(12) United States Patent
Brown, Jr. et al.

(10) Patent No.: US 9,039,179 B2
(45) Date of Patent: May 26, 2015

(54) UNOBTRUSIVE ACTIVE EYE INTERROGATION

(71) Applicant: Elwha LLC, Bellevue, WA (US)

(72) Inventors: Allen L. Brown, Jr., Bellevue, WA (US); Douglas C. Burger, Bellevue, WA (US); Eric Horvitz, Kirkland, WA (US); Roderick A. Hyde, Redmond, WA (US); Edward K. Y. Jung, Bellevue, WA (US); Eric C. Leuthardt, St. Louis, MO (US); Jordin T. Kare, Seattle, WA (US); Chris Demetrios Karkanias, Sammamish, WA (US); John L. Manferdelli, San Francisco, CA (US); Craig J. Mundie, Seattle, WA (US); Nathan P. Myhrvold, Medina, WA (US); Barney Pell, San Francisco, CA (US); Clarence T. Tegreene, Mercer Island, WA (US); Willard H. Wattenburg, Walnut Creek, CA (US); Charles Whitmer, North Bend, WA (US); Lowell L. Wood, Jr., Bellevue, WA (US); Richard N. Zare, Stanford, CA (US)

(73) Assignee: Elwha LLC, Bellevue, WA (US)

( * ) Notice: Subject to any disclaimer, the term of this patent is extended or adjusted under 35 U.S.C. 154(b) by 90 days.

(21) Appl. No.: 13/711,436

(22) Filed: Dec. 11, 2012

(65) Prior Publication Data
US 2014/0160433 A1    Jun. 12, 2014

(51) Int. Cl.
*A61B 3/14*  (2006.01)
*A61B 3/10*  (2006.01)
*A61B 3/113* (2006.01)

(52) U.S. Cl.
CPC .................................. *A61B 3/113* (2013.01)

(58) Field of Classification Search
USPC .......... 351/208, 200, 203, 205, 211, 206, 221, 351/222, 237, 243–245, 210
See application file for complete search history.

(56) References Cited

U.S. PATENT DOCUMENTS

| | | | |
|---|---|---|---|
| 3,948,248 | A | 4/1976  | Zuckerman et al. |
| 4,494,881 | A | 1/1985  | Everest |
| 4,641,349 | A | 2/1987  | Flom et al. |
| 5,115,815 | A | 5/1992  | Hansen |
| 5,398,681 | A | 3/1995  | Kupershmidt |
| 5,433,197 | A | 7/1995  | Stark |
| 5,572,596 | A | 11/1996 | Wildes et al. |

(Continued)

FOREIGN PATENT DOCUMENTS

EP    2 508 931 A1    10/2012

OTHER PUBLICATIONS

"24-Bit, 102.4 kS/s, 8 and 4-Channel Dynamic Signal Acquisition", National Instruments, bearing a date of 2004, pp. 1-4, National Instruments Corporation.

(Continued)

*Primary Examiner* — Scott J Sugarman
*Assistant Examiner* — Brandi Thomas

(57) ABSTRACT

Methods and systems for determining a physiological parameter of a subject through interrogation of an eye of the subject with an optical signal are described. Interrogation is performed unobtrusively. The physiological parameter is determined from a signal sensed from the eye of a subject when the eye of the subject is properly aligned with regard to an interrogation signal source and/or response signal sensor.

23 Claims, 67 Drawing Sheets

(56) References Cited

U.S. PATENT DOCUMENTS

| | | | |
|---|---|---|---|
| 5,995,856 | A | 11/1999 | Mannheimer et al. |
| 6,053,738 | A | 4/2000 | Ivey, Jr. |
| 6,110,110 | A | 8/2000 | Dublin, Jr. et al. |
| 6,149,589 | A | 11/2000 | Diaconu et al. |
| 6,198,532 | B1 | 3/2001 | Cabib et al. |
| 6,276,798 | B1 | 8/2001 | Gil et al. |
| 6,305,804 | B1 | 10/2001 | Rice et al. |
| 6,542,442 | B2 | 4/2003 | Kaslon |
| 6,556,853 | B1 | 4/2003 | Cabib et al. |
| 6,958,039 | B2 | 10/2005 | Burd et al. |
| 6,961,599 | B2 | 11/2005 | Lambert et al. |
| 7,187,960 | B2 | 3/2007 | Abreu |
| 7,272,431 | B2 | 9/2007 | McGrath |
| 7,811,234 | B2 | 10/2010 | McGrath |
| 8,248,217 | B2 | 8/2012 | Kang et al. |
| 8,308,558 | B2 | 11/2012 | Thorner |
| 2004/0123667 | A1 | 7/2004 | McGrath |
| 2004/0127778 | A1 | 7/2004 | Lambert et al. |
| 2004/0257585 | A1 | 12/2004 | Cornsweet |
| 2006/0178572 | A1 | 8/2006 | March |
| 2006/0183986 | A1 | 8/2006 | Rice et al. |
| 2008/0045832 | A1 | 2/2008 | McGrath |
| 2008/0273768 | A1 | 11/2008 | Dennis et al. |
| 2008/0287821 | A1 | 11/2008 | Jung et al. |
| 2009/0018419 | A1 | 1/2009 | Torch |
| 2009/0105605 | A1 | 4/2009 | Abreu |
| 2010/0220289 | A1 | 9/2010 | Hearn et al. |
| 2011/0184262 | A1 | 7/2011 | Menon |
| 2012/0179380 | A1 | 7/2012 | Taylor et al. |
| 2014/0160432 | A1* | 6/2014 | Brown et al. ............... 351/208 |
| 2014/0160434 | A1* | 6/2014 | Brown et al. ............... 351/210 |
| 2014/0163329 | A1* | 6/2014 | Brown et al. ............... 600/301 |

OTHER PUBLICATIONS

"Characterisation", Warfarin IR Spectrum, http://www.chi.ic.ac.uk/local/projects/bhonoah/characterisation.html, bearing a date of Oct. 25, 2012, pp. 1-3.

Chi et al., "Key Techniques of Eye Gaze Tracking Based on Pupil Corneal Reflection", Global Congress on Intelligent Systems, 2009, pp. 133-138, IEEE.

"Crossmatch Retinal Scan 2 Iris Scanner", http://bayometric.com/products/i-scan-2-usb-iris-scanner-iris-scanning.htm, bearing a date of Oct. 22, 2012, pp. 1-2, Bayometric Inc.

Corcoran et al., "Real-Time Eye Gaze Tracking for Gaming Design and Consumer Electronics Systems", IEEE Transactions on Consumer Electronics, May 2012, published Jun. 22, 2012, pp. 347-355, vol. 58, No. 2, IEEE.

"faceLAB 5", Specification Sheet, 2012, pp. 1, Seeing Machines.

"Fluke Industrial/Electrical Thermal Imagers, Models: Ti25 and Ti10" bearing a date of 2009-2011, pp. 1-3, Fluke Corporation.

Hansen et al., "In the Eye of the Beholder: A Survey of Models for Eyes and Gaze", IEEE Transactions on Pattern Analysis and Machine Intelligence, Mar. 2010, published Jan. 23, 2009pp. 478-500, vol. 32, No. 3, IEEE.

Hennessey et al., "Fixation Precision in High-Speed Noncontact Eye-Gaze Tracking", IEEE Transactions on Systems, Man, and Cybernetics—Part B: Cybernetics, Apr. 2008, Revised May 28, 2007, pp. 289-298, vol. 38, No. 2, IEEE.

"HL-2000 Tungsten Halogen Light Sources", Ocean Optics, bearing dates of 1989-2012, created on Oct. 30, 2012, pp. 1-3, Ocean Optics, Inc.

Kessel et al., "The Relationship between Body and Ambient Temperature and Corneal Temperature", Investigative Ophthalmology & Visual Science, Dec. 2010, pp. 6593-6597, vol. 51, No. 12, Association for Research in Vision and Ophthalmology.

Klinger, Jeff, "Measuring Cognitive Load During Visual Tasks by Combining Pupillometry and Eye Tracking", A dissertation submitted to the department of computer science and the committee on graduate studies of Stanford University, May 2010, pp. i-xvi, 1-116, Jeffrey Michael Klinger.

Mikhelson et al., "Remote Sensing of Heart Rate and Patterns of Respiration on a Stationary Subject Using 94-GHz Millimeter-Wave Interferometry", IEEE Transactions on Biomedical Engineering, Jun. 2011, published Feb. 4, 2011, pp. 1671-1677, vol. 58, No. 6, IEEE.

"MIR8025™ Modular IR Fourier Spectrometers", http://www.newport.com/MIR8025-Modular-IR-Fourier-Spectrometers/378421/1033/info.aspx#tab_Specifications, 1996-2012, bearing a date of Oct. 25, 2012, pp. 1-2, Newport Corporation.

Pastoor et al., "An Experimental Multimedia System Allowing 3-D Visualization and Eye-Controlled Interaction Without User-Worn Devices", IEEE Transactions on Multimedia, Mar. 1999, Revised Nov. 23, 1998, pp. 41-47, vol. 1, No. 1, IEEE.

Palinko et al., "Estimating Cognitive Load Using Remote Eye Tracking in a Driving Simulator", Proceedings of the 2010 Symposium on Eye Tracking Research and Applications, 2010, pp. 141-144, Austin, TX.

"Picomotor Piezo Linear Actuators", http://www.newport.com/Picomotor-Piezo-Linear-Actuators/853235/1033/info.aspx#tab_Specifications, 1996-2012, bearing a date of Oct. 22, 2012, pp. 1-2 Newport Corporation.

Saha et al., "The Impact of Cardiac Index on Cerebral Hemodynamics", Stroke, Nov. 1993, accepted Jun. 8, 1993, pp. 1686-1690, vol. 24, No. 11.

"Sensitivity", Avantes, http://www.avantes.com website, printed on Oct. 23, 2012, pp. 1-3.

"Über Tuner™ Broad Tuning Pulsed Lasers", http://www.daylightsolutions.com/products/lasers/tunable-laser-uber.htm, 2011, bearing a date of Oct. 24, 2012, pp. 1-4, Daylight Solutions.

"USB2000+ Miniature Fiber Optic Spectrometer", http://www.oceanoptics.com/Products/usb2000+.asp, 1989-2012, printed on Oct. 18, 2012, pp. 1-3, Ocean Optics, Inc.

Zhu et al., "Novel Eye Gaze Tracking Techniques Under Natural Head Movement", IEEE Transactions on Biomedical Engineering, Dec. 2007, revised Dec. 11, 2007, pp. 2246-2260, vol. 54, No. 12, IEEE.

PCT International Search Report; International App. No. PCT/US2013/074313; Mar. 7, 2014; pp. 1-2.

* cited by examiner

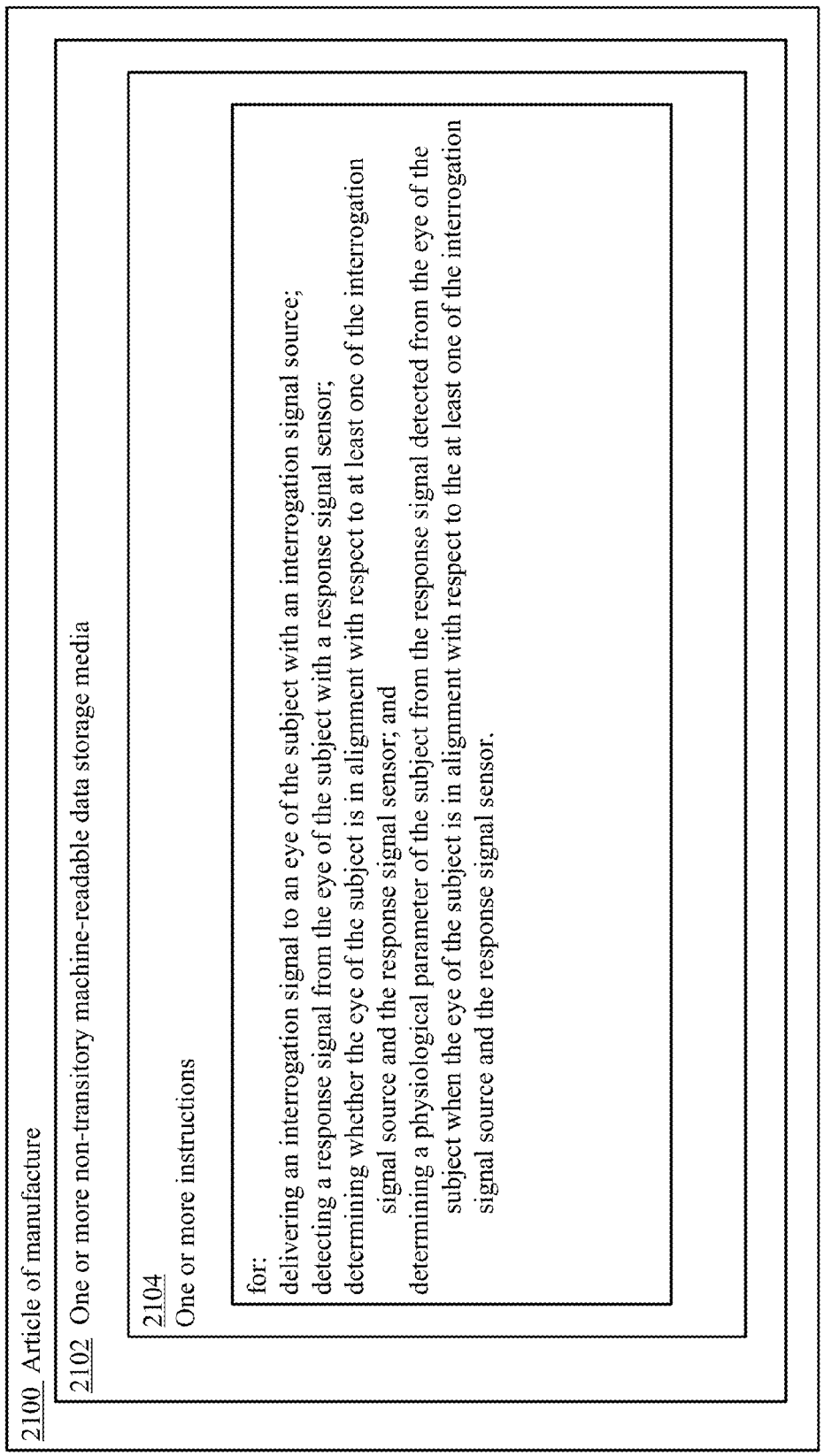

FIG. 21

2100 Article of manufacture

2102 One or more non-transitory machine-readable data storage media

2104 One or more instructions for:
delivering an interrogation signal to an eye of the subject with an interrogation signal source;
detecting a response signal from the eye of the subject with a response signal sensor;
determining whether the eye of the subject is in alignment with respect to at least one of the interrogation signal source and the response signal sensor; and
determining a physiological parameter of the subject from the response signal detected from the eye of the subject when the eye of the subject is in alignment with respect to the at least one of the interrogation signal source and the response signal sensor.

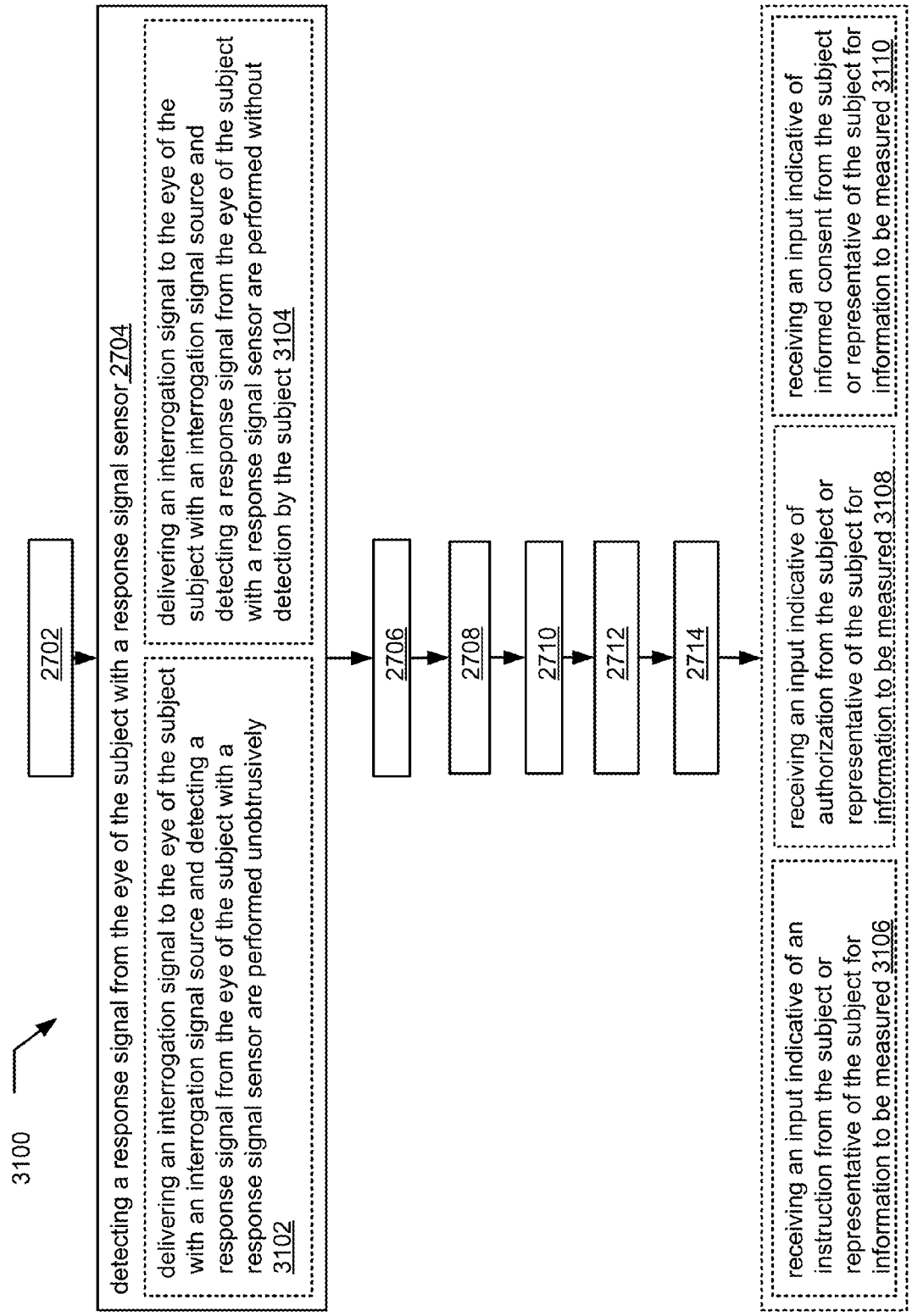

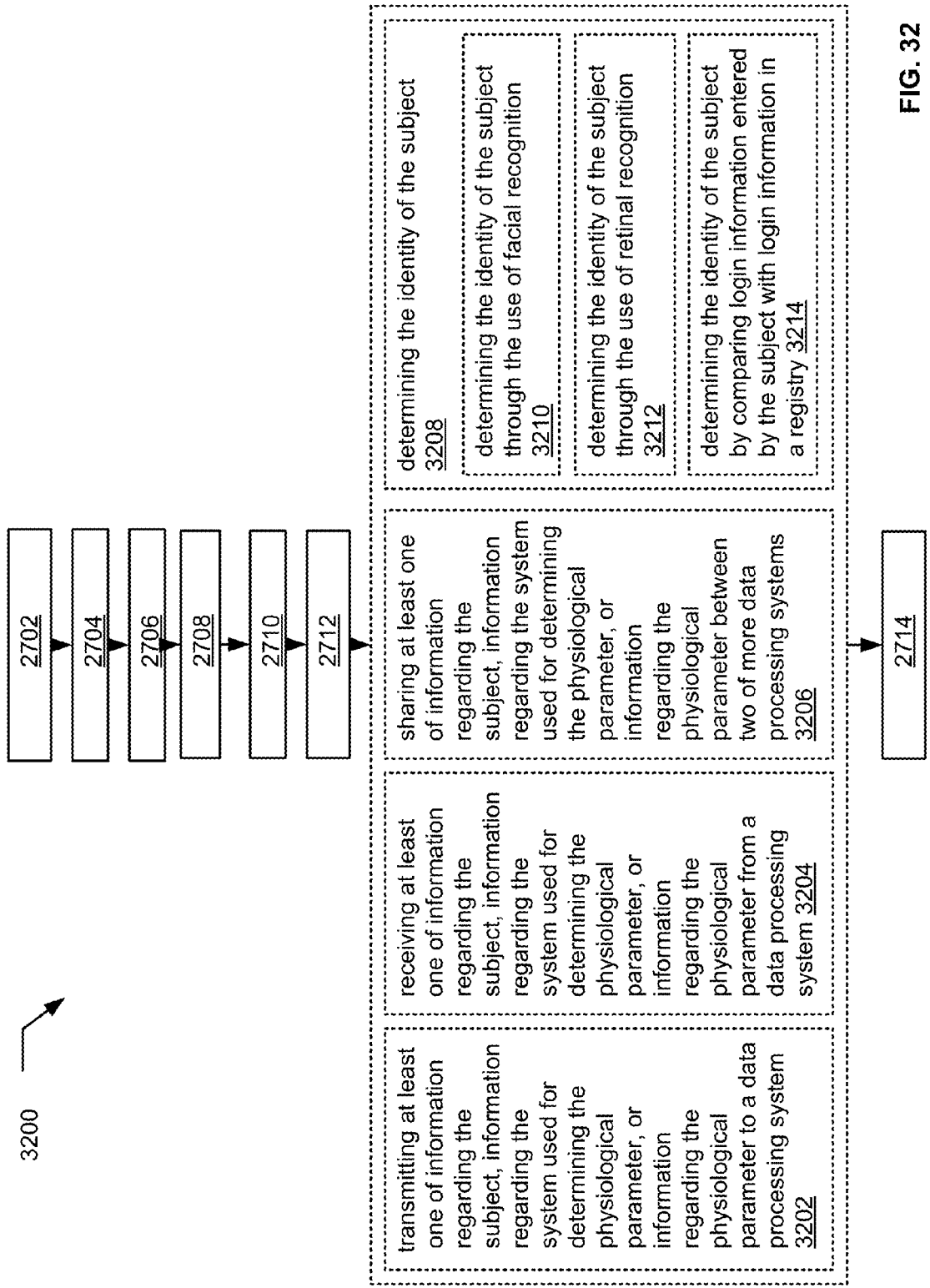

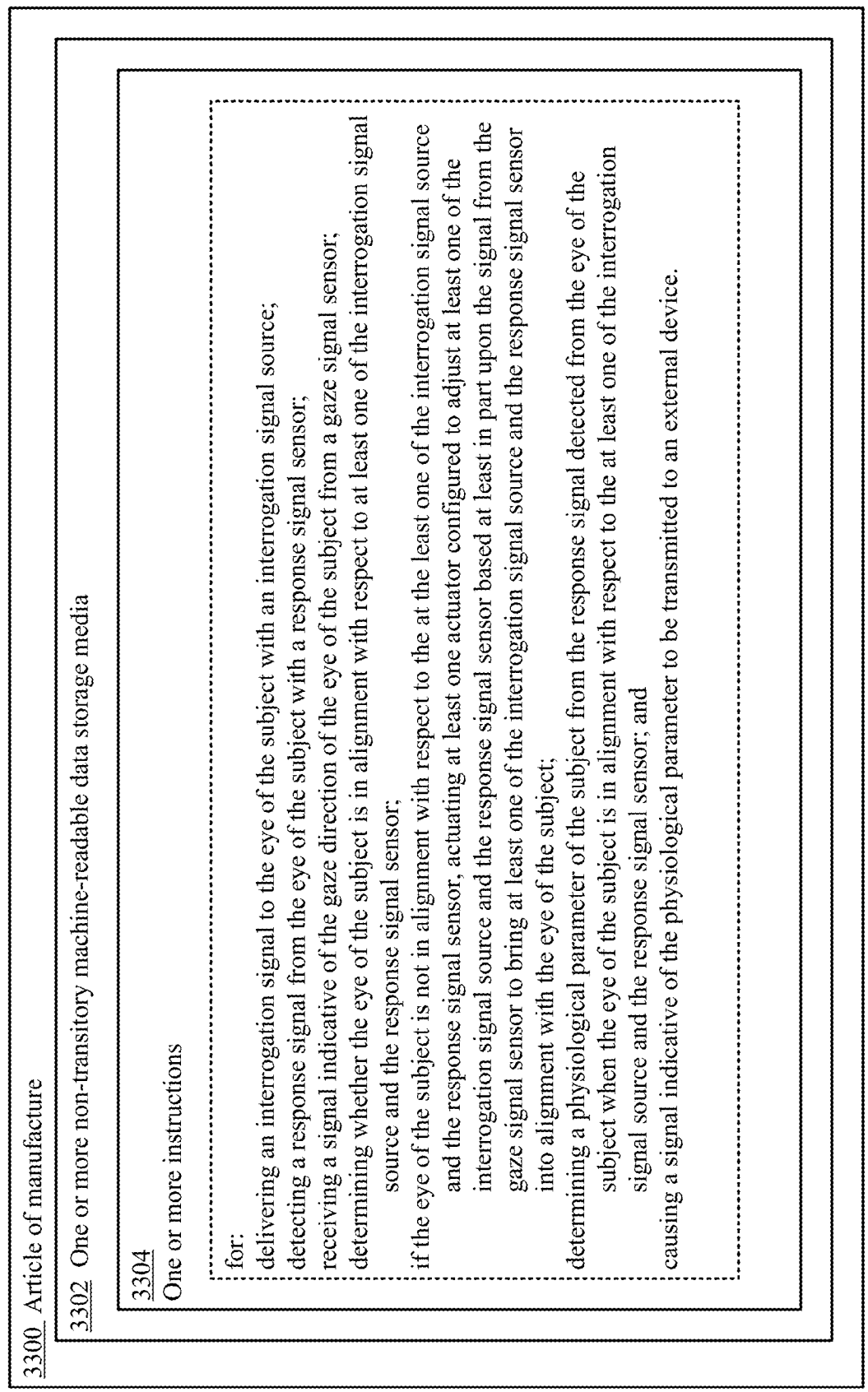

FIG. 33

3300 Article of manufacture

3302 One or more non-transitory machine-readable data storage media

3304
One or more instructions for:
delivering an interrogation signal to the eye of the subject with an interrogation signal source;
detecting a response signal from the eye of the subject with a response signal sensor;
receiving a signal indicative of the gaze direction of the eye of the subject from a gaze signal sensor;
determining whether the eye of the subject is in alignment with respect to at least one of the interrogation signal source and the response signal sensor;
if the eye of the subject is not in alignment with respect to the at the least one of the interrogation signal source and the response signal sensor, actuating at least one actuator configured to adjust at least one of the interrogation signal source and the response signal sensor based at least in part upon the signal from the gaze signal sensor to bring at least one of the interrogation signal source and the response signal sensor into alignment with the eye of the subject;
determining a physiological parameter of the subject from the response signal detected from the eye of the subject when the eye of the subject is in alignment with respect to the at least one of the interrogation signal source and the response signal sensor; and
causing a signal indicative of the physiological parameter to be transmitted to an external device.

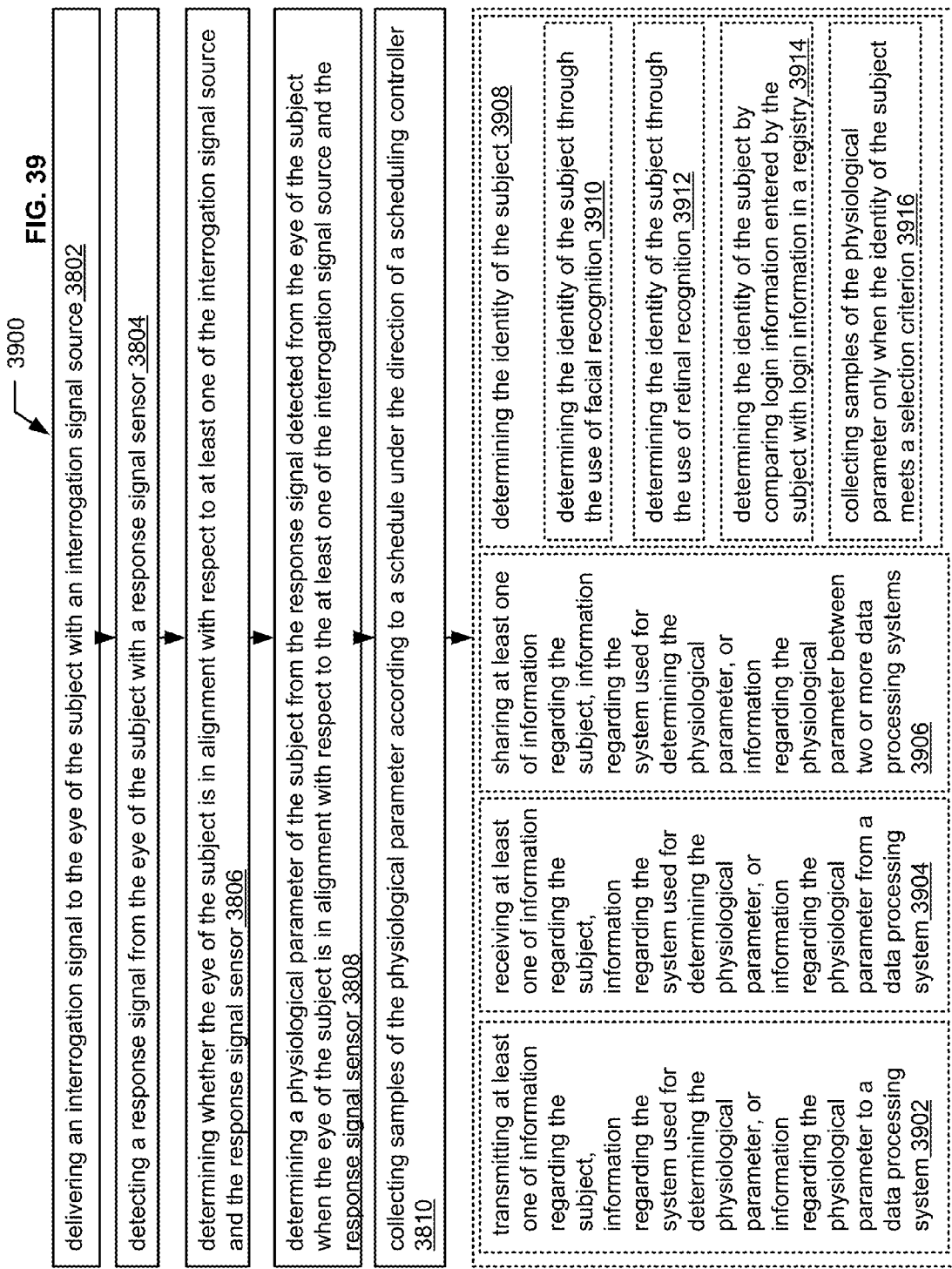

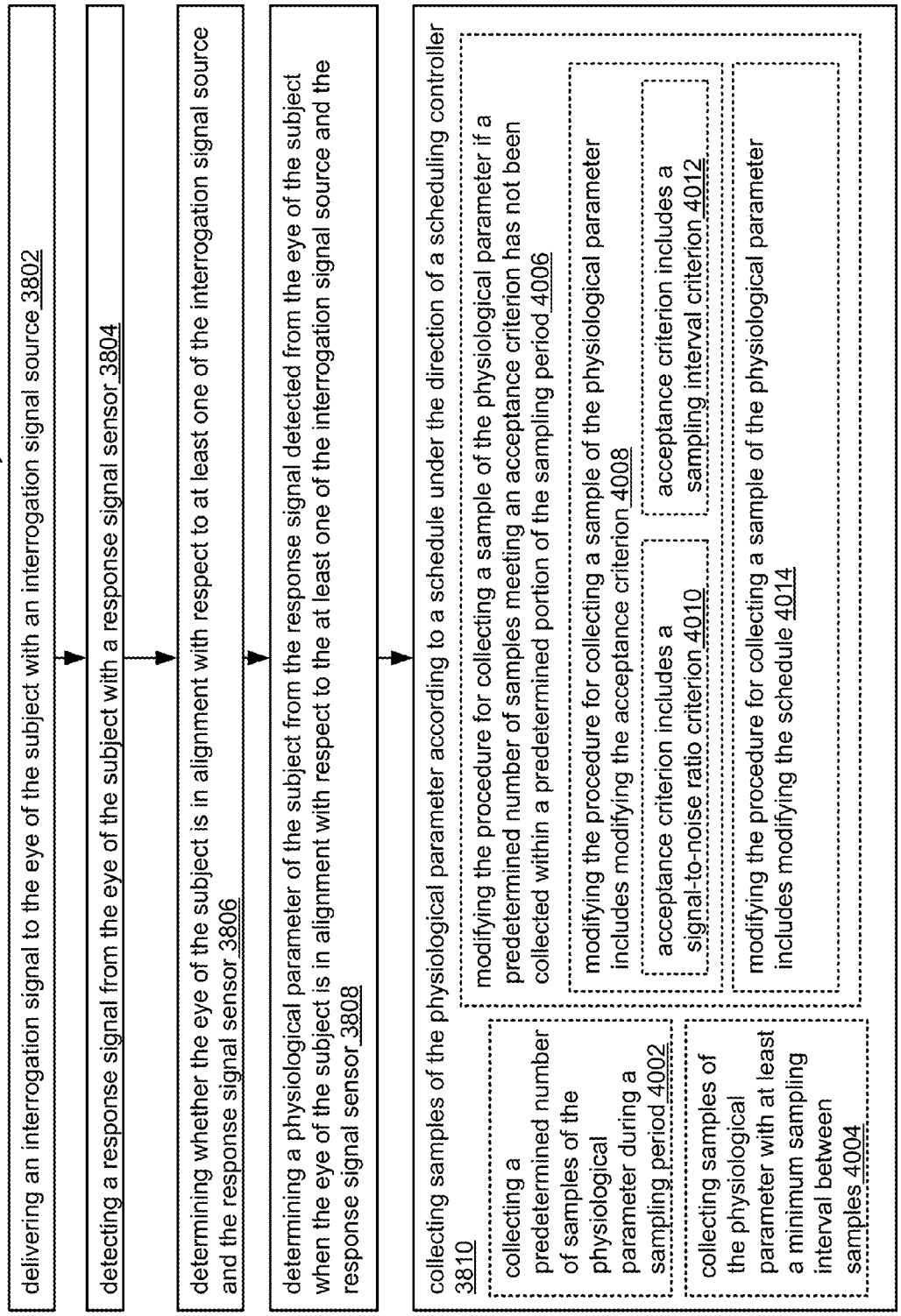

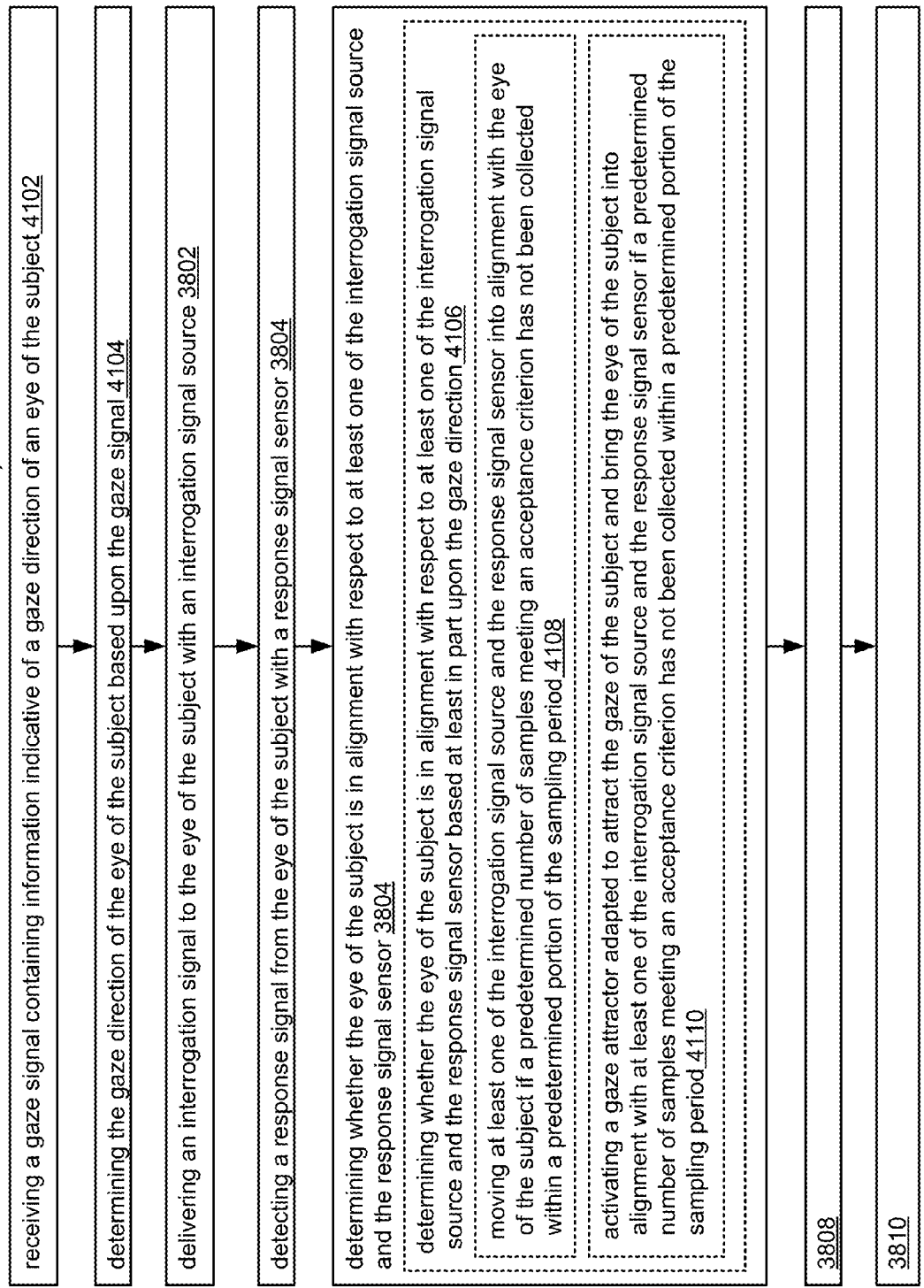

- delivering an interrogation signal to the eye of the subject with an interrogation signal source 3802
  - delivering the interrogation signal includes delivering a pulsed interrogation signal 4202
  - gating detection of the response signal relative to the pulsed interrogation signal 4204
  - detecting multiple response signals produced by the eye of the subject in response to multiple pulses of the pulsed interrogation signal 4206
    - combining the multiple response signals produced by the eye of the subject in response to multiple pulses of the pulsed interrogation signal by summing the multiple response signals 4208
    - including combining the multiple response signals produced by the eye of the subject in response to multiple pulses of the pulsed interrogation signal by averaging the multiple response signals 4210
    - combining the multiple response signals produced by the eye of the subject in response to multiple pulses of the pulsed interrogation signal by determining a moving average of the multiple response signals 4212
    - combining the multiple response signals produced by the eye of the subject in response to multiple pulses of the pulsed interrogation signal by determining a weighted sum of the multiple response signals 4214

- detecting a response signal from the eye of the subject with a response signal sensor 3804

- determining whether the eye of the subject is in alignment with respect to at least one of the interrogation signal source and the response signal sensor 3806

- determining a physiological parameter of the subject from the response signal detected from the eye of the subject when the eye of the subject is in alignment with respect to the at least one of the interrogation signal source and the response signal sensor 3808

- collecting samples of the physiological parameter according to a schedule under the direction of a scheduling controller 3810

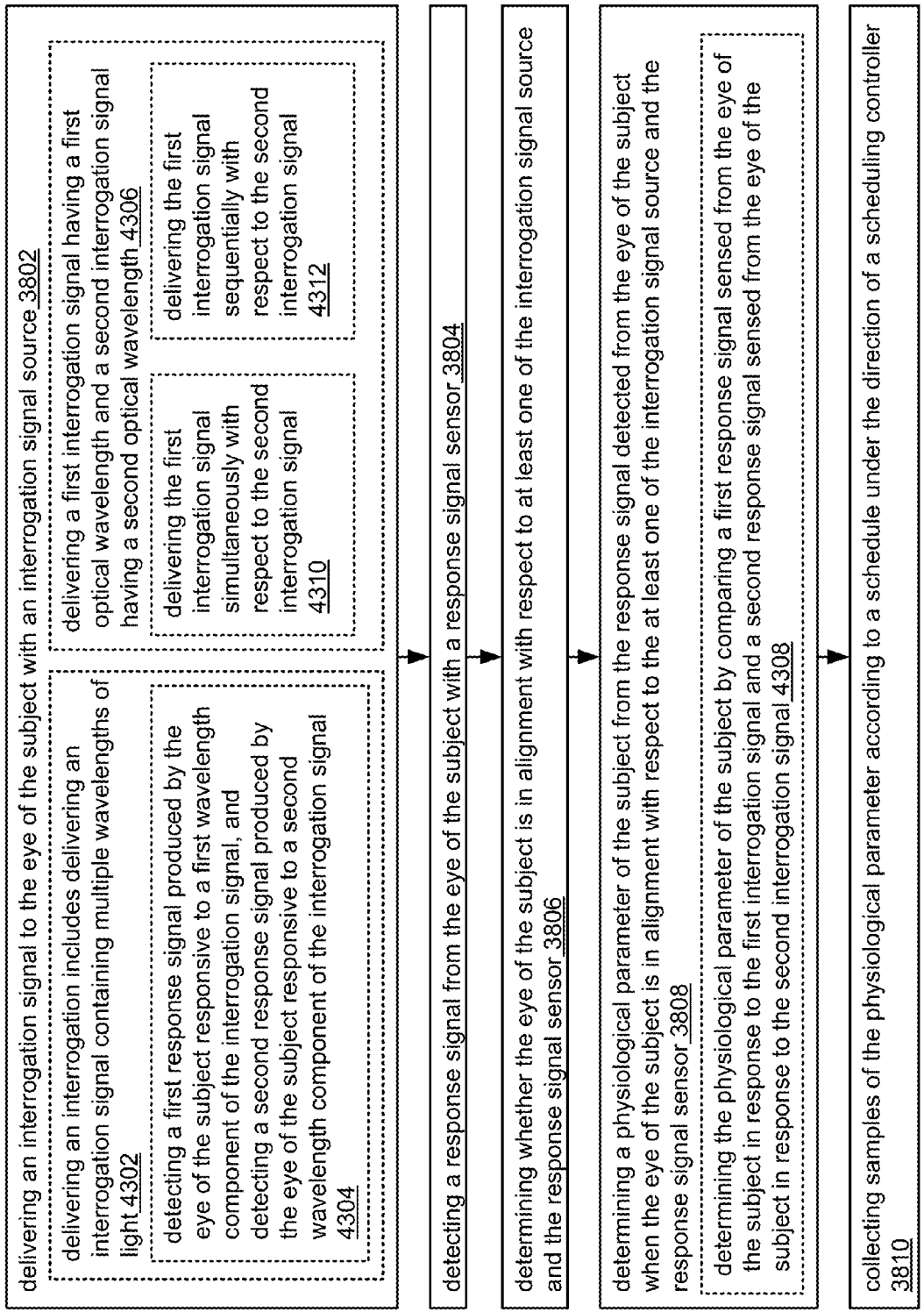

UNOBTRUSIVE ACTIVE EYE INTERROGATION

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

None.

RELATED APPLICATIONS

U.S. patent application Ser. No. 13/711,445, entitled SELF-ALIGNING UNOBTRUSIVE ACTIVE EYE INTERROGATION naming ALLEN L. BROWN, DOUGLAS C. BURGER, ERIC HORVITZ, RODERICK A. HYDE, EDWARD K. Y. JUNG, ERIC C. LEUTHARDT, JORDIN T. KARE, CHRIS DEMETRIOS KARKANIAS, JOHN L. MANFERDELLI, CRAIG J. MUNDIE, NATHAN P. MYHRVOLD, BARNEY PELL, CLARENCE T. TEGREENE, WILLARD H. WATTENBURG, CHARLES WHITMER, LOWELL L. WOOD, Jr., AND RICHARD N. ZARE as inventors, filed 11 Dec. 2012, is related to the present application.

U.S. patent application Ser. No. 13/711,453, entitled TIME-BASED UNOBTRUSIVE ACTIVE EYE INTERROGATION naming ALLEN L. BROWN, DOUGLAS C. BURGER, ERIC HORVITZ, RODERICK A. HYDE, EDWARD K. Y. JUNG, ERIC C. LEUTHARDT, JORDIN T. KARE, CHRIS DEMETRIOS KARKANIAS, JOHN L. MANFERDELLI, CRAIG J. MUNDIE, NATHAN P. MYHRVOLD, BARNEY PELL, CLARENCE T. TEGREENE, WILLARD H. WATTENBURG, CHARLES WHITMER, LOWELL L. WOOD, Jr., AND RICHARD N. ZARE as inventors, filed 11 Dec. 2012, is related to the present application.

U.S. patent application Ser. No. 13/711,459, entitled UNOBTRUSIVE ACTIVE EYE INTERROGATION WITH GAZE ATTRACTOR naming ALLEN L. BROWN, DOUGLAS C. BURGER, ERIC HORVITZ, RODERICK A. HYDE, EDWARD K. Y. JUNG, ERIC C. LEUTHARDT, JORDIN T. KARE, CHRIS DEMETRIOS KARKANIAS, JOHN L. MANFERDELLI, CRAIG J. MUNDIE, NATHAN P. MYHRVOLD, BARNEY PELL, CLARENCE T. TEGREENE, WILLARD H. WATTENBURG, CHARLES WHITMER, LOWELL L. WOOD, Jr., AND RICHARD N. ZARE as inventors, filed 11 Dec. 2012, is related to the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

To the extent that the listings of applications provided above may be inconsistent with the listings provided via an ADS, it is the intent of the Application to claim priority to all applications listed in the Priority Applications section of either document.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

In one aspect, a system for sensing information from an eye of a subject includes, but is not limited to a gaze signal sensor adapted for receiving a gaze signal containing information indicative of a gaze direction of an eye of the subject; an interrogation signal source for delivering an interrogation signal to an eye of a subject; a response signal sensor for sensing a response signal produced by the eye of the subject responsive to the interrogation signal; signal processing circuitry including: a gaze signal processor configured to determine the gaze direction of the eye of the subject based upon the gaze signal; an alignment detector configured to determine whether the eye of the subject is in alignment with respect to at least one of the interrogation signal source and the response signal sensor based at least in part upon the gaze direction; and a response signal processor configured to process the response signal sensed from the eye of the subject by the response signal sensor when the eye of the subject is in alignment with respect to the at least one of the interrogation signal source and the response signal sensor to determine a physiological parameter from the response signal. In addition to the foregoing, other system aspects are described in the claims, drawings, and text forming a part of the disclosure set forth herein.

In one aspect, a system for controlling the sensing of information from an eye of a subject includes, but is not limited to signal processing circuitry including: a gaze signal input adapted to receive a gaze signal containing information indicative of a gaze direction of the eye of the subject sensed from at least an eye of the subject; a response signal input adapted to receive a response signal sensed from the eye of the subject by a response signal sensor responsive to delivery of an interrogation signal to the eye of the subject; a gaze signal processor configured to determine the gaze direction of the eye of the subject based upon the gaze signal; an alignment detector configured to determine whether the eye of the subject is in alignment with respect to at least one of the interrogation signal source and the response signal sensor based at least in part upon the gaze direction; and a response signal processor configured to process the response signal sensed from the eye of the subject by the response signal sensor when the eye of the subject is in alignment with respect to the at least one of the interrogation signal source and the response signal sensor to determine a physiological parameter from the response signal. In addition to the foregoing, other system aspects are described in the claims, drawings, and text forming a part of the disclosure set forth herein.

In one aspect, a system includes, but is not limited to a housing; an interrogation signal source housed in the housing and adapted for delivering an interrogation signal to an eye of a subject, the interrogation signal source including at least one light source and at least one optical system; a response signal sensor housed within the housing and adapted for sensing a response signal produced by the eye of the subject responsive to the interrogation signal, the response signal containing information regarding a physiological parameter of the subject; an output structure adapted for transmitting an output signal; mounting means adapted for mounting the housing with respect to a display in such a manner that the interrogation signal source and response signal sensor are alignable with the eye of the subject during normal use of the display by the subject. In addition to the foregoing, other system aspects are described in the claims, drawings, and text forming a part of the disclosure set forth herein.

In one aspect, a method of measuring information from an eye of a subject includes, but is not limited to; delivering an interrogation signal to the eye of the subject with an interrogation signal source; detecting a response signal from the eye of the subject with a response signal sensor; determining whether the eye of the subject is in alignment with respect to at least one of the interrogation signal source and the response signal sensor; and determining a physiological parameter of the subject from the response signal detected from the eye of the subject when the eye of the subject is in alignment with respect to the at least one of the interrogation signal source and the response signal sensor. In addition to the foregoing, other method aspects are described in the claims, drawings, and text forming a part of the disclosure set forth herein.

In one aspect, an article of manufacture includes, but is not limited to, one or more non-transitory machine-readable data storage media bearing one or more instructions for: delivering an interrogation signal to an eye of the subject with an interrogation signal source; detecting a response signal from the eye of the subject with a response signal sensor; determining whether the eye of the subject is in alignment with respect to at least one of the interrogation signal source and the response signal sensor; and determining a physiological parameter of the subject from the response signal detected from the eye of the subject when the eye of the subject is in alignment with respect to the at least one of the interrogation signal source and the response signal sensor. In addition to the foregoing, other aspects of articles of manufacture including one or more non-transitory machine-readable data storage media bearing one or more instructions are described in the claims, drawings, and text forming a part of the disclosure set forth herein.

In one aspect, a system for sensing information from an eye of a subject includes, but is not limited to: an interrogation signal source for delivering an interrogation signal to an eye of a subject; a response signal sensor for sensing a response signal produced by the eye of the subject responsive to the interrogation signal; a gaze signal sensor adapted for receiving a gaze signal containing information indicative of a gaze direction of an eye of the subject; at least one actuator configured to adjust at least one of the interrogation signal source and the response signal sensor to bring at least one of the interrogation signal source and the response signal sensor into alignment with the eye of the subject; and signal processing circuitry including: a response signal processor configured to process a response signal sensed from the eye of the subject to determine a physiological parameter from the response signal; a gaze signal processor configured to determine the gaze direction of the eye of the subject based upon the gaze signal; an alignment detector configured to determine whether the eye of the subject is in alignment with respect to at least one of the interrogation signal source and the response signal sensor based at least in part upon the gaze direction; and an actuator controller configured to: determine a target position for at least one of the interrogation signal source and the response signal sensor based at least in part on the gaze direction; and generate an actuator control signal to drive the at least one actuator to adjust at least one of the interrogation signal source and the response signal sensor to bring at least one of the interrogation signal source and the response signal sensor into alignment with the eye of the subject. In addition to the foregoing, other system aspects are described in the claims, drawings, and text forming a part of the disclosure set forth herein.

In one aspect, a system for controlling the sensing of information from an eye of a subject includes, but is not limited to: signal processing circuitry including: a gaze signal input adapted to receive a gaze signal containing information indicative of a gaze direction of the eye of the subject sensed from at least an eye of the subject; a response signal input adapted to receive a response signal sensed from the eye of the subject by a response signal sensor responsive to delivery of an interrogation signal to the eye of the subject; a response signal processor configured to process a response signal sensed from the eye of the subject to determine a physiological parameter from the response signal; a gaze signal processor configured to determine the gaze direction of the eye of the subject based upon the gaze signal; an alignment detector configured to determine whether the eye of the subject is in alignment with respect to at least one of the interrogation signal source and the response signal sensor based at least in part upon the gaze direction; and an actuator controller configured to: determine a target position for at least one of the interrogation signal source and the response signal sensor based at least in part on the gaze direction; and generate an actuator control signal to drive the at least one actuator to adjust at least one of the interrogation signal source and the response signal sensor to bring at least one of the interrogation signal source and the response signal sensor into alignment with the eye of the subject. In addition to the foregoing, other system aspects are described in the claims, drawings, and text forming a part of the disclosure set forth herein.

In one aspect, a system includes, but is not limited to a housing; an interrogation signal source housed in the housing and adapted for delivering an interrogation signal to an eye of a subject, the interrogation signal source including at least one light source and at least one optical system; a response signal sensor housed within the housing and adapted for sensing a response signal produced by the eye of the subject responsive to the interrogation signal, the response signal containing information regarding a physiological parameter of the subject; an input structure adapted for receiving an input signal; at least one actuator configured to adjust at least one of the interrogation signal source and the response signal sensor based at least in part upon the input signal to bring at least one of the interrogation signal source and the response signal sensor into alignment with the eye of the subject; an output structure adapted for transmitting an output signal; and mounting means adapted for mounting the housing with respect to a display in such a manner that the interrogation signal source and response signal sensor are alignable with the eye of the subject during normal use of the display by the subject. In addition to the foregoing, other system aspects are described in the claims, drawings, and text forming a part of the disclosure set forth herein.

In one aspect, a method of measuring information from an eye of a subject includes, but is not limited to delivering an interrogation signal to the eye of the subject with an interrogation signal source; detecting a response signal from the eye of the subject with a response signal sensor; receiving a signal indicative of the gaze direction of the eye of the subject from a gaze signal sensor; determining whether the eye of the subject is in alignment with respect to at least one of the interrogation signal source and the response signal sensor; if the eye of the subject is not in alignment with respect to the at least one of the interrogation signal source and the response signal sensor, actuating at least one actuator configured to adjust at least one of the interrogation signal source and the response signal sensor based at least in part upon the signal from the gaze signal sensor to bring at least one of the interrogation signal source and the response signal sensor into alignment with the eye of the subject; determining a physiological parameter of the subject from the response signal detected from the eye of the subject when the eye of the subject is in alignment with respect to the at least one of the interrogation signal source and the response signal sensor; and causing a signal indicative of the physiological parameter to be transmitted to an external device. In addition to the foregoing, other method aspects are described in the claims, drawings, and text forming a part of the disclosure set forth herein.

In one aspect, an article of manufacture includes, but is not limited to, one or more non-transitory machine-readable data storage media bearing one or more instructions for: delivering an interrogation signal to the eye of the subject with an interrogation signal source; detecting a response signal from the eye of the subject with a response signal sensor; receiving a signal indicative of the gaze direction of the eye of the subject from a gaze signal sensor; determining whether the eye of the subject is in alignment with respect to at least one of the interrogation signal source and the response signal sensor; if the eye of the subject is not in alignment with respect to the at least one of the interrogation signal source and the response signal sensor, actuating at least one actuator configured to adjust at least one of the interrogation signal source and the response signal sensor based at least in part upon the signal from the gaze signal sensor to bring at least one of the interrogation signal source and the response signal sensor into alignment with the eye of the subject; determining a physiological parameter of the subject from the response signal detected from the eye of the subject when the eye of the subject is in alignment with respect to the at least one of the interrogation signal source and the response signal sensor; and causing a signal indicative of the physiological parameter to be transmitted to an external device. In addition to the foregoing, other aspects of articles of manufacture including one or more non-transitory machine-readable data storage media bearing one or more instructions are described in the claims, drawings, and text forming a part of the disclosure set forth herein.

In one aspect, a system for sensing information from an eye of a subject includes, but is not limited to: an interrogation signal source for delivering an interrogation signal to an eye of a subject; a response signal sensor for sensing a response signal produced by the eye of the subject responsive to the interrogation signal; and signal processing circuitry including: a response signal processor configured to process a response signal sensed from the eye of the subject to determine a physiological parameter from the response signal; and a scheduling controller configured to direct collection of samples of the physiological parameter according to a schedule. In addition to the foregoing, other system aspects are described in the claims, drawings, and text forming a part of the disclosure set forth herein.

In one aspect, a system for controlling the sensing of information from an eye of a subject includes, but is not limited to: signal processing circuitry including: a response signal input adapted to receive a response signal sensed from the eye of the subject by a response signal sensor responsive to delivery of an interrogation signal to the eye of the subject; and a response signal processor configured to process the response signal sensed from the eye of the subject by the response signal sensor to determine a physiological parameter from the response signal; and a scheduling controller configured to direct collection of samples of the physiological parameter according to a schedule. In addition to the foregoing, other system aspects are described in the claims, drawings, and text forming a part of the disclosure set forth herein.

In one aspect, a system includes, but is not limited to a housing; an interrogation signal source housed in the housing and adapted for delivering an interrogation signal to an eye of a subject, the interrogation signal source including at least one light source and at least one optical system; a response signal sensor housed within the housing and adapted for sensing a response signal produced by the eye of the subject responsive to the interrogation signal, the response signal containing information regarding a physiological parameter of the subject; signal processing circuitry including: a response signal processor configured to process a response signal sensed from the eye of the subject to determine a physiological parameter from the response signal; and a scheduling controller configured to direct collection of samples of the physiological parameter according to a schedule; an output structure adapted for transmitting an output signal; and mounting means adapted for mounting the housing with respect to a display in such a manner that the interrogation signal source and response signal sensor are alignable with the eye of the subject during normal use of the display by the subject. In addition to the foregoing, other system aspects are described in the claims, drawings, and text forming a part of the disclosure set forth herein.

In one aspect, a method of measuring information from an eye of a subject includes, but is not limited to; delivering an interrogation signal to the eye of the subject with an interrogation signal source; detecting a response signal from the eye of the subject with a response signal sensor; processing a response signal sensed from the eye of the subject to determine a physiological parameter from the response signal; determining whether the eye of the subject is in alignment with respect to at least one of the interrogation signal source and the response signal sensor; determining a physiological parameter of the subject from the response signal detected from the eye of the subject when the eye of the subject is in alignment with respect to the at least one of the interrogation signal source and the response signal sensor; and collecting samples of the physiological parameter according to a schedule under the direction of a scheduling controller. In addition to the foregoing, other method aspects are described in the claims, drawings, and text forming a part of the disclosure set forth herein.

In one aspect, an article of manufacture includes, but is not limited to, one or more non-transitory machine-readable data storage media bearing one or more instructions for: delivering an interrogation signal to the eye of the subject with an interrogation signal source; detecting a response signal from the eye of the subject with a response signal sensor; processing a response signal sensed from the eye of the subject to determine a physiological parameter from the response signal; determining whether the eye of the subject is in alignment with respect to at least one of the interrogation signal source and the response signal sensor; determining a physiological parameter of the subject from the response signal detected from the eye of the subject when the eye of the subject is in alignment with respect to the at least one of the interrogation signal source and the response signal sensor; and collecting samples of the physiological parameter according to a schedule under the direction of a scheduling controller. In addition to the foregoing, other aspects of articles of manufacture including one or more non-transitory machine-readable data storage media bearing one or more instructions are described in the claims, drawings, and text forming a part of the disclosure set forth herein.

In one aspect, a system for sensing information from an eye of a subject includes, but is not limited to: an interrogation signal source for delivering an interrogation signal to an eye of a subject; a response signal sensor for sensing a response signal produced by the eye of the subject responsive to the interrogation signal; a gaze attractor adapted to attract the gaze of the subject to thereby cause the eye of the subject to move into alignment with at least one of the interrogation signal source and the response signal sensor; and signal processing circuitry including: a response signal processor configured to process a response signal sensed from the eye of the subject when the eye of the subject is in alignment with respect to the at least one of the interrogation signal source and the response signal sensor to determine a physiological parameter from the response signal. In addition to the foregoing, other system aspects are described in the claims, drawings, and text forming a part of the disclosure set forth herein.

In one aspect, a system for controlling the sensing of information from an eye of a subject includes, but is not limited to: signal processing circuitry including: a gaze attractor controller adapted to drive a gaze attractor to cause the eye of the subject to move into alignment with at least one of the interrogation signal source and the response signal sensor; a response signal input adapted to receive a response signal sensed from the eye of the subject by a response signal sensor responsive to delivery of an interrogation signal to the eye of the subject; and a response signal processor configured to process a response signal sensed from the eye of the subject when the eye of the subject is in alignment with respect to the at least one of the interrogation signal source and the response signal sensor to determine a physiological parameter from the response signal. In addition to the foregoing, other system aspects are described in the claims, drawings, and text forming a part of the disclosure set forth herein.

In one aspect, a system includes, but is not limited to a housing; an interrogation signal source housed in the housing and adapted for delivering an interrogation signal to an eye of a subject, the interrogation signal source including at least one light source and at least one optical system; a response signal sensor housed within the housing and adapted for sensing a response signal produced by the eye of the subject responsive to the interrogation signal, the response signal containing information regarding a physiological parameter of the subject; a gaze attractor adapted to attract the gaze of the subject to thereby cause the eye of the subject to move into alignment with at least one of the interrogation signal source and the response signal sensor; an output structure adapted for transmitting an output signal; mounting means adapted for mounting the housing with respect to a display in such a manner that the interrogation signal source and response signal sensor are alignable with the eye of the subject during normal use of the display by the subject. In addition to the foregoing, other system aspects are described in the claims, drawings, and text forming a part of the disclosure set forth herein.

In one aspect, a method of measuring information from an eye of a subject includes, but is not limited to; delivering an interrogation signal to the eye of the subject with an interrogation signal source; detecting a response signal from the eye of the subject with a response signal sensor; controlling a gaze attractor to cause the eye of the subject to move into alignment with at least one of the interrogation signal source and the response signal sensor; and determining a physiological parameter of the subject from the response signal detected from the eye of the subject when the eye of the subject is in alignment with respect to the at least one of the interrogation signal source and the response signal sensor. In addition to the foregoing, other method aspects are described in the claims, drawings, and text forming a part of the disclosure set forth herein.

In one aspect, an article of manufacture includes, but is not limited to, one or more non-transitory machine-readable data storage media bearing one or more instructions for: delivering an interrogation signal to the eye of the subject with an interrogation signal source; detecting a response signal from the eye of the subject with a response signal sensor; controlling a gaze attractor to cause the eye of the subject to move into alignment with at least one of the interrogation signal source and the response signal sensor; and determining a physiological parameter of the subject from the response signal detected from the eye of the subject when the eye of the subject is in alignment with respect to the at least one of the interrogation signal source and the response signal sensor. In addition to the foregoing, other aspects of articles of manufacture including one or more non-transitory machine-readable data storage media bearing one or more instructions are described in the claims, drawings, and text forming a part of the disclosure set forth herein.

In addition to the foregoing, various other method and/or system and/or articles of manufacture including one or more non-transitory machine-readable data storage media bearing one or more instructions are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent by reference to the detailed description, the corresponding drawings, and/or in the teachings set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

For a more complete understanding of embodiments, reference now is made to the following descriptions taken in connection with the accompanying drawings. The use of the same symbols in different drawings typically indicates similar or identical items, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 21 illustrates an article of manufacture including non-transitory machine-readable data storage media bearing instructions for performing a method of measuring information from an eye of a subject.

FIG. 31 is a flow diagram of a method of measuring information from an eye of a subject.

FIG. 32 is a flow diagram of a method of measuring information from an eye of a subject.

FIG. 33 illustrates an article of manufacture including non-transitory machine-readable data storage media bearing instructions for performing a method of measuring information from an eye of a subject.

FIG. 39 is a flow diagram of a method of measuring information from an eye of a subject.

FIG. 40 is a flow diagram of a method of measuring information from an eye of a subject.

FIG. 41 is a flow diagram of a method of measuring information from an eye of a subject.

FIG. 42 is a flow diagram of a method of measuring information from an eye of a subject.

FIG. 43 is a flow diagram of a method of measuring information from an eye of a subject.

DETAILED DESCRIPTION

Figure 1:
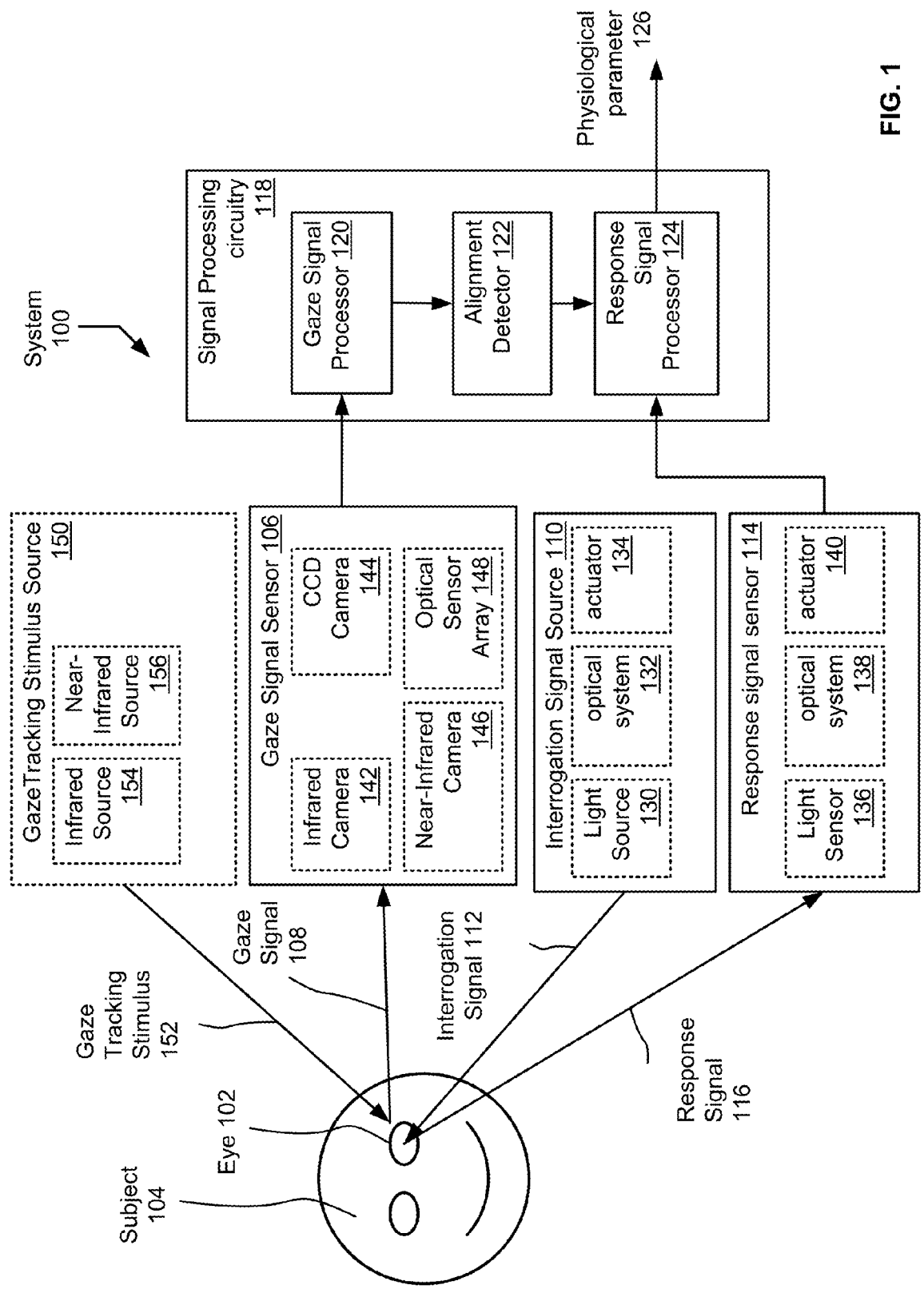
FIG. 1 is a block diagram of a system for sensing information from an eye of a subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts a system 100 for sensing information from an eye 102 of a subject 104, which includes a gaze signal sensor 106 adapted for receiving a gaze signal 108 containing information indicative of a gaze direction of eye 102 of subject 104; an interrogation signal source 110 for delivering an interrogation signal 112 to eye 102 of subject 104; a response signal sensor 114 for sensing response signal 116 produced by the eye 102 responsive to interrogation signal 112; signal processing circuitry 118 including a gaze signal processor 120 configured to determine the gaze direction of eye 102 based upon gaze signal 108; alignment detector 122 configured to determine whether eye 102 of subject 104 is in alignment with respect to at least one of the interrogation signal source 110 or response signal sensor 114 based at least in part upon the gaze direction; and response signal processor 124 configured to process response signal 116 sensed from eye 102 of subject 104 by the response signal sensor 114 when eye 102 is in alignment with respect to the at least one of the interrogation signal source 110 or response signal sensor 114 to determine a physiological parameter 126 from response signal 116.

Interrogation signal source 110 includes light source 130, optical system 132, and actuator 134 for adjusting light source 130 and/or optical system 132 to control the position and focal distance of interrogation signal 112. Response signal sensor 114 includes light sensor 136, optical system 138, and actuator 140 for manipulating the light sensor 136 and/or optical system 138. Optical systems 132 and 138 (and other optical systems described herein) may include various components for controlling different aspects of the optical signals, (e.g. focus, direction, collimation, light polarization, wavelength composition) including, for examples, lenses, mirrors, reflectors, filters, diffraction gratings, etc. as are well known to those having skill in the optical arts. Response signal sensor 114 may be adapted to sense response signal 116 from an interior of the eye 102 of subject 104 responsive to the interrogation signal. For example, response signal generally may be focused to detect a response signal reflect from a particular structure in the interior eye 102, and or be adapted to sense frequency components found in signals reflected from a region/structure of interest within eye 102.

Figure 2:
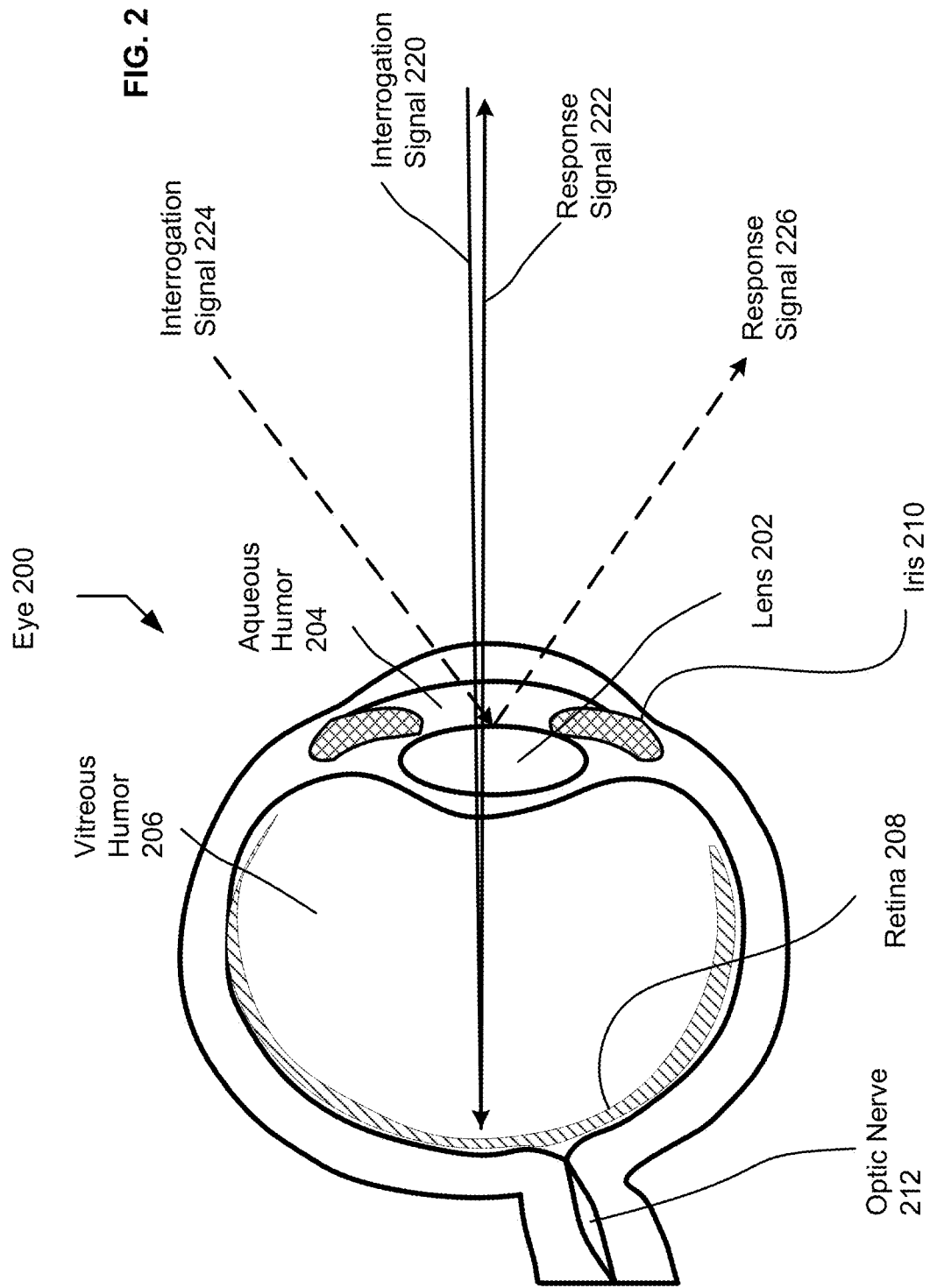
FIG. 2 is an illustration of the anatomy of an eye.

FIG. 2 depicts an eye 200 showing various internal structures from which a response signal can be detected responsive to an interrogation signal, including lens 202, aqueous humor 204, vitreous humor 206, or retina 208. Also depicted are iris 210 and optic nerve 212. As two specific examples, FIG. 2 depicts interrogation signal 220 that is reflected off a front surface of lens 202 to form response signal 222, and interrogation signal 224 that is reflected off retina 208 to form response signal 226.

Figure 3:
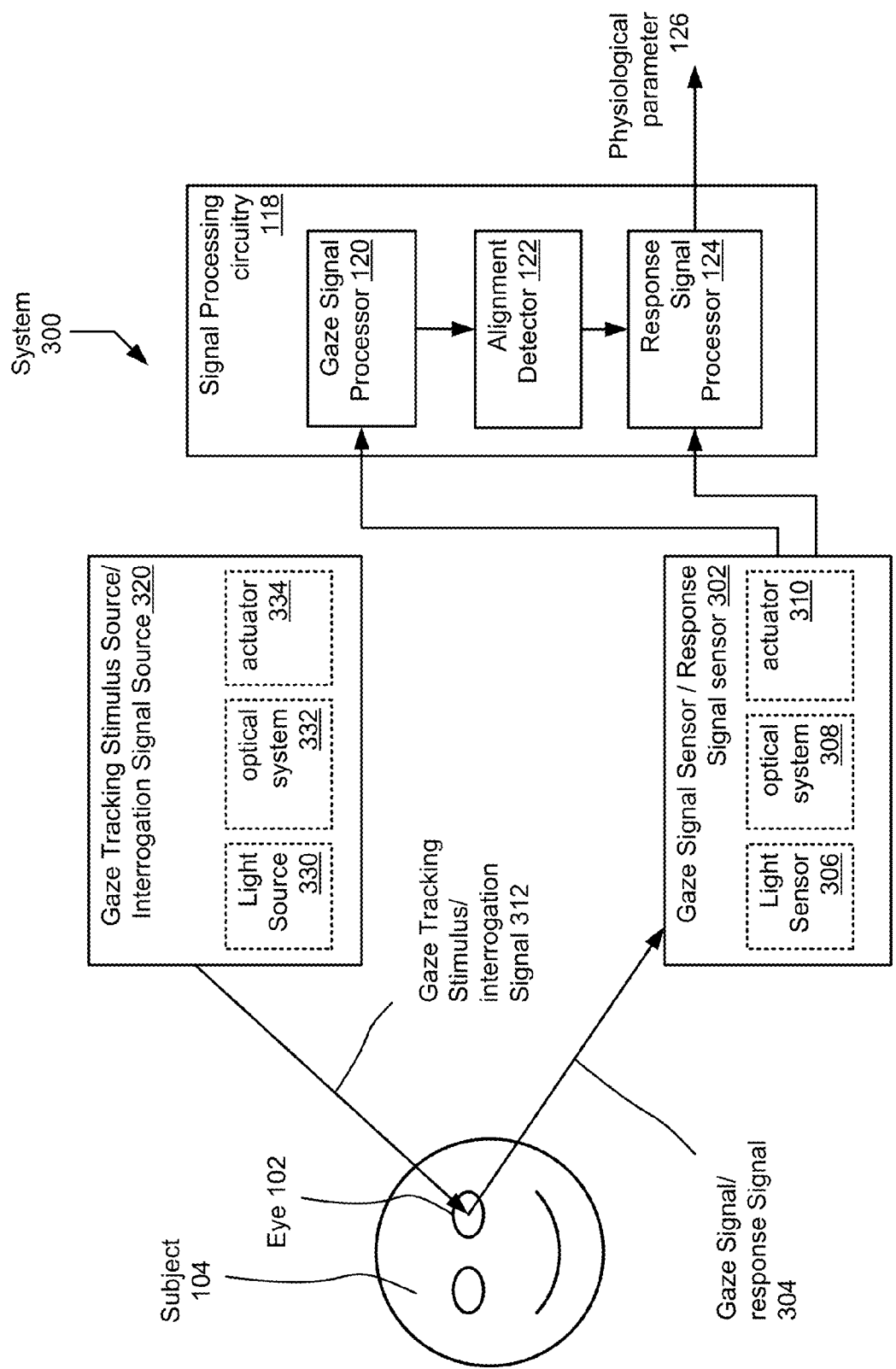
FIG. 3 is a block diagram of a system for sensing information from an eye of a subject.

Referring back to FIG. 1, gaze signal sensor 106 may include various types of sensing devices, including, e.g. an infrared camera 142 or a CCD camera 144. Gaze signal sensor 106 and response signal sensor 114 may be different sensors, as depicted in FIG. 1, or the same sensor as depicted in FIG. 3. If different sensors, they may be different sensors of the same type, or different sensors of different types. FIG. 3 depicts a system 300 in which a single signal source is used as a combined gaze tracking stimulus source interrogation signal source 320, which includes light source 330, optical system 332 and actuator 334, and a single sensor is used as gaze signal sensor/response signal sensor 302, which includes light sensor 306, optical system 308 and actuator 310. Gaze signal/response signal 304 is produced by eye 102 in response to gaze tracking stimulus/interrogation signal 312. The sensed response signal is directed to gaze signal processor 120 and response signal processor 124, which along with alignment detector 122, components of signal processing circuitry 118.

As shown in FIG. 1, system 100 for sensing information from eye 102 of subject 104 may also include at least one gaze tracking stimulus source 150 adapted to deliver gaze tracking stimulus 152 to at least eye 102 of subject 104, wherein the gaze signal 108 is produced in response to gaze tracking stimulus 152. Here and elsewhere, elements of a figure indicated with a dashed line are not required in all embodiments.

Gaze tracking stimulus source 150 may include, for example, an infra-red source 154 or a near infra-red source 156. A gaze signal sensor 106 that includes an infra-red sensor (e.g., an infrared camera 142) may be used in combination with an infra-red source 154, and a gaze signal sensor that includes a near infra-red sensor (for example, a near infra-red camera 146) may be used in combination with a near infra-red source 156. Gaze tracking stimulus source 150 may include one or a plurality of light sources. Gaze signal sensor 106 may include one or a plurality of optical sensors, an optical sensor array, and/or a camera (142, 144, 146, or 148).

Eye tracking to determining gaze direction is performed by analysis of gaze signal 108 sensed by gaze signal sensor 106 with gaze signal processor 120. As depicted in FIG. 1, gaze signal sensor can include a camera, which can be a smart camera that can capture images of a user's eyes, process them and issue control commands within a millisecond time frame. Image data may include results of visual spectrum imaging, infrared imaging, ultrasound imaging. Smart cameras are commercially available (e.g., Hamamatsu's Intelligent Vision System; http://jp.hamamatsu.com/en/product_info/index.html). Such image capture systems may include dedicated processing elements for each pixel image sensor. Other camera systems for use as gaze signal sensors may include, for example, a pair of infrared charge coupled device cameras to continuously monitor pupil size and position. This can be done as the eye follows a moving visual target, and can provide real-time data relating to pupil accommodation relative to objects on a display (e.g., http://jp.hamamatsu.com/en/rd/publication/scientific_american/common/pdf/scientific_0608.pdf). FIG. 1 depicts gaze signal processor 120 as separate from gaze signal sensor 106; however, in some embodiments, some or all of the gaze signal processor 120 may be packaged with and/or formed integrally with the gaze signal sensor 106.

Eye movement and/or pupil movement may also be measured by video-based eye trackers. In these systems, a camera (the gaze signal sensor 106) focuses on one or both eyes and records eye movement as the viewer looks at a stimulus. Contrast may be used to locate the center of the pupil, and infrared and near-infrared non-collimated light (the gaze tracking stimulus source 150) may be used to create a corneal reflection. The vector between these two features can be used to compute gaze intersection with a surface after a calibration for a subject.

Two types of eye tracking techniques include bright pupil eye tracking and dark pupil eye tracking. Their difference is based on the location of the illumination source (gaze tracking stimulus source) with respect to the optical system. If the illumination is coaxial with the optical path, then the eye acts as a retroreflector as the light reflects off the retina, creating a bright pupil effect similar to red eye. If the illumination source is offset from the optical path, then the pupil appears dark. Thus, in some embodiments, the gaze tracking stimulus source and the gaze response signal sensor are co-aligned. Alternatively, the gaze tracking stimulus source and the gaze response signal sensor be separately aligned and located.

Bright Pupil tracking creates greater iris/pupil contrast allowing for more robust eye tracking that is less dependent upon iris pigmentation and greatly reduces interference caused by eyelashes and other obscuring features. It also allows for tracking in lighting conditions ranging from total darkness to very bright light. However, bright pupil techniques are not recommended for tracking outdoors as extraneous infrared (IR) sources may interfere with monitoring.

Most eye tracking systems use a sampling rate of at least 30 Hz. Although 50/60 Hz is most common, many video-based eye trackers run at 240, 350 or even 1000/1250 Hz, which is recommended in order to capture the detail of the very rapid eye movements during reading, for example.

Eye movements are typically divided into fixations, when the eye gaze pauses in a certain position, and saccades, when the eye gaze moves to another position. A series of fixations and saccades is called a scanpath. Most information from the eye is made available during a fixation, not during a saccade. The central one or two degrees of the visual angle (the fovea) provide the bulk of visual information; input from larger eccentricities (the periphery) generally is less informative. Therefore the locations of fixations along a scanpath indicate what information loci on the stimulus were processed during an eye tracking session. On average, fixations last for around 200 milliseconds during the reading of linguistic text, and 350 milliseconds during the viewing of a scene. Preparing a saccade towards a new goal takes around 200 milliseconds. Scanpaths are useful for analyzing cognitive intent, interest, and salience. Other biological factors (some as simple as gender) may affect the scanpath as well. Eye tracking in human-computer interaction typically investigates the scanpath for usability purposes, or as a method of input in gaze-contingent displays, also known as gaze-based interfaces.

Commercial eye tracking software packages can analyze eye tracking and show the relative probability of eye fixation at particular locations. This allows for a broad analysis of which locations received attention and which ones were ignored. Other behaviors such as blinks, saccades, and cognitive engagement can be reported by commercial software packages.

Signal processing circuitry 118 includes alignment detector 122. As used herein, the interrogation signal source being "in alignment" with respect to the eye of the subject refers to positioning of the eye of the subject with respect to the interrogation signal source such that, for example, an interrogation signal 112 from the interrogation signal source 110 is able to enter and/or interact with the eye 102 of the subject so that a measurement can be obtained from the eye of the subject. Alignment of eye 102 of subject 104 with respect to response signal sensor 114 refers to positioning of eye 102 of subject 104 with respect to the response signal sensor 114 such that response signal 116 from eye 102 of subject 104 can reach and can be sensed by the response signal sensor 114. Determining alignment of the eye of the subject with respect to the interrogation signal source 110 and the response signal sensor 114 may include determining the gaze direction of the eye of the subject, and comparing the gaze direction of the eye with information regarding the position and orientation of the interrogation signal source and/or response signal sensor. Alternatively, or in addition, alignment of the eye of the subject with respect to the interrogation signal source and the response signal sensor can be detected through the quality of the signal, e.g., by higher signal strength in wavelengths of interest. Such determining or detection of alignment is carried out by alignment detector 122. It will be appreciated that the eye may be considered "in alignment" with the response signal sensor 114 or interrogation signal source 110 when the response signal sensor or interrogation signal source lies within a specified number of degrees of the gaze direction, and may not necessarily be located exactly in line with the gaze direction. In particular, if the interrogation signal source has a broad output angle, or the response signal sensor has a broad input angle, then components may be considered to be "in alignment," in that a measurement may be obtained, even if the components are not exactly in line. In some embodiments, the system may be configured to deliver the interrogation signal to the eye of the subject with the interrogation signal source only when the eye of the subject is in alignment with the interrogation signal source and the response signal sensor.

Interrogation signal source 110 and response signal sensor 114 are selected such that a signal produced by the eye in response to the interrogation signal 112 is detectable by response signal sensor 114. For example, as depicted in FIG. 1, the interrogation signal source is an optical signal source, and an optical response signal is produced in response thereto, which is detectable by an optical response signal sensor. Optical signal sources may be characterized in terms of wavelength/waveband of light emitted (which may be visible, infrared, near-infrared, or mid-infrared, for example). Wavelength, phase, amplitude and polarization of light emitted by an optical interrogation signal source may be modified, e.g. through the use of filters or diffraction gratings. An optical response signal sensor used in combination with an optical interrogation signal source may be configured (e.g. through the use of suitable filters or diffraction gratings) to sense an optical signal having particular properties, e.g., wavelength or polarization, which may be the same or different that the wavelength or polarization of the light produced by the interrogation signal source. In one aspect, the interrogation signal source is adapted to produce light having a first polarization, wherein the response signal sensor is adapted to detect light having a second polarization. The first polarization and the second polarization may be the same or different.

Figure 4:
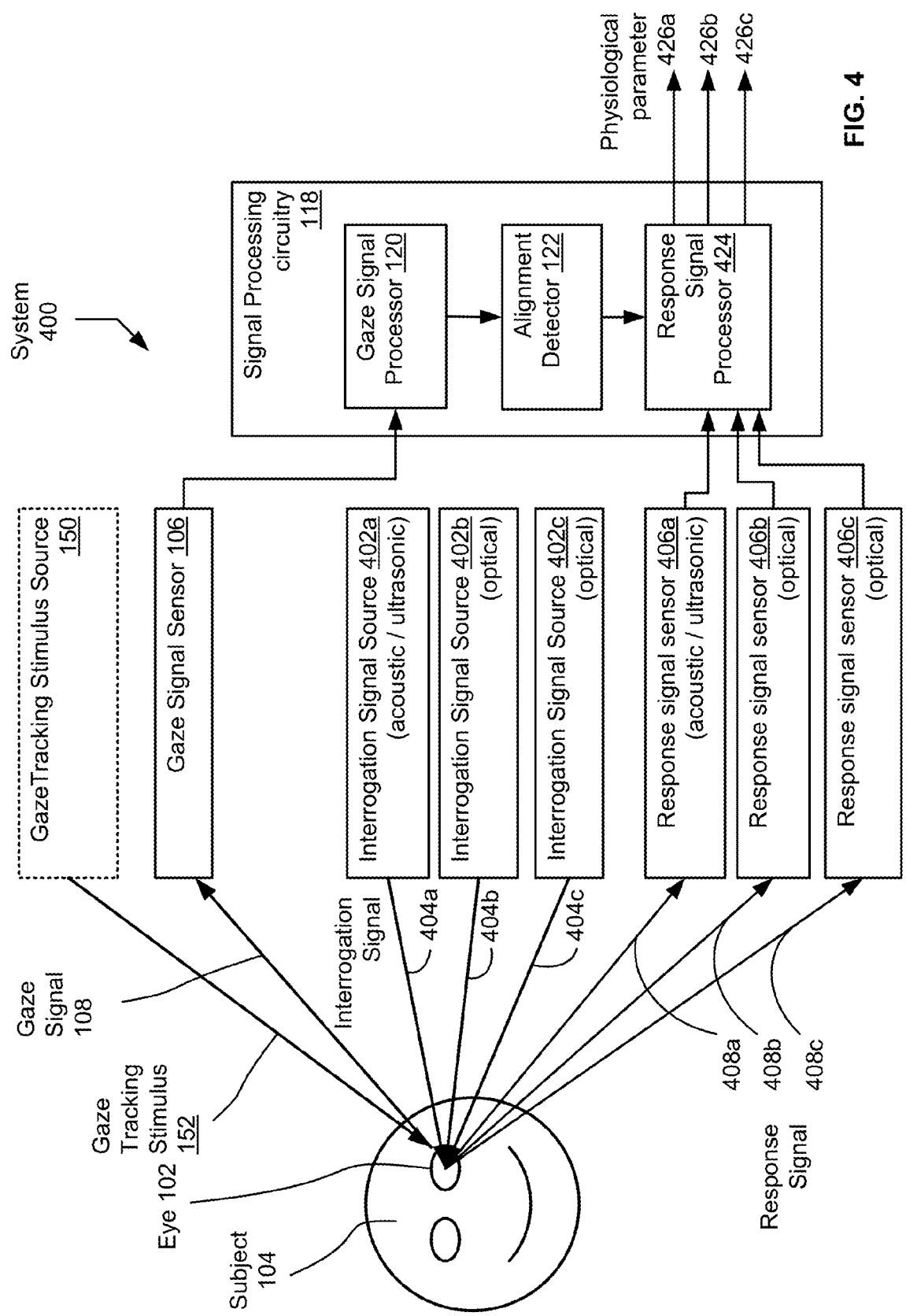
FIG. 4 is a block diagram of a system for sensing information from an eye of a subject.

In some embodiments described herein, a system may include other types of interrogation signal source and response signal sensor. For example, as shown in FIG. 4, an acoustic (ultrasonic) interrogation signal source 402a and acoustic (ultrasonic) response signal sensor 406a are used. An ultrasonic interrogation signal 404a can be used to measure a subject's hear rate, for example, as will be described in greater detail herein below. In some embodiments, more than one interrogation signal source and response signal sensor may be used. FIG. 4 depicts optical interrogation signal sources 402b and 402c which generate optical interrogation signals 404b and 404c, respectively, in addition to ultrasonic interrogation signal source 402a, and optical signal sensors 406b and 406c in addition to ultrasonic response signal sensor 406a. Use of multiple different interrogation signal sources and sensors permits detection of multiple different physiological parameters 426a, 426b, and 426c. Gaze signal sensor 106, gas tracking stimulus source 150, gaze signal processor and alignment detector 122 are as described in connection with FIG. 1. Response signal processor 424 is configured to process response signals 408a, 408b, and 408c to determine physiological parameters 426a, 426b, and 426c. In some aspects, multiple sensors may be used to detect multiple different physiological parameters. However, in some embodiments it may be desirable to use multiple sensors in the detection of a single parameter.

Figure 5:
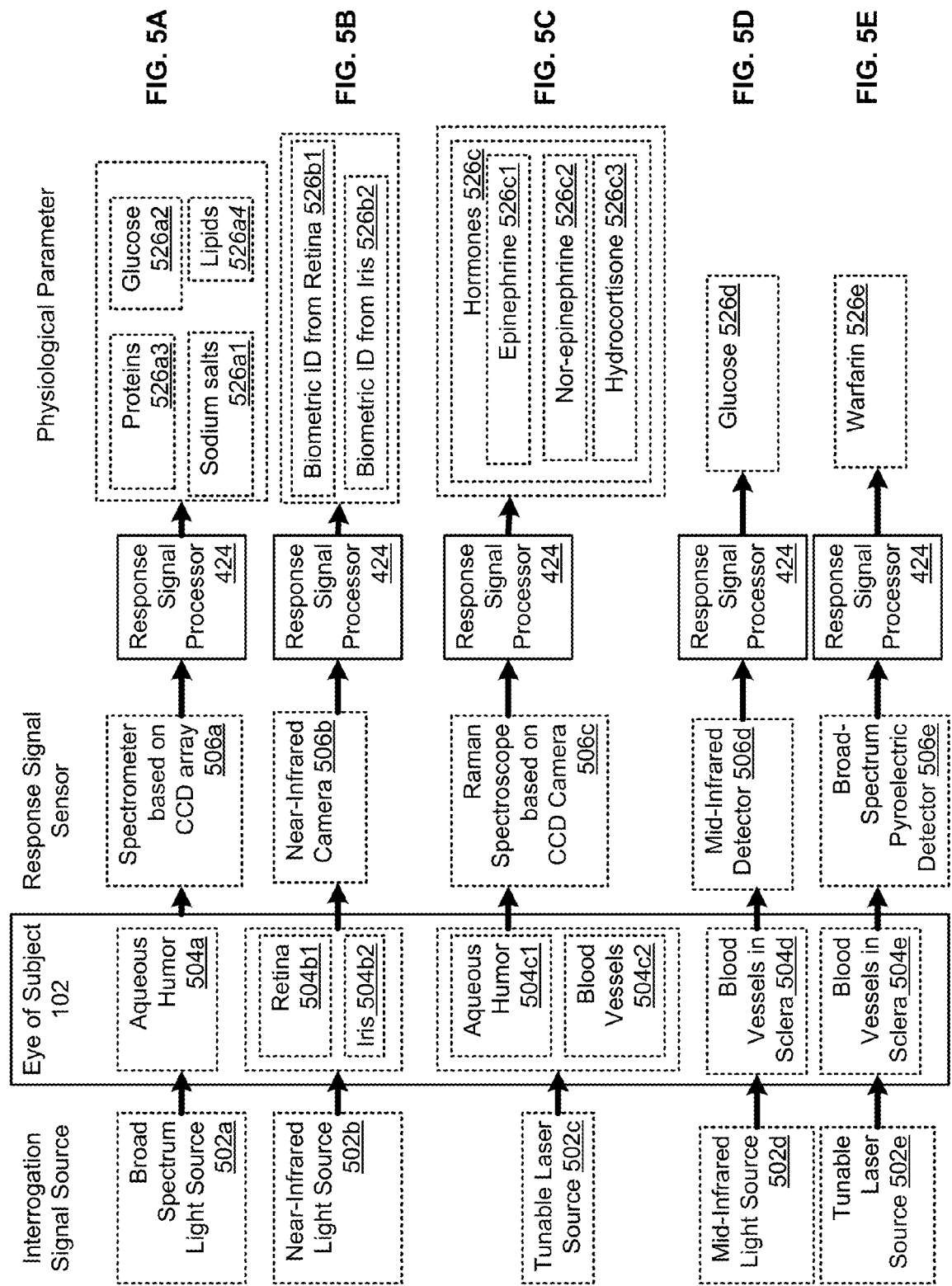
FIG. 5A depicts an example of an interrogation signal source and response signal sensor combination for detecting various physiological parameters.
FIG. 5B depicts an example of an interrogation signal source and response signal sensor combination for detecting various physiological parameters.
FIG. 5C depicts an example of an interrogation signal source and response signal sensor combination for detecting various physiological parameters.
FIG. 5D depicts an example of an interrogation signal source and response signal sensor combination for detecting a physiological parameter.
FIG. 5E depicts example of an interrogation signal source and response signal sensor combination for detecting a physiological parameter.

Different source/sensor combinations can be used to detect different physiological parameters. Examples of combinations of interrogation signal source and response signal sensor and sensed parameters are depicted in FIGS. 5A-5E. For example, as shown in FIG. 5A, the combination of interrogation signal source that includes a broad spectrum light source 502a and response signal sensor that includes a spectrometer 506a based on a CCD array may be suited for detecting a variety of analytes, e.g. sodium salts 526a1, glucose 526a2, proteins 526a3, or lipids 526a4 from the aqueous humor 504a of the eye 102, as well as other analytes, for example as described U.S. Patent Appl. No. 2011/0184262 by Menon published on Jul. 28, 2011, which is incorporated herein by reference.

As shown in FIG. 5B, the combination of an interrogation signal source that includes a near-infrared light source 502b and response signal sensor that includes near-infrared camera 506b may be suited for detecting biometric identification 526b1 from retina 504b1 or biometric identification 526b2 from iris 504b2, for example as described in U.S. Pat. No. 5,572,596 issued to Wildes et al. on Nov. 5, 1996 and U.S. Pat. No. 4,641,349 issued to Flom et al. on Feb. 3, 1987, each of which is incorporated herein by reference.

As shown in FIG. 5C, the combination of interrogation signal source that includes a tunable laser source 502c and response signal sensor that includes a Raman spectroscope 506c based on a CCD camera may be suited for detecting, e.g. hormones 526c such as epinephrine 526c1, norepinephrine 526c2, or hydrocortisone 526c3, in aqueous humor 504c1, or blood vessels 504c2 in conjunctiva or retina, for example as described U.S. Pat. No. 6,961,599 issued to Lambert et al. on Nov. 1, 2005, which is incorporated herein by reference.

As shown in FIG. 5D, the combination of interrogation signal source that includes a mid-infrared light source 502d and response signal sensor that includes a mid-infrared detector 506d may be suited for detecting, e.g. glucose 526d in blood vessels 504d in sclera, for example as described in U.S. Pat. No. 6,958,039 issued to Burd et al. on Oct. 25, 2005, which is incorporated herein by reference.

As shown in FIG. 5E, The combination of interrogation signal source that includes tunable laser 502e and response signal sensor that includes broad spectrum pyroelectric detector 506e may be suited for detecting, e.g. warfarin 526e in blood vessels in the sclera 504e, (see e.g., the Data Sheet: "Warfarin IR Spectrum" which is incorporated herein by reference).

The detection methods summarized in FIGS. 5A-5E are described in greater detail in connection with various examples of embodiments described herein. The response signal may be indicative of, e.g., a feature of the vasculature of the eye of the subject, or a biometric identification of the subject. A response signal detected by a camera may be an image, such as an image of the vasculature of the retina, which may be used in a biometric identification. Other characteristics of the vasculature of the eye (e.g. movement of the vasculature of the eye) may be indicative of other physiological parameters, which may be derived therefrom.

In various embodiment described herein, the physiological parameter may be a measurement of and/or indicative of heart rate or pulse rate, blood flow, a temperature (e.g. body temperature), or a substance (e.g., a chemical component) in the eye of the subject, which may be, for example, a substance in the aqueous humor or vitreous humor, or in the blood of the retina, conjunctiva, or sclera. A wide variety of substances in blood, aqueous humor or vitreous humor can be detected using spectroscopic methods, as described herein and as known to those of skill in the relevant art. Substances that may be detected include, but are not limited to, glucose, oxygen, glycosylated hemoglobin, salts, proteins, lipids, gases, hormones, and drugs. The physiological parameter may be measured directly, or derived from a parameter that is measured directly. Blood flow may be determined, for example, with laser Doppler or thermal flowmetry based on optical temperature measurements. Heart rate or pulse rate can be determined from ocular pulse measurements (see e.g., U.S. Pat. No. 3,948,248 issued to Zuckerman et al. on Apr. 6, 1976 which is incorporated herein by reference). Other physiological parameters may be measured by methods known to those having skill in the art.

Multiple physiological parameters can be determined from a subject through the use of multiple interrogation signal sources and sensors, or by using different processing signal approaches on data obtained with the same interrogation signal source(s)/response signal.

Figure 6:
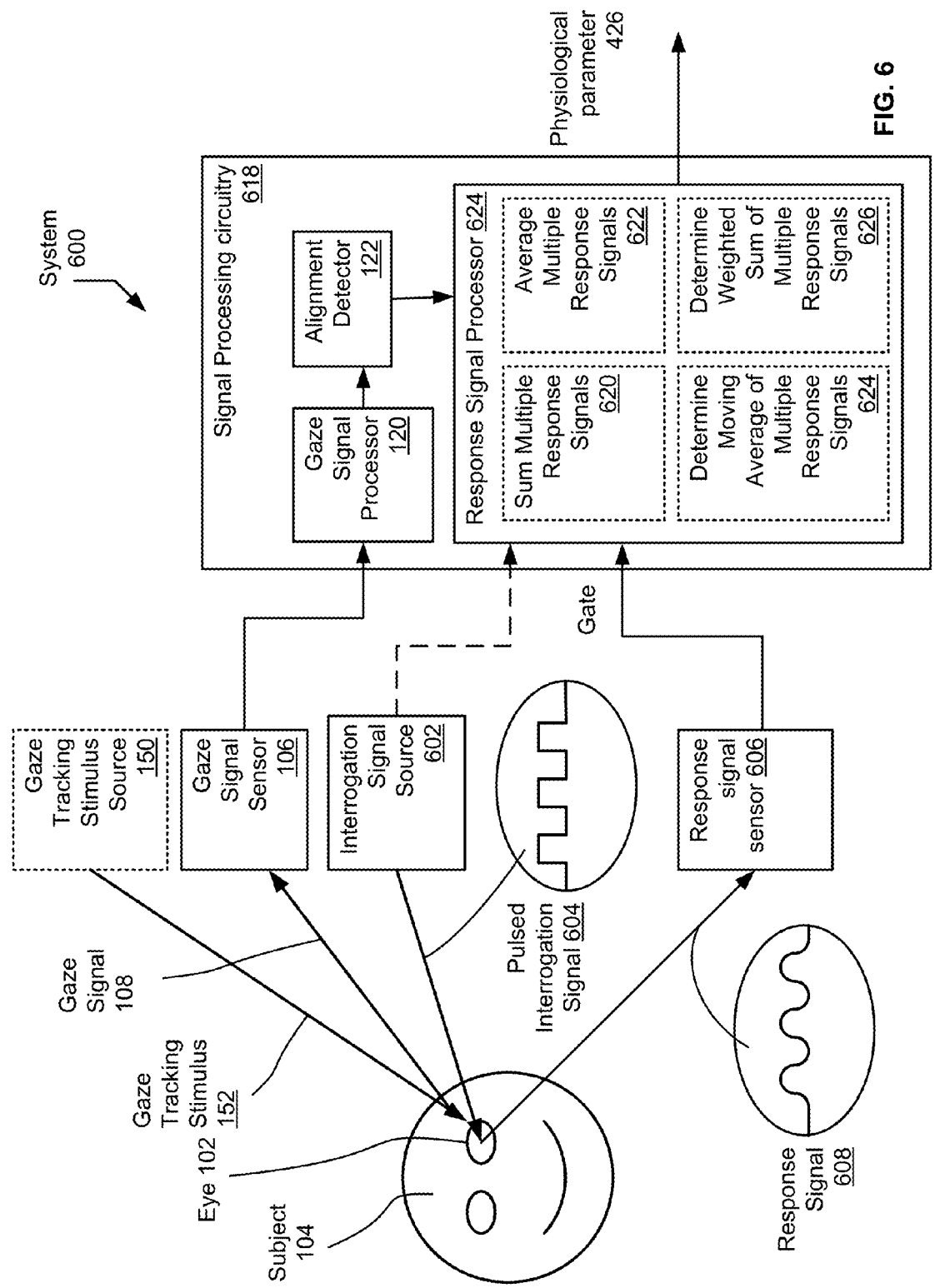
FIG. 6 is a block diagram of a system for sensing information from an eye of a subject.

As shown in FIG. 6, in an embodiment, interrogation signal source 602 may be adapted to deliver a pulsed interrogation signal 604. At least one of response signal sensor 606 and signal processing circuitry 618 is configured to gate detection of the response signal 608 relative to the pulsed interrogation signal 604. In an aspect, signal processing circuitry 618 is configured to combine multiple response signals produced by the eye of the subject in response to multiple pulses of the pulsed interrogation signal. Signal processing circuitry 618 may combine the multiple response signals by various methods, e.g., by summing and/or averaging the multiple response signals, as indicated at 620 and 622, respectively, or by determining a moving average or weighted sum of the multiple response signals, as indicated at 624 and 626, respectively. Combining response signals may be beneficial in order to produce physiological parameter data 426 that has an improved signal-to-noise ratio or that more accurately represents the physiological parameter being measured. As used herein, the term "signal" refers to a signal of interest within the relevant context, and the term "noise" refers to any signal that is not of interest within the relevant context.

Figure 7:
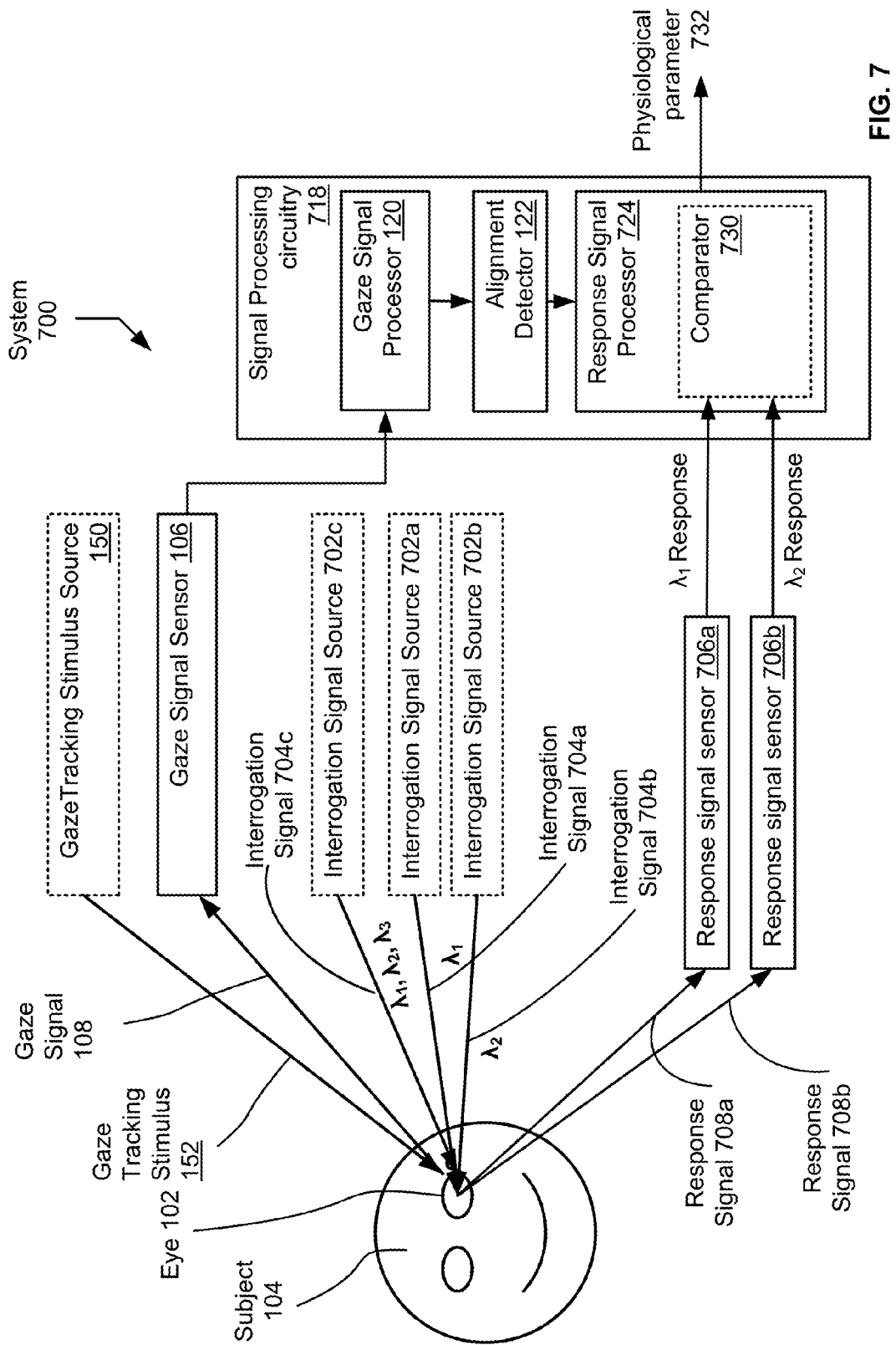
FIG. 7 is a block diagram of a system for sensing information from an eye of a subject.

As shown in FIG. 7, an interrogation signal source 702c may be adapted to deliver an interrogation signal containing multiple wavelengths of light $\lambda_1$, $\lambda_2$, $\lambda_3$ (for example, interrogation signal source may be a broad spectrum source). The system may include a first response signal sensor 706a configured to sense a first response signal 708a produced by the eye of the subject responsive to a first wavelength component ($\lambda_1$) of the interrogation signal 704c, and a second response signal sensor 706b configured to sense a second response signal 708b produced by the eye of the subject responsive to a second wavelength component ($\lambda_2$) of the interrogation signal 704c. Alternatively, a single sensor may sense response signals produced at two or more different wavelengths.

Alternatively, the system may include at least a first interrogation signal source 702a configured to deliver a first interrogation signal 704a having a first optical wavelength ($\lambda_1$) and at least a second interrogation signal source 702b configured to deliver a second interrogation signal 704b having a second optical wavelength ($\lambda_2$). Response signals 708a and 708b are produced in response to first interrogation signal 704a and second interrogation signal 704b, and detected by response signal sensors 706a and 706b respectively. Signal processing circuitry 718 including response signal processor 724 may be configured to process a first response signal 708a sensed from eye 102 of subject 104 in response to the first interrogation signal 704a and a second response signal 708b sensed from eye 102 of subject 104 in response to second interrogation signal 704b by comparing the first and second response signals with comparator 730 to determine the physiological parameter 732. System 700 may be configured to deliver the first interrogation signal 704a simultaneously with respect to the second interrogation signal 704b, or sequentially with respect to the second interrogation signal 704b.

In an embodiment, the interrogation signal source and the response signal sensor are co-aligned. Alternatively, the interrogation signal source and the response signal sensor may be separately aligned and located. If the interrogation signal source and response signal sensor are co-aligned, it may be necessary to only detect the alignment of the eye of the subject with one of the interrogation signal source and response signal sensor, in that alignment with one is indicative of alignment with the other. If, on the other hand, interrogation signal source and response signal sensor are separately located and aligned, it may be necessary to detect the alignment of the eye with regard to each. This is particularly the case if the output angle of the interrogation signal source and the input angle of the response signal sensor are narrowly focused and tight alignment is required in order to obtain a good measurement. If one of the interrogation signal source and response signal sensor is relatively unfocused and/or untargeted (having a wide input/output angle) and one has a narrow/focused input/output angle, its alignment with the eye may not be critical and detection of such alignment may not be required. In addition, if a detector but no source is used (e.g., in the case that a detectable response signal can be obtained in ambient light), again, it would only be necessary to detect alignment of the eye of the subject with respect to the response signal sensor.

Figure 8:
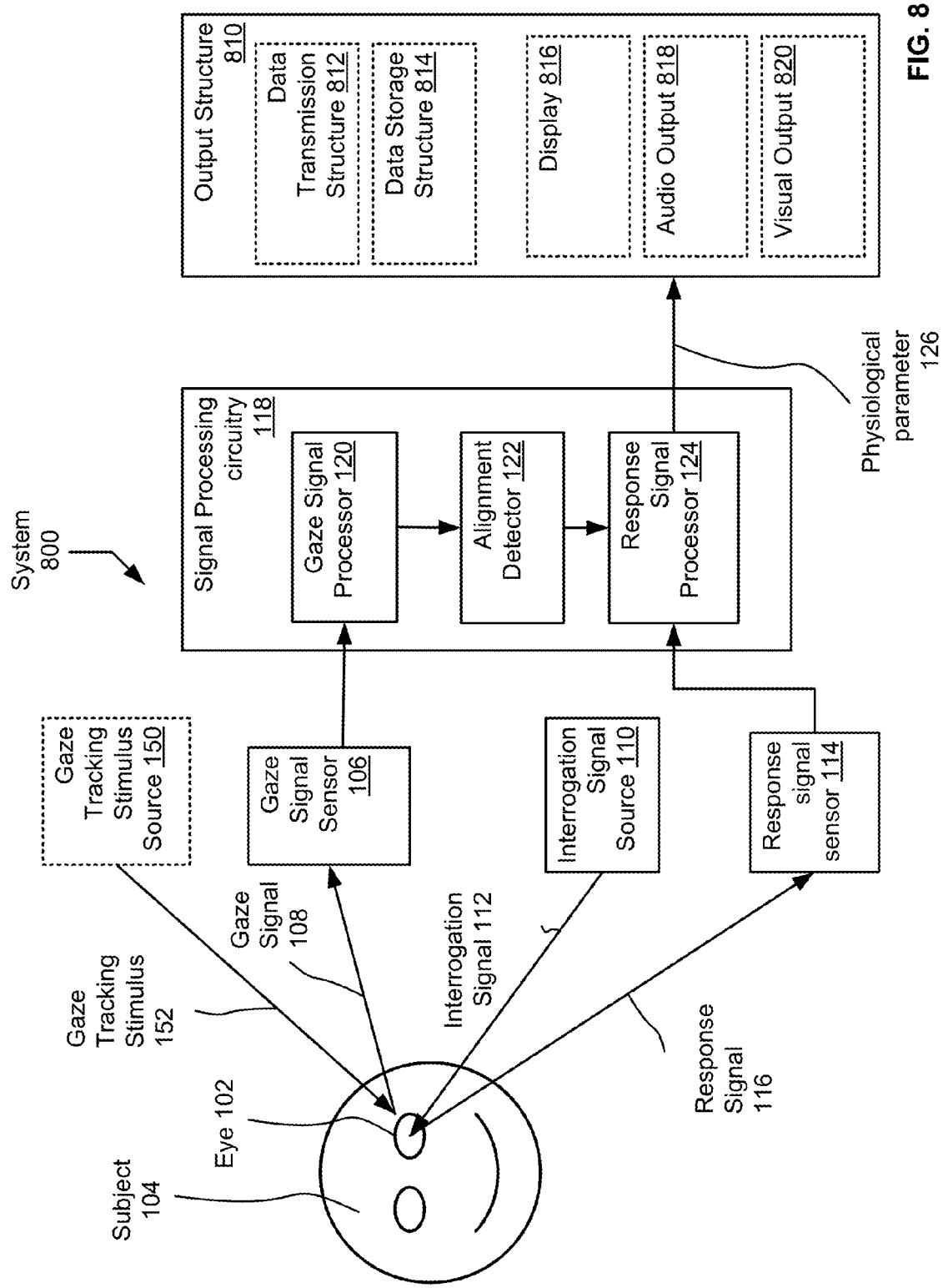
FIG. 8 is a block diagram of a system for sensing information from an eye of a subject.

As depicted in FIG. 8, a system 800 for sensing information from eye 102 of subject 104 may also include an output structure 810 adapted to output a signal relating to the determined physiological parameter 126. For example, output structure 810 can include data transmission structure 812, a data storage structure 814, a display 816, an audio output 818, or a visual output 820. As an example, the system may include a display adapted to display information relating to the determined physiological parameter. The display may be a video monitor (including but not limited to a television display), a computer display (including but not limited to a display on a desktop, laptop, tablet computer, personal digital assistance, or any other stationary, portable or handheld computing devices), a video game display, a telephone display (including, but not limited to, a display on a smart phone), or a terminal of a data processing device (any type of device having data processing capability). The display may be incorporated in a wearable item (e.g. eyewear, headware, jewelry, an article of clothing, a badge, a bandage, an adhesive patch, a wristwatch, a cuff, a sleeve, a wristband, an armband, a helmet, a physiological support such as a cast or brace, or a wearable a positioning structure configured to surround a portion of the subject), an article of furniture, an article of medical or health-care related equipment (e.g., for use in a hospital, clinic, physician's office, care facility, or home), an article of exercise equipment (e.g., a treadmill, exercise bicycle, elliptical trainer), or a vehicle (e.g. as a display in a dashboard, control panel, or drop-down or seat-back display of an automobile, a truck, a train, an airplane, a motorcycle, or a boat). The particular choice of display may depend upon the intended application of the system, e.g. whether it is to be used for a medical or health-related application or business or security application, or for individual or institutional use, as illustrated by the examples provided herein. System 800 may include multiple output structures to permit data or information to be output in more than one format or for more than one purpose.

EXAMPLE 1

Figure 9:
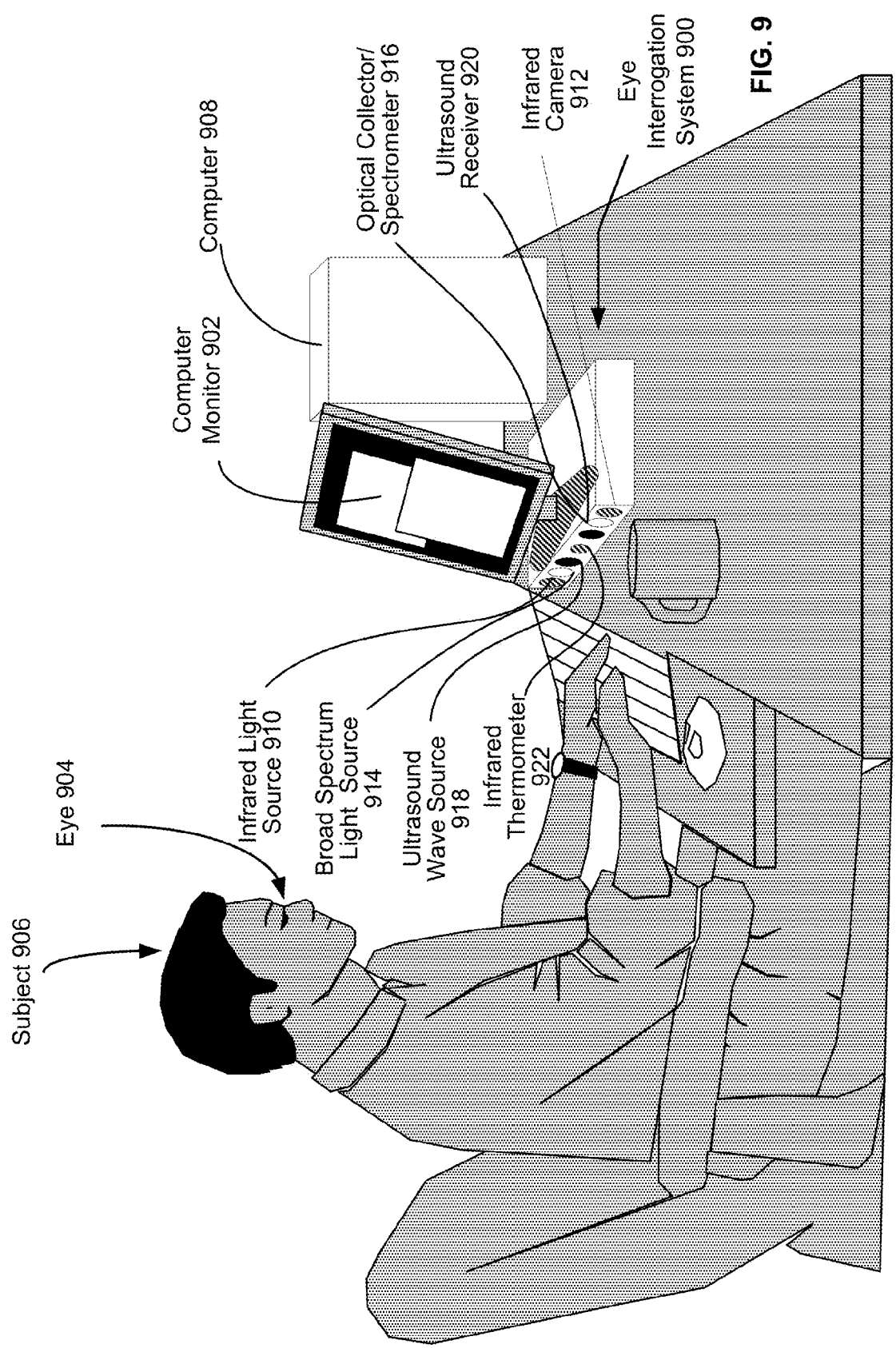
FIG. 9 is an illustration of an example a system used for monitoring health parameters of a computer user.

An Unobtrusive Eye Interrogation System Attached to a Computer Monitor to Measure Health Parameters of a Computer User FIG. 9 illustrates an example of a system as described generally in connection with FIG. 1. FIG. 9 illustrates an eye interrogation system 900 positioned relative to computer monitor 902. Eye interrogation system 900 detects gaze alignment and interrogates the eye 904 of a subject (computer user) 906 to determine health parameters while subject 906 works at the computer 908. To detect gaze alignment, a gaze tracking system is used to detect when the subject 906 looks at the interrogation source and/or the interrogation sensor. The gaze tracking system includes gaze tracking stimulus source which includes IR light source 910 and gaze signal sensor which includes IR camera 912, which detects the reflection of IR light from the eyes 904 of the subject 906. For example, a gaze tracking system for monitoring eye position is available from Seeing Machines Inc., Tucson, Ariz. (see e.g., the Specification Sheet: "faceLAB™ 5 Specifications" which is incorporated herein by reference). Eye position, eye rotation, eye gaze position against screen, pupil diameter and eye vergence distance may be monitored. Eye rotation measurements of up to +/−45 degrees around the y-axis and +/−22 degrees around the x-axis are possible. Typical static accuracy of gaze direction measurement is 0.5-1 degree rotational error. The gaze tracking system includes software and circuitry forming a part of gaze signal processor (in eye interrogation system 900; the processing capability of computer 908 may also be used, through special purpose software or hardware installed therein) to analyze the gaze tracking data and to detect alignment of the user's gaze with an broad spectrum light source (interrogation signal source) 914 and/or an optical collector/spectrometer (response signal sensor) 916. Alignment of the user's eyes with the interrogation signal source 914 or the response signal sensor 916 triggers activation of the interrogation signal 914 source by the circuitry in system 900.

An interrogation signal source 914 and response signal sensor 916 are incorporated in eye interrogation system 900 to determine health parameters of the computer user. Interrogation signal source 914 includes a light source which generates broad spectrum light (approximate wavelengths: 360 nm to 900 nm) located in the interrogation system to deliver light to the eye. For example a tungsten halogen light source with a wavelength range of 360 nm to 2000 nm in wavelength is available from Ocean Optics, Dunedin, Fla. See e.g., the Specification Sheet: "HL-2000 Tungsten Halogen Light Sources" which is incorporated herein by reference. Light from the source strikes the cornea, reflects off the iris and passes through the anterior chamber of the eye which contains aqueous humor with bioanalytes. Methods and systems for analyzing reflected light to determine bioanalytes in the eye are described (see e.g., U.S. Patent Appl. No. 2011/0184262 by Menon published on Jul. 28, 2011 which is incorporated herein by reference). Light reflected from the eye is detected by a response signal sensor 916 which is also located in the system (See FIG. 2). The response signal sensor 916 may include an optical collector and a spectrometer to determine the reflected spectrum. For example the collector may be a collimating lens assembly with a single aspheric lens with a field of view of approximately 45 degrees (e.g., a 74-DA Collimating Lens (200-2000 nm) is available from Ocean Optics, Dunedin, Fla.). The lens attaches to a spectrometer for increased light throughput and collects collimated light in a straight path of open air and focuses it on to a spectrometer's slit. The spectrometer may be a fiber optic spectrometer with a CCD-array detector and an analog to digital converter with programmable electrical circuitry. For example a miniature fiber optic spectrometer with a 2048-element CCD-array detector with a range of 200-1100 nm and a grating with a spectral range of 625 nm with best efficiency from 530 nm to 1100 nm is available from Ocean Optics, Dunedin, Fla. (see e.g., the Specification Sheet: USB2000+ Miniature Fiber Optic Spectrometer which is incorporated herein by reference). The spectrometer has a microcontroller and USB connector to allow activation and programming of the spectrometer by computer 908, using software/hardware installed therein. To summarize, when the gaze tracking system detects alignment of the user's eyes, the signal processing circuitry activates the interrogation signal source 914 and the response signal sensor 916 (spectrometer) to collect data from the user's eyes.

Health parameters for subject 906 are routinely monitored during use of the computer to provide information to subject 906 for example. Information regarding the subject's health parameters may also be provided to a health care provider or other party, for example via the internet. The interrogation system may monitor analytes present in the anterior chamber of the eye, for example, sodium salts, glucose, proteins, lipids and other metabolites. For example the concentration of sodium salts in the aqueous humor in the anterior chamber of the eye may be determined by reflectance spectroscopy and reference to a spectrum from a healthy subject with blood sodium levels in the normal range. Computer algorithms to determine sodium salt concentration based on reflection spectra are described (see e.g., U.S. Patent Appl. No. 2011/0184262, Ibid.). For example, user reflectance spectra are compared with reference spectra to compute analyte concentration. Multivariate analysis, e.g., Least Square analysis, may be used to calibrate the reference data and evaluate analyte concentrations. Sodium salt concentrations in aqueous humor of the eye may be correlated with blood sodium levels and hydration. To measure glucose levels of the subject reflectance spectra are obtained for concentrations of glucose as a function of wavelength. The intensity of light measured at a specific wavelength and the ratio of intensities at two or more wavelengths are characteristic for glucose in the aqueous humor of the eye. A characteristic pattern for glucose solutions at different wavelengths (e.g., 400 nm to 600 nm) may be established in vitro with the eye interrogation system, and an algorithm may be used to determine the concentration of glucose present in the aqueous humor of the eye. Noncontact optical systems to measure glucose in the eye including: energy sources emitting wavelengths in the visible and near-infrared regions of the spectrum; reflectance detectors, e.g., spectrometers, and computer algorithms to analyze spectral data have been described (see e.g., Patent Application No. 2011/0184262, Ibid. and U.S. Pat. No. 5,433,197 issued to Stark on Jul. 18, 1995 is incorporated herein by reference). Glucose concentrations in the anterior chamber of the eye are correlated with blood glucose levels and since the aqueous humor is continuously replaced, changes in blood glucose concentrations are reflected in the aqueous humor with a delay of approximately 10 minutes (see e.g., U.S. Pat. No. 5,433,197, Ibid.). Eye interrogation may be used to monitor the computer user's glycemic control. For example, the eye interrogation system may routinely monitor glucose levels in the eye and alert the user when hyperglycemia is evident.

To monitor the subject's heart rate, the eye interrogation system includes an ultrasound system to measure ocular pulse. Ocular pulsation results from pulsatile blood flow in vasculature of the eye and reflects heart rate. Systolic heartbeat results in pulsatile ocular blood flow which generates a pressure wave at the retina which is transmitted through the intraocular media to the cornea which distends, moving 1-50 microns and then reverts back to its original position during the diastolic portion of the heartbeat. To measure ocular pulse the eye interrogation system includes an ultrasound wave source 918 and a receiver 920 to measure movement of the cornea based on Doppler frequency shift (see e.g., U.S. Pat. No. 3,948,248 issued to Zuckerman et al. on Apr. 6, 1976, which is incorporated herein by reference). For example the ultrasound source may be a piezoelectric-based transducer that produces a continuous ultrasonic wave at approximately 1 MHz frequency which is collimated into a beam 2 mm to 3 mm in diameter that is focused on the cornea. Ultrasonic waves are reflected from the moving cornea and detected by a receiver 920 which converts the ultrasonic energy into an electrical signal that is processed by demodulation circuitry to reduce noise, amplify the signal and determine the frequency shift (a.k.a., the Doppler shift) of the reflected ultrasound waves. The frequency shift of the reflected ultrasound waves is used to calculate the movement, i.e., pulsation, of the cornea with respect to time, and the velocity of movement versus time is used to calculate heart rate. The relationship between ocular pulse and heart rate are described by linear equations (see e.g., Saha et al., *Stroke* 24: 1686-1690, 1993 which is incorporated herein by reference). A plot of ocular pulsation velocity versus time correlates with a simultaneous electrocardiogram (see e.g., U.S. Pat. No. 3,948,248 Ibid.). Heart rates are determined by eye interrogation with ultrasound waves and transmitted to a computer for storage and comparison to average values for the computer user. Abnormal heart rate is reported to the computer user. Moreover, ocular pulsation data may be used to identify other diseases. For example, ocular pulse distortions may indicate: carotid stenosis, potential stroke and glaucoma. The eye interrogation system may alert the computer user when ocular pulsation data indicate potential diseases exist.

To monitor the computer user's temperature the eye interrogation system may include an infrared thermometer which remotely measures temperature in the eye. An infrared thermometer 922 comprised of a detector, collecting optical system, e.g., lens and filter and processing circuitry is incorporated in the eye interrogation system. The filter limits the spectrum of infrared radiation that is detected, and the lens optical characteristics determine the target size within the eye and the allowed distance from the user's eye. The detector converts infrared energy into an electrical signal which is amplified and processed by the associated computer with programs to calculate temperature of the eye. An infrared thermometer suitable for sensitive temperature measurement (i.e., approximately 0.1 degree Centigrade) that may be targeted to the iris/pupil region or to the sclera is described (see e.g., U.S. Pat. No. 5,115,815 issued to Hansen on May 26, 1992 which is incorporated herein by reference). For example an infrared camera may be used to measure corneal temperature (see e.g., Kessel et al., *Investigative Ophthalmology and Visual Science* 51: 6593-6597, 2010 which is incorporated herein by reference). An infrared camera with a focal plane array detector, thermal sensitivity ≤0.09 degrees C. and an accuracy of 0.1 degrees C. is available from Fluke Corp., Everett, Wash. (see e.g., Fluke_Ti25 Datasheet which is incorporated herein by reference). The gaze tracking system (see above) detects alignment of the infrared thermometer's detector with the user's eye and activates the infrared thermometer. Temperature readings are stored in the computer associated with the eye interrogation system and the user may be alerted when temperature at the eye is above or below the normal range relative to the ambient temperature (see e.g., Kessel et al., Ibid.). Signal processing may be performed in eye interrogation system 900, and/or in computer 908. For example, physiological parameter values may also be sent to computer 908 for data analysis, storage, reporting, and/or transmission to another party (e.g. a medical caregiver). Accordingly, system 900 permits blood glucose, heart rate, and temperature of subject 906 to be measured unobtrusively while subject 906 uses computer 908.

In some embodiments, signal processing circuitry is packaged separately from signal sources and sensors. Signal processing circuitry (which may include hardware or software) is readily reconfigurable for use with different types and/or numbers of signal sources and sensors, e.g. for measuring different physiological parameters. A user (either the subject or a caregiver, for example) thus has the option to configure the system as desired for a specific application.

Figure 10:
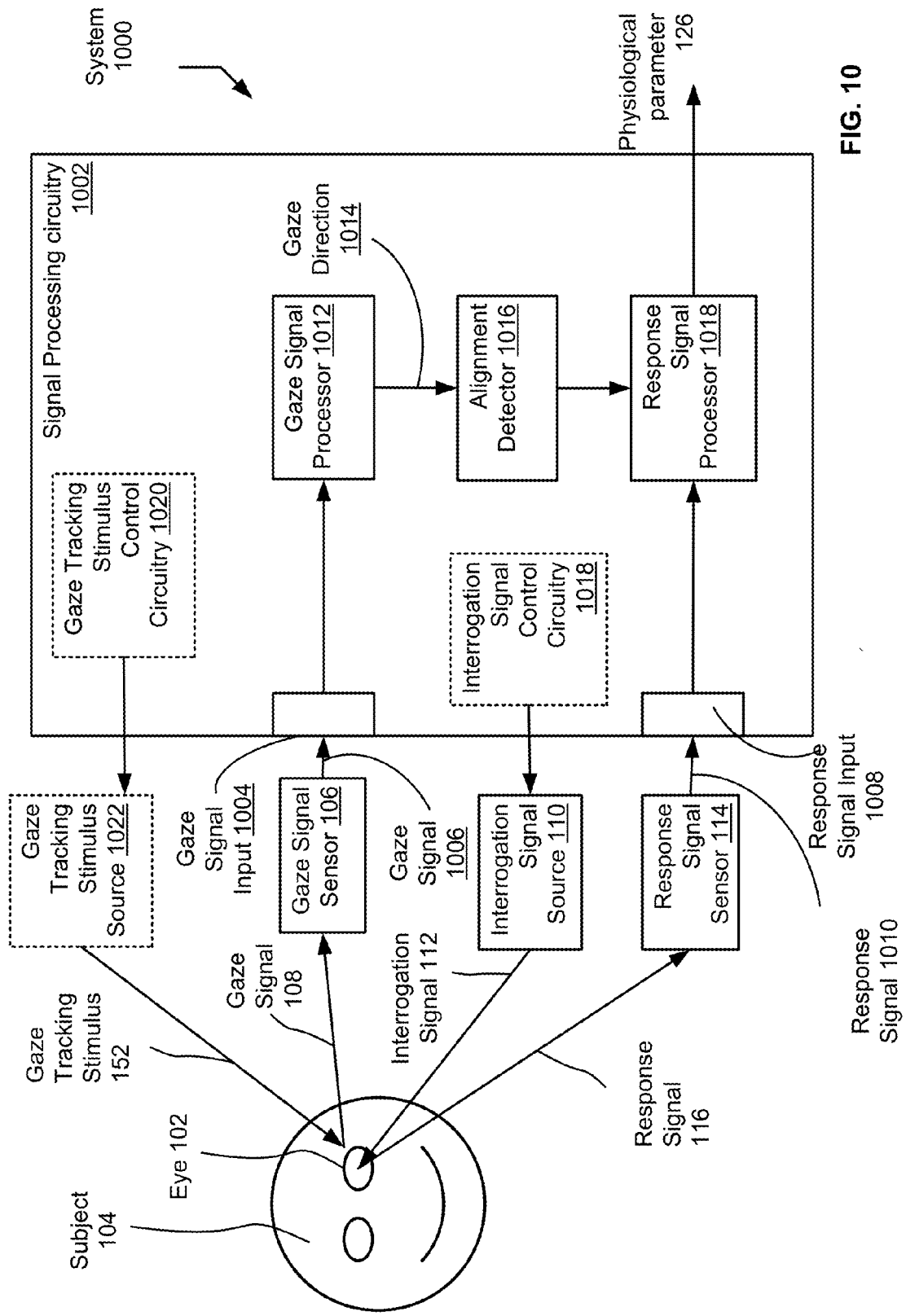
FIG. 10 is a block diagram of a system for controlling the sensing of information from an eye of a subject.

FIG. 10 depicts a system 1000 for controlling the sensing of information from an eye 102 of a subject 104, which includes signal processing circuitry 1002 including a gaze signal input 1004 adapted to receive a gaze signal 1006 containing information indicative of a gaze direction of the eye 102 of subject 104 sensed from at least an eye 102 of the subject; a response signal input 1008 adapted to receive a response signal 1010 sensed from the eye 102 of the subject 104 by a response signal sensor 114 responsive to delivery of an interrogation signal 112 to the eye 102 of the subject 104; a gaze signal processor 1012 configured to determine the gaze direction 1014 of the eye of the subject based upon the gaze signal 1006; an alignment detector 1016 configured to determine whether the eye of the subject is in alignment with respect to at least one of the interrogation signal source 110 or the response signal sensor 114 based at least in part upon the gaze direction; and a response signal processor 1018 configured to process the response signal 1010 sensed from the eye 102 of the subject 104 by the response signal sensor 114 when the eye of the subject is in alignment with respect to the at least one of the interrogation signal source 110 or the response signal sensor 114 to determine a physiological parameter 126 from the response signal.

As can be seen from FIG. 10, system 1000 is used in combination with at least gaze signal sensor 106, interrogation signal source 110, and response signal sensor 114. System 1000, used in combination with these additional components, provides functionality similar to that offered by system 100 as depicted in and described in connection with FIG. 1, for example. System 1000 is adapted for use in a system including modular components.

System 1000 can include interrogation signal control circuitry 1018 configured to drive production of the interrogation signal 112 by interrogation signal source 110.

System 1000 can include gaze tracking stimulus control circuitry 1020 configured to drive production of a gaze tracking stimulus 152 by a gaze tracking stimulus source 1022. In an embodiment, gaze tracking stimulus control circuitry 1020 is configured to drive production of a gaze tracking stimulus by a plurality of gaze tracking stimulus sources. Response signal processor 1018 may be adapted to process a response signal 1010 sensed from an interior of the eye of the subject responsive to the interrogation signal, e.g., from a lens, aqueous humor, vitreous humor, or retina of the eye of the subject, as discussed in connection with FIG. 2. Response signal processor 1018 may be configured to process the response signal to determine a feature of the vasculature of the eye of the subject or a biometric identification of the subject, as discussed herein above.

Figure 11:
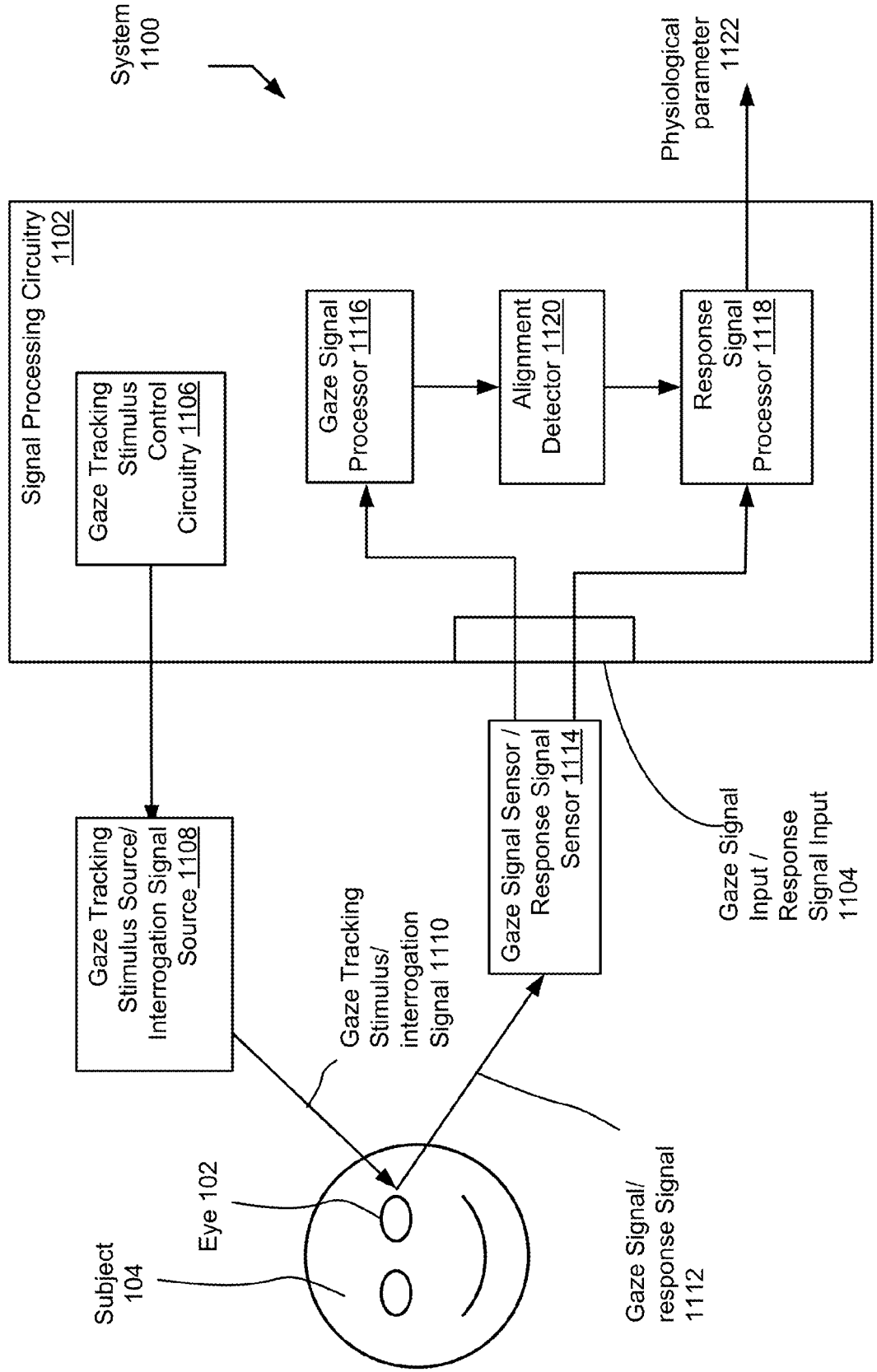
FIG. 11 is a block diagram of a system for controlling the sensing of information from an eye of a subject.

The gaze signal input and the response signal input be may separate inputs, as depicted in FIG. 10, or the same input, as depicted in FIG. 11. FIG. 11 depicts a system 1100 in which a single signal source is used as a combined gaze tracking stimulus source/interrogation signal source 1108, driven by gaze tracking stimulus control circuitry 1106 and a single sensor is used as gaze signal sensor/response signal sensor 1114. Gaze signal/response signal 1112 is produced by eye 102 of subject 104 in response to gaze tracking stimulus/interrogation signal 1110. The sensed response signal 1104 is directed to gaze signal processor 1116 and response signal processor 1118, which along with alignment detector 1120 and gaze tracking stimulus control circuitry 1106, are components of signal processing circuitry 1102. Physiological parameter 1122 is determined by Response Signal Processor 1118.

Figure 12:
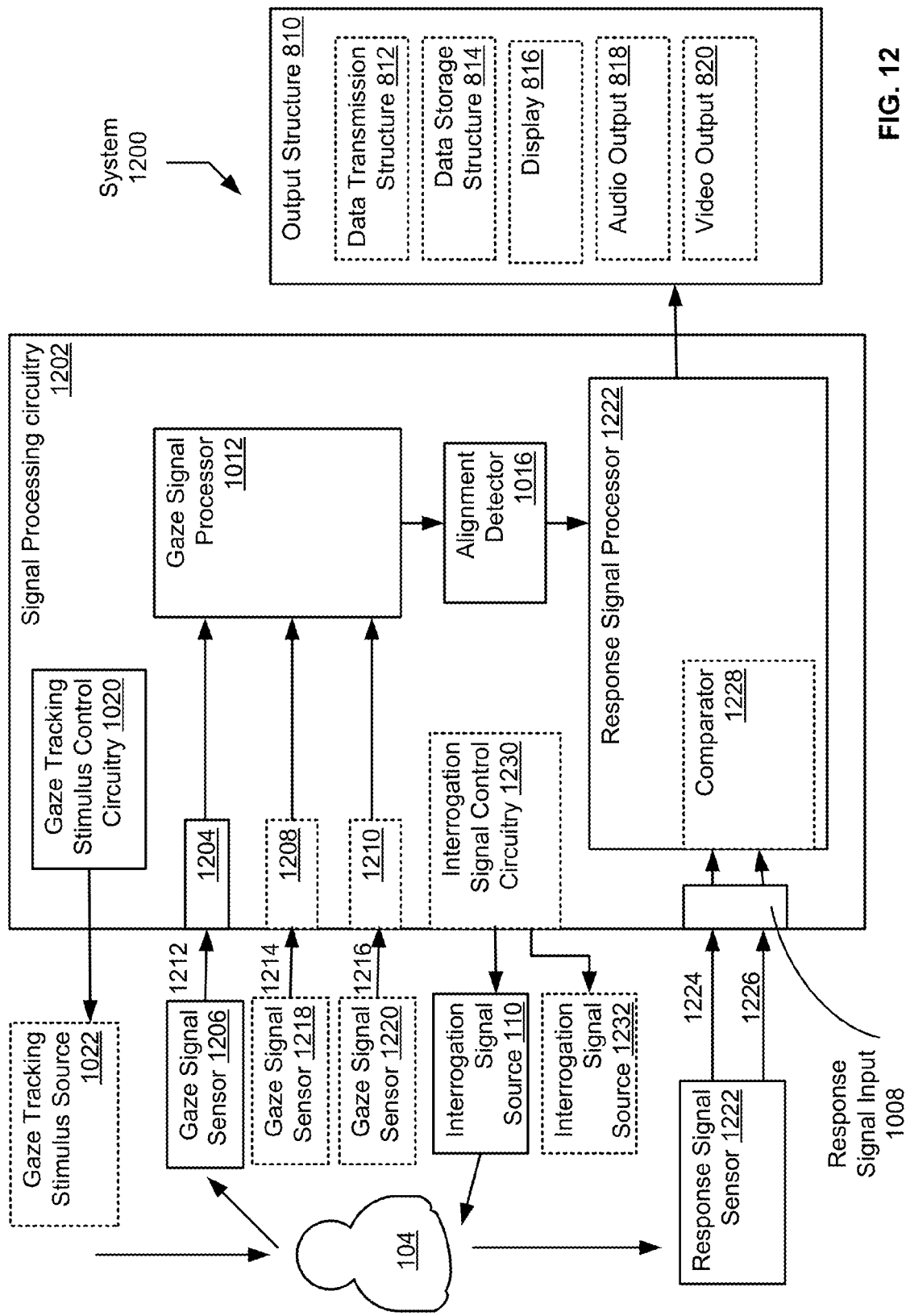
FIG. 12 is a block diagram of a system for controlling the sensing of information from an eye of a subject.

FIG. 12 depicts a system 1200, signal processing circuitry 1202 in which gaze signal input 1204 is adapted to receive a signal from a gaze signal sensor 1206. In related embodiments, signal processing circuitry 1202 includes a plurality of gaze signal inputs, e.g., 1204, 1208, and 1210, adapted to receive a plurality of gaze signals 1212, 1214, and 1216 containing information indicative of a gaze direction of the eye of the subject 104 sensed from at least an eye of the subject, from a plurality of gaze signal sensors 1206, 1218, and 1220.

In an embodiment, response signal processor 1222 is configured to process a response signal by determining a first response signal 1224 at a first polarization, determining a second response signal 1226 at a second polarization, and comparing the response signal 1224 determined at the first polarization to the response signal 1226 determined at the second polarization with comparator 1228, wherein the first polarization and the second polarization are different. Response signal processor 1222 may be configured to process the response signal sensed from the eye of the subject by the response signal sensor when the eye of the subject is in alignment with respect to the at least one of the interrogation signal source 110 or the response signal sensor 1222 to determine, for example, a measurement of oxygenation, blood glucose, heart rate, glycosylated hemoglobin, temperature (e.g., body temperature), blood flow, a substance in the eye of the subject, or other physiological parameters as discussed elsewhere herein, from the response signal.

In an embodiment, system 1200 includes interrogation signal control circuitry 1230. Interrogation signal control circuitry 1230 may be configured to drive production of a pulsed interrogation signal by interrogation signal source 110, as described in connection with FIG. 6. Signal processing circuitry 1202 may be configured to gate detection of the response signal (e.g. 1224 or 1226) relative to the pulsed interrogation signal. Signal processing circuitry 1202 may be configured to combine multiple response signals produced by the eye of the subject in response to multiple pulses of the pulsed interrogation signal, e.g. by summing or averaging the multiple response signals, or by determining a moving average or weighted sum of the multiple response signals, as illustrated and discussed in connection with FIG. 6.

In an embodiment, interrogation signal control circuitry 1230 may be configured to drive production of a first interrogation signal having a first optical wavelength and production of a second interrogation signal having a second optical wavelength, as described in connection with FIG. 8. System 1200 may be used with two or more interrogation signal sources, e.g. 110 and 1232 as shown in FIG. 12. As Signal processing circuitry 1202 may be configured to process a first response signal sensed from the eye of the subject in response to the first interrogation signal and a second response signal sensed from the eye of the subject in response to the second interrogation signal by comparing the first and second response signals in order to determine the physiological parameter, e.g. with comparator 1228. Signal processing circuitry 1202 may be configured to drive production of the first interrogation signal simultaneously or sequentially with respect to the second interrogation signal.

System 1200 may include an output structure 810 adapted to output a signal relating to the determined physiological parameter. The output structure can include, e.g., a data transmission structure 812, a data storage structure 814, a display 816, an audio output 818, or a visual output 820, as described in connection with FIG. 8. The system can include a display adapted to display information relating to the determined physiological parameter. The system can include one or multiple output structures, to permit one or more signals relating to the determine physiological parameter to be used for various purposes, such as providing feedback directly to the subject (in various formats, such as numerical, graphical, or narrative), reporting to a medical care giver or institution, sending information to a data storage device, which may be local or remote, or to a computer network, where it may be accessed by various parties.

Figure 13:
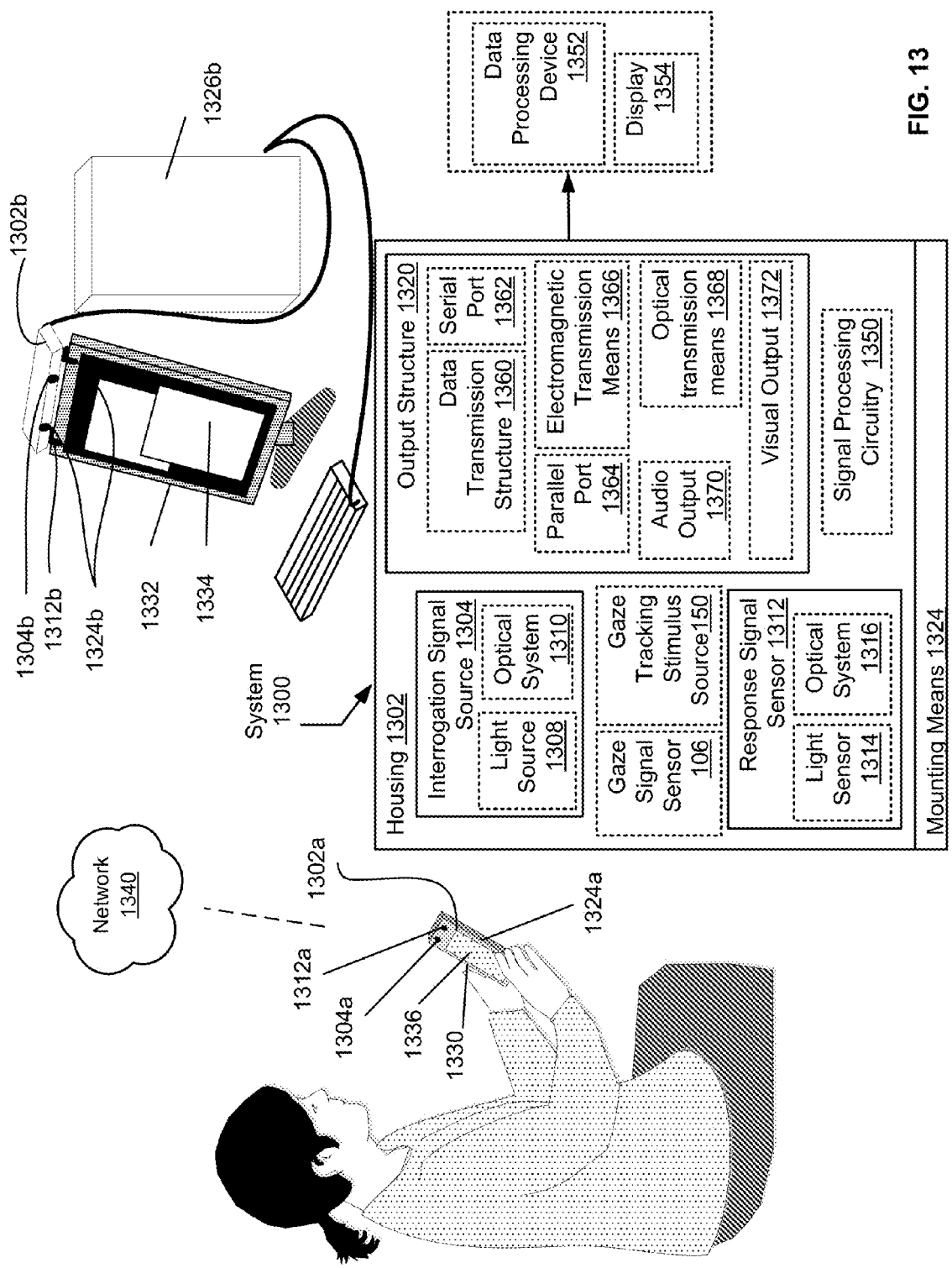
FIG. 13 illustrates several embodiments of a system for sensing information from an eye of a subject.

FIG. 13 depicts several examples of systems in which various components are packaged in a housing suitable for use in combination with a conventional display device such as, for example, a computer. System 1300 is depicted in schematic form, including a housing 1302; an interrogation signal source 1304 housed in the housing 1302 and adapted for delivering an interrogation signal to an eye of a subject, the interrogation signal source 1304 including at least one light source 1308 and at least one optical system 1310; response signal sensor 1312 housed within housing 1302 and adapted for sensing a response signal produced by the eye of the subject responsive to the interrogation signal, the response signal containing information regarding a physiological parameter of the subject; output structure 1320 adapted for transmitting an output signal; mounting means 1324 adapted for mounting housing 1302 with respect to a display in such a manner that the interrogation signal source 1304 and response signal sensor 1312 are alignable with the eye of the subject during normal use of the display by the subject.

In various embodiments, housing 1302 has a size and configuration that permits it to be conveniently attached to or otherwise positioned with respect to an existing device incorporating a display, e.g. a television, computer (including but not limited to a desktop, laptop, or tablet computer), telephone, or various displays as described herein above. For example, in FIG. 13, housing 1302a is configured to mount to a telephone 1330 by fitting around it in the same manner as a conventional telephone case. Interrogation signal source 1304a and response signal sensor 1312a are positioned in housing 1302a. In another example, housing 1302b is configured to mount to computer display 1332 by means of clips 1324b that serve as mounting means.

In an aspect, mounting means 1324 (see examples 1324a and 1324b) is adapted for mounting the housing 1302 with respect to the display such that during normal use of the display by the subject, the interrogation signal source 1304 (see examples 1304a and 1304b) and response signal sensor 1312 (see examples 1312a and 1312b) are positioned within the visual field of at least one eye of the subject. In an aspect, mounting means 1324 (see examples 1324a and 1324b) is adapted for mounting the housing 1302 with respect to the display such that the interrogation signal source and response signal sensor are oriented in substantially the same direction as the display surface of the display (see display surface 1334 of computer display 1332, and display surface 1336 of telephone 1330). Mounting means 1324 can be any of a variety of mounting means well known to those skilled in the art and can be adapted for use with a particular types of display. For example, mounting means can include one or more clamps, clips, brackets, screws, adhesives, hook and loop strips, pegs, tongue and groove structures, tab and slot structures, to name a few examples.

As depicted in FIG. 13, system 1300 can include a gaze signal sensor 106 adapted for receiving a gaze signal containing information indicative of a gaze direction of an eye of the subject. Gaze signal sensor can include an optical sensor, or optical sensor array, which may include for example, camera and/or a plurality of gaze signal sensors, as depicted in and described in connection with FIG. 1, for example.

System 1300 may also include at least one gaze tracking stimulus source 150 adapted to deliver a gaze tracking stimulus to at least an eye of a subject, wherein the gaze signal is produced in response to the gaze tracking stimulus, as described in connection with FIG. 1. The gaze tracking stimulus source 150 may include an infra-red source; in connection therewith, the gaze signal sensor may include an infra-red sensor. Gaze tracking stimulus source 150 may include a near infra-red source; in connection therewith, the gaze signal sensor may include a near infra-red sensor. Gaze tracking stimulus source 150 can include one or a plurality of light sources.

Response signal sensor 1312, which includes light sensor 1314 and optical system 1316, may be adapted to sense a response signal from various portions of the eye of the subject responsive to the interrogation signal; e.g., from an interior of the eye, lens, aqueous humor, vitreous humor, or retina of the eye of the subject responsive to the interrogation signal. Gaze signal sensor and the response signal sensor can be the same sensor or different sensors, e.g. as shown in FIG. 3. Gaze signal sensor may include an infrared camera, and/or a CCD camera.

Various combinations of interrogation signal source 1304 and response signal sensor 1312 can be used in the various embodiments, as described herein above. Suitable combinations include, but are not limited to, an interrogation signal source 1304 that includes a broad spectrum light source and a response signal sensor 1312 that includes a spectrometer based on a CCD array; interrogation signal source 1304 that includes a near-infrared light source and response signal sensor 1312 that includes a near-infrared camera; interrogation signal source 1314 that includes a tunable laser source and response signal sensor 1312 that includes a Raman spectrometer based on a CCD camera; interrogation signal source 1304 that includes a mid-infrared light source and response signal sensor 1312 that includes a mid-infrared detector; or interrogation signal source 1304 that includes a tunable laser source and response signal sensor 1312 that includes a broad spectrum pyroelectric detector.

The interrogation signal source 1304 may be adapted to produce light having a first polarization, with the response signal sensor is adapted to detect light having a second polarization, where the first polarization and the second polarization are the same, or, alternatively, where the first polarization and the second polarization are different, as shown in FIG. 12. This may be useful, for example, if detection of the physiological parameter is based on detection of a change in polarization caused by the presence (or absence) of a material of interest.

In various embodiments, the physiological parameter can be a measurement of oxygenation, blood glucose, heart rate, glycosylated hemoglobin, temperature, (e.g., a body temperature), blood flow, a substance in the eye of the subject, or various other physiological parameters as described herein above. As noted previously, the response signal may be indicative of a feature of the vasculature of the eye of the subject or a biometric identification of the subject.

System 1300 can be modified so that the interrogation signal source is adapted to deliver a pulsed interrogation signal, as depicted generally in FIG. 6. The response signal sensor 1312 may be configured to gate detection of the response signal relative to the pulsed interrogation signal. In an embodiment, system 1300 includes signal processing circuitry 1350 adapted to process the response signal. In one aspect, interrogation signal source 1304 is adapted to deliver a pulsed interrogation signal, and signal processing circuitry 1350 is configured to gate detection of the response signal relative to the pulsed interrogation signal. Signal processing circuitry 1350 includes hardware and/or software located in housing 1302, or, alternatively, or in addition, in an external data processing device 1352 (for example computer 1326b or phone 1330) or in one or more remote locations (represented by network 1340) or distributed across multiple such locations. Signal processing circuitry 1350 may be configured to combine multiple response signals produced by the eye of the subject in response to multiple pulses of the pulsed interrogation signal. For example, the signal processing circuitry may be configured to combine the multiple response signals by summing the multiple response signals or averaging the multiple response signals, or by determining a moving average or weighted sum of the multiple response signals.

As in other embodiment described herein, e.g. as described in connection with FIG. 7, in an aspect, the interrogation signal source 1304 is adapted to deliver an interrogation signal containing multiple wavelengths of light. System 1300 may include at least a first response signal sensor configured to sense a first response signal produced by the eye of the subject responsive to a first wavelength component of the interrogation signal, and a second response signal sensor configured to sense a second response signal produced by the eye of the subject responsive to a second wavelength component of the interrogation signal. In an aspect, the system includes at least a first interrogation signal source configured to deliver a first interrogation signal having a first optical wavelength and at least a second interrogation signal source configured to deliver a second interrogation signal having a second optical wavelength. Signal processing circuitry 1350 can be configured to process a first response signal sensed from the eye of the subject in response to the first interrogation signal and a second response signal sensed from the eye of the subject in response to the second interrogation signal by comparing the first and second response signals to determine the physiological parameter. System 1300 can be configured to deliver the first interrogation signal simultaneously with respect to the second interrogation signal, or sequentially with respect to the second interrogation signal. Interrogation signal source 1304 and response signal sensor 1312 can be co-aligned, or in another embodiment, interrogation signal source 1304 and response signal sensor 1312 can be separately aligned and located.

System 1300 includes output structure 1320, which may include, for example, a data transmission structure 1360, a serial port 1362, a parallel port 1364, an electromagnetic transmission means 1366, or an optical transmission means 1368. Output structure 1320 may be adapted to transmit an output signal to the display 1354 (for example computer display 1332 or telephone display 1336), or to a data processing device 1352 (which may be computer 1326, for example), wherein, for example, the display is controlled by the data processing device. The output structure can include an audio output 1370 and/or a visual output 1372. A visual output 1372 can include a display on housing 1302 (e.g., an alphanumeric display, a screen, or simply a light emitting diode or other indicator light) in addition to or in alternative to the display to which housing 1302 is mounted.

Display 1354 (also visual output 1370) can be configured to display information relating to the determined physiological parameter. Display 1354 can be a video monitor, computer display, video game display, telephone display, or terminal of a data processing device. Display 1354 can be incorporated in a wearable item (e.g., eyewear, headwear, jewelry, an article of clothing, a badge, a bandage, an adhesive patch, a wristwatch, a cuff, a sleeve, a wristband, an armband, a helmet, a physiological support such as a cast or brace, or a wearable a positioning structure configured to surround a portion of the subject). Display 1354 can be incorporated in an article of furniture, an article of medical or health-care related equipment, an article of exercise equipment, or a vehicle, for example. Examples of such displays are described in greater detail herein above.

Figure 14:
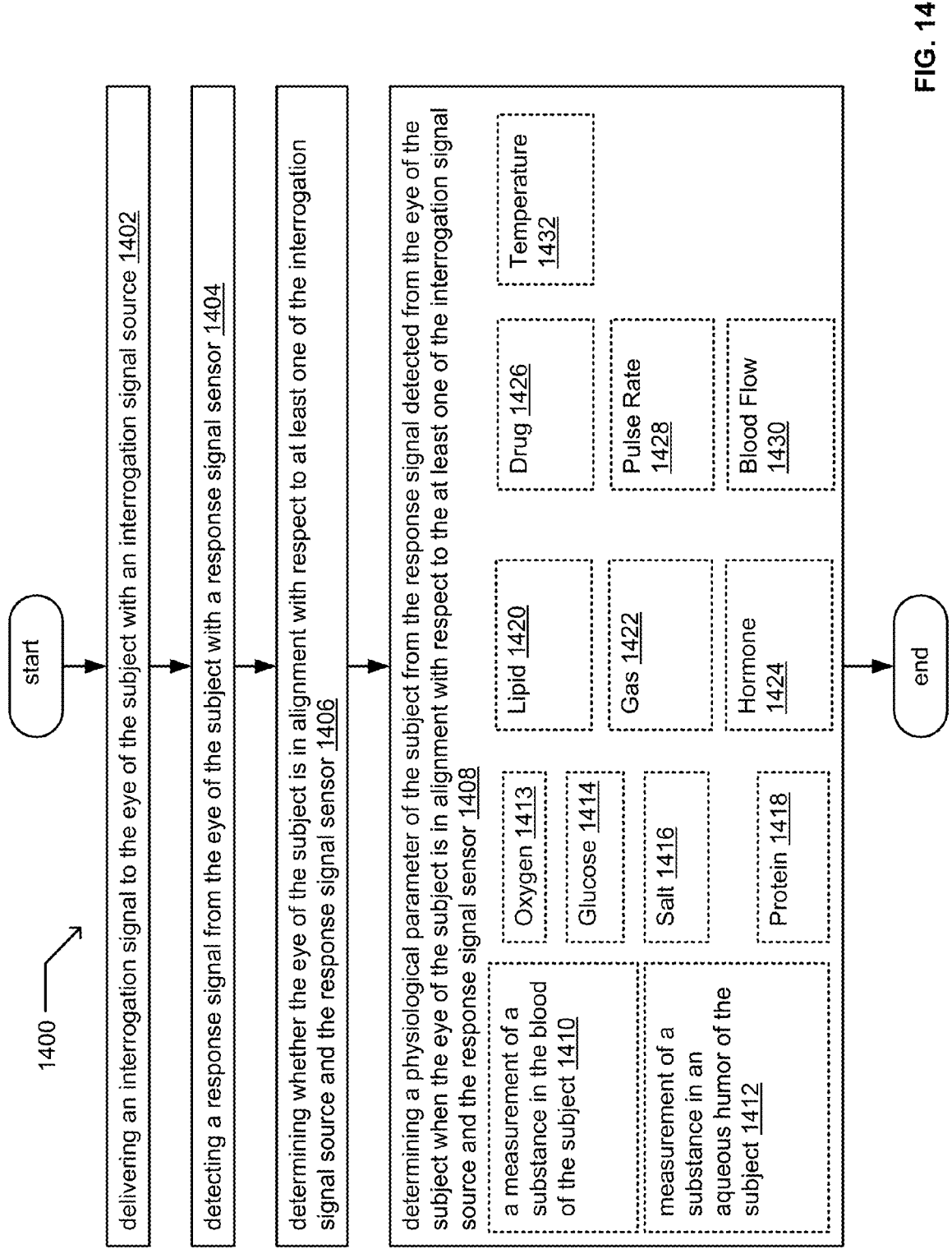
FIG. 14 is a flow diagram of a method of measuring information from an eye of a subject.

FIG. 14 is a flow chart of a method 1400 of measuring information from an eye of a subject, including delivering an interrogation signal to the eye of the subject with an interrogation signal source at 1402; detecting a response signal from the eye of the subject with a response signal sensor at 1404; determining whether the eye of the subject is in alignment with respect to at least one of the interrogation signal source and the response signal sensor at 1406; and determining a physiological parameter of the subject from the response signal detected from the eye of the subject when the eye of the subject is in alignment with respect to the at least one of the interrogation signal source and the response signal sensor at 1408. Additional variations and expansions of method 1400 are illustrated in FIGS. 15-20.

In some method embodiments, the physiological parameter is a measurement of a substance in the blood of the subject, as indicated at 1410, and in some embodiments, the physiological parameter is a measurement of a substance in an aqueous humor of the subject, as indicated at 1412. The physiological parameter can be a measurement of oxygen 1413, glucose 1414, a salt 1416, a protein 1418, a lipid 1420, a gas 1422 (e.g. oxygen), a hormone 1424, a drug 1426. The physiological parameter can be a pulse rate 1428, a blood flow 1430, or a temperature 1432.

Figure 15:
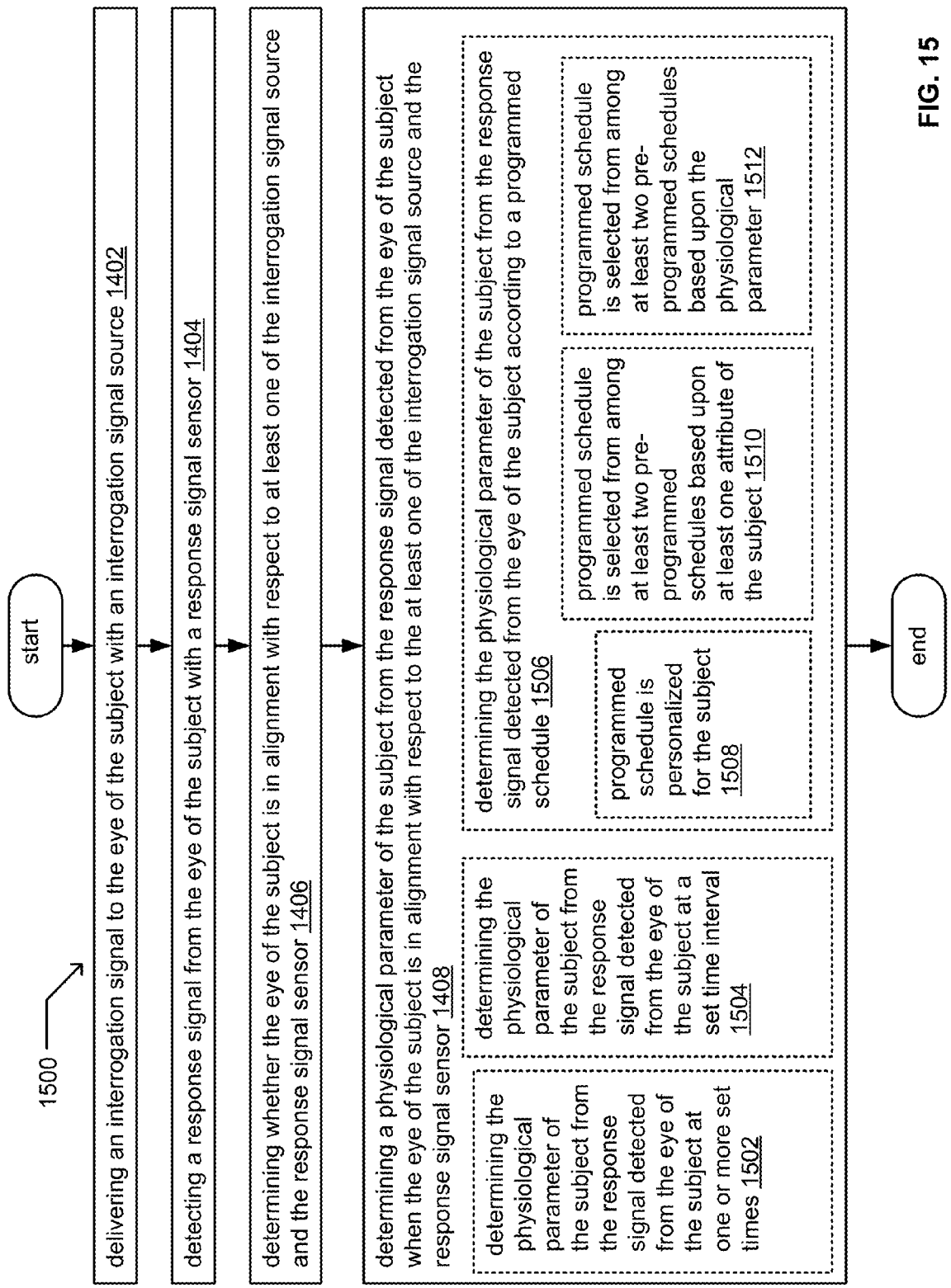
FIG. 15 is a flow diagram of a method of measuring information from an eye of a subject.

As shown in FIG. 15, a related method 1500 includes determining the physiological parameter of the subject from the response signal detected from the eye of the subject at one or more set times 1502, at a set time interval 1504, and/or according to a programmed schedule 1506. For example, the programmed schedule can be personalized for the subject 1508. That is, the schedule may be set depending upon the needs or desires of the subject. In one aspect, the programmed schedule is selected from among at least two pre-programmed schedules based upon at least one attribute of the subject 1510. For example, several schedules may pre-programmed into the system, with each schedule suitable for subjects having a particular attribute or attributes; e.g., the temperature of a subject may be monitored at according to a schedule having lower sampling rates if the subject is generally healthy, and according to a schedule having higher sampling rates if the subject is known to be sick and/or if a previous high temperature reading has been detected from the subject. As another example, the schedule for sampling blood glucose may be set depending upon how quickly the subject's blood glucose is expected to change at different times during a measurement period; that is, measurements may be taken more frequently immediately after a meal and less frequently several hours after the meal if it is expected that blood glucose will change most rapidly immediately after a meal. Sampling more be performed at a higher rate if a new treatment regimen is being tried than if the subject is using a well-established treatment regimen. Furthermore, the schedule may be selected based on the subject's current health status, recent activities, or other attributes which may be entered into the system by the subject or a care provider or the subject, or sensed with the system. The programmed schedule can be selected from among at least two pre-programmed schedules based upon the physiological parameter 1512.

Figure 16:
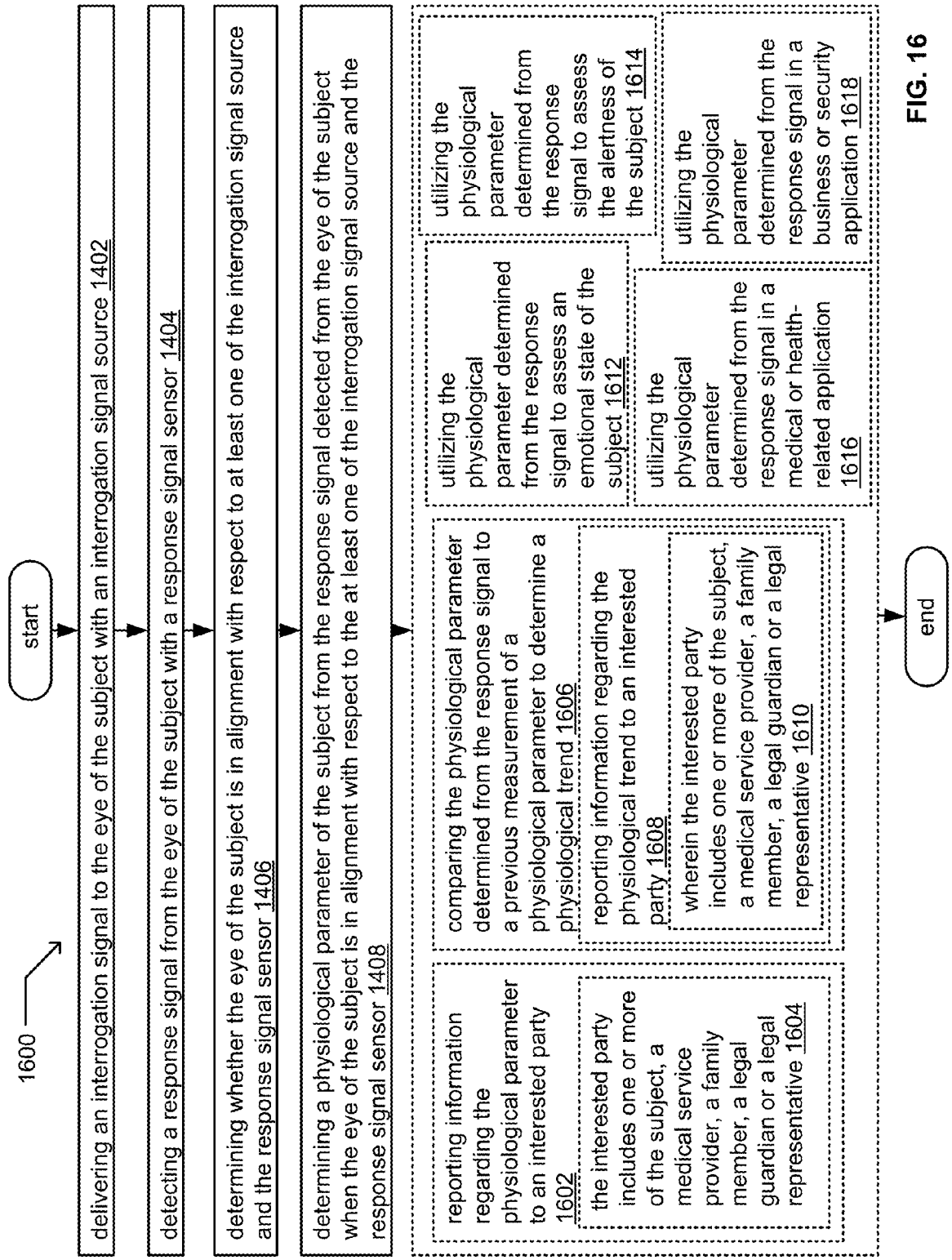
FIG. 16 is a flow diagram of a method of measuring information from an eye of a subject.

As shown in FIG. 16, a method 1600 can include various additional steps, such as reporting information regarding the physiological parameter to an interested party 1602, which may be, for example one or more of the subject, a medical service provider, a family member, a legal guardian or a legal representative 1604. Alternatively, or in addition, the method can include comparing the physiological parameter determined from the response signal to a previous measurement of a physiological parameter to determine a physiological trend 1606. The method may then also include reporting information regarding the physiological trend to an interested party 1608, which may be, for example one or more of the subject, a medical service provider, a family member, a legal guardian or a legal representative 1610.

Method 1600 method may include utilizing the physiological parameter determined from the response signal to assess an emotional state of the subject 1612, or alertness of the subject 1614. For example, heart rate, hormone levels, body temperature, and various other physiological parameters as described herein can be used to determine aspects of the subject's emotional state (e.g., nervousness, excitement, relaxation, etc.) or alertness, as is known to those having skill in the relevant arts. The method can include utilizing the physiological parameter determined from the response signal in a medical or health-related application 1616 or in a business or security application 1618, or both.

Figure 17:
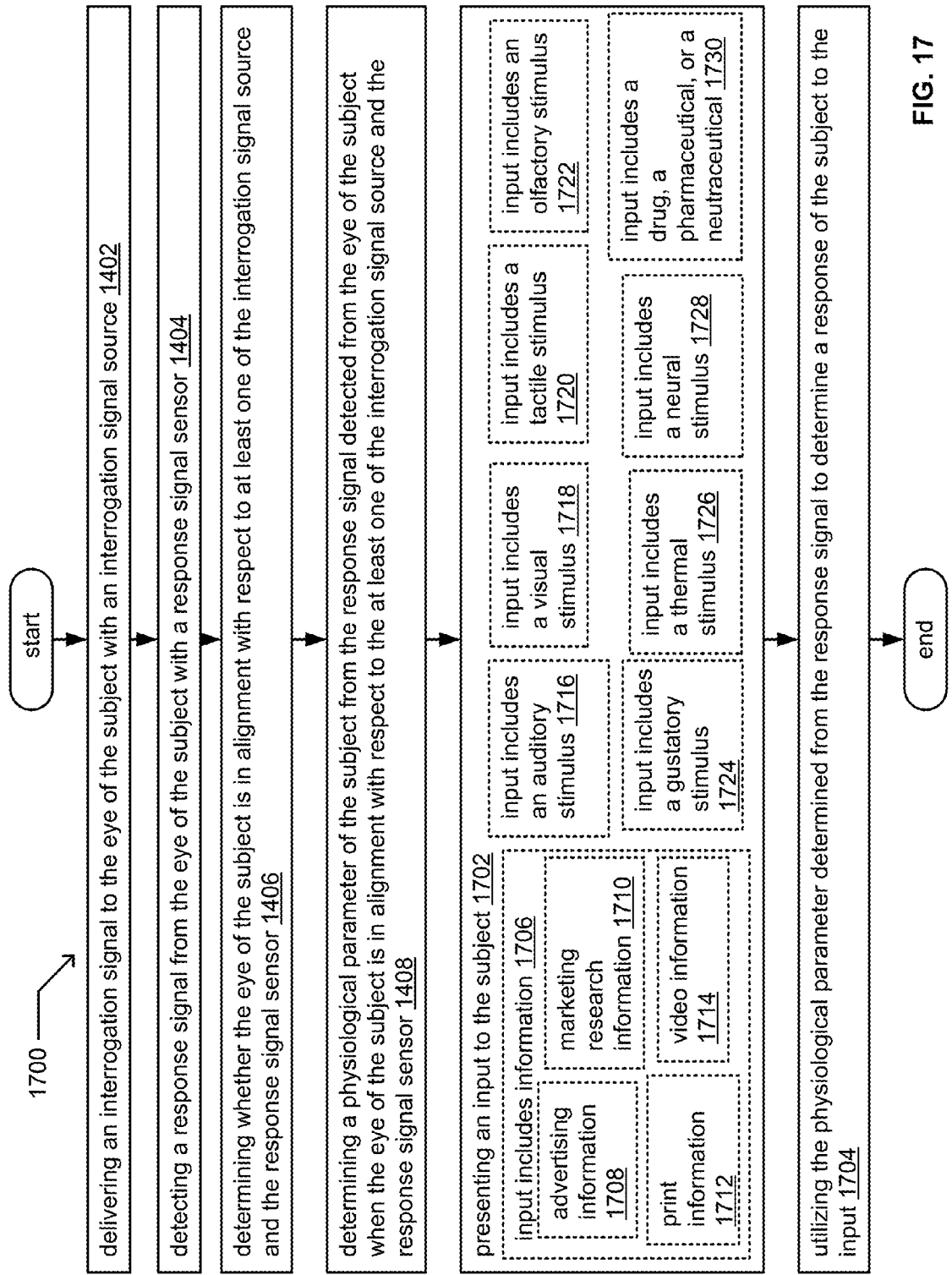
FIG. 17 is a flow diagram of a method of measuring information from an eye of a subject.

As shown in FIG. 17, method 1700 may include presenting an input to the subject 1702 and utilizing the physiological parameter determined from the response signal to determine a response of the subject to the input 1704. In some aspects, the input includes information 1706 (including, but not limited to, advertising information 1708, marketing research information 1710, print information 1712, or video information 1714). In some aspects, the input includes an auditory stimulus 1716, a visual stimulus 1718, a tactile stimulus 1720, an olfactory stimulus 1722, a gustatory stimulus 1724, a thermal stimulus 1726, a neural stimulus 1728, or a drug, a pharmaceutical, anutraceutical, or a nutrient 1730. Physiological response of the subject to advertising information or marketing research information may be used to assess the subject's response to such information, for example, for product development, marketing purposes or other business purposes. Similarly, response of the subject to various other stimulus (auditory, visual, olfactory, gustatory, etc.) may be used to determine whether or not the subject has a favorable response to the stimulus, which may be useful for marketing, product development or other business purposes. Alternatively, information relating to the subject's response to such stimuli may indicate a medical condition of the subject, or the subject's response to treatment, for monitoring or diagnostic purposes.

Figure 18:
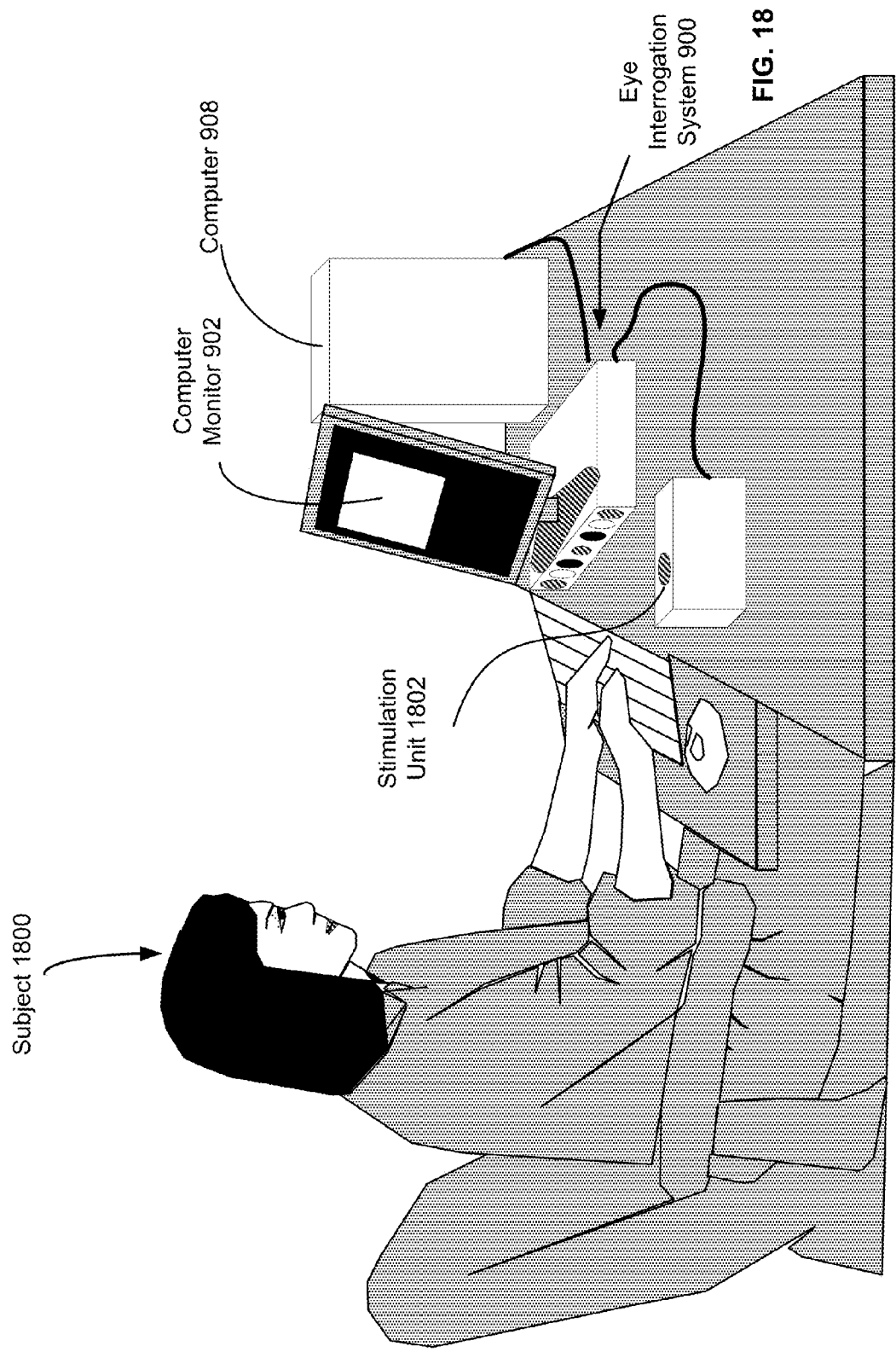
FIG. 18 illustrates an embodiment of a system including a stimulation unit.

FIG. 18 illustrates an example of a system that can be used for presenting stimuli and assessing the response of the subject to stimuli by means of eye interrogation. An eye interrogation system, computer monitor 902 and computer 908 are provided, as depicted in FIG. 8. Interrogation system 900 may be configured to detect one or more physiological parameters indicative of the response of subject 1800 to a stimulus presented by stimulus unit 1802. Presenting an input to subject 1800 may include presenting an input to the subjected in an automated fashion, under the control of and/or with monitoring by electrical or other circuitry (monitoring may include providing an input to a computer reporting delivery of the input to the subject, or receipt of the input by the subject, which does not necessarily require that the delivery of the input is controlled by the computer). For example, "presenting information," which may include presenting print, video, audio, auditory, or visual or graphical information, can be done by displaying information on a screen and/or delivering sound via speakers or headphone (e.g. playing recorded voice, music, sound, etc.). In broad terms, these are considered auditory stimuli and visual stimuli, which, however, are not limited to auditory and visual inputs having any particular information content. Visual and auditory stimuli can readily be presented to a user by via a computer system that includes a display and speakers, under control of appropriate software. Other types of stimuli can be presented using special-purpose stimulus units. See e.g., U.S. Pat. No. 6,053,738 (describing scent, flavor and tactile/texture stimuli), U.S. Pat. No. 6,542,442 (describing scent stimuli), and U.S. Pat. Nos. 8,308,558 and 8,248,217 (describing tactile/haptic stimuli), each of which is incorporated herein by reference). A tactile stimulus may include, but is not limited to, pressure or vibration, (e.g. delivered via a probe or air puff), or electrical or electromechanical stimulation, for example. An olfactory stimulus may include delivery or release of an odorant, while a gustatory stimulus may include delivery or release of a flavoring agent, or provision of a food or other flavored item. Thermal stimuli can be delivered via a beam of light or other electromagnetic energy, by application of a heated probe, or delivery of heated air or water. A neural stimulus can be, for example, an electrical, magnetic, or electromagnetic stimulus delivered with implanted or external (transcutaneous) stimulator. A drug, pharmaceutical, nutraceutical, or a nutrient can be delivered in a controlled fashion via an implanted or external controlled delivery device. Delivery/release of a stimulus may be via one or more stimulus delivery devices controlled by electrical circuitry (or other types of circuitry, e.g. optical circuitry, electromechanical devices, etc.); alternatively, delivery of a stimulus may include action of a human (including the subject) delivering a stimulus to the subject in accordance with the method. The timing of delivery of a human-delivered stimulus can be controlled by delivering a computer- or other electrical circuitry-controlled prompt for the stimulus to be delivered, or by receiving an input indicating delivery of the stimulus via a user-input to a computer or other electrical circuitry (e.g. by depressing a button or switch, providing an input via a mouse, keyboard, or microphone, or via other input devices as are known to those skilled in the art).

Figure 19:
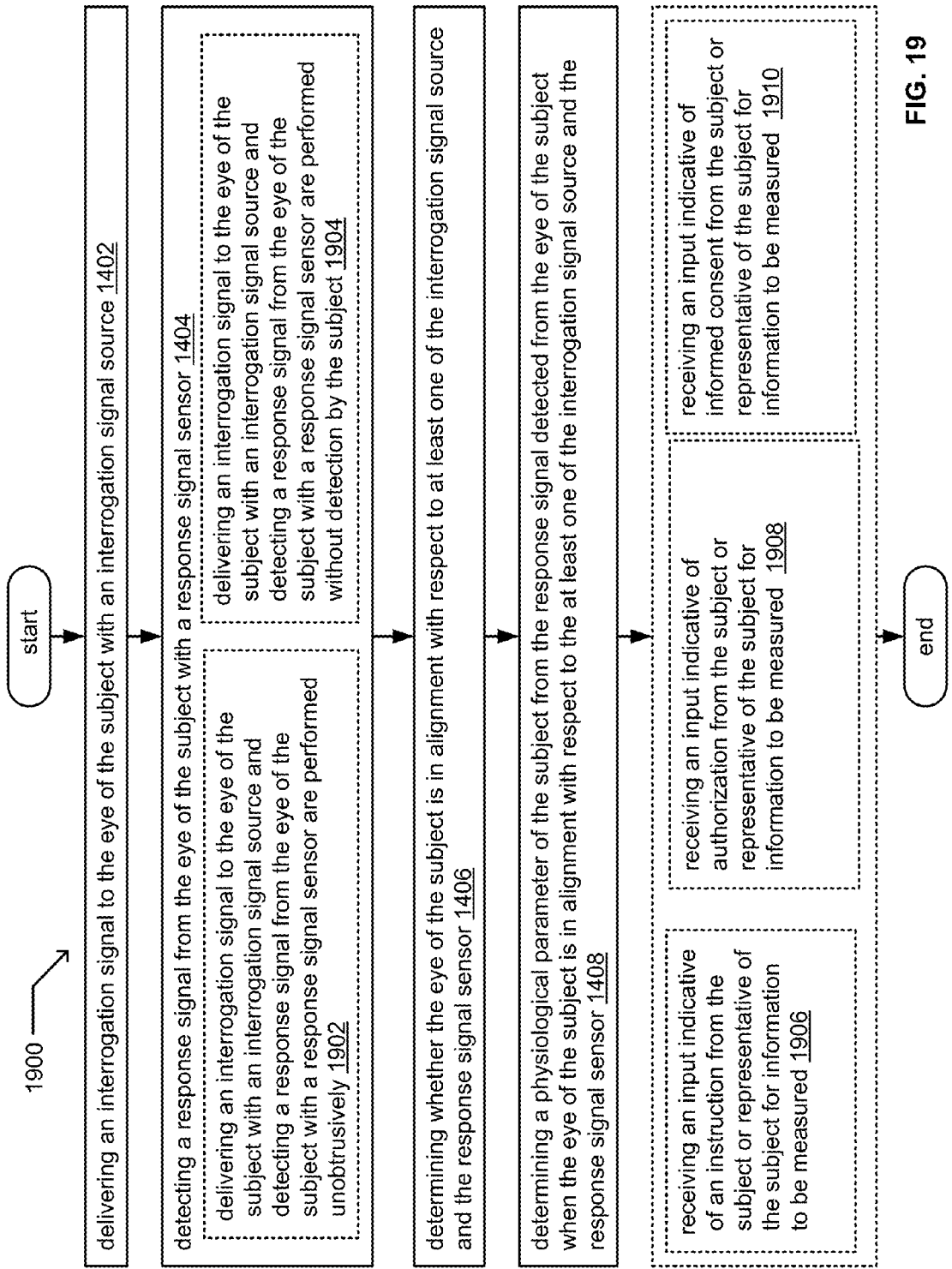
FIG. 19 is a flow diagram of a method of measuring information from an eye of a subject.

As shown in FIG. 19, in one aspect, a method 1900 includes, delivering an interrogation signal to the eye of the subject with an interrogation signal source and detecting a response signal from the eye of the subject with a response signal sensor are performed unobtrusively 1902. It is contemplated that performance of the methods as described herein can be done unobtrusively, e.g., that the measurement of information from the eye of a subject does not appreciably interfere with the subject's activities, and does not require or elicit any appreciable effort or attention from the subject. In some embodiments a method may be considered unobtrusive even if a modest level of effort or attention (either conscious or subconscious) is required of the subject. In some embodiments, delivering an interrogation signal to the eye of the subject with an interrogation signal source and detecting a response signal from the eye of the subject with a response signal sensor are performed without detection (i.e. without conscious detection and/or without subconscious detection) by the subject 1904. For example, if detection is performed for medical monitoring purposes, the subject may request or authorize performance of detection. It may be more convenient (or, in some cases more accurate information may be obtained) if the detection is performed unobtrusively or without detection by the subject. In some applications, e.g. monitoring of a public space such as a government building or airport, or in various private spaces such as a place of employment, monitoring may be performed to detect health or security risks, and subjects may be informed that monitoring will take place, although the actual taking of measurements may be unobtrusive or undetectable to the subject.

In some embodiments it may be desired to perform the method unobtrusively and/or without detection by the subject (at the time the measurement is being made) but to notify the subject about the performance of the method, or perform the method at the request of or with the consent of the subject. For example, the method may include receiving an input indicative of an instruction from the subject or representative of the subject for information to be measured 1906, receiving an input indicative of authorization from the subject or representative of the subject for information to be measured 1908, or receiving an input indicative of informed consent from the subject or representative of the subject for information to be measured 1910.

Figure 20:
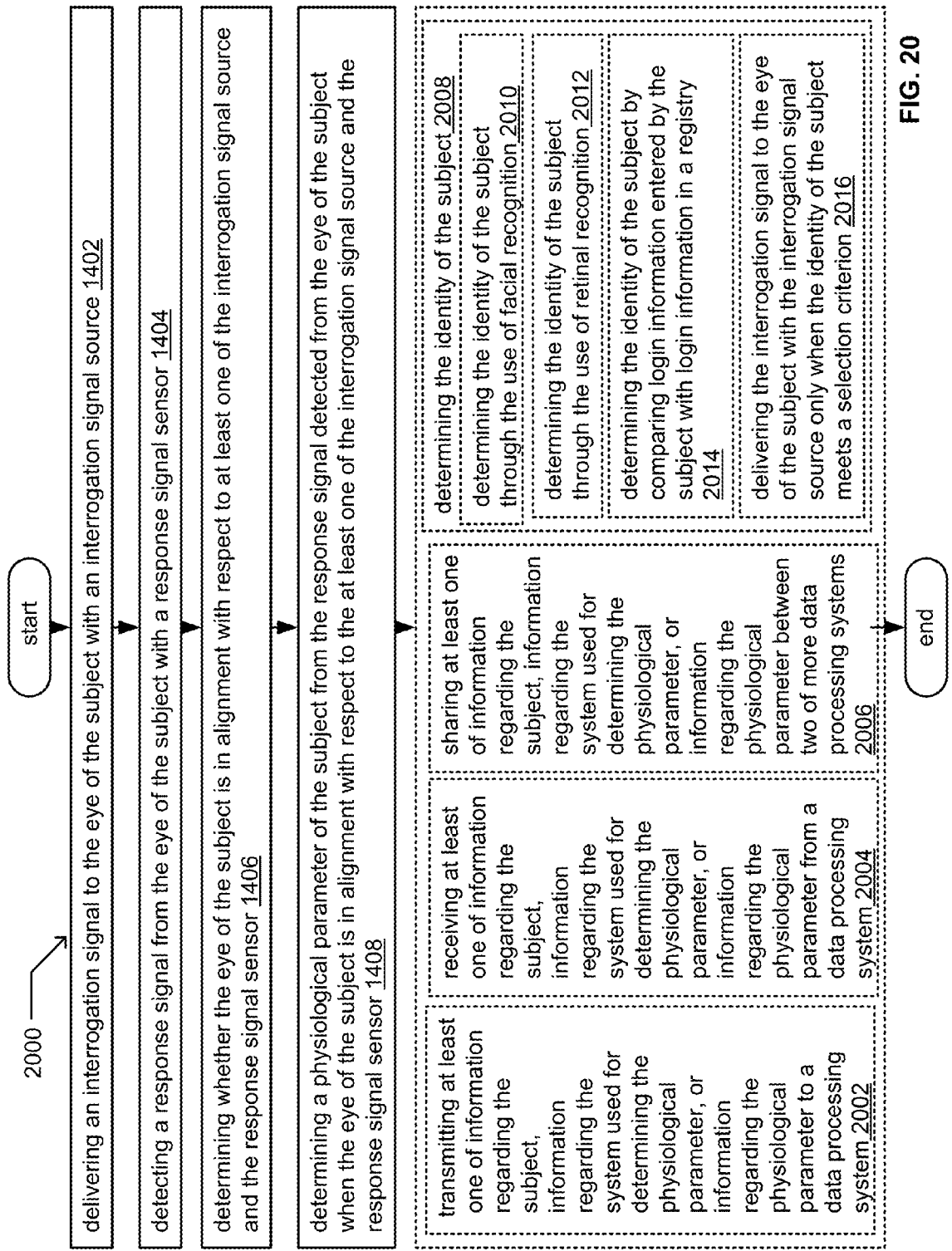
FIG. 20 is a flow diagram of a method of measuring information from an eye of a subject.

As shown in FIG. 20, in an embodiment, method 2000 includes transmitting at least one of information regarding the subject, information regarding the system used for determining the physiological parameter, or information regarding the physiological parameter to a data processing system 2002. In embodiment the method includes receiving at least one of information regarding the subject, information regarding the system used for determining the physiological parameter, or information regarding the physiological parameter from a data processing system 2004. In an embodiment, the method includes sharing at least one of information regarding the subject, information regarding the system used for determining the physiological parameter, or information regarding the physiological parameter between two of more data processing systems 2006.

In an aspect, the method includes determining the identity of the subject 2008. Determining the identity of the subject may be done, e.g., through the use of facial recognition 2010, through the use of retinal recognition 2012, or by determining the identity of the subject by comparing login information entered by the subject with login information in a registry 2014, by methods known to those having skill in the relevant arts. In an aspect, delivering the interrogation signal to the eye of the subject with the interrogation signal source can be done only when the identity of the subject meets a selection criterion, as indicated at 2016; for example, once the identity of the subject has been determined, the identity of the subject may be compared with an identity of one or more approved subjects, and if the identity matches an identity of an approved subject, the selection criterion is met and the interrogation signal is delivered.

In various embodiments, methods as described herein may be performed according to instructions implementable in either hardware, software, and/or firmware. Such instructions may be stored in non-transitory machine-readable data storage media, for example. Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware in one or more machines, compositions of matter, and articles of manufacture, limited to patentable subject matter under 35 USC 101. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware. In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components.

Implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled// implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof, limited to patentable subject matter under 35 U.S.C. §101. In an embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, limited to patentable subject matter under 35 U.S.C. §101, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to non-transitory machine-readable data storage media such as a recordable type medium such as a floppy disk, a hard disk drive, a Compact Disc (CD), a Digital Video Disk (DVD), a digital tape, a computer memory, etc. A signal bearing medium may also include transmission type medium such as a digital and/or an analog communication medium (e.g., a fiber optic cable, a waveguide, a wired communications link, a wireless communication link (e.g., transmitter, receiver, transmission logic, reception logic, etc), etc.).

FIG. 21 illustrates in schematic form an article of manufacture 2100 that includes one or more non-transitory machine-readable data storage media 2102 bearing one or more instructions 2104 for delivering an interrogation signal to an eye of the subject with an interrogation signal source; detecting a response signal from the eye of the subject with a response signal sensor; determining whether the eye of the subject is in alignment with respect to at least one of the interrogation signal source and the response signal sensor; and determining a physiological parameter of the subject from the response signal detected from the eye of the subject when the eye of the subject is in alignment with respect to the at least one of the interrogation signal source and the response signal sensor. As discussed herein above, the physiological parameter can be a measurement of a substance in the blood of the subject (e.g. as oxygen, glucose, a salt, a protein, or a lipid), a measurement of a substance in an aqueous humor of the subject (e.g., oxygen, glucose, a salt, a protein, or a lipid, a hormone, a drug), or a pulse rate, for example.

The one or more non-transitory machine-readable data storage media 2102 can bear one or more instructions 2104 for performing method steps as depicted in FIG. 15 for determining the physiological parameter of the subject from the response signal detected from the eye of the subject at one or more set times, one or more instructions for determining the physiological parameter of the subject from the response signal detected from the eye of the subject at a set time interval, and/or one or more instructions for determining the physiological parameter of the subject from the response signal detected from the eye of the subject according to a programmed schedule. The programmed schedule can be personalized for the subject. The one or more non-transitory machine-readable data storage media can be bear one or more instructions for selecting the programmed schedule from among at least two pre-programmed schedules based upon at least one attribute of the subject. For example, the one or more non-transitory machine-readable data storage media bear one or more instructions for selecting the programmed schedule from among at least two pre-programmed schedules based upon the physiological parameter.

In an embodiment, the one or more non-transitory machine-readable data storage media 2102 bear one or more instructions for performing steps of method 1600 as depicted in FIG. 16, for reporting information regarding the physiological parameter to an interested party, one or more instructions for comparing the physiological parameter determined from the response signal to a previous measurement of a physiological parameter to determine a physiological trend, and may also include one or more instructions for reporting information regarding the physiological trend to an interested party. In an embodiment, the article of manufacture 2100 includes one or more non-transitory machine-readable data storage media 2102 bearing one or more instructions for utilizing the physiological parameter determined from the response signal to assess an emotional state of the subject, or one or more instructions for utilizing the physiological parameter determined from the response signal to assess the alertness of the subject. The article of manufacture may include one or more non-transitory machine-readable data storage media that bear one or more instructions for utilizing the physiological parameter determined from the response signal in a medical or health-related application, or one or more instructions for utilizing the physiological parameter determined from the response signal in a business or security application.

In an embodiment, the article of manufacture 2100 includes one or more non-transitory machine-readable data storage media 2102 that bear one or more instructions for performing method 1799 as depicted in FIG. 17, including presenting an input to the subject; and utilizing the physiological parameter determined from the response signal to determine a response of the subject to the input. In an embodiment, the one or more non-transitory machine-readable data storage media bear one or more instructions for presenting information to the subject, for example, advertising information, marketing research information, print information, or video information. In various embodiments, the one or more non-transitory machine-readable data storage media bear one or more instructions for presenting various stimuli to the subject, e.g., an auditory stimulus, a visual stimulus, a tactile stimulus, an olfactory stimulus, a gustatory stimulus, a thermal stimulus, a neural stimulus, or a drug or pharmacologically active substance.

As noted above, the method may be performed unobtrusively or without detection, at the instruction of the subject, or with or without the permission or notification of the subject. The article of manufacture 2100 may include one or more non-transitory machine-readable data storage media 2102 that bear one or more instructions 2104 for receiving an input indicative of an instruction from the subject or representative of the subject for information to be measured, receiving an input indicative of authorization from the subject or representative of the subject for information to be measured, and/or receiving an input indicative of informed consent from the subject or representative of the subject for information to be measured, as depicted in FIG. 19.

In some embodiments, the article of manufacture 2100 may include one or more non-transitory machine-readable data storage media 2102 that bear one or more instructions for transmitting at least one of information regarding the subject, information regarding the system used for determining the physiological parameter, or information regarding the physiological parameter to a data processing system, as depicted in FIG. 20 at 2002.

In some embodiments, the article of manufacture 2100 may include one or more non-transitory machine-readable data storage media 2102 that bear one or more instructions for receiving at least one of information regarding the subject, information regarding the system used for determining the physiological parameter, or information regarding the physiological parameter from a data processing system, as depicted in FIG. 20 at 2004.

In some embodiments, the article of manufacture 2100 may include one or more non-transitory machine-readable data storage media 2102 that bear one or more instructions for sharing at least one of information regarding the subject, information regarding the system used for determining the physiological parameter, or information regarding the physiological parameter between two of more data processing systems, as depicted in FIG. 20 at 2006.

In some embodiments, the article of manufacture 2100 may include one or more non-transitory machine-readable data storage 2102 media that bear one or more instructions 2104 for determining the identity of the subject, which may be, for example, instructions for determining the identity of the subject through the use of facial recognition, determining the identity of the subject through the use of retinal recognition, and/or determining the identity of the subject by comparing login information entered by the subject with login information in a registry, as depicted in FIG. 20 at 2008-2014.

Figure 22:
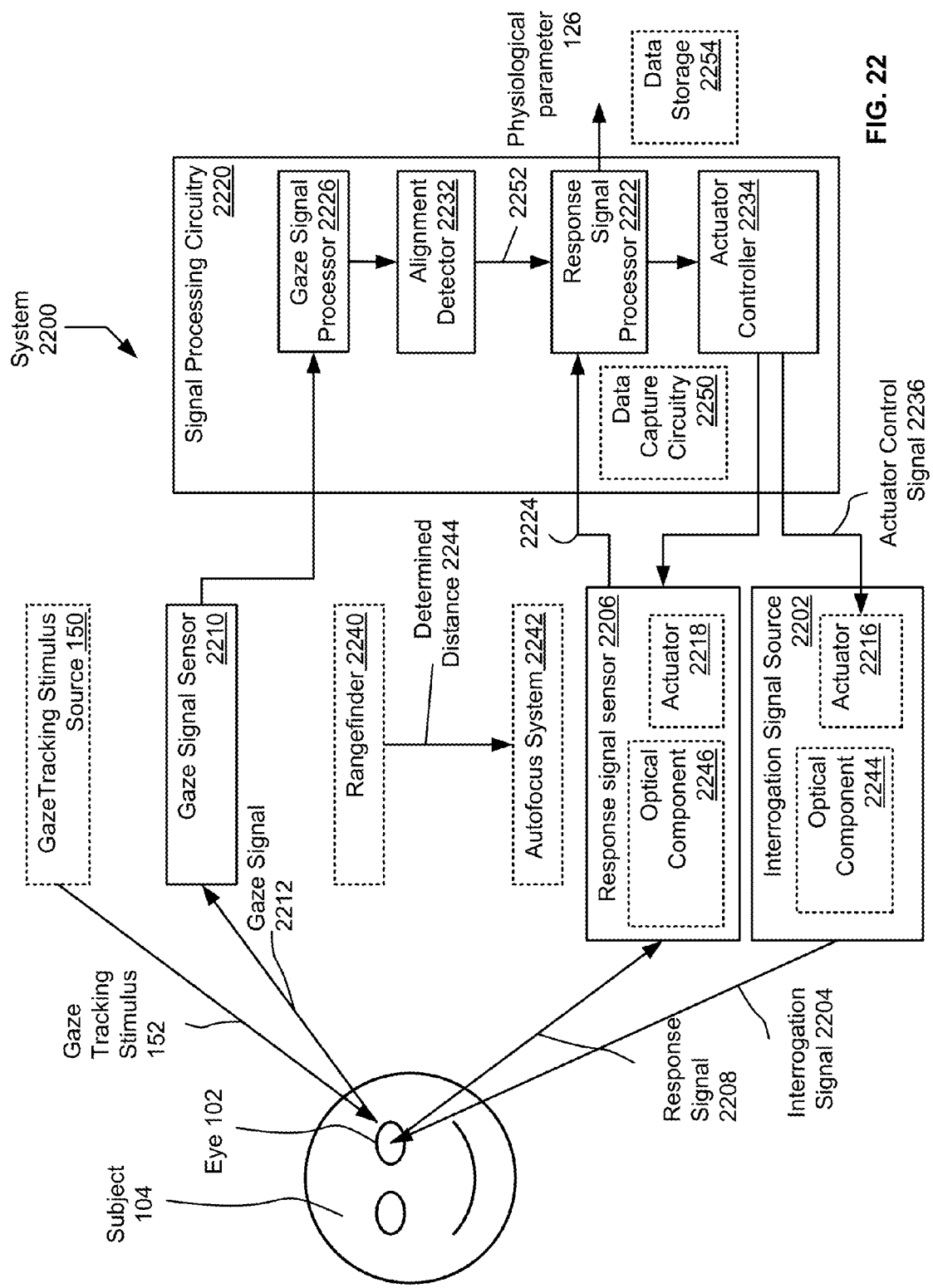
FIG. 22 is a block diagram of a system for sensing information from an eye of a subject.

FIG. 22 depicts a system 2200 for sensing information from an eye 102 of a subject 104, the system including an interrogation signal source 2202 for delivering an interrogation signal 2204 to an eye 102 of a subject 104; a response signal sensor 2206 for sensing a response signal 2208 produced by the eye of the subject responsive to interrogation signal 2204; a gaze signal sensor 2210 adapted for receiving a gaze signal 2212 containing information indicative of a gaze direction of an eye 102 of the subject 104; at least one actuator 2216, 2218 configured to adjust at least one of the interrogation signal source 2202 or the response signal sensor 2206 to bring at least one of the interrogation signal source 2202 or the response signal sensor 2206 into alignment with the eye 102 of the subject 104; and signal processing circuitry 2220 including: a response signal processor 2222 configured to process a response signal 2224 sensed from the eye of the subject to determine a physiological parameter 126 from the response signal, a gaze signal processor 2226 configured to determine the gaze direction of the eye of the subject based upon the gaze signal 2212; an alignment detector 2232 configured to determine whether the eye 102 of the subject 104 is in alignment with respect to at least one of the interrogation signal source 2202 or the response signal sensor 2206 based at least in part upon the gaze direction; and an actuator controller 2234 configured to: determine a target position for at least one of the interrogation signal source and the response signal sensor based at least in part on the gaze direction; and generate an actuator control signal 2236 to drive the at least one actuator 2216, 2218 to adjust at least one of the interrogation signal source 2202 or the response signal sensor 2206 to bring at least one of the interrogation signal source 2202 or the response signal sensor 2206 into alignment with the eye 102 of the subject 104.

In an embodiment, the system includes a rangefinder 2240 adapted for determining the distance between the eye 102 of the subject and the interrogation signal source 2202 and an autofocus system 2242 for focusing the interrogation signal source 2202 responsive to the determined distance 2244. Alternatively, or in addition, rangefinder 2240 may be adapted for determining the distance between the eye of the subject and the response signal sensor 2206; and an autofocus system 2242 may be adapted for focusing the response signal sensor 2206 responsive to the determined distance.

In an embodiment, the at least one actuator 2216 is configured to adjust the interrogation signal source 2202 by adjusting the position of at least a portion of the interrogation signal source. The interrogation signal source can include at least one optical component 2244, and the at least one actuator 2216, can be configured to adjust the interrogation signal source 2202 by adjusting at least one optical component 2244 of the interrogation signal source.

In an embodiment, the at least one actuator 2218 is configured to adjust the response signal sensor 2206 by adjusting the position of at least a portion of the response signal sensor 2206. The response signal sensor 2206 can include at least one optical component 2246, and the at least one actuator 2216 can be configured to adjust the response signal sensor 2206 by adjusting at least one optical component 2246 of the response signal sensor.

Adjusting the position of interrogation signal source 2202 or response signal sensor 2206 can include rotational or translation motion of the light source or sensor, or movement or adjustment of a component that can control the position/focal distance of the light beam being generated or sensed (e.g., a mirror, lens, or reflector). In an embodiment, the least one actuator is configured to scan the at least one of the interrogation signal source 2202 or the response signal sensor 2206 through a region in which the eye of the subject is located such that the at least one of the interrogation signal source and the response signal sensor will be brought into alignment with the eye of the subject at at least one position within the scanned region.

Interrogation signal source 2202 and the response signal sensor 2206 can be co-aligned, or separately aligned and located, as discussed herein above.

The system may also include data capture circuitry 2250 configured to capture a response signal 2224 from the eye of the subject in connection with determination by the signal processing circuitry that the eye of the subject is in alignment with respect to at least one of the interrogation signal source and the response signal sensor, as indicated by signal 2252 from alignment detector 2232. Data capture circuitry 2250 provides for capture (acquisition and/or storage e.g. in data storage 2254) of data obtained while system components are aligned such data may contain information measured from eye 102 of subject 104.

Figure 23:
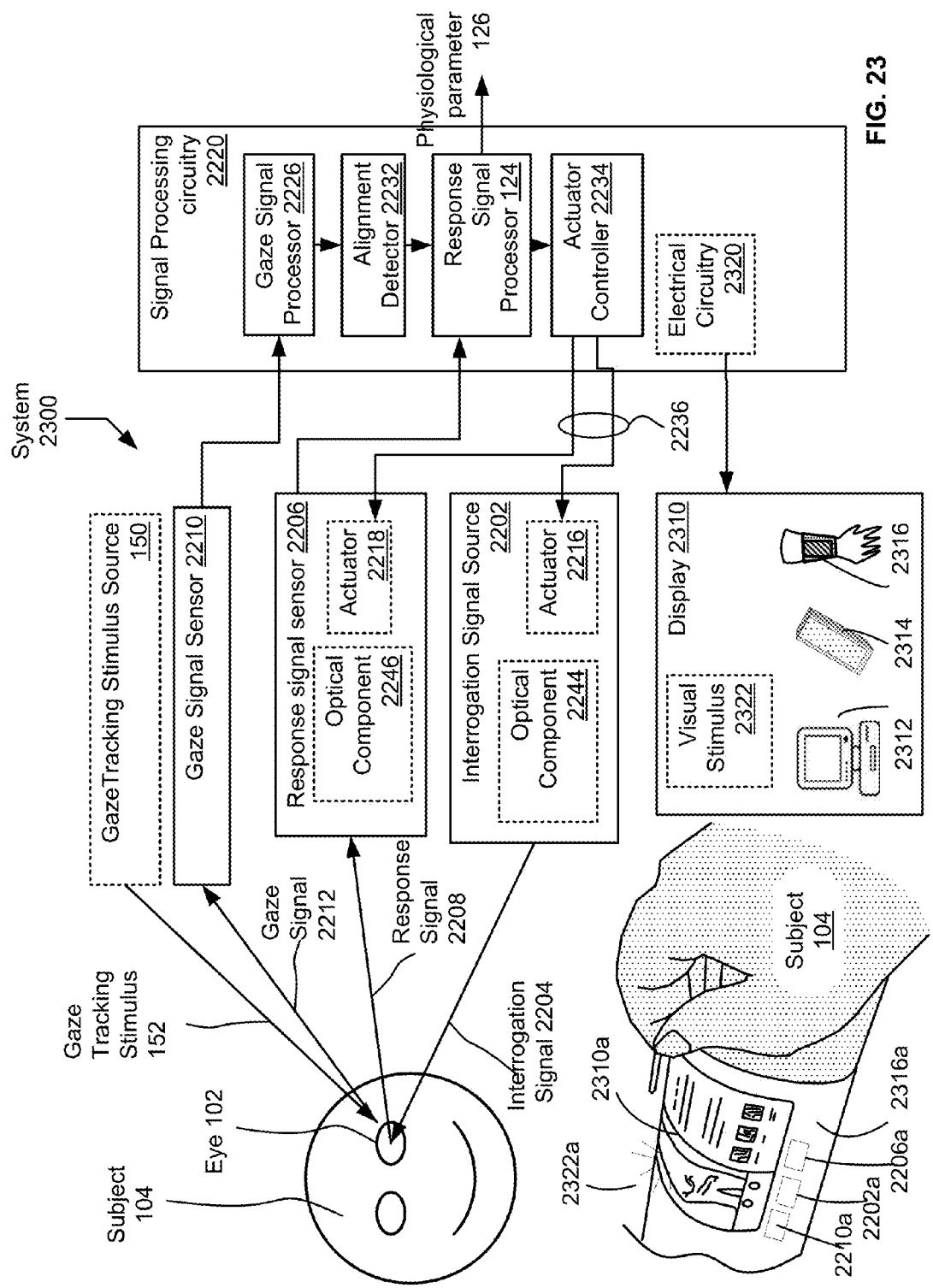
FIG. 23 is a block diagram of a system for sensing information from an eye of a subject.

As shown in FIG. 23, system 2300 may also include a display 2310, which may be, for example, a computer display 2312, a telephone display 2314, or a video monitor, a video game display, a terminal of a data processing device (not shown). The display can be incorporated in a wearable item, which may be, for example, eyewear, headware, jewelry, an article of clothing, a badge, a bandage, an adhesive patch, a wristwatch, a cuff, a sleeve, a wristband 2316 (depicted in FIG. 23), an armband, a helmet, a physiological support such as a cast or brace, or a wearable a positioning structure configured to surround a portion of the subject. The display can be incorporated in an article of furniture, an article of medical equipment, an article of health-care related equipment, an article of exercise equipment, or a vehicle. Examples of such displays are described in greater detail herein above.

The system 2300 can include electrical circuitry 2320 configured to cause a visual stimulus 2322 to be displayed on the display 2310 to attract the gaze of the subject 104. The electrical circuitry may include at least one of hardware, software, or firmware. In an embodiment, the electrical circuitry 2320 is configured to cause the visual stimulus 2322 to be displayed at a location on the display 2310 such that when the gaze of the subject is directed toward the visual stimulus 2322 the eye 102 of the subject 104 will be brought into alignment with respect to the at least one of the interrogation signal source 2202 or the response signal sensor 2206. In various embodiments, the electrical circuitry 2320 is configured to cause a visual stimulus 2322 to be displayed on the display 2310 that includes a different light intensity relative to a visual background, a different optical wavelength relative to a visual background, a different temporal pattern of light intensity or optical wavelength relative to a visual background, or a different spatial pattern of light intensity or optical wavelength relative to a visual background. The electrical circuitry 2320 can be configured to cause a visual stimulus 2322 to be displayed on the display that includes any or all of an image, a moving image, or text. The visual stimulus can include or be displayed in connection with other text and/or graphics displayed on the screen (for example as a button that the subject must select or click, a text box with text to be read by the subject, or a flashing icon or moving image on the screen).

As an example, FIG. 23 illustrates a wristband 2316a on the wrist of a subject 104, including gaze signal sensor 2210a, interrogation signal source 2202a, response signal sensor 2206a and display 2310a showing visual stimulus 2322a. For example, visual stimulus 2322a can be a flashing image on display 2310a on wristband 2316a. Components on wristband 2316a can be microfabricated/MEMS components. Signal processing circuitry associated with armband 2316a (not depicted) may be located on wristband 2316a, or located fully or in part at a remote location, operably linked to components on 2316a via a wireless connection.

EXAMPLE 2

Figure 24:
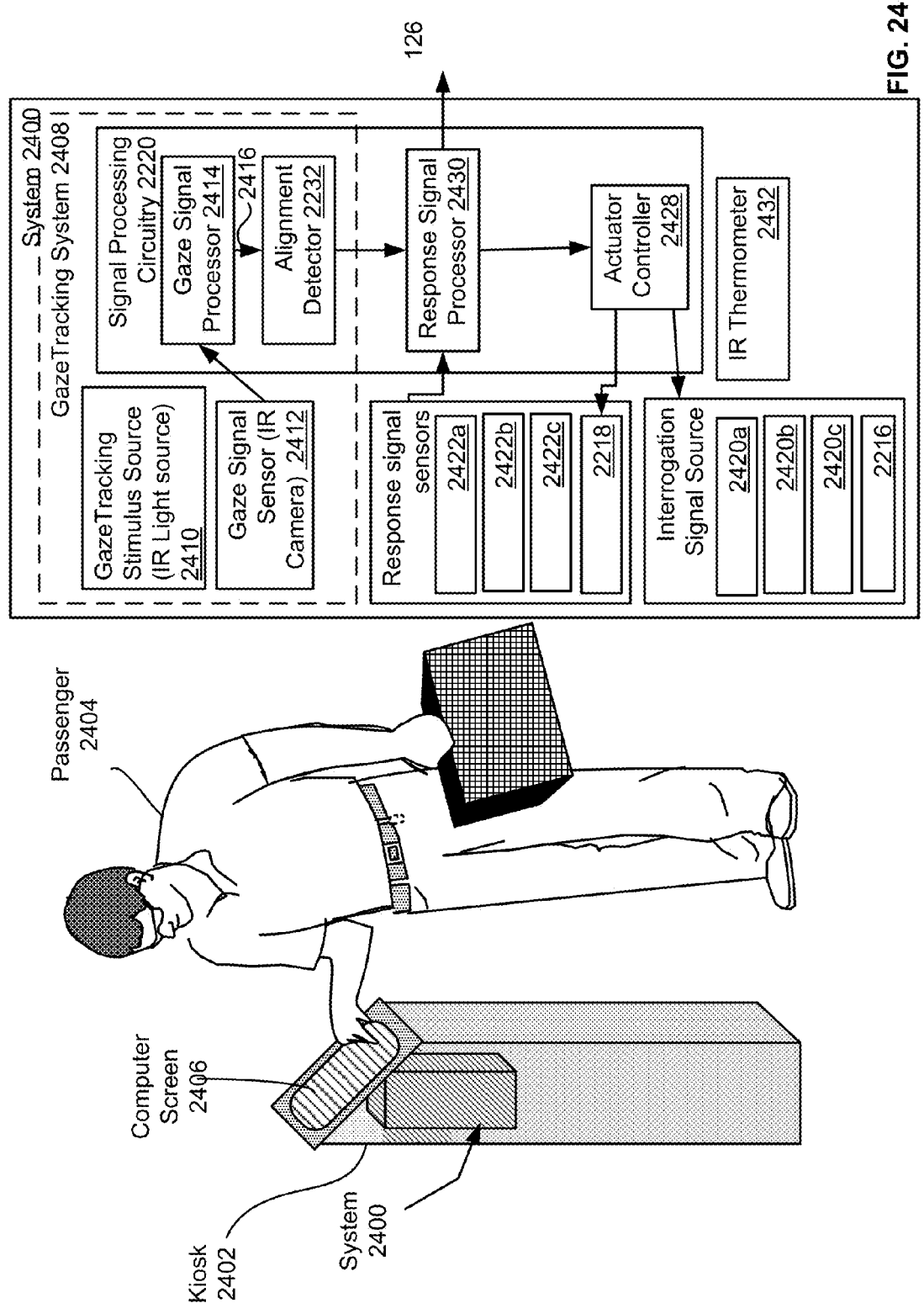
FIG. 24 illustrates an embodiment of a system for sensing information from an eye of a subject at an airline ticket kiosk.

An Unobtrusive Eye Interrogation System to Monitor Passengers Upon Check-in at the Airport FIG. 24 depicts an example of an unobtrusive eye interrogation system 2400 that is used for monitoring passenger 2404 upon check-in at an airport. Eye interrogation system 2400, which collects biometric and physiologic data from passengers, is incorporated in a check-in kiosk 2402 at the airport. The system automatically detects the gave of passenger 2404 and aligns with his eyes at the computer monitor at check-in. The system measures biometric parameters to identify passenger 2404 and physiological parameters to screen for stress, nervousness, anxiety and signs of contagious disease. The eye interrogation system transmits the passenger's biometric and physiological data 126 to computers at the airlines and to airport security. The system alerts airport security and the airlines if the passenger's identification and/or physiological parameters indicate they may be a potential security or health risk.

The eye interrogation system 2400 is constructed in association with the computer screen 2406 at the check-in kiosk 2402. The system 2400 has an active gaze alignment system to align the interrogation system and the passengers' eyes. Gaze tracking system 2408 is used to detect where the passenger's gaze strikes the computer screen. The gaze tracking system is comprised of an IR light source (gaze tracking stimulus source 2410) and an IR camera (gaze signal sensor 2412 which detects the reflection of IR light from the eyes of the passenger. For example, a gaze tracking system for monitoring eye position is available from Seeing Machines Inc., Tucson, Ariz. (see e.g., the Specification Sheet: "faceLAB™ 5 Specifications" which is incorporated herein by reference). Eye position, eye rotation, eye gaze position against screen, pupil diameter and eye vergence distance may be monitored. Eye rotation measurements of up to +/−45 degrees around the y-axis and +/−22 degrees around the x-axis are possible. Typical static accuracy of gaze direction measurement is 0.5-1 degree rotational error. The gaze tracking system includes electric circuitry 2414, including e.g. software and hardware, to analyze the reflected IR waves and to determine the position of the passenger's gaze and the location of the passenger's eyes. Gaze tracking data 2416 is used by alignment detector 2232 and actuator controller 2428 to control actuator (s) 2216 align eye interrogation sources (e.g. 2420a, 2420b, 2420c) and sensors (e.g. 2422a, 2422b, 2422c) with the passenger's eyes. An active alignment system comprised of actuators and controllers moves the sources and sensors into alignment with the passenger's eyes. An actuated optical system to control alignment of light sources or light sensors with a viewer's eyes is described (see e.g., European Patent Application No. EP 2 508 931 A1 by Oellers published on Oct. 10, 2012 which is incorporated herein by reference). Eye location data from the gaze tracking system (see above) is provided to a controller which is programmed to activate linear actuators 2216, 2218 to align the eye interrogation sources 2420a, 2420b, 2420c4 and sensors 2422a, 2422b 2422c with the passenger's eyes. Controllers capable of motion control in six dimensions and linear actuators are available from Newport Corp., Irvine, Calif. (see e.g. the Specification sheet: Picomotor Piezo Linear Actuators which is incorporated herein by reference). Rapid alignment of the eye interrogation system with the passenger's eyes is followed by activation of the interrogation sources 2420, 2420b, 2420c and sensors 2422a, 2422b, 2422c by system 2400.

The eye interrogation system 2400 includes electromagnetic radiation sources and sensors which are contained within the check-in kiosk. A light source 2424a for iris scanning and a camera 2422a to capture iris images is incorporated in the system to identify the passenger checking in. Systems and algorithms to obtain iris images, identify unique signatures and rapidly compare key features of iris images to a large database of iris images are described (see e.g., U.S. Pat. No. 5,572,596 issued to Wildes et al. on Nov. 5, 1996 and U.S. Pat. No. 4,641,349 issued to Flom et al. on Feb. 3, 1987 which are incorporated herein by reference). An iris scanning system which includes a near-infrared (approximately 700-900 nm) illumination source, a 1.3 megapixel camera and algorithms to analyze and compare iris images is available from Bayometric Inc., San Jose, Calif. (see e.g., the Specification Sheet: "Crossmatch Retinal Scan 2 Iris Scanner" which is incorporated herein by reference). Biometric information obtained by the iris scanner is compared to the passenger's ticket, passport and visa information, and discrepancies are transmitted to airport security personnel as well as the airlines.

To detect passengers who may be a health risk, e.g., have a fever associated with an infectious disease, an infrared thermometer 2432 is placed in the eye interrogation system which remotely measures temperature in the eye. Following active alignment of the infrared thermometer with the passenger's eye the thermometer is activated. An infrared thermometer comprised of a detector, collecting optical system (e.g., lens and filter) and signal processing circuitry (in response signal processor 2430) is incorporated in the eye interrogation system. The filter limits the spectrum of infrared radiation detected and the lens' optical characteristics determine the target size within the eye and the allowed distance from the passenger's eye. The detector converts infrared energy into an electrical signal which is amplified and processed by the associated signal processors to calculate temperature of the eye. An infrared thermometer suitable for sensitive temperature measurement (i.e., approximately 0.1 degree Centigrade) that may be targeted to the iris/pupil region or to the sclera is described (see e.g., U.S. Pat. No. 5,115,815 issued to Hansen on May 26, 1992 which is incorporated herein by reference). For example an infrared camera may be used to measure corneal temperature (see e.g., Kessel et al., Investigative Opthalmology and Visual Science 51: 6593-6597, 2010 which is incorporated herein by reference). An infrared camera with a focal plane array detector, thermal sensitivity ≤0.09 degrees C. and an accuracy of 0.1 degrees C. is available from Fluke Corp., Everett, Wash. (see e.g., Fluke_Ti25 Datasheet which is incorporated herein by reference). To summarize, the gaze tracking system (see above) detects the passenger's gaze and eye location which are signaled to actuators which align the infrared detector with the passenger's eye. Next the system controller activates the infrared thermometer and signal processors determine eye temperature. Corneal eye temperatures may be correlated with body temperatures and ambient temperatures (see e.g., Kessel et al., Ibid.). Temperature data are stored and analyzed by a computer associated with the eye interrogation system, and security personnel and the airlines are alerted when temperature in the eye is outside the normal range and may indicate an infectious disease is present.

To identify passengers who may represent other types of risk such as terrorism the eye interrogation system uses a bioanalyte detection system in conjunction with biometric identification, e.g., iris scanning. Unobtrusive, noncontact detection and quantitation of biological, metabolites, and chemicals may be done using a remote spectroscopic device to interrogate the passenger's eye and processors and algorithms to process the spectroscopic signals. For example, a spectroscopic system to obtain Raman spectral data may include a laser source, spatial filters, a beam splitter, notch filters, confocal optics, a CCD detector and a low pass electrical filter (see e.g., U.S. Pat. No. 6,961,599 issued to Lambert et al. on Nov. 1, 2005 which is incorporated herein by reference). The eye interrogation source may be a tunable laser 2420b to provide excitation beams of wavelengths from about 400 nm to 900 nm (e.g., a tunable external cavity diode laser is available from Thorlabs, Newton, N.J.). For example the excitation beam may be at wavelength approximately 785 nm which is barely visible to the passenger and thus elicits Raman spectra unobtrusively A confocal optic system allows one to focus the excitation beam on selected regions of the eye, for example, the aqueous humor in the anterior chamber of the eye, or the blood vessels in the conjunctiva or the retina. A CCD detector 2422b with high quantum efficiency in the 400-1100 nm wavelength range is used to detect Raman spectra (e.g., a silicon CCD linear array (Sony 2048) is available from Avantes, Broomfield, Colo.; see "Table 4 Detector Specifications" in "Sensitivity", Avantes, http://www.avantes.com website, which is incorporated herein by reference).

To identify passengers who are under stress or agitated and who may represent a risk to other passengers, such as that posed by a terrorist, the eye interrogation system may detect "fight or flight hormones". When passenger 2404 views the check-in monitor, the active gaze alignment system aligns and activates the interrogation source, i.e., the tunable laser 2420b, and an excitation beam of approximately 500 nm wavelength is focused on the blood vessels in the conjunctiva of the passenger's eye. Reflected spectra, including any resonant Raman spectra are detected by the CCD array 2422b and transmitted as electronic signals to the signal processor (response signal processor 2430) of the eye interrogation system 2400. Raman spectra which arise from stress hormones are identified by the signal processing software from a database of reference Raman spectra for epinephrine, norepinephrine and hydrocortisone in blood. The concentration of stress hormones may be determined by signal processing algorithms which correlate emission spectra intensity with analyte concentration (see e.g., U.S. Pat. No. 6,961,599, Ibid.). Passengers with elevated concentrations of stress hormones in their blood may also be tested for elevated heart rate, another indication of stress or agitation.

The eye interrogation system may also use pupillometry to detect passengers who are under stress and/or a high cognitive load. Data on pupil diameter, mean pupil diameter change (MPDC), and mean pupil diameter change rate (MPDCR) are collected with the gaze tracking system 2408 described above (see e.g., a gaze tracking system available from Seeing Machines Inc., Tucson, Ariz.; the Specification Sheet: "faceLAB™ 5 Specifications" which is incorporated herein by reference), and parameters determined by signal processing circuitry 2220. Methods and calculations employing remote imaging to measure MPDC and MPDCR and to monitor cognitive load are described (see e.g., Klingner, Dissertation submitted to Stanford University May 2010: Measuring Cognitive Load During Visual Tasks by Combining Pupillometry and Eye Tracking, available at http://purl.stanford.edu/mv271zd7591 and Palinko et al., *Proceedings of the 2010 Symposium on Eye Tracking Research and Applications* pp. 141-144, Austin, Tex. which are incorporated herein by reference). For example, a remote eye tracking system (e.g., Tobii 1750 video eye tracker available from Tobi Technology, Inc., Falls Church, Va.) may be used to measure pupil diameters with an accuracy of 0.34 mm and a precision of 0.12 mm. To measure cognitive load multiple measurements are made in a time scale of fractions of a second and the change in pupil diameter at the initiation of a task is averaged over many repetitions. Mean pupil diameter may vary by approximately 0.1-0.5 mm within about 2 seconds after an increase in cognitive load (see e.g., Klingner, Ibid.). To measure the passenger's cognitive load visual tasks are presented on the video monitor and multiple measurements of pupil diameter are recorded and the MPDC and MPDCR are calculated. The corresponding cognitive load and stress level is computed by comparison to baseline data collected for the passenger and cumulative data for multiple passengers analyzed by the eye interrogation system. The calculated cognitive load is compared to other parameters (e.g., cortisol level, heart rate) and passengers who display abnormal stress parameters are reported to airport security and to airlines personnel.

To monitor the passenger's heart rate and respiration the eye interrogation system is equipped with an interferometry system that detects movement of an individual's chest wall. Construction of an interferometer, data acquisition systems and signal processing algorithms to determine heart rate and respiration are described (see e.g., Mikhelson et al., IEEE Transactions on Biomedical Engineering, 58: 1671-1677, 2011 which is incorporated herein by reference). For example a continuous wave millimeter-wave interferometer is constructed integral to the eye interrogation system. A continuous wave 94-GHz signal is generated by a cavity-tuned Gunn diode oscillator 2420c and transmitted at the computer user with a Gaussian (quasi-optical) antenna with a lens that results in a far-field starting at approximately 0.5 meter and a beam divergence of approximately 1.5 degrees. The gaze tracking system 2408 (see above) is used to infer alignment of the oscillator and antenna on the user's chest and to signal activation of the interferometer. Interferometer components include: a Gunn diode oscillator (94 GHz) a circulator, a Gaussian antenna and beam splitters and mixers. To acquire the reflected wave signals (via the antenna), a 24 bit data acquisition device 2422c (DAQ) (e.g., a PCI-4474 DAQ available from National Instruments, Austin, Tex.; see the Data sheet: "DAQ Device" which is incorporated herein by reference) is used with LabView data acquisition software. The vibration signals may be processed with programs written in MATLAB to derive chest displacements (respiration) and heart beats from the reflected wave signals (see e.g., Mikhelson et al., Ibid.). Heart rate and respiration data are accumulated and analyzed by computer software and authorities and airline personnel may be alerted when, for example, a passenger's heart rate and/or respiration rate exceeds the normal range.

Figure 25:
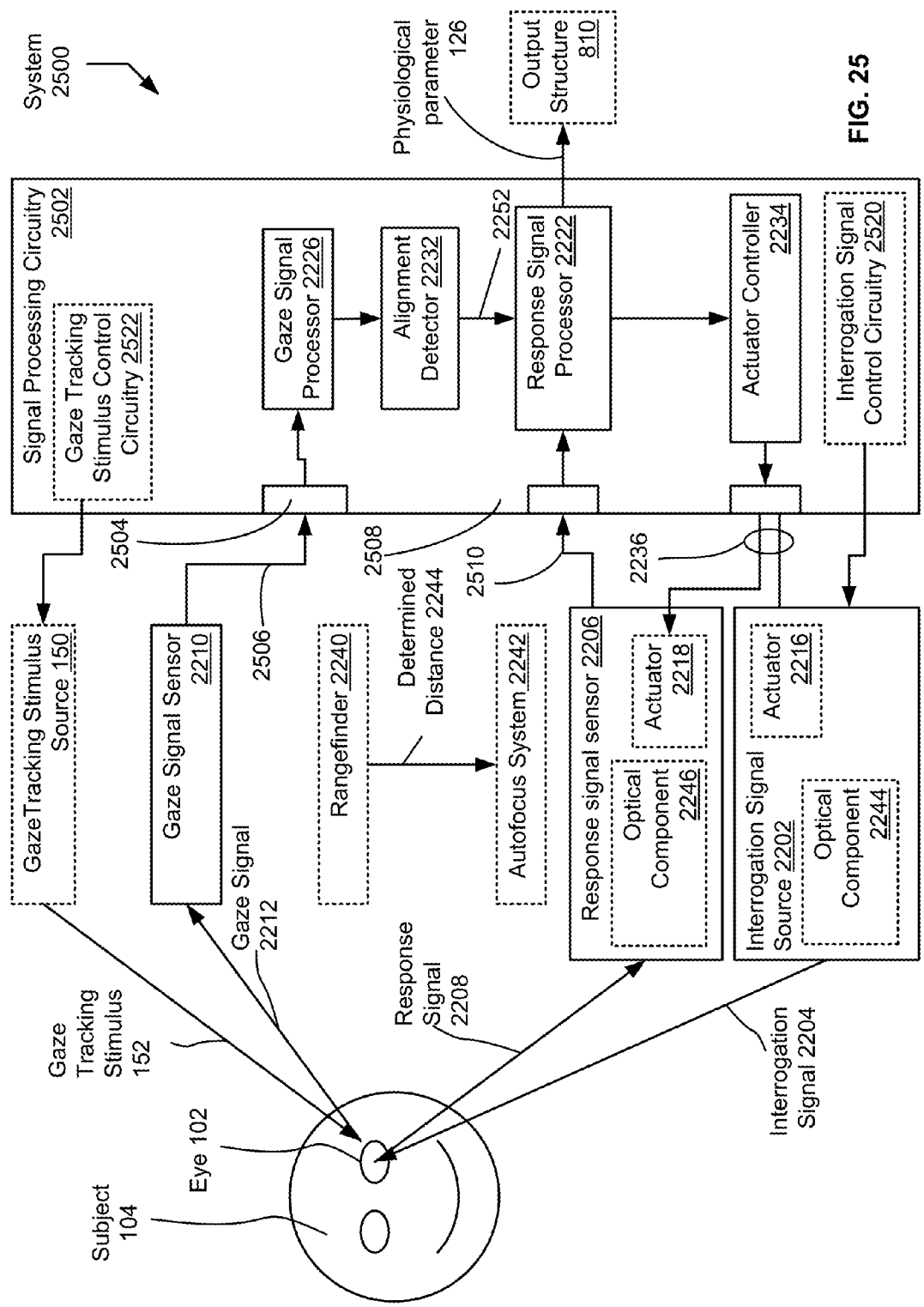
FIG. 25 is a block diagram of a system for controlling the sensing of information from an eye of a subject.

FIG. 25 depicts a system 2500 for controlling the sensing of information from an eye 102 of a subject 104, including signal processing circuitry 2502 including a gaze signal input 2504 adapted to receive a gaze signal 2506 containing information indicative of a gaze direction of the eye of the subject sensed from at least an eye of the subject; a response signal input 2508 adapted to receive a response signal 2510 sensed from the eye of the subject by a response signal sensor 2206 responsive to delivery of an interrogation signal 2204 to the eye of the subject; a response signal processor 2222 configured to process a response signal sensed from the eye of the subject to determine a physiological parameter 216 from the response signal; a gaze signal processor 2226 configured to determine the gaze direction of the eye of the subject based upon the gaze signal; an alignment detector 2232 configured to determine whether the eye of the subject is in alignment with respect to at least one of the interrogation signal source 2202 or the response signal sensor 2206 based at least in part upon the gaze direction; and an actuator controller 2234 configured to: determine a target position for at least one of the interrogation signal source 2202 or the response signal sensor 2206 based at least in part on the gaze direction; and generate an actuator control signal 2236 to drive the at least one actuator 2216, 2218 to adjust at least one of the interrogation signal source 2202 or the response signal sensor 2206 to bring at least one of the interrogation signal source 2202 or the response signal sensor 2206 into alignment with the eye 102 of the subject 104.

The system may also include interrogation signal control circuitry 2520 configured to drive production of the interrogation signal 2204 by an interrogation signal source 2202.

In an embodiment, the system includes gaze tracking stimulus control circuitry 2522 configured to drive production of a gaze tracking stimulus 152 by a gaze tracking stimulus source 150, including, e.g. gaze tracking stimulus control circuitry configured to drive production of a gaze tracking stimulus by a plurality of gaze tracking stimulus sources. In an aspect, the gaze signal input 2504 and the response signal input 2508 are separate inputs. In another, the gaze signal input 2504 and the response signal input 208 are the same input, as discussed generally in connection with, e.g. FIG. 3.

The response signal processor 2222 may be adapted to process a response signal sensed from an interior of the eye of the subject responsive to the interrogation signal, e.g. from a lens, aqueous humor, vitreous humor, or retina of the eye of the subject, as discussed herein above. In an embodiment, the response signal processor is configured to process the response signal to determine a feature of the vasculature of the eye of the subject, and or determine a biometric identification of the subject.

Gaze signal input 2504 may be adapted to receive a signal from a camera, for example. In some embodiments, signal processing circuitry 2502 includes a plurality of gaze signal inputs (only one is depicted) adapted to receive a plurality of gaze signals containing information indicative of a gaze direction of the eye of the subject sensed from at least an eye of the subject.

In an embodiment, response signal processor 2222 is configured to process the response signal by determining a first response signal at a first polarization, determining a second response signal at a second polarization, and comparing the response signal determined at the first polarization to the response signal determined at the second polarization, wherein the first polarization and the second polarization are different, as discussed in connection with FIG. 12.

The response signal processor 2222 can be configured to process the response signal sensed from the eye 102 of the subject 104 by the response signal sensor to determine a measurement of oxygenation, blood glucose, heart rate, glycosylated hemoglobin, temperature, body temperature, blood flow, or a substance in the eye of the subject from the response signal, for example, as discussed herein above.

In an embodiment, interrogation signal control circuitry 2520 can be configured to drive production of a pulsed interrogation signal by the interrogation signal source. Signal processing circuitry may then be configured to gate detection of the response signal relative to the pulsed interrogation signal. Signal processing circuitry can be configured to combine multiple response signals produced by the eye of the subject in response to multiple pulses of the pulsed interrogation signal. For example, signal processing circuitry can be configured to combine the multiple response signals by summing or averaging the multiple response signals, or by determining a moving average or weighted sum of the multiple response signals. Such an approach is illustrated in and described in connection with FIG. 6, for example.

The system can include interrogation signal control circuitry 2520 configured to drive production of a first interrogation signal having a first optical wavelength and production of a second interrogation signal having a second optical wavelength. Signal processing circuitry is configured to process a first response signal sensed from the eye of the subject in response to the first interrogation signal and a second response signal sensed from the eye of the subject in response to the second interrogation signal by comparing the first and second response signals in order to determine the physiological parameter, as described in connection with FIG. 7. Signal processing circuitry 2502 can be configured to drive production of the first interrogation signal simultaneously or sequentially with respect to the second interrogation signal.

In an embodiment, the system includes an output structure 810 adapted to output a signal relating to the determined physiological parameter. Output structure 810 can be, for example, a data transmission structure, a data storage structure, a display, an audio output, or a visual output, as discussed in connection with FIG. 8. The system may include a display adapted to display information relating to the determined physiological parameter.

Figure 26:
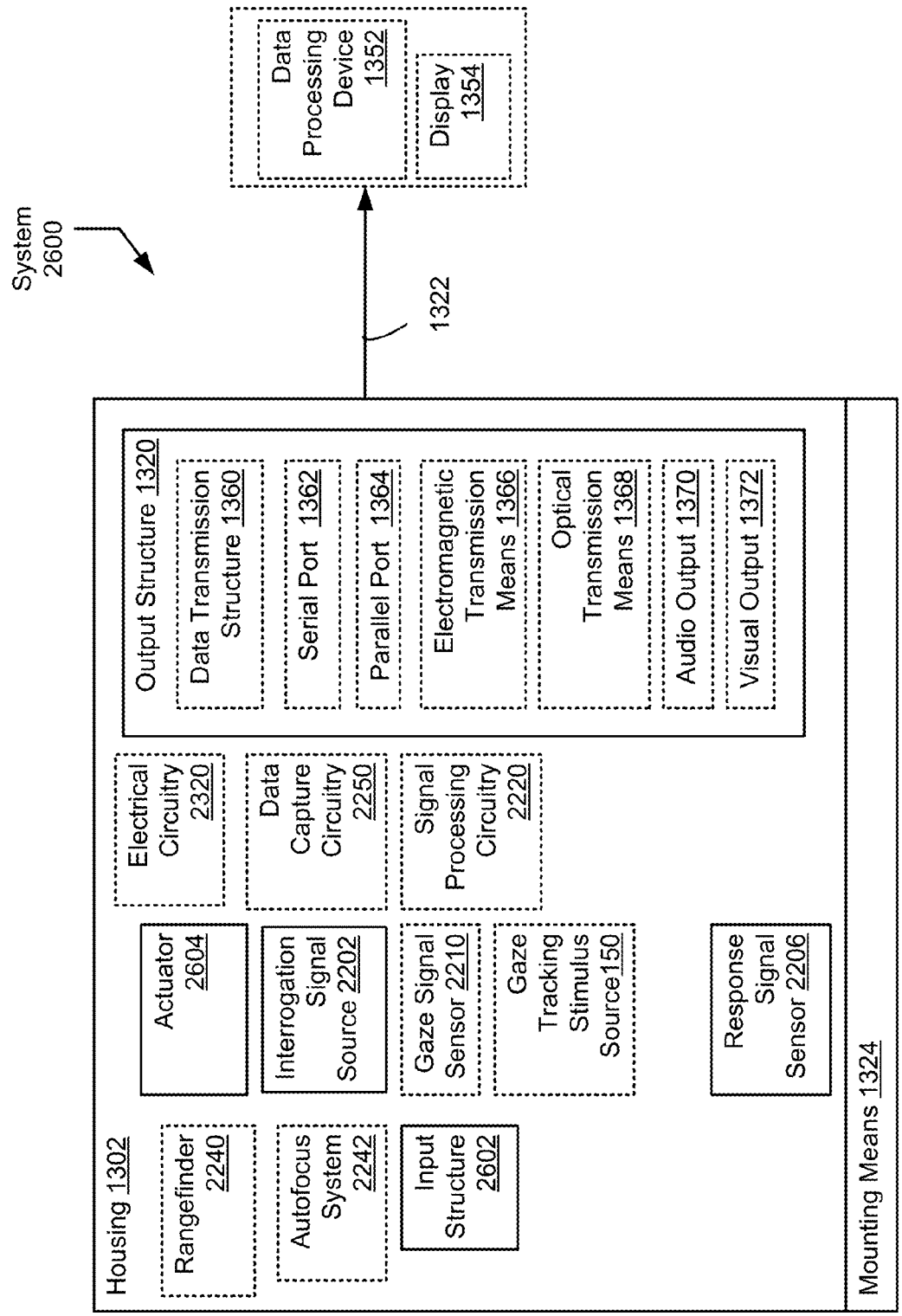
FIG. 26 is a block diagram of a system for sensing of information from an eye of a subject.

FIG. 26 depicts a system 2600 that includes a housing 1302; an interrogation signal source 2202 housed in the housing 1302 and adapted for delivering an interrogation signal to an eye of a subject, the interrogation signal source 2202 including at least one light source and at least one optical system; a response signal sensor 2206 housed within the housing 1302 and adapted for sensing a response signal produced by the eye of the subject responsive to the interrogation signal, the response signal containing information regarding a physiological parameter of the subject; an input structure 2602 adapted for receiving an input signal; at least one actuator 2604 configured to adjust at least one of the interrogation signal source 2202 or the response signal sensor 2206 based at least in part upon the input signal to bring at least one of the interrogation signal source 2292 or the response signal sensor 2206 into alignment with the eye of the subject; an output structure 1320 adapted for transmitting an output signal 1322; and mounting means 1324 adapted for mounting the housing 1302 with respect to a display in such a manner that the interrogation signal source 2202 and response signal sensor 2206 are alignable with the eye of the subject during normal use of the display by the subject. Interrogation signal source 2202 and response signal sensor 2206 are described herein above in connection with FIG. 22. Output structure 1320 is as described in connection with FIG. 13. Various examples of mounting means 1324 are described herein above, in connection with FIG. 13. In an embodiment, system 2600 includes a gaze signal sensor 2210 adapted for receiving a gaze signal containing information indicative of a gaze direction of an eye of the subject.

In an embodiment, system 2600 includes signal processing circuitry 2220 adapted for determining a target position for the at least one of the interrogation signal source and the response signal sensor and for providing an input signal indicative of the target position to the input structure.

System 2600 may also include at least one gaze tracking stimulus source 150, as described herein above, adapted to deliver a gaze tracking stimulus to at least an eye of a subject, wherein the gaze signal is produced in response to the gaze tracking stimulus. For example, gaze tracking stimulus source can include an infra-red source, in which case gaze signal sensor may include an infra-red sensor, or a near infra-red source, which may be used in combination with a gaze signal sensor that includes a near infra-red sensor. Gaze tracking stimulus source may include a plurality of light sources. In an embodiment gaze signal sensor and the response signal sensor are the same sensor. In another embodiment, gaze signal sensor and the response signal sensor are different sensors. In an embodiment, 2600 system includes signal processing circuitry 2220 adapted for determining at least one instruction for controlling actuator 2604.

In one aspect, mounting means 1324 can be adapted for mounting the housing 1302 with respect to the display such that during normal use of the display by the subject, the interrogation signal source 2202 and response signal sensor 2206 are positioned within the visual field of at least one eye of the subject. In one aspect, the mounting means 1324 is adapted for mounting the housing 1302 with respect to the display such that the interrogation signal source 2202 and response signal sensor 2206 are oriented in substantially the same direction as the display surface of the display.

Response signal sensor 2206 may be adapted to sense a response signal from an interior of the eye of the subject responsive to the interrogation signal, e.g., from a lens, an aqueous humor, a vitreous humor, or a retina of the eye of the subject. Gaze signal sensor 2210 may include an infrared camera, or a CCD camera. Gaze signal sensor 2210 can include an optical sensor or an optical sensor array, which may include, for example, a camera or a plurality of gaze signal sensors.

As discussed above, various combinations of interrogation signal source 2202 and response signal sensor 2206 can be selected for detecting particular analytes. For example, in an embodiment, interrogation signal source 2202 includes a broad spectrum light source, and response signal sensor 2206 includes a spectrometer based on a CCD array. In another embodiment, interrogation signal source 2202 includes a near-infrared light source and the response signal sensor 2206 includes a near-infrared camera. In another embodiment, interrogation signal source 2202 includes a tunable laser source and wherein the response signal sensor 2206 includes a Raman spectrometer based on a CCD camera. Other combinations include an interrogation signal source 2202 that includes a mid-infrared light source and response signal sensor 2206 that includes a mid-infrared detector; and an interrogation signal source 2202 that includes a tunable laser source and response signal sensor 2206 that includes a broad spectrum pyroelectric detector.

In an embodiment, interrogation signal source 2202 is adapted to produce light having a first polarization, wherein the response signal sensor 2206 is adapted to detect light having a second polarization, and wherein the first polarization and the second polarization are the same. In an embodiment, the interrogation signal source 2202 is adapted to produce light having a first polarization, wherein the response signal sensor 2206 is adapted to detect light having a second polarization, and wherein the first polarization and the second polarization are different.

The response signal may be indicative of a feature of the vasculature of the eye of the subject or a biometric identification of the subject. The physiological parameter can be, for example, a measurement of oxygenation, blood glucose, heart rate, or glycosylated hemoglobin. The physiological parameter can be a temperature, e.g. a body temperature, a measurement of blood flow, or a measurement of a substance in the eye of the subject.

In one aspect, the interrogation signal source 2202 is adapted to deliver a pulsed interrogation signal, as discussed herein above. In connection therewith, the response signal sensor 2206 can be configured to gate detection of the response signal relative to the pulsed interrogation signal.

In an embodiment, system 2600 includes signal processing circuitry 2220 adapted to process the response signal. For example, the interrogation signal source 2202 may be adapted to deliver a pulsed interrogation signal, and the signal processing circuitry 2229 may be configured to gate detection of the response signal relative to the pulsed interrogation signal. In one aspect, signal processing circuitry 2220 is configured to combine multiple response signals produced by the eye of the subject in response to multiple pulses of the pulsed interrogation signal. Multiple response signals can be combined, e.g., by summing or averaging the multiple response signals, or by determining a moving average or weighted sum of the multiple response signals.

In one aspect the interrogation signal source 2202 is adapted to deliver an interrogation signal containing multiple wavelengths of light. System 2600 can include at least a first response signal sensor configured to sense a first response signal produced by the eye of the subject responsive to a first wavelength component of the interrogation signal, and a second response signal sensor configured to sense a second response signal produced by the eye of the subject responsive to a second wavelength component of the interrogation signal, as described herein above, e.g. in connection with FIG. 7.

In an aspect, system 2600 includes at least a first interrogation signal source 2202 configured to deliver a first interrogation signal having a first optical wavelength and at least a second interrogation signal source (not shown) configured to deliver a second interrogation signal having a second optical wavelength, as discussed in connection with FIG. 7. Signal processing circuitry 2220 can be configured to process a first response signal sensed from the eye of the subject in response to the first interrogation signal and a second response signal sensed from the eye of the subject in response to the second interrogation signal by comparing the first and second response signals to determine the physiological parameter. System 2600 can be configured to deliver the first interrogation signal simultaneously with respect to the second interrogation signal, or sequentially with respect to the second interrogation signal.

In some embodiments, interrogation signal source and the response signal sensor are co-aligned. In other embodiments, interrogation signal source and the response signal sensor can be separately aligned and located.

Output structure 1320 can include one or more of various structures, e.g. a data transmission structure, serial port, parallel port, electromagnetic transmission means, optical transmission means, audio output, or visual output. Output structure 1320 can be adapted to transmit an output signal to the display (e.g. display 1354), or to a data processing device 1352, for example. In an embodiment, the display is controlled by the data processing device 1352. Display 1354 can be configured to display information relating to the determined physiological parameter. Display 1354 can be, for example, a video monitor, computer display, video game display, telephone display, terminal of a data processing device, or other display as known to those having skill in the relevant art. The display can be incorporated in a wearable item (e.g., as described herein above), an article of furniture, an article of medical or health-care related equipment, an article of exercise equipment, or a vehicle. Examples of such displays are described in greater detail herein above.

In an embodiment, system 2600 also includes a rangefinder 2240 adapted for determining the distance between the eye of the subject and the interrogation signal source; and an autofocus system 2242 for focusing the interrogation signal source responsive to the determined distance. In an embodiment, system 2600 includes a rangefinder 2240 adapted for determining the distance between the eye of the subject and the response signal sensor; and an autofocus system 2242 for focusing the response signal sensor responsive to the determined distance. Rangefinder 2240 and autofocus system 2242 are discussed in greater detail in connection with FIG. 22.

In one aspect, actuator 2604 is configured to adjust the interrogation signal source 2202 by adjusting the position of at least a portion of the interrogation signal source. Interrogation signal source can at least one optical component, and the at least one actuator can be configured to adjust the interrogation signal source by adjusting at least one optical component of the interrogation signal source.

In one aspect, actuator 2604 can be configured to adjust the response signal sensor 2206 by adjusting the position of at least a portion of the response signal sensor. Response signal sensor 2206 can include at least one optical component, and the at least one actuator 2604 can be configured to adjust the response signal sensor by adjusting at least one optical component of the response signal sensor. The interrogation signal source 2202 and the response signal sensor 2206 can be co-aligned, or alternatively, the interrogation signal source and the response signal sensor can be separately aligned and located.

In an embodiment, the at least one actuator 2604 is configured to scan the at least one of the interrogation signal source 2202 or the response signal sensor 2206 through a region in which the eye of the subject is located such that the least one of the interrogation signal source and the response signal sensor will be brought into alignment with the eye of the subject at at least one position within the scanned region.

System 2600 can include data capture circuitry 2250 configured to capture a response signal from the eye of the subject in connection with determination by the signal processing circuitry that the eye of the subject is in alignment with respect to at least one of the interrogation signal source and the response signal sensor.

System 2600 may also include electrical circuitry 2320 configured to cause a visual stimulus to be displayed on the display to attract the gaze of the subject. The electrical circuitry 2320 can include at least one of hardware, software, or firmware, and may be configured to cause the visual stimulus to be displayed at a location on the display such that when the gaze of the subject is directed toward the visual stimulus the eye of the subject will be brought into alignment with respect to the at least one of the interrogation signal source and the response signal sensor. Electrical circuitry 2320 can be configured to cause a visual stimulus to be displayed on the display that differs from a visual background. For example, electrical circuitry can be configured to cause a visual stimulus to be displayed on the display that includes a different light intensity, different optical wavelength, different temporal pattern of light intensity, different temporal pattern of optical wavelength, different spatial pattern of light intensity, or different spatial pattern of optical wavelength relative to a visual background. Electrical circuitry 2320 can be configured to cause a visual stimulus to be displayed on the display that includes an image, a moving image, or text.

Figure 27:
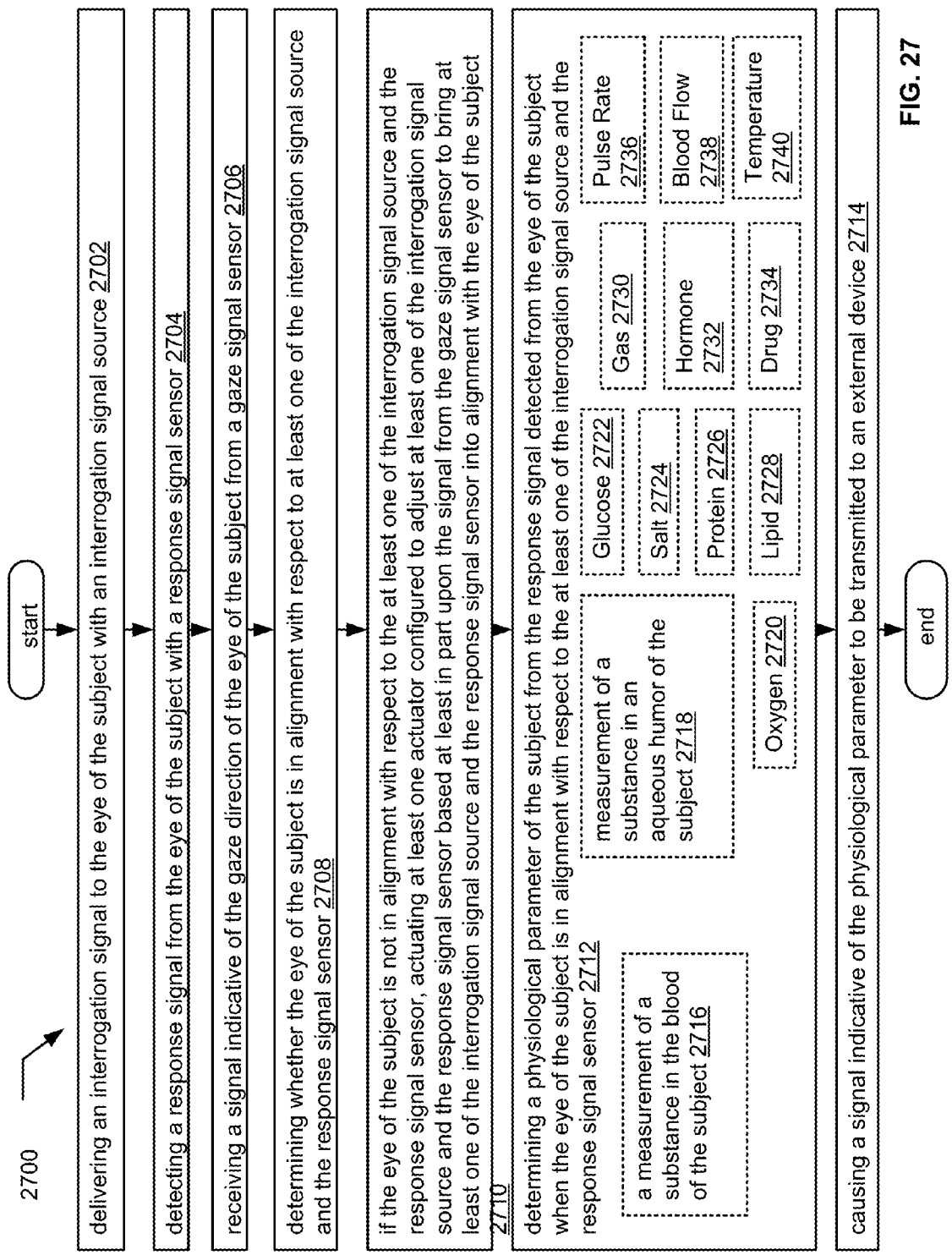
FIG. 27 is a flow diagram of a method of measuring information from an eye of a subject.

FIG. 27 is a flow diagram of a method 2700 of measuring information from an eye of a subject, including; delivering an interrogation signal to the eye of the subject with an interrogation signal source 2702; detecting a response signal from the eye of the subject with a response signal sensor 2704; receiving a signal indicative of the gaze direction of the eye of the subject from a gaze signal sensor 2706; determining whether the eye of the subject is in alignment with respect to at least one of the interrogation signal source and the response signal sensor 2708; if the eye of the subject is not in alignment with respect to the at least one of the interrogation signal source and the response signal sensor, actuating at least one actuator configured to adjust at least one of the interrogation signal source and the response signal sensor based at least in part upon the signal from the gaze signal sensor to bring at least one of the interrogation signal source and the response signal sensor into alignment with the eye of the subject 2710; determining a physiological parameter of the subject from the response signal detected from the eye of the subject when the eye of the subject is in alignment with respect to the at least one of the interrogation signal source and the response signal sensor 2712; and causing a signal indicative of the physiological parameter to be transmitted to an external device 2714.

As discussed elsewhere herein, various physiological parameters can be measured. In some method embodiments, the physiological parameter is a measurement of a substance in the blood of the subject, as indicated at 2716, and in some embodiments, the physiological parameter is a measurement of a substance in an aqueous humor of the subject, as indicated at 2718. The physiological parameter can be a measurement of oxygen 2720, glucose 2722, a salt 2724, a protein 2726, a lipid 2728, a gas 2730 (e.g. oxygen), a hormone 2732, a drug 2734. The physiological parameter can be a pulse rate 2736, a blood flow 2738, or a temperature 2740.

Figure 28:
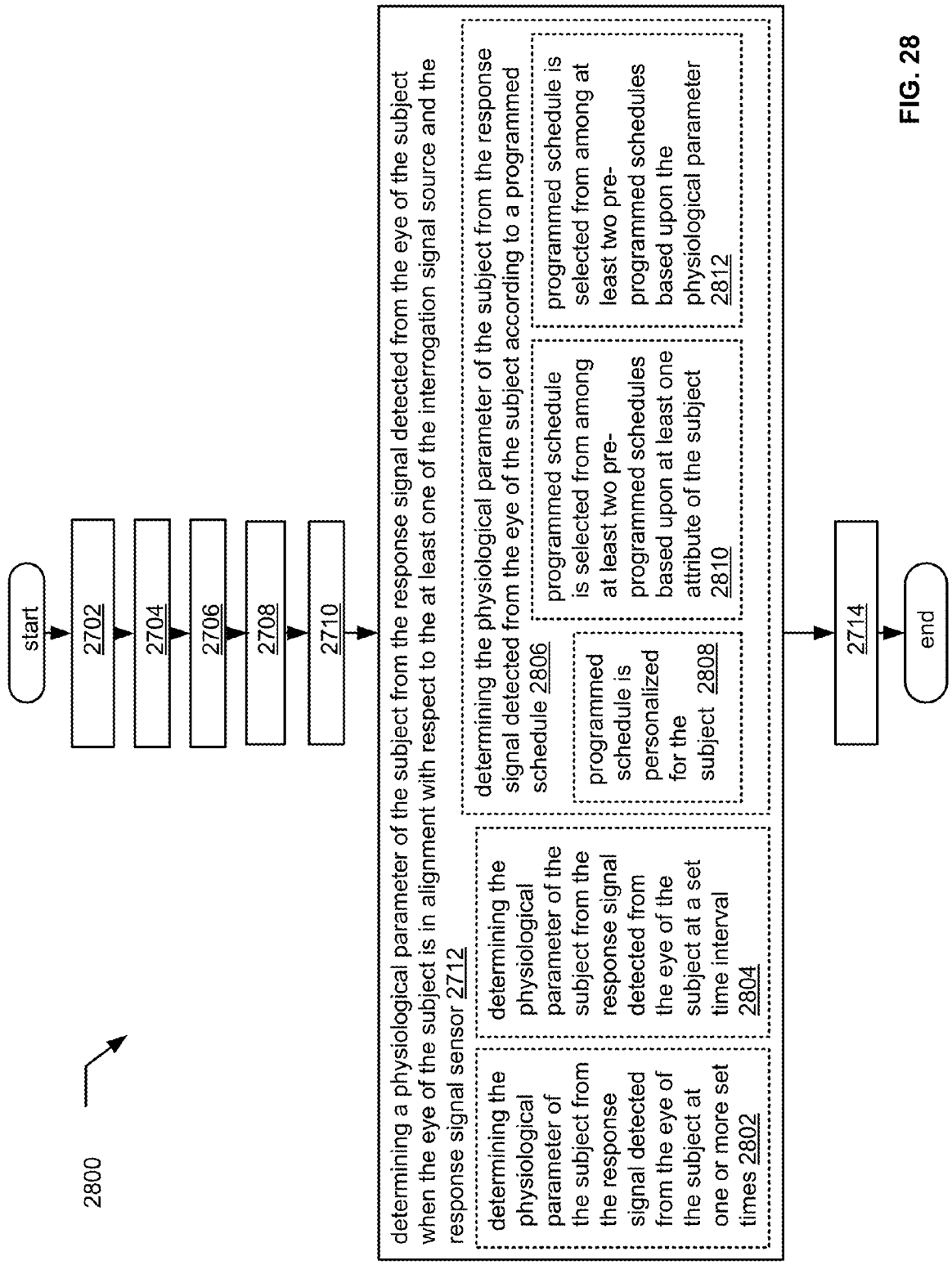
FIG. 28 is a flow diagram of a method of measuring information from an eye of a subject.

As shown in FIG. 28, a method 2800 is an expansion of the method shown in FIG. 27, which includes include determining the physiological parameter of the subject from the response signal detected from the eye of the subject at one or more set times 2802, determining the physiological parameter of the subject from the response signal detected from the eye of the subject at a set time interval 2804, or determining the physiological parameter of the subject from the response signal detected from the eye of the subject according to a programmed schedule 2806. For example, the programmed schedule can be personalized for the subject 2808, selected from among at least two pre-programmed schedules based upon at least one attribute of the subject 2810, or selected from among at least two pre-programmed schedules based upon the physiological parameter 2812.

Figure 29:
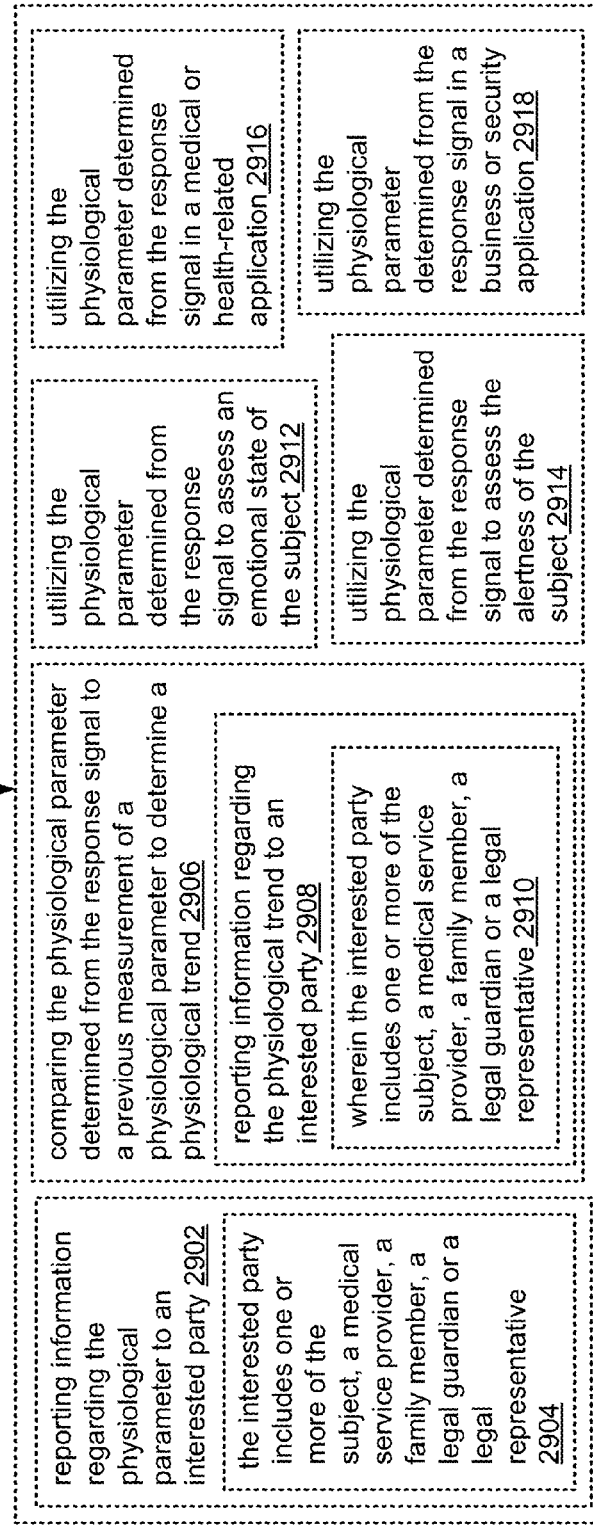
FIG. 29 is a flow diagram of a method of measuring information from an eye of a subject.

A shown in FIG. 29, a method 2900 also includes reporting information regarding the physiological parameter to an interested party 2902. For example, the interested party may include one or more of the subject, a medical service provider, a family member, a legal guardian or a legal representative 2904. Method 2900 may include comparing the physiological parameter determined from the response signal to a previous measurement of the physiological parameter to determine a physiological trend 2906, and reporting information regarding the physiological trend to an interested party 2908, e.g. one or more of the subject, a medical service provider, a family member, a legal guardian or a legal representative 2910. In an aspect, method 2900 may include utilizing the physiological parameter determined from the response signal to assess various states of the subject, e.g. an emotional state of the subject 2912, or alertness of the subject 2914. The physiological parameter determined from the response signal can be used in a medical or health-related application 2916, or in a business or security application 2918.

Figure 30:
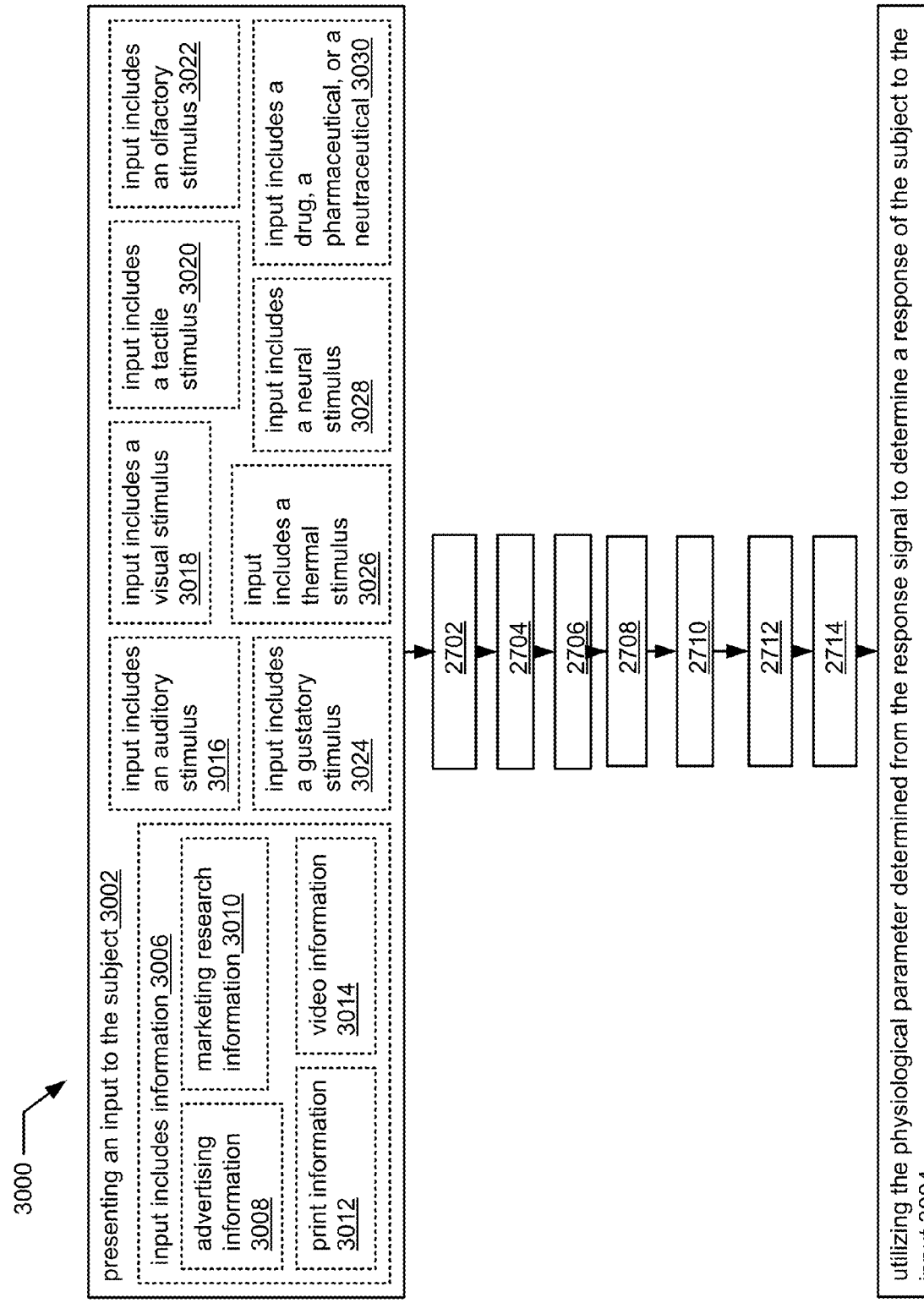
FIG. 30 is a flow diagram of a method of measuring information from an eye of a subject.

FIG. 30 depicts a method 3000 which includes steps 2702-2714 as depicted in FIG. 27. Method 3000 also includes presenting an input to the subject 3002 and utilizing the physiological parameter determined from the response signal to determine a response of the subject to the input 3004. The input may include, for example, information 3006 (e.g. advertising information 3008, marketing research information 3010, print information 3012, or video information 3014), an auditory stimulus 3016, a visual stimulus 3018, a tactile stimulus 3020, an olfactory stimulus 3022, a gustatory stimulus 3024, a thermal stimulus 3026, a neural stimulus 3028, or a drug, a pharmaceutical, a nutraceutical, or a nutrient 3030.

FIG. 31 depicts a method 3100 which includes steps 2702-2714 as described in connection with FIG. 27. In addition method 3100 includes delivering an interrogation signal to the eye of the subject with an interrogation signal source and detecting a response signal from the eye of the subject with a response signal sensor can be performed unobtrusively, as indicated at 3102, or, in some applications, without detection by the subject, as indicated at 3104. As discussed herein above, the method may include receiving an input indicative of an instruction from the subject or representative of the subject for information to be measured 3106, receiving an input indicative of authorization from the subject or representative of the subject for information to be measured 3108, or receiving an input indicative of informed consent from the subject or representative of the subject for information to be measured 3110.

In an aspect, a method 3200 depicted in FIG. 32 includes steps 2702-2714 as shown in FIG. 27, and also includes transmitting at least one of information regarding the subject, information regarding the system used for determining the physiological parameter, or information regarding the physiological parameter to a data processing system 3202. In an aspect, a method includes receiving at least one of information regarding the subject, information regarding the system used for determining the physiological parameter, or information regarding the physiological parameter from a data processing system 3204. A method may also include sharing at least one of information regarding the subject, information regarding the system used for determining the physiological parameter, or information regarding the physiological parameter between two or more data processing systems 3206.

In an aspect, the method includes determining the identity of the subject 3208, e.g. through the use of facial recognition 3210 or retinal recognition 3212, or by comparing login information entered by the subject with login information in a registry 3214. As discussed herein above in connection with FIG. 20, in an aspect, delivering the interrogation signal to the eye of the subject with the interrogation signal source can be done only when the identity of the subject meets a selection criterion, e.g., matching an identity of an approved subject.

FIG. 33 depicts an article of manufacture 3300 as generally described in connection with FIG. 21, the article of manufacture including one or more non-transitory machine-readable data storage media 3302 bearing one or more instructions 3304 for carrying out a method as shown in FIG. 27, including delivering an interrogation signal to the eye of the subject with an interrogation signal source; detecting a response signal from the eye of the subject with a response signal sensor; receiving a signal indicative of the gaze direction of the eye of the subject from a gaze signal sensor; determining whether the eye of the subject is in alignment with respect to at least one of the interrogation signal source and the response signal sensor; if the eye of the subject is not in alignment with respect to the at least one of the interrogation signal source and the response signal sensor, actuating at least one actuator configured to adjust at least one of the interrogation signal source and the response signal sensor based at least in part upon the signal from the gaze signal sensor to bring at least one of the interrogation signal source and the response signal sensor into alignment with the eye of the subject; determining a physiological parameter of the subject from the response signal detected from the eye of the subject when the eye of the subject is in alignment with respect to the at least one of the interrogation signal source and the response signal sensor; and causing a signal indicative of the physiological parameter to be transmitted to an external device, as shown in FIG. 27. As discussed above, the physiological parameter can be a measurement of a substance in the blood of the subject (e.g., oxygen, glucose, a salt, a protein, or a lipid), a measurement of a substance in an aqueous humor of the subject (e.g., oxygen, glucose, a salt, a protein, or a lipid, a hormone, a drug), or pulse rate.), or other parameters as discussed elsewhere herein.

The data storage media 3302 can bear one or more instructions 3304 for performing a method as shown in FIG. 28, including determining the physiological parameter of the subject from the response signal detected from the eye of the subject at one or more set times, determining the physiological parameter of the subject from the response signal detected from the eye of the subject at a set time interval, or determining the physiological parameter of the subject from the response signal detected from the eye of the subject according to a programmed schedule. The data storage media can bear one or more instructions for personalizing the programmed schedule for the subject, for example by selecting the programmed schedule from among at least two pre-programmed schedules based upon at least one attribute of the subject, or selecting the programmed schedule from among at least two pre-programmed schedules based upon the physiological parameter.

In an embodiment, the data storage media 3302 can bear one or more instructions for reporting information regarding the physiological parameter to an interested party, for example, one or more of the subject, a medical service provider, a family member, a legal guardian or a legal representative. In an embodiment, the data storage media can bear one or more instructions for comparing the physiological parameter determined from the response signal to a previous measurement of the physiological parameter to determine a physiological trend. In addition, the data storage media can bear one or more instructions for reporting information regarding the physiological trend to an interested party, for example one or more of the subject, a medical service provider, a family member, a legal guardian or a legal representative.

The data storage media 3302 can bear instructions for utilizing the physiological parameter determined from the response signal to assess an emotional state of the subject, or assess the alertness of the subject. In an embodiment, the data storage media can bear one or more instructions for utilizing the physiological parameter determined from the response signal in a medical or health-related application. Alternatively, or in addition, the data storage media can bear one or more instructions for utilizing the physiological parameter determined from the response signal in a business or security application.

The data storage media 3302 can bear one or more instructions for performing a method as shown in FIG. 30, including one or more instructions for presenting an input to the subject; and utilizing the physiological parameter determined from the response signal to determine a response of the subject to the input. For example, the input can include information (e.g., advertising information, marketing research information, print information, or video information), an auditory stimulus, a visual stimulus, a tactile stimulus, an olfactory stimulus, a gustatory stimulus, a thermal stimulus, a neural stimulus, a drug, a pharmaceutical, a nutraceutical, or a nutrient.

The data storage media 3302 can bear one or more instructions for performing a method as shown in FIG. 31, including one more instructions for delivering an interrogation signal to the eye of the subject with an interrogation signal source and detecting a response signal from the eye of the subject with a response signal sensor unobtrusively, or one or more instructions for: delivering an interrogation signal to the eye of the subject with an interrogation signal source and detecting a response signal from the eye of the subject with a response signal sensor are performed without detection by the subject.

In addition, data storage media 3302 can bear instructions for receiving an input indicative of an instruction from the subject or representative of the subject for information to be measured, receiving an input indicative of authorization from the subject or representative of the subject for information to be measured, or receiving an input indicative of informed consent from the subject or representative of the subject for information to be measured, as discussed above.

In an embodiment, the data storage media 3302 can bear one or more instructions for performing a method as shown in FIG. 32, including transmitting at least one of information regarding the subject, information regarding the system used for determining the physiological parameter, or information regarding the physiological parameter to a data processing system. The data storage media can bear one or more instructions for receiving at least one of information regarding the subject, information regarding the system used for determining the physiological parameter, or information regarding the physiological parameter from a data processing system. In an embodiment, the data storage media 3302 bear one or more instructions for sharing at least one of information regarding the subject, information regarding the system used for determining the physiological parameter, or information regarding the physiological parameter between two of more data processing systems. In an embodiment, data storage media 3302 bear one or more instructions for determining the identity of the subject, e.g. through the use of facial recognition or retinal recognition, or by comparing login information entered by the subject with login information in a registry.

Figure 34:
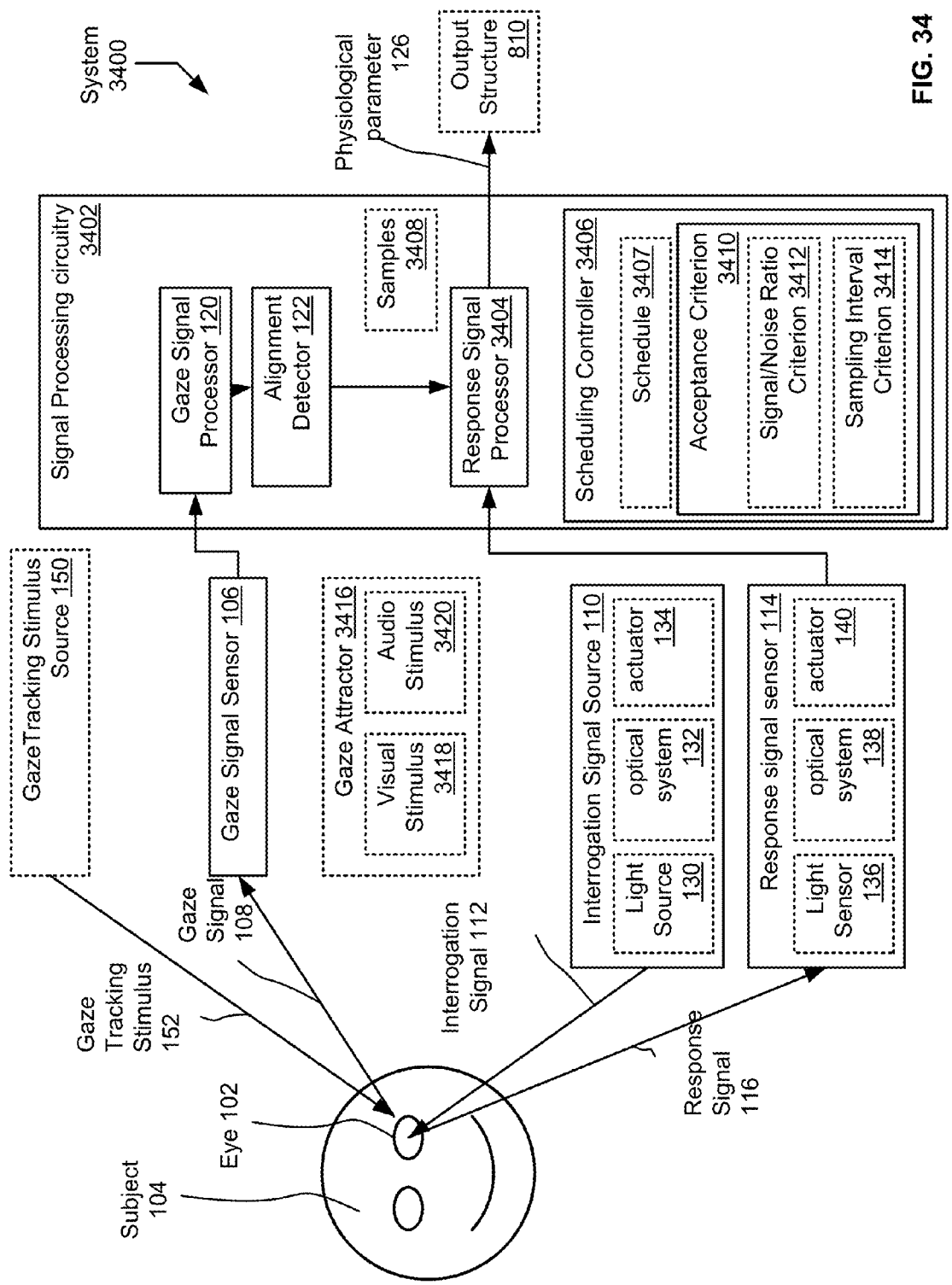
FIG. 34 is a block diagram of a system for sensing information from an eye of a subject.

FIG. 34 is a schematic diagram of a system 3400 for sensing information from an eye 102 of a subject 104, including an interrogation signal source 110 for delivering an interrogation signal 112 to an eye 102 of a subject 104; a response signal sensor 114 for sensing a response signal 116 produced by the eye 102 of the subject 104 responsive to the interrogation signal 112; and signal processing circuitry 3402 including: a response signal processor 3404 configured to process a response signal sensed 116 from the eye 102 of the subject 104 to determine a physiological parameter 126 from the response signal 116; and a scheduling controller 3406 configured to direct collection of samples of the physiological parameter according to a schedule 3407.

In one aspect, scheduling controller 3406 can be configured to direct collection of a predetermined number of samples 3408 of the physiological parameter during a sampling period. In one aspect, scheduling controller 3406 can be configured to direct collection of samples with at least a minimum sampling interval between samples. Scheduling controller 3406 can be configured to modify the procedure for collecting a sample of the physiological parameter if a predetermined number of samples meeting an acceptance criterion 3410 has not been collected within a predetermined portion of the sampling period. For example, modifying the procedure for collecting a sample of the physiological parameter can include modifying the acceptance criterion 3410, which may be, for example, a signal-to-noise ratio criterion 3412 or a sampling interval criterion 3414. For example, if not enough samples meeting an acceptance signal-to-noise ratio acceptance criterion have been met, a lower signal-to-noise ratio criterion ratio may be set, so that a larger number of samples meet the acceptance criterion. It will be appreciated that in some embodiments of methods described herein, sampling of data is performed continuously or substantially continuously, while collection of samples includes retaining a subset of the sampled data, based upon a schedule and according to other acceptance criterion, as discussed herein above, for further analysis. For example, sampled data may be retained temporarily in a buffer or other location, whereas collected samples may be stored in a separate memory location or transmitted to a remote location for longer term storage and/or analysis. In other embodiments, data sampling is performed only when certain criterion are met (e.g. alignment of the eye of the subjects with interrogation signal source and/or response signal sensor, schedule criterion, acceptance criterion, etc.) and collecting samples is consequently substantially the same as sampling data.

As shown in FIG. 34, system 3400 can include a gaze signal sensor 106 adapted for receiving a gaze signal 108 containing information indicative of a gaze direction of an eye 102 of the subject 104; and wherein the signal processing circuitry 3402 includes: a gaze signal processor 120 configured to determine the gaze direction of the eye of the subject based upon the gaze signal; and an alignment detector 122 configured to determine whether the eye 102 of the subject 104 is in alignment with respect to at least one of the interrogation signal source 110 or the response signal sensor 114; wherein the response signal processor is configured to process the response signal 116 sensed from the eye 102 of the subject 104 when the eye of the subject is in alignment with respect to the at least one of the interrogation signal source and the response signal sensor to determine the physiological parameter 126 from the response signal.

Signal processing circuitry 3402 may be configured to cause the alignment of the eye 102 of the subject 104 with respect to the at least one of the interrogation signal source and the response signal sensor if a predetermined number of samples meeting an acceptance criterion 3410 has not been collected within a predetermined portion of the sampling period. Alignment of eye 102 with interrogation signal source 110 and/or response signal sensor 114 can be achieved by causing the subject 104 to direct his or her gaze toward interrogation signal source 110 and/or response signal sensor 114, and/or by directing interrogation signal source 110 and/or response signal sensor 114 toward eye 102.

System 3400 can include at least one actuator (134 or 140) configured to move at least one of the interrogation signal source 110 or the response signal sensor 114, respectively; wherein the signal processing circuitry 3402 is configured to cause the alignment of the eye of the subject with respect to the at least one of the interrogation signal source 110 or the response signal sensor 114 by directing the actuator (134 or 140) to move at least one of the interrogation signal source 110 or the response signal sensor 114 into alignment with the eye 102 of the subject 104.

In an embodiment, system 3400 also includes a gaze attractor 3416 adapted to attract the gaze of the subject 104 to thereby cause the eye 102 of the subject 104 to move into alignment with at least one of the interrogation signal source 110 or the response signal sensor 114; wherein the signal processing circuitry 3402 is configured to activate the gaze attractor 3416 to cause the alignment of the eye of the subject with respect to the at least one of the interrogation signal source 110 or the response signal sensor 114 if a predetermined number of samples meeting an acceptance criterion has not been collected within a predetermined portion of the sampling period. Gaze attractor may be 3416 any structure capable of attracting the gaze of the subject, by attracting the attention of the subject such that the subject directs his or her gaze toward the gaze attractor. For example, gaze attractor may be capable of delivering a visual stimulus 3418, an audio stimulus 3420, or both, simultaneously or in sequence, as discussed in connection with FIG. 23.

Response signal sensor 114 can be adapted to sense a response signal from an interior of the eye of the subject responsive to the interrogation signal, e.g. from a lens, aqueous humor, vitreous humor, or a retina of the eye of the subject.

In some embodiments, gaze signal sensor 106 and the response signal sensor 114 may be different sensors, as depicted in FIG. 34, or, as depicted in FIG. 3, gaze signal sensor 106 and the response signal sensor 114 are may be the same sensor. Gaze signal sensor can be an infrared camera or a CCD camera, as discussed herein above.

Various combinations of interrogation signal source 110 and response signal sensor 114 can be used, depending on the physiological parameter to be sensed, as discussed herein above. For example, in one embodiment, interrogation signal source 110 includes a broad spectrum light source and response signal sensor 114 includes a spectrometer based on a CCD array. In another embodiment, wherein the interrogation signal source 110 includes a near-infrared light source and the response signal sensor 114 includes a near-infrared camera. Other such combinations include interrogation signal source 110 includes a tunable laser source and the response signal sensor 114 includes a Raman spectrometer based on a CCD camera, interrogation signal source 110 includes a mid-infrared light source and the response signal sensor 114 includes a mid-infrared detector, and interrogation signal source 110 includes a tunable laser source and the response signal sensor 114 includes a broad spectrum pyroelectric detector.

Response signal may be indicative of a feature of the vasculature of the eye of the subject or a biometric identification of the subject.

In an embodiment, system also includes at least one gaze tracking stimulus 150 source adapted to deliver a gaze tracking stimulus 152 to at least an eye of a subject, wherein the gaze signal 108 is produced in response to the gaze tracking stimulus 152. Gaze tracking stimulus source 150 may include, for example, an infra-red source, which may be used in combination with a gaze signal sensor 106 that includes an infra-red sensor. Gaze tracking stimulus source may include a near infra-red source, which may be used in combination with a gaze signal sensor 106 that includes a near infra-red sensor. Gaze tracking stimulus source 150 may include one or a plurality of light sources. Gaze signal sensor 106 may include an optical sensor, an optical sensor array, or a camera. System may include a plurality of gaze signal sensors.

In an embodiment, the interrogation signal source 110 is adapted to produce light having a first polarization, and the response signal sensor 114 is adapted to detect light having a second polarization, as discussed herein above in connection with FIG. 12. The first polarization and the second polarization may be the same, or different.

As in other embodiments discussed herein, various physiological parameters can be measured. The physiological parameter may be a measurement of oxygenation, measurement of blood glucose, a heart rate, a measurement of glycosylated hemoglobin, a temperature, e.g., a body temperature, a measurement of blood flow, or a measurement of a substance in the eye of the subject, for example.

As discussed generally in connection with FIG. 6, interrogation signal source 110 may be adapted to deliver a pulsed interrogation signal. In connection therewith, at least one of the response signal sensor 114 and the signal processing circuitry 3402 may be configured to gate detection of the response signal relative to the pulsed interrogation signal. Signal processing circuitry 3402 may be configured to combine multiple response signals produced by the eye of the subject in response to multiple pulses of the pulsed interrogation signal. For example, signal processing circuitry may be configured to combine the multiple response signals by summing or averaging the multiple response signals, or by determining a moving average or weighted sum of the multiple response signals.

In an embodiment, interrogation signal source 110 is adapted to deliver an interrogation signal containing multiple wavelengths of light. In connection therewith system 3400 may include includes at least a first response signal sensor configured to sense a first response signal produced by the eye of the subject responsive to a first wavelength component of the interrogation signal, and a second response signal sensor (not shown) configured to sense a second response signal produced by the eye of the subject responsive to a second wavelength component of the interrogation signal. See, e.g. FIG. 7.

In an embodiment, system 3400 includes at least a first interrogation signal source configured to deliver a first interrogation signal having a first optical wavelength and at least a second interrogation signal source configured to deliver a second interrogation signal having a second optical wavelength. Signal processing circuitry may be configured to process a first response signal sensed from the eye of the subject in response to the first interrogation signal and a second response signal sensed from the eye of the subject in response to the second interrogation signal by comparing the first and second response signals to determine the physiological parameter. See, e.g. FIG. 7. System 3400 may be configured to deliver the first interrogation signal simultaneously with respect to the second interrogation signal, or sequentially with respect to the second interrogation signal.

Interrogation signal source 110 and response signal sensor 114 can be co-aligned, or separately aligned and located.

In an embodiment, system 3400 includes an output structure 810 adapted to output a signal relating to the determined physiological parameter. The output structure can be a data transmission structure, a data storage structure, a display, an audio output, or a visual output, for example, as discussed in connection with FIG. 8. In one aspect, system 3400 can include a display adapted to display information relating to the determined physiological parameter. The display can be, for example, a video monitor, a computer display, a video game display, a telephone display, or a data processing device. The display may be incorporated in a wearable item, an article of furniture, an article of medical or health-care related equipment, an article of exercise equipment, or a vehicle. Examples of such displays are described in greater detail herein above.

Figure 35:
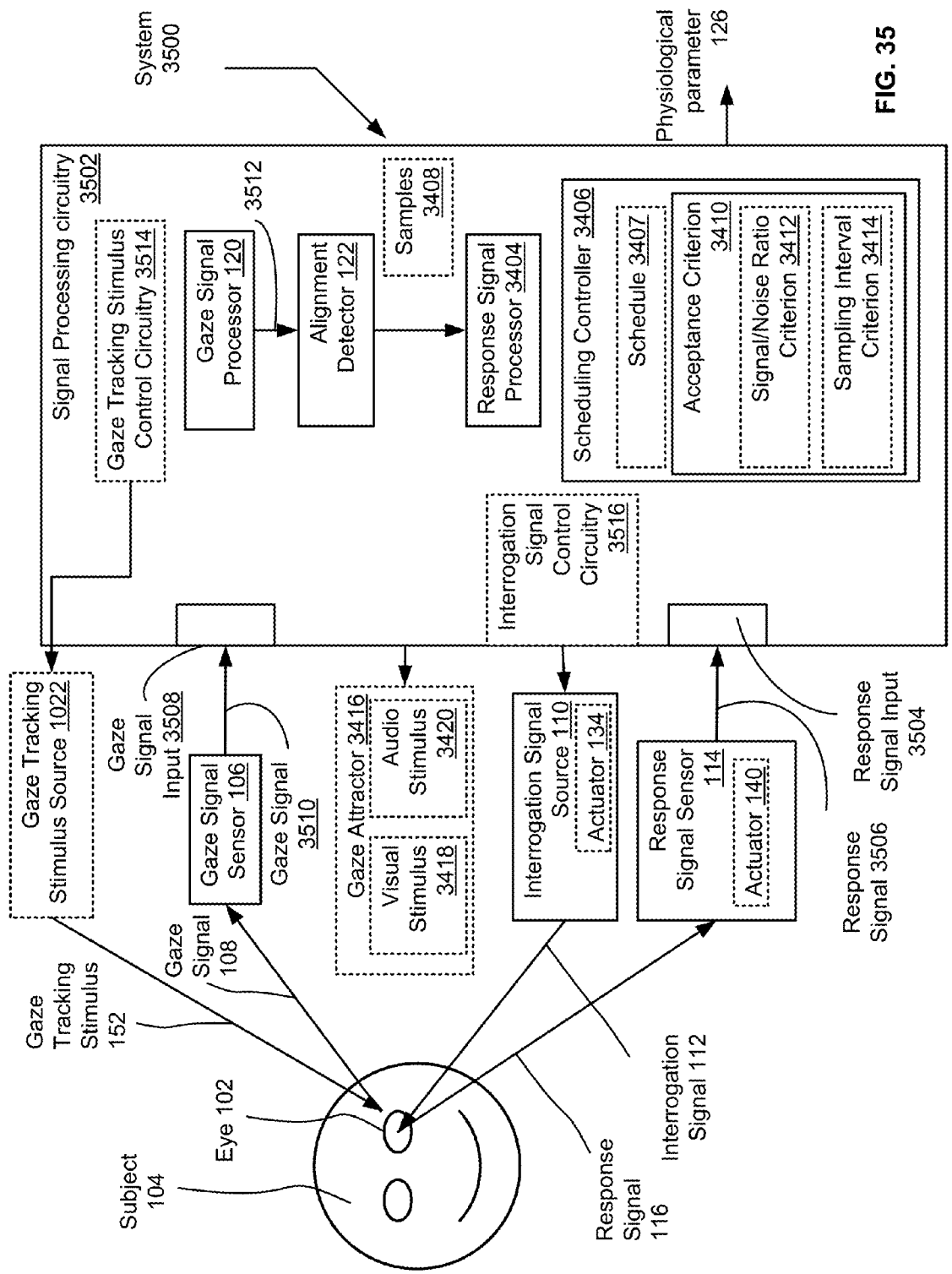
FIG. 35 is a block diagram of an embodiment of a system for controlling the sensing of information from an eye of a subject.

FIG. 35 depicts a system 3500 for controlling the sensing of information from an eye 102 of a subject 104, including signal processing circuitry 3502 including: a response signal input 3504 adapted to receive a response signal 3506 sensed from the eye 102 of the subject 104 by a response signal sensor 114 responsive to delivery of an interrogation signal 112 to the eye 102 of the subject 104; and a response signal processor 3404 configured to process the response signal sensed from the eye of the subject by the response signal sensor to determine a physiological parameter 126 from the response signal; and a scheduling controller 3406 configured to direct collection of samples 3408 of the physiological parameter according to a schedule 3407.

System 3500 may include a gaze signal input 3508 adapted to receive a gaze signal 3510 containing information indicative of a gaze direction of the eye of the subject sensed from at least an eye of the subject; and a gaze signal processor 120 configured to determine the gaze direction 3512 of the eye 102 of the subject 104 based upon the gaze signal 3510; and an alignment detector 122 configured to determine whether the eye of the subject is in alignment with respect to at least one of the interrogation signal source 110 or the response signal sensor 114 based at least in part upon the gaze direction 3512.

System may 3500 include gaze tracking stimulus control circuitry 3514 configured to drive production of gaze tracking stimulus 152 by a gaze tracking stimulus source 1022, wherein the gaze signal 108 is produced responsive to the gaze tracking stimulus 1022. In an embodiment, gaze tracking stimulus control circuitry 3514 is configured to drive production of a gaze tracking stimulus by a plurality of gaze tracking stimulus sources (not shown). Gaze signal input 3508 and the response signal input 3504 can be the same input (e.g. if same sensor is used as the gaze signal sensor and the response signal sensor). Alternatively, the gaze signal input 3508 and the response signal input 3504 can be separate inputs, e.g. gaze signal sensor and response signal sensor are separate sensors. The gaze signal input 3508 may be configured to receive various types of signals. In an embodiment, gaze signal input 3508 is adapted to receive a signal from a camera. In an embodiment, signal processing circuitry includes a plurality of gaze signal inputs (not shown in FIG. 35, but generally as depicted in FIG. 12) adapted to receive a plurality of gaze signals containing information indicative of a gaze direction of the eye of the subject sensed from at least an eye of the subject. System 3500 may also include interrogation signal control circuitry 3516 configured to drive production of interrogation signal 112 by interrogation signal source 110.

Response signal processor 3404 may be adapted to process a response signal 3506 sensed from an interior of the eye of the subject responsive to the interrogation signal, e.g. a response signal sensed from a lens, aqueous humor, vitreous humor, or retina of the eye of the subject. Response signal processor 3404 can be configured to process the response signal 3506 to determine a feature of the vasculature of the eye of the subject or determine a biometric identification of the subject, as described herein above. In an embodiment, response signal processor 3404 is configured to process the response signal by determining a first response signal at a first polarization, determining a second response signal at a second polarization, and comparing the response signal determined at the first polarization to the response signal determined at the second polarization, wherein the first polarization and the second polarization are different, discussed above in connection with FIG. 12.

Response signal processor 3404 can be configured to process the response signal 3506 sensed from the eye of the subject by the response signal sensor 114 when the eye of the subject is in alignment with respect to the at least one of the interrogation signal source and the response signal sensor to determine a measurement of a physiological parameter from the response signal, including, for example, oxygenation, blood glucose, heart rate, glycosylated hemoglobin, temperature, body temperature, blood flow, or a substance in the eye of the subject from the response signal.

In an embodiment, interrogation signal control circuitry 3516 is configured to drive production of a pulsed interrogation signal by the interrogation signal source, as discussed above in connection with FIG. 6. Signal processing circuitry 3502 may be configured to gate detection of the response signal relative to the pulsed interrogation signal. In one aspect, signal processing circuitry 3502 is configured to combine multiple response signals produced by the eye of the subject in response to multiple pulses of the pulsed interrogation signal, by summing or averaging the multiple response signals, or by determining a moving average or weighted sum of the multiple response signals.

In an embodiment, system includes interrogation signal control circuitry 3516 configured to drive production of a first interrogation signal having a first optical wavelength and production of a second interrogation signal having a second optical wavelength, as described in connection with FIG. 7. Signal processing circuitry 3516 may be configured to process a first response signal sensed from the eye of the subject in response to the first interrogation signal and a second response signal sensed from the eye of the subject in response to the second interrogation signal by comparing the first and second response signals in order to determine the physiological parameter. Signal processing circuitry 3516 may be configured to drive production of the first interrogation signal simultaneously with respect to the second interrogation signal, or sequentially with respect to the second interrogation signal.

In an embodiment, scheduling controller 3406 is configured to direct collection of a predetermined number of samples of the physiological parameter during a sampling period. In an embodiment, scheduling controller 3406 is configured to direct collection of samples with at least a minimum sampling interval between samples. In an aspect, scheduling controller 3406 is configured to modify the procedure for collecting a sample of the physiological parameter if a predetermined number of samples meeting an acceptance criterion 3410 has not been collected within a predetermined portion of the sampling period. Modifying the procedure for collecting a sample of the physiological parameter may be done, for example by modifying the acceptance criterion 3410. Acceptance criterion may include one or more of signal-to-noise ratio criterion 3412 and sampling interval criterion 3414.

In an embodiment, signal processing circuitry 3502 is configured to cause the alignment of the eye of the subject with respect to the at least one of the interrogation signal source and the response signal sensor if a predetermined number of samples meeting an acceptance criterion has not been collected within a predetermined portion of the sampling period. System 3500 may also include at least one actuator (134 or 140) configured to move at least one of the interrogation signal source 110 or the response signal sensor 114; wherein the signal processing circuitry 3502 is configured to cause the alignment of the eye of the subject with respect to the at least one of the interrogation signal 110 source or the response signal sensor 114 by directing an actuator 134 or 140, respectively, to move at least one of the interrogation signal 110 source or the response signal sensor 114 into alignment with the eye 102 of the subject 104. In an embodiment, signal processing circuitry 3502 may be configured to activate a gaze attractor 3416 to cause the alignment of the eye of the subject with respect to the at least one of the interrogation signal source and the response signal sensor if a predetermined number of samples meeting an acceptance criterion has not been collected within a predetermined portion of the sampling period. The response signal 3506 may be indicative of a feature of the vasculature of the eye of the subject or a biometric identification of the subject.

Figure 36:
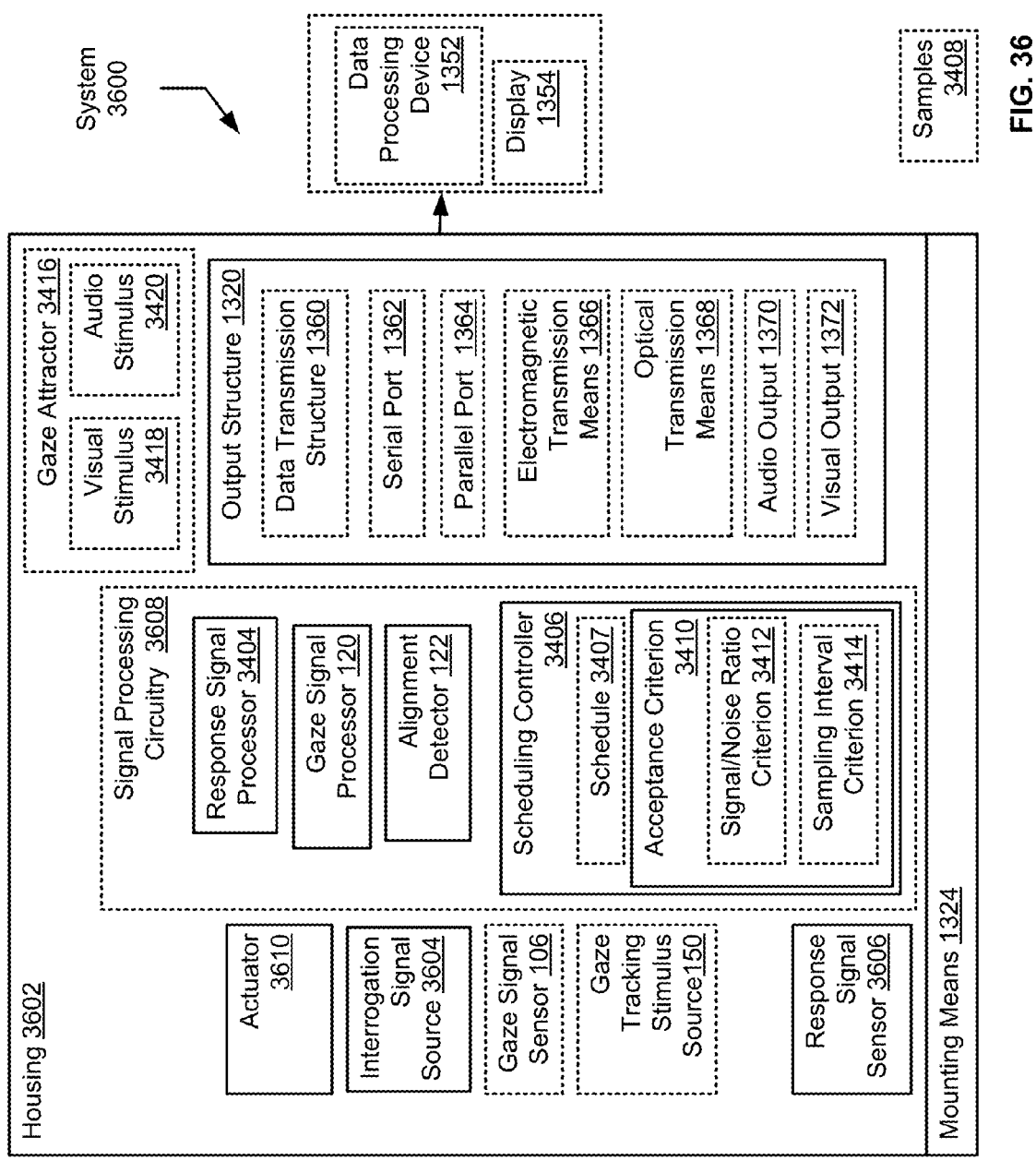
FIG. 36 is a block diagram of a system for sensing information from an eye of a subject.

FIG. 36 depicts a system 3600 that includes a housing 3602; an interrogation signal source 3604 housed in the housing 3602 and adapted for delivering an interrogation signal to an eye of a subject, the interrogation signal source 3604 including at least one light source and at least one optical system; a response signal sensor 3606 housed within the housing 3602 and adapted for sensing a response signal produced by the eye of the subject responsive to the interrogation signal, the response signal containing information regarding a physiological parameter of the subject; signal processing circuitry 3608 including: a response signal processor 3404 configured to process a response signal sensed from the eye of the subject to determine a physiological parameter from the response signal; and a scheduling controller 3406 configured to direct collection of samples of the physiological parameter according to a schedule 3407; an output structure 810 adapted for transmitting an output signal; and mounting means 1324 adapted for mounting the housing 3602 with respect to a display in such a manner that the interrogation signal source

3604 and response signal sensor 3606 are alignable with the eye of the subject during normal use of the display by the subject.

In one aspect, scheduling controller 3406 is configured to direct collection of a predetermined number of samples of the physiological parameter during a sampling period. In one aspect, scheduling controller 3406 is configured to direct collection of samples with at least a minimum sampling interval between samples. Scheduling controller 3406 may be configured to modify the procedure for collecting a sample of the physiological parameter if a predetermined number of samples meeting an acceptance criterion 3410 has not been collected within a predetermined portion of the sampling period, for example by modifying the acceptance criterion. Acceptance criterion 3410 may include, for example, a signal-to-noise ratio criterion 3412 and/or a sampling interval criterion 3414.

In an embodiment, a system 3600 includes a gaze signal sensor 106 adapted for receiving a gaze signal containing information indicative of a gaze direction of an eye of the subject; and wherein the signal processing circuitry includes: a gaze signal processor 120 configured to determine the gaze direction of the eye of the subject based upon the gaze signal; and an alignment detector 122 configured to determine whether the eye of the subject is in alignment with respect to at least one of the interrogation signal source 3604 or the response signal sensor 3606; wherein the response signal processor 3404 is configured to process the response signal sensed from the eye of the subject when the eye of the subject is in alignment with respect to the at least one of the interrogation signal source 3604 or the response signal sensor 3606 to determine the physiological parameter from the response signal. The physiological parameter may be a measurement of oxygenation, blood glucose, heart rate, glycosylated hemoglobin, temperature, body temperature, blood flow, or a substance in the eye of the subject, for example.

System 3600 may also include at least one actuator 3610 configured to move at least one of the interrogation signal source 3604 or the response signal sensor 3606; wherein the signal processing circuitry 3608 is configured to cause the alignment of the eye of the subject with respect to the at least one of the interrogation signal source 3604 or the response signal sensor 3606 by directing the actuator 3610 to move at least one of the interrogation signal source 3604 or the response signal sensor 3606 into alignment with the eye of the subject.

In an embodiment, system 3600 includes a gaze attractor 3416 adapted to attract the gaze of the subject to thereby cause the eye of the subject to move into alignment with at least one of the interrogation signal source and the response signal sensor; wherein the signal processing circuitry 3608 is configured to activate the gaze attractor 3416 to cause the alignment of the eye of the subject with respect to the at least one of the interrogation signal source 3604 or the response signal sensor 3606 if a predetermined number of samples meeting an acceptance criterion has not been collected within a predetermined portion of the sampling period. As discussed above, response signal sensor 3606 may be adapted to sense a response signal from an interior of the eye of the subject responsive to the interrogation signal, for example from a lens, aqueous humor, vitreous humor or retina of the eye of the subject responsive to the interrogation signal. Gaze signal sensor 106 and the response signal sensor 3606 may be the same sensor, or different sensors, depending on the parameter to be sensed and preferred method for determining gaze direction. For example, gaze signal sensor can include an infrared camera or a CCD camera.

Various combinations of interrogation signal source 3604 and response signal sensor 3606 may be used, as discussed herein above. For example, in an embodiment, the interrogation signal source 3604 includes a broad spectrum light source and the response signal sensor 3606 includes a spectrometer based on a CCD array. Other combinations include an interrogation signal source 3604 that includes a near-infrared light source and response signal sensor 3606 that includes a near-infrared camera, an interrogation signal source 3604 that includes a tunable laser source and response signal sensor 3606 that includes a Raman spectrometer based on a CCD camera, an interrogation signal source 3604 that includes a mid-infrared light source and response signal sensor 3606 that includes a mid-infrared detector, and an interrogation signal source 3604 that includes a tunable laser source and response signal sensor 3606 that includes a broad spectrum pyroelectric detector.

System 3600 may include at least one gaze tracking stimulus source 150 adapted to deliver a gaze tracking stimulus to at least an eye of a subject, wherein the gaze signal is produced in response to the gaze tracking stimulus. Gaze tracking stimulus source 150 may include, for example, an infrared source, while gaze signal sensor 106 includes an infra-red sensor. Gaze tracking stimulus source 150 may include a near infra-red source, and gaze signal sensor 106 may include a near infra-red sensor. In some embodiment, gaze tracking stimulus source 150 includes a plurality of light sources. Gaze signal sensor 106 can include an optical sensor, an optical sensor array, a camera, and/or a plurality of gaze signal sensors, for example.

In an embodiment, interrogation signal source 3604 is adapted to produce light having a first polarization, and response signal sensor 3606 is adapted to detect light having a second polarization, wherein the first polarization and the second polarization are the same. Alternatively, interrogation signal source 3604 may be adapted to produce light having a first polarization, and the response signal sensor 3606 is adapted to detect light having a second polarization, wherein the first polarization and the second polarization are different.

In an embodiment, interrogation signal source 3604 is adapted to deliver a pulsed interrogation signal, as described in connection with FIG. 6. In one aspect, at least one of response signal sensor 3606 and signal processing circuitry 3608 is configured to gate detection of the response signal relative to the pulsed interrogation signal. Signal processing circuitry 3608 may be configured to combine multiple response signals produced by the eye of the subject in response to multiple pulses of the pulsed interrogation signal, for example by summing or averaging the multiple response signals, or by determining a moving average or weighted sum of the multiple response signals.

In an embodiment, a system 3600 includes an interrogation signal source 3604 adapted to deliver an interrogation signal containing multiple wavelengths of light. As discussed generally elsewhere herein, system 3600 may include at least a first response signal sensor configured to sense a first response signal produced by the eye of the subject responsive to a first wavelength component of the interrogation signal, and a second response signal sensor (not shown) configured to sense a second response signal produced by the eye of the subject responsive to a second wavelength component of the interrogation signal. In an embodiment, a system includes a first interrogation signal source configured to deliver a first interrogation signal having a first optical wavelength and at least a second interrogation signal source (not shown) configured to deliver a second interrogation signal having a second optical wavelength. Signal processing circuitry 3608 may be configured to process a first response signal sensed from the eye of the subject in response to the first interrogation signal and a second response signal sensed from the eye of the subject in response to the second interrogation signal by comparing the first and second response signals to determine the physiological parameter. The system may be configured to deliver the first interrogation signal simultaneously with respect to the second interrogation signal, sequentially with respect to the second interrogation signal. Interrogation signal source 3604 and the response signal sensor 3606 may be co-aligned, or separately aligned and located.

In one aspect, mounting means 1324 is adapted for mounting the housing 3602 with respect to the display such that during normal use of the display by the subject, the interrogation signal source 3604 and response signal sensor 3606 are positioned within the visual field of at least one eye of the subject. In one aspect, mounting means 1324 is adapted for mounting the housing 3602 with respect to the display such that the interrogation signal source 3604 and response signal sensor 3606 are oriented in substantially the same direction as the display surface of the display.

Output structure 1320 may include a data transmission structure, which may be, for example, a serial port, a parallel port, an electromagnetic transmission means, an optical transmission means, an audio output or a visual output, as discussed herein above. Output structure 1320 may be adapted to transmit an output signal to display 1354, or data processing device 1352. In a related embodiment, the display 1354 is controlled by the data processing device. Display 1354 may be configured to display information relating to the determined physiological parameter, and may be any of various types of displays, for example, a video monitor, computer display, video game display, telephone display, or terminal of a data processing device. Display 1354 can be incorporated in a wearable item, article of furniture, article of medical or health-care related equipment, article of exercise equipment, or vehicle. Examples of such displays are described in greater detail herein above.

EXAMPLE 3

Figure 37:
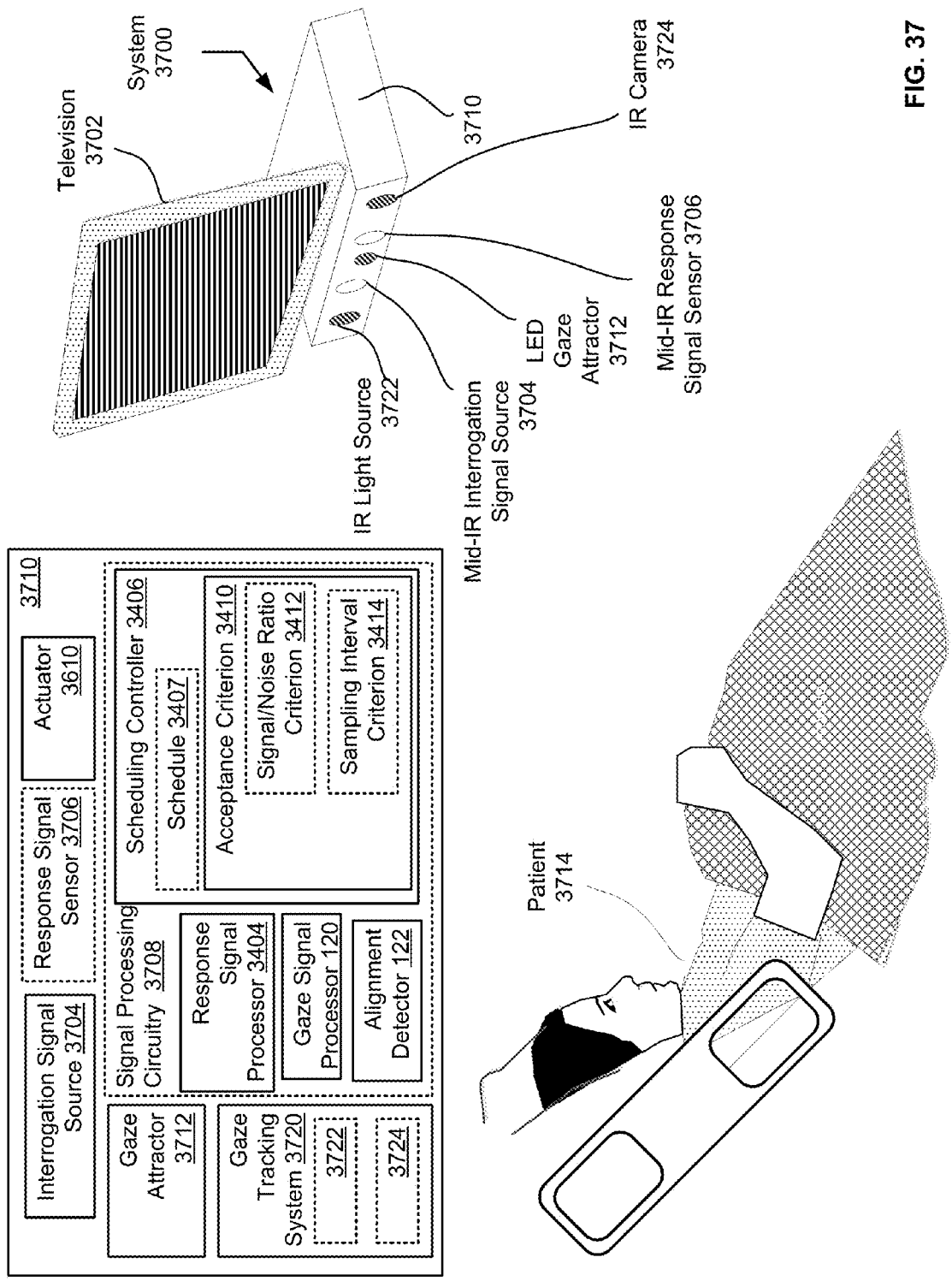
FIG. 37 illustrates an embodiment of a system for sensing information from a hospital patient according to a schedule.

An Unobtrusive Eye Interrogation System Associated with a Hospital TV to Measure Health Parameters on a Predetermined Schedule FIG. 37 illustrates an eye interrogation system 3700 that is used to measure a patient's health parameters according to a schedule. Eye interrogation system 3700 is placed adjacent to a hospital patient's television 3702 to measure health parameters according to a predetermined schedule. The eye interrogation system includes an interrogation signal source 3704, a response signal sensor 3706 and a signal processing circuitry 3708 which are housed in the unit 3710 that is mounted with respect to the patient's TV 3702. Eye interrogation system 3700 also includes a scheduling controller 3406 and a gaze attractor 3712 to engage the eyes of the patient 3714 to collect health parameter data according to a schedule.

The eye interrogation system employs a mid-infrared wavelength interrogation signal source 3704 and response signal sensor 3706 to noninvasively identify bioanalytes and determine their concentration in the eye. The system includes a gaze attractor 3712 to attract the patients gaze to interrogation signal source 3704 and response signal sensor 3706. For example, gaze attractor 3712 may include a light emitting diode (LED) which draws the patient's gaze to interrogation signal source 3704 and response signal sensor 3706 when a bioanalyte determination is scheduled. For example the LED may flash to attract the patients' attention. A gaze tracking system 3720 is used to detect when the user looks at the LED gaze attractor 3712 and the interrogation signal source and/or the response signal sensor. The gaze tracking system 3720 is comprised of an IR light source 3722 and an IR camera 3724 which detects the reflection of IR light from the eyes of the patient. Eye position, eye rotation, eye gaze position against screen, pupil diameter and eye vergence distance may be monitored. The gaze tracking system 3720 includes software and circuitry to analyze the gaze tracking data and to detect alignment of the patient's gaze with the interrogation source and/or the interrogation detectors. Alignment of the patient's eyes with the interrogation sources and detectors triggers activation of the interrogation source by the system controller.

Interrogation signal source 3704 interrogates the patient's eyes with mid-infrared light, which may be approximately 2.5 to 50.0 microns in wavelength. A range of mid-infrared wavelengths is sourced from tunable external cavity lasers which provide multiple wavelengths for spectroscopy of bioanalytes (e.g., the Uber Tuner™ Lasers available from Daylight Solutions Inc., San Diego, Calif.; see the Product Sheet: "Uber Tuner™ Broad Tuning Pulsed Lasers" which is incorporated herein by reference). For example, tunable lasers emitting mid-infrared radiation at wavelengths between about 8 microns and about 11 microns may be used to identify glucose which displays an absorption signature at those wavelengths. Irradiation of the blood vessels in the sclera of the eye with 8-11 micron wavelength light results in reflected spectra that may be detected by mid-infrared detectors. For example a deuterated tri-glycine sulfate pyroelectric detector may be used to detect the reflected mid-infrared radiation and determine the absorption pattern. Broad spectrum pyroelectric detectors to detect wavelengths between approximately 700 nm and 28 microns are available from Newport Corp., Irvine, Calif. (see the Specification Sheet: "MIR8025™ Modular IR Fourier Spectrometers" which is incorporated herein by reference). Signal processors and associated software determine the radiation pattern and correlate the pattern with the known radiation signatures in a reference database. For example, an absorption pattern at wavelengths between approximately 8 and 11 microns may be used to identify glucose and to determine its concentration (see e.g. U.S. Pat. No. 6,958,039 issued to Burd et al. on Oct. 25, 2005 which is incorporated herein by reference).

Eye interrogation system 3700 includes signal processing circuitry 3708 to analyze bioanalyte concentrations, compare them to reference values or to values determined previously for the patient. For example, glucose concentration in conjunctiva blood vessels may be compared to correlated glucose concentrations in the peripheral circulation and to a normal range for glucose. Also the glucose concentrations determined according to a predetermined schedule may be compared. Blood glucose concentrations outside the normal range or trending rapidly to hyperglycemia are reported electronically to computer terminals of the responsible health caregivers.

Eye interrogation system 3700 may be used to monitor a patient's blood concentration of a pharmaceutical such as warfarin. A hospital patient at risk of thrombosis and thromboembolism is treated with an anticoagulant, warfarin, which prevents blood clots from forming but dosing must be monitored closely to avoid excessive bleeding and yet prevent clots from forming. Instead of measuring clotting time with an ex vivo blood test the concentration of warfarin in the blood can be monitored by scheduled eye interrogations. Warfarin (also known as Coumadin) displays a characteristic IR spectrum with absorption peaks at 3200 cm$^{-1}$ and 1747 cm$^{-1}$ (see e.g., the Data Sheet: "Warfarin IR Spectrum" in "Characterisation" which is incorporated herein by reference). After a loading dose of warfarin is administered the eye interrogation system is scheduled to attract the patient's gaze and determine the warfarin concentration in the blood vessels of the eye every 4 hours. Warfarin concentrations determined by mid-infrared spectroscopy in the eye are correlated to blood clotting times determined ex vivo and stored in a reference database. If the warfarin concentration and the corresponding clotting time are outside safe boundaries the patient's physician is notified and the dose of warfarin is adjusted. Data on the scheduled interrogation times and corresponding warfarin concentrations is stored in a database for analysis by the physician or pharmacist to predict future doses of warfarin.

Eye interrogation system 3700 may also include sources and sensors to detect other physiological parameters to monitor the patient's health according to a predetermined schedule. For example the eye interrogation system may be scheduled to measure the patient's heart rate, respiration rate and temperature. The corresponding components including interrogation sources and detectors are described above in Example 2. The health parameter data obtained from the eye interrogation system is analyzed by signal processing circuitry 3708 and provided to health caregivers. Moreover the health parameters may be consolidated to provide an overview of the patient's health over a time frame determined by the scheduled eye interrogations.

Figure 38:
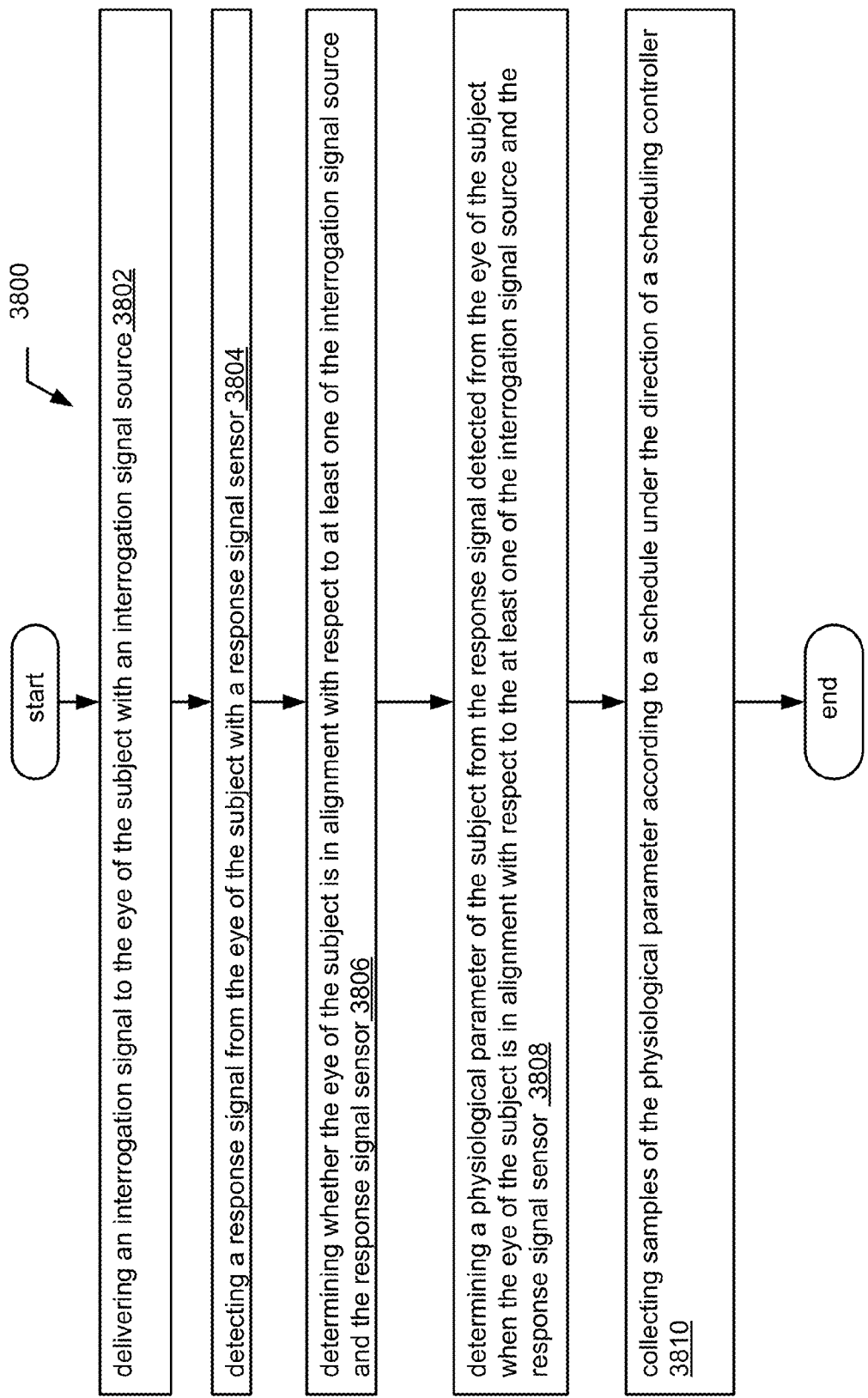
FIG. 38 is a flow diagram of a method of measuring information from an eye of a subject.

FIG. 38 is a flow diagram of a method 3800 of measuring information from an eye of a subject, which includes delivering an interrogation signal to the eye of the subject with an interrogation signal source 3802; detecting a response signal from the eye of the subject with a response signal sensor; processing a response signal sensed from the eye of the subject to determine a physiological parameter from the response signal 3804; determining whether the eye of the subject is in alignment with respect to at least one of the interrogation signal source and the response signal sensor 3806; determining a physiological parameter of the subject from the response signal detected from the eye of the subject when the eye of the subject is in alignment with respect to the at least one of the interrogation signal source and the response signal sensor 3808; and collecting samples of the physiological parameter according to a schedule under the direction of a scheduling controller 3810.

As shown in FIG. 39, a method 3900 also includes transmitting at least one of information regarding the subject, information regarding the system used for determining the physiological parameter, or information regarding the physiological parameter to a data processing system 3902. In various embodiments, the method may include receiving at least one of information regarding the subject, information regarding the system used for determining the physiological parameter, or information regarding the physiological parameter from a data processing system 3904; or sharing at least one of information regarding the subject, information regarding the system used for determining the physiological parameter, or information regarding the physiological parameter between two or more data processing systems 3906.

Method 3900 may include determining the identity of the subject 3908, for example, through the use of facial recognition 3910 or retinal recognition 3912, or comparing login information entered by the subject with login information in a registry 3914. As indicated at 3916, in some aspects the method may include collecting samples of the physiological parameter only when the identity of the subject meets a selection criterion. For example, once the identity of the subject has been determined, the identity of the subject may be compared with an identity of one or more approved subjects, and if the identity matches an identity of an approved subject, the selection criterion is met.

In an embodiment shown in FIG. 40, a method 4000 includes collecting a predetermined number of samples of the physiological parameter during a sampling period 4002. The method may include collecting samples of the physiological parameter with at least a minimum sampling interval between samples 4004. The method may include modifying the procedure for collecting a sample of the physiological parameter if a predetermined number of samples meeting an acceptance criterion has not been collected within a predetermined portion of the sampling period 4006. Modifying the procedure for collecting a sample of the physiological parameter may include modifying the acceptance criterion 4008, for example a signal-to-noise ratio criterion 4010 or sampling interval criterion 4012, as discussed herein above. In another aspect, modifying the procedure for collecting a sample of the physiological parameter may include modifying the schedule, as indicated at 4014.

As depicted in FIG. 41, in an embodiment, a method 4100 includes receiving a gaze signal containing information indicative of a gaze direction of an eye of the subject 4102; determining the gaze direction of the eye of the subject based upon the gaze signal 4104; determining whether the eye of the subject is in alignment with respect to at least one of the interrogation signal source and the response signal sensor based at least in part upon the gaze direction 4106. Method 4100 may include moving at least one of the interrogation signal source and the response signal sensor into alignment with the eye of the subject if a predetermined number of samples meeting an acceptance criterion has not been collected within a predetermined portion of the sampling period 4108. In one aspect, method 4100 includes activating a gaze attractor adapted to attract the gaze of the subject and bring the eye of the subject into alignment with at least one of the interrogation signal source and the response signal sensor if a predetermined number of samples meeting an acceptance criterion has not been collected within a predetermined portion of the sampling period 4110.

As shown in FIG. 42, in method 4200 delivering the interrogation signal includes delivering a pulsed interrogation signal 4202. The method may also include gating detection of the response signal relative to the pulsed interrogation signal 4204. The method may include detecting multiple response signals produced by the eye of the subject in response to multiple pulses of the pulsed interrogation signal 4206, and may include combining the multiple response signals produced by the eye of the subject in response to multiple pulses of the pulsed interrogation signal, for example by summing the multiple response signals 4208, averaging the multiple response signals 4210, determining a moving average of the multiple response signals 4212, and or determining a weighted sum of the multiple response signals 4214.

As shown in FIG. 43, in method 4300 delivering an interrogation includes delivering an interrogation signal containing multiple wavelengths of light 4302. The method may include detecting a first response signal produced by the eye of the subject responsive to a first wavelength component of the interrogation signal, and detecting a second response signal produced by the eye of the subject responsive to a second wavelength component of the interrogation signal 4304. In an embodiment, a method includes delivering a first interrogation signal having a first optical wavelength and a second interrogation signal having a second optical wavelength 4306. The method may include determining the physiological parameter of the subject by comparing a first response signal sensed from the eye of the subject in response to the first interrogation signal and a second response signal sensed from the eye of the subject in response to the second interrogation signal 4308. In an embodiment, the method includes delivering the first interrogation signal simultaneously with respect to the second interrogation signal 4310. In another embodiment, the method includes delivering the first interrogation signal sequentially with respect to the second interrogation signal 4312.

Figure 44:
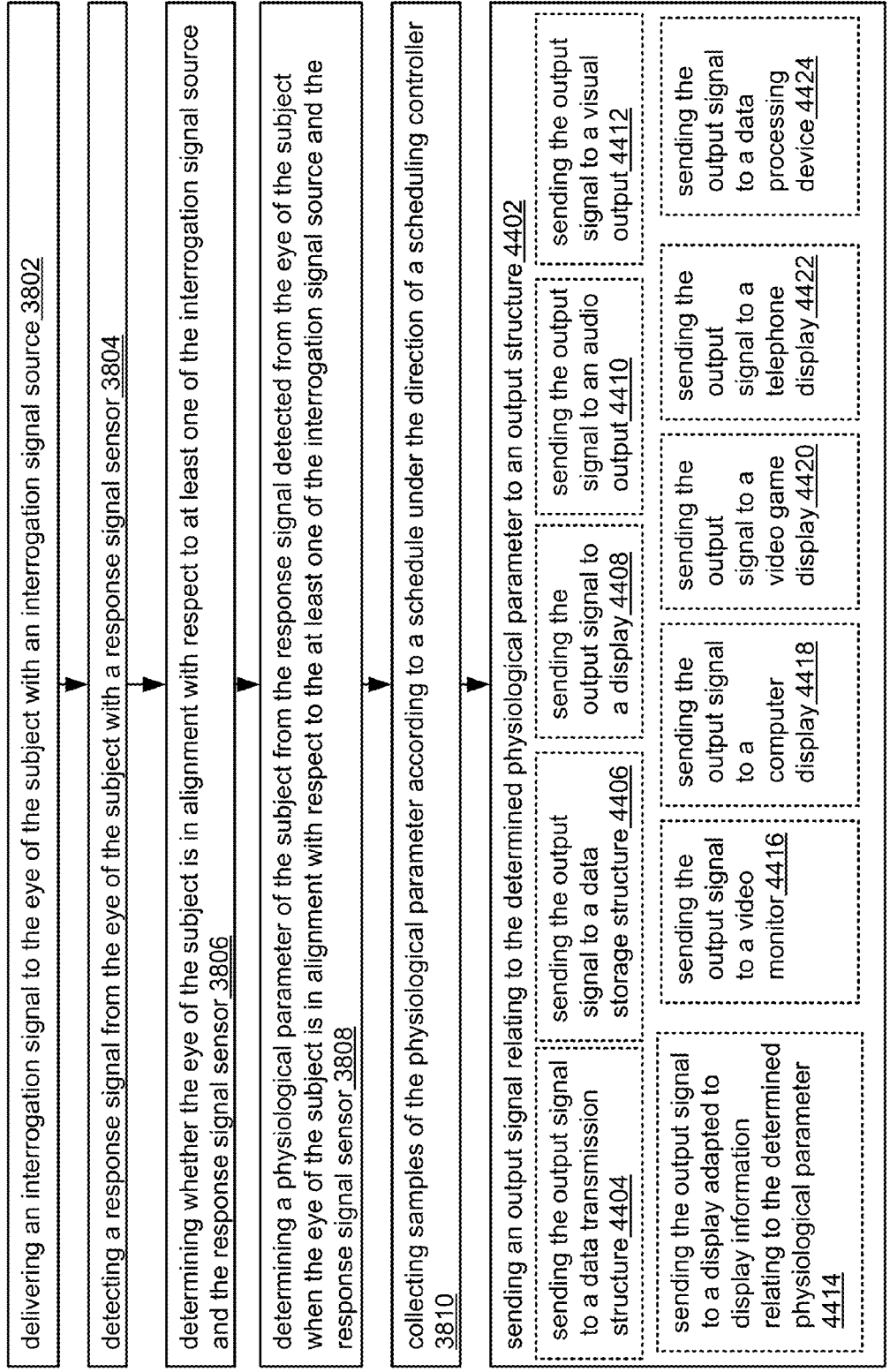
FIG. 44 is a flow diagram of a method of measuring information from an eye of a subject.

In another aspect, as shown in FIG. 44, a method 4400 includes sending an output signal relating to the determined physiological parameter to an output structure 4402, which may include, for example, a data transmission structure 4404, data storage structure 4406, display 4408, audio output 4410, or visual output 4412. The method may include sending the output signal to a display adapted to display information relating to the determined physiological parameter 4414. The method may include sending the output signal to a video monitor 4416, computer display 4418, video game display 4420, telephone display 4422, or data processing device 4424.

Figure 45:
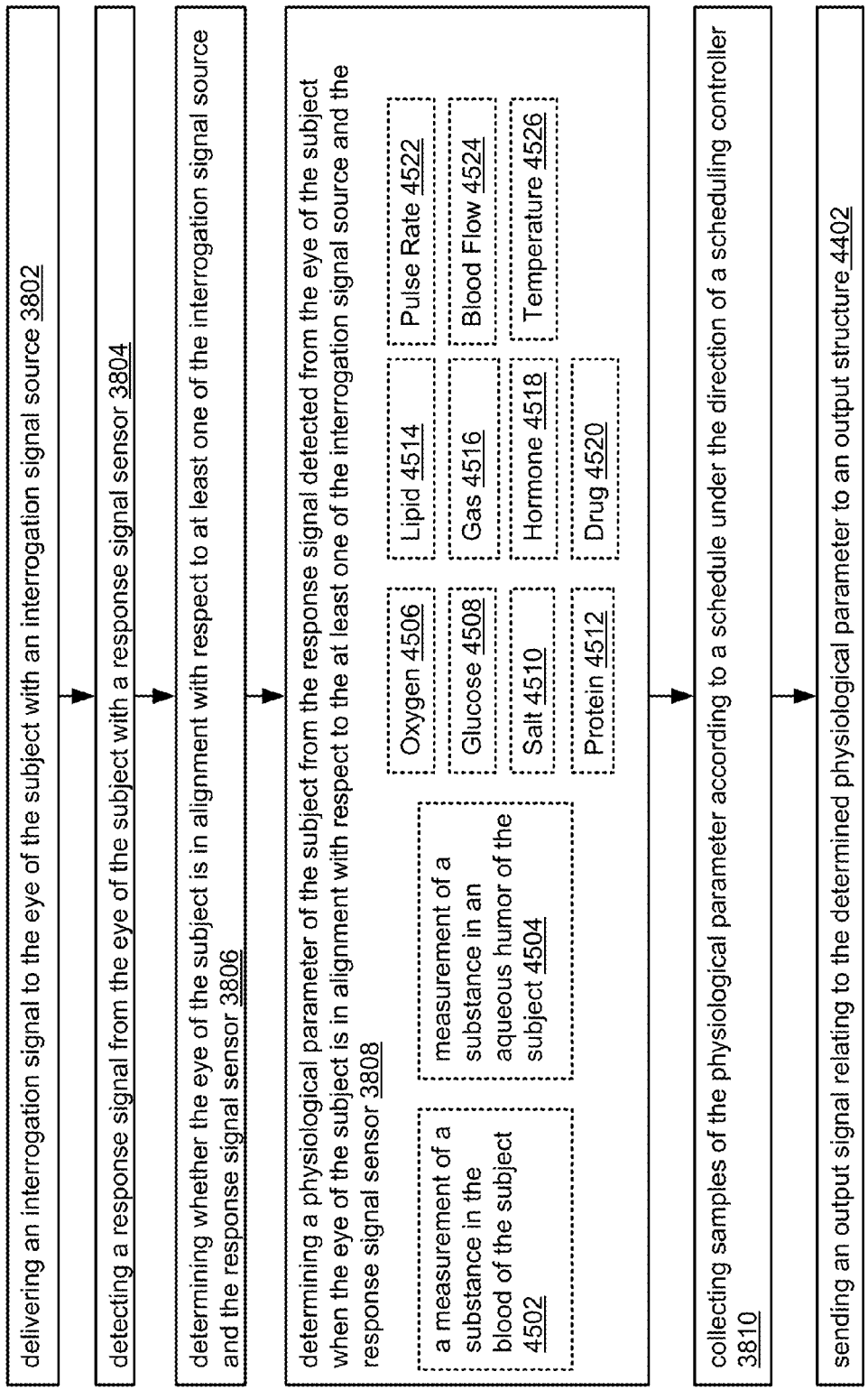
FIG. 45 is a flow diagram of a method of measuring information from an eye of a subject.

As shown FIG. 45, in a method 4500, a measurement of a substance in the blood of the subject, as indicated at 4512, and in some embodiments, the physiological parameter is a measurement of a substance in an aqueous humor of the subject, as indicated at 4504. The physiological parameter can be a measurement of oxygen 4506, glucose 4508, a salt 4510, a protein 4512, a lipid 4514, a gas 4516, a hormone 4518, or a drug 4520. The physiological parameter can be a pulse rate 4522, a blood flow 4524, or a temperature 4526.

Figure 46:
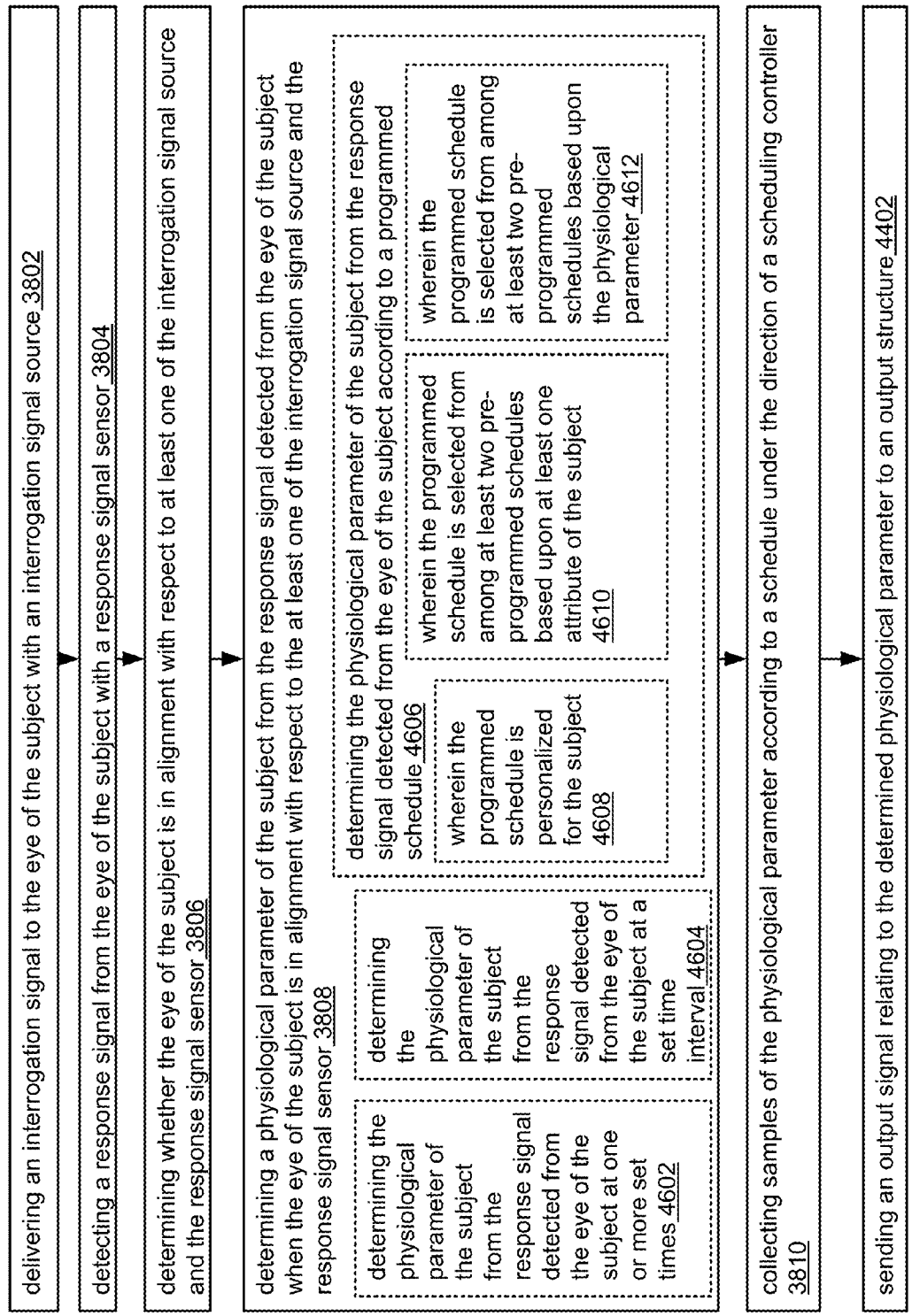
FIG. 46 is a flow diagram of a method of measuring information from an eye of a subject.

As shown in FIG. 46, a method 4600 may include determining the physiological parameter of the subject from the response signal detected from the eye of the subject at one or more set times 4602, determining the physiological parameter of the subject from the response signal detected from the eye of the subject at a set time interval 4604, or determining the physiological parameter of the subject from the response signal detected from the eye of the subject according to a programmed schedule 4606. In an embodiment, a programmed schedule can be personalized for the subject 4608. The programmed schedule can be selected from among at least two pre-programmed schedules based upon at least one attribute of the subject 4610, or selected from among at least two pre-programmed schedules based upon the physiological parameter 4612.

Figure 47:
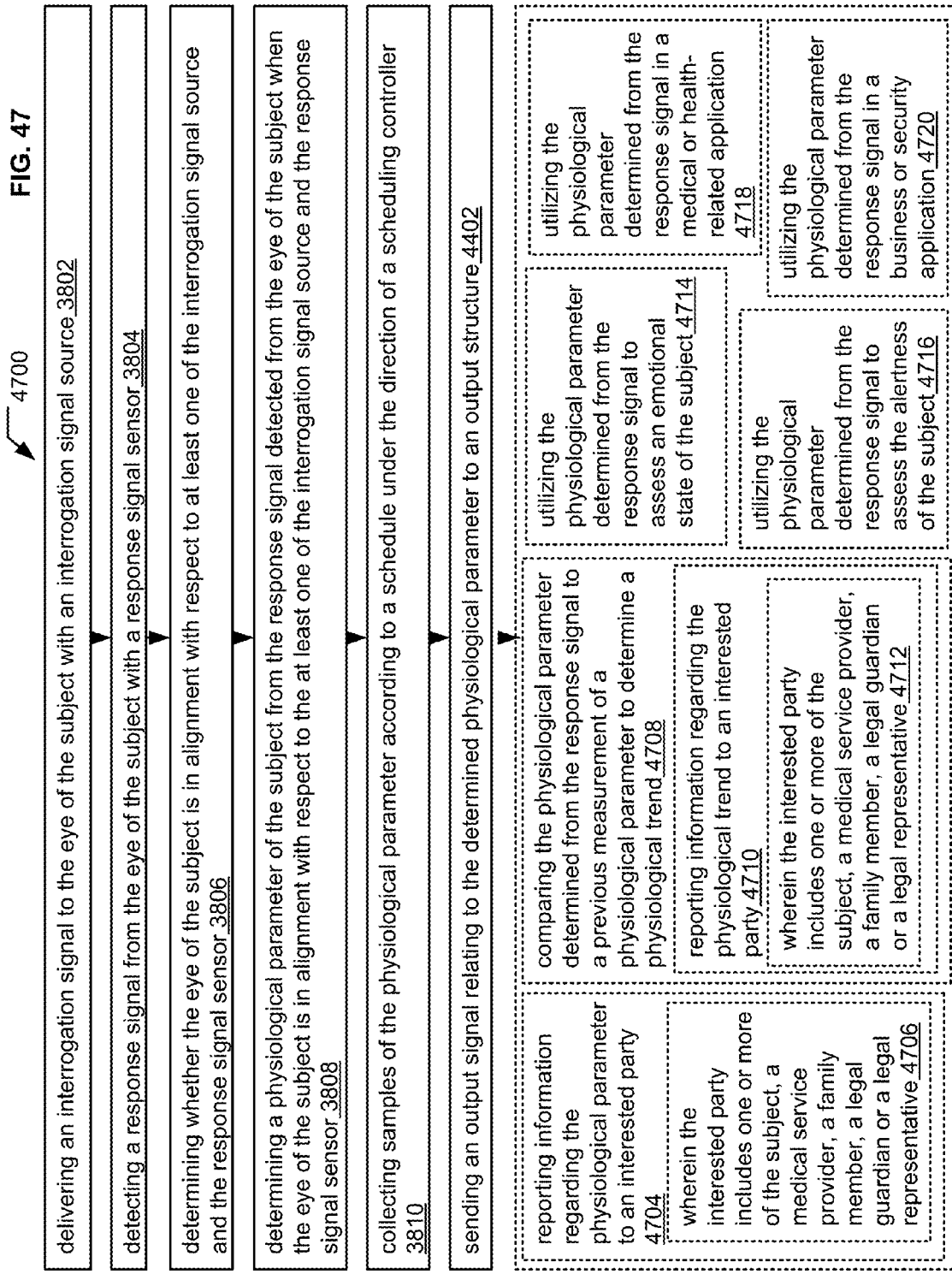
FIG. 47 is a flow diagram of a method of measuring information from an eye of a subject.

As shown in FIG. 47, a method 4700 includes reporting information regarding the physiological trend to an interested party 4704, for example, one or more of the subject, a medical service provider, a family member, a legal guardian or a legal representative 4706. In an embodiment, method 4700 includes comparing the physiological parameter determined from the response signal to a previous measurement of a physiological parameter to determine a physiological trend 4708. Method 4700 may also include reporting information regarding the physiological trend to an interested party 4710, for example one or more of the subject, a medical service provider, a family member, a legal guardian or a legal representative 4712.

In an aspect, method 4700 includes utilizing the physiological parameter determined from the response signal to assess an emotional state of the subject 4714 or utilizing the physiological parameter determined from the response signal to assess the alertness of the subject 4716. In an aspect, method 4700 includes utilizing the physiological parameter determined from the response signal in a medical or health-related application 4718. In another aspect, method 4700 includes utilizing the physiological parameter determined from the response signal in a business or security application 4720.

Figure 48:
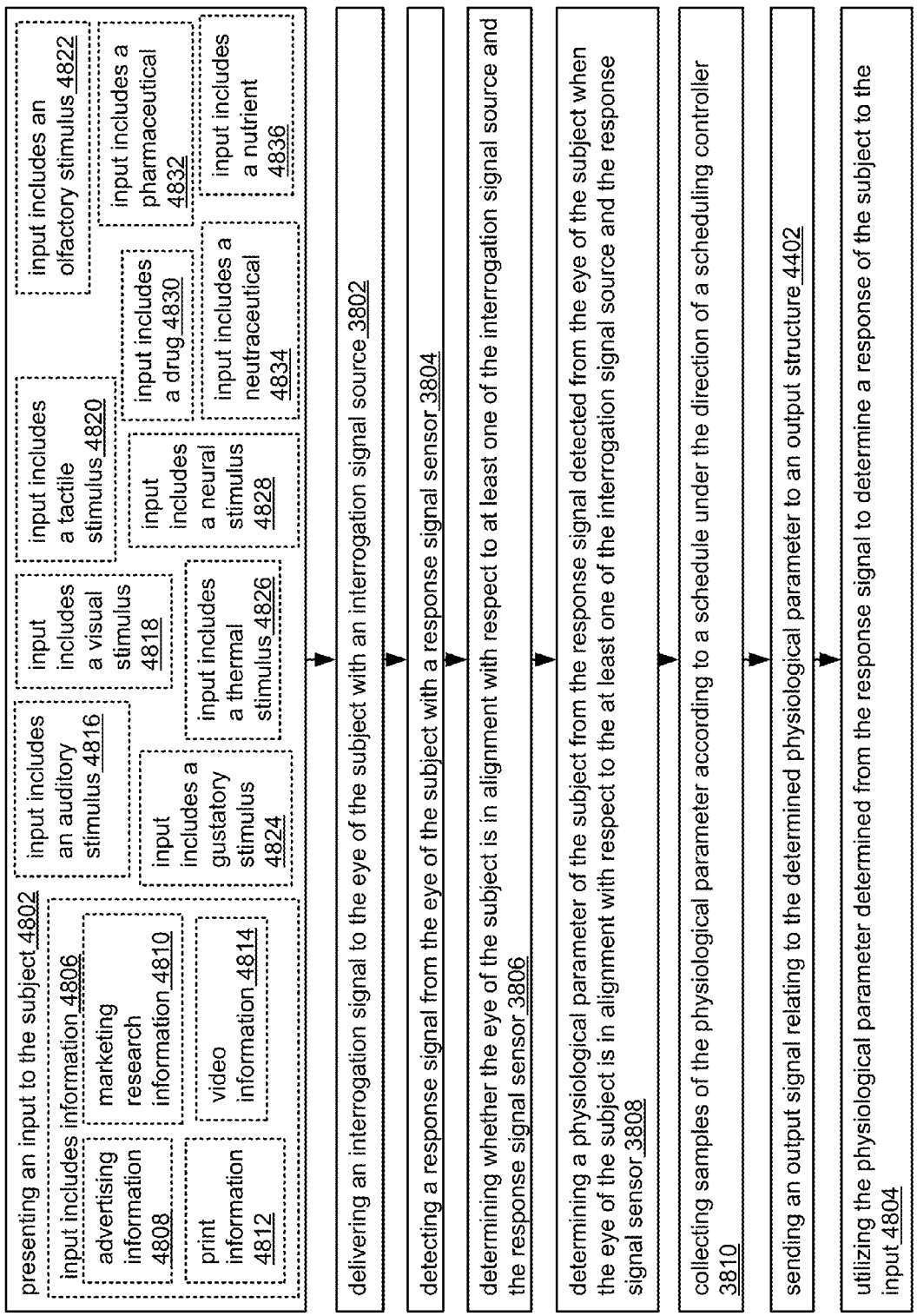
FIG. 48 is a flow diagram of a method of measuring information from an eye of a subject.

A method 4800 shown in FIG. 48 also includes presenting an input to the subject 4802; and utilizing the physiological parameter determined from the response signal to determine a response of the subject to the input 4804. The input can include information 4806 (including, but not limited to advertising information 4808, marketing research information 4810, print information 4812, or video information 4814). The input may include an auditory stimulus 4816, visual stimulus 4818, tactile stimulus 4820, olfactory stimulus 4822, gustatory stimulus 4824, thermal stimulus 4826, neural stimulus 4828, a drug 4830, a pharmaceutical 4832, a nutraceutical 4834, or a nutrient 4836.

Figure 49:
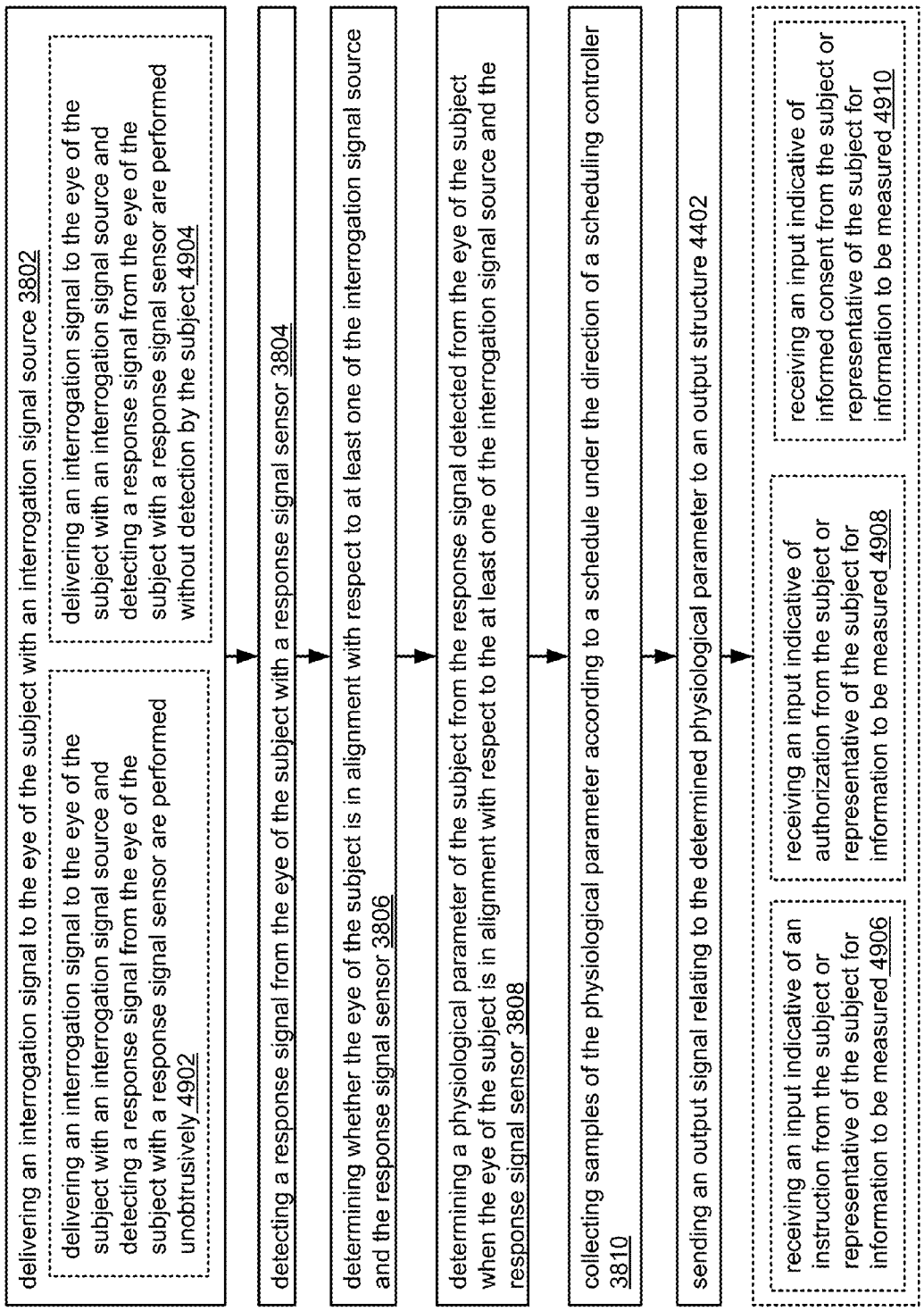
FIG. 49 is a flow diagram of a method of measuring information from an eye of a subject.

As shown in FIG. 49, a method 4900 includes delivering an interrogation signal to the eye of the subject with an interrogation signal source and detecting a response signal from the eye of the subject with a response signal sensor may be performed unobtrusively 4902, as described herein above. In some embodiments, delivering an interrogation signal to the eye of the subject with an interrogation signal source and detecting a response signal from the eye of the subject with a response signal sensor may be performed without detection by the subject 4904. In various aspects, the method may include receiving an input indicative of an instruction from the subject or representative of the subject for information to be measured 4906, receiving an input indicative of authorization from the subject or representative of the subject for information to be measured 4908, or receiving an input indicative of informed consent from the subject or representative of the subject for information to be measured 4910.

Figure 50:
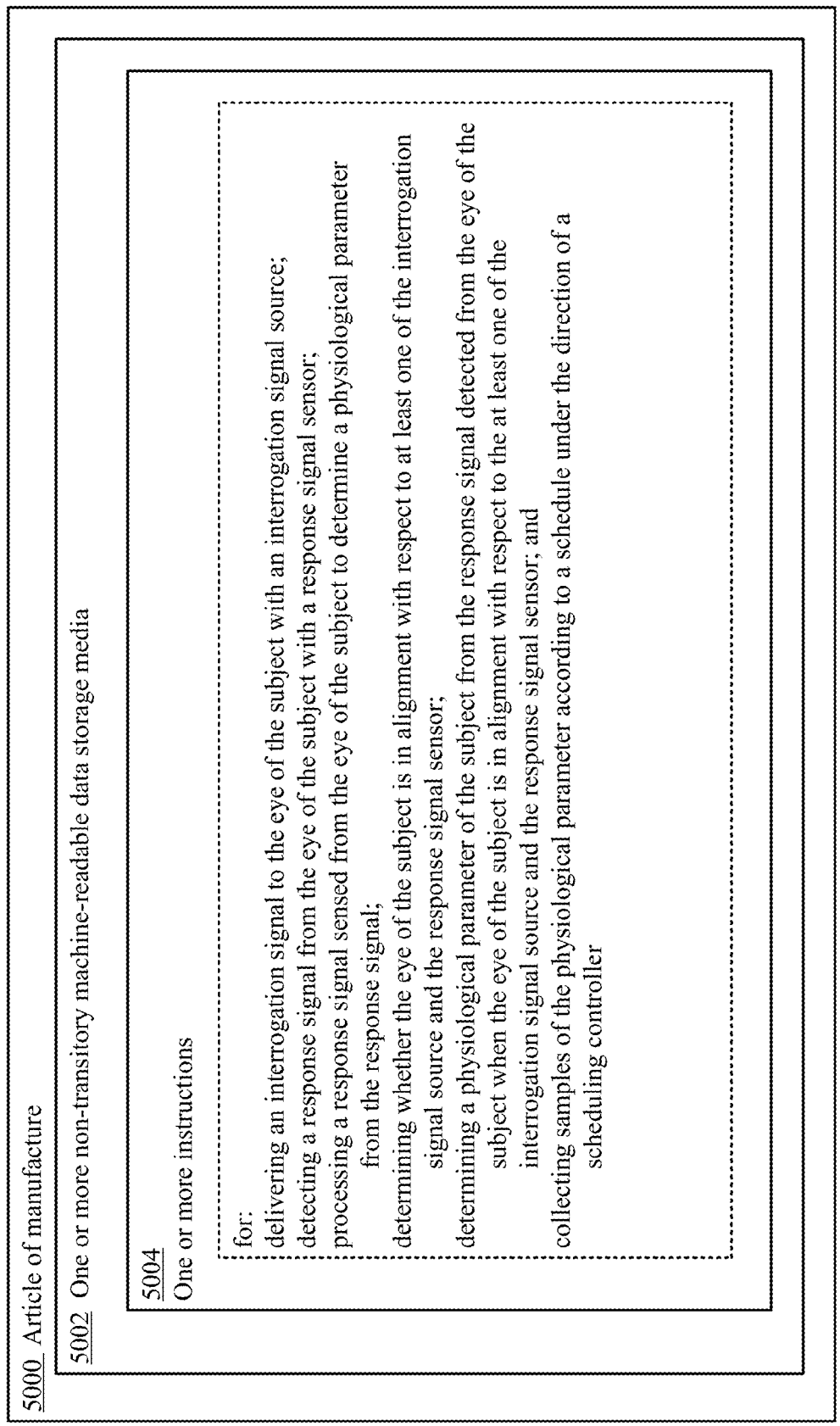
FIG. 50 illustrates an article of manufacture including non-transitory machine-readable data storage media bearing instructions for performing a method of measuring information from an eye of a subject.

FIG. 50 depicts an article of manufacture 5000 that includes one or more non-transitory machine-readable data storage media 5002 bearing one or more instructions 5004 for performing a method as shown in FIG. 38, including delivering an interrogation signal to the eye of the subject with an interrogation signal source; detecting a response signal from the eye of the subject with a response signal sensor; processing a response signal sensed from the eye of the subject to determine a physiological parameter from the response signal; determining whether the eye of the subject is in alignment with respect to at least one of the interrogation signal source and the response signal sensor; determining a physiological parameter of the subject from the response signal detected from the eye of the subject when the eye of the subject is in alignment with respect to the at least one of the interrogation signal source and the response signal sensor; and collecting samples of the physiological parameter according to a schedule under the direction of a scheduling controller.

In one aspect, the one or more non-transitory machine-readable data storage media 5002 bear one or more instructions performing method steps as shown in FIG. 39, e.g. instructions for transmitting at least one of information regarding the subject, information regarding the system used for determining the physiological parameter, or information regarding the physiological parameter to a data processing system. The data storage media 5002 bear one or more instructions for receiving at least one of information regarding the subject, information regarding the system used for determining the physiological parameter, or information regarding the physiological parameter from a data processing system. Data storage media 5002 may bear one or more instructions for sharing at least one of information regarding the subject, information regarding the system used for determining the physiological parameter, or information regarding the physiological parameter between two of more data processing systems. Data storage media 5002 may bear one or more instructions for determining the identity of the subject, for example through the use of facial recognition or retinal recognition, or by comparing login information entered by the subject with login information in a registry, also as shown in FIG. 39.

The data storage media 5002 may bear one or more instructions for performing a method as shown in FIG. 40, including collecting a predetermined number of samples of the physiological parameter during a sampling period. In an aspect data storage media 5002 bear one or more instructions for collecting samples of the physiological parameter with at least a minimum sampling interval between samples. Data storage media 5002 may bear one or more instructions for modifying the procedure for collecting a sample of the physiological parameter if a predetermined number of samples meeting an acceptance criterion has not been collected within a predetermined portion of the sampling period. In another aspect, data storage media bear one or more instructions for modifying the procedure for collecting a sample of the physiological parameter includes modifying the acceptance criterion. The acceptance criterion may include, for example, a signal-to-noise ratio criterion, or a sampling interval criterion.

Data storage media 5002 may bear one or more instructions 5004 for performing a method as shown in FIG. 41, including receiving a gaze signal containing information indicative of a gaze direction of an eye of the subject; determining the gaze direction of the eye of the subject based upon the gaze signal; determining whether the eye of the subject is in alignment with respect to at least one of the interrogation signal source and the response signal sensor based at least in part upon the gaze direction; and determining whether the eye of the subject is in alignment with respect to at least one of the interrogation signal source and the response signal sensor. Data storage media 5002 may bear one or more instructions for determining the physiological parameter from the response signal when the eye of the subject is in alignment with respect to the at least one of the interrogation signal source and the response signal sensor. This may include, for example, one or more instructions for causing alignment of the eye of the subject with respect to the at least one of the interrogation signal source and the response signal sensor if a predetermined number of samples meeting an acceptance criterion has not been collected within a predetermined portion of the sampling period; one or more instructions for causing the alignment of the eye of the subject with respect to the at least one of the interrogation signal source and the response signal sensor by moving at least one of the interrogation signal source and the response signal sensor into alignment with the eye of the subject; or bear one or more instructions for: causing the alignment of the eye of the subject with respect to the at least one of the interrogation signal source and the response signal sensor by activating a gaze attractor adapted to attract the gaze of the subject to thereby cause the eye of the subject to move into alignment with at least one of the interrogation signal source and the response signal sensor.

Data storage media 5002 may include one or more instructions for performing a method as shown in FIG. 42, including one or more instructions for delivering the interrogation signal includes delivering a pulsed interrogation signal. In one aspect, the data storage media may bear one or more instructions for gating detection of the response signal relative to the pulsed interrogation signal. In one aspect, the data storage media may bear one or more instructions for detecting multiple response signals produced by the eye of the subject in response to multiple pulses of the pulsed interrogation signal. The data storage media may in addition bear one or more instructions for combining the multiple response signals produced by the eye of the subject in response to multiple pulses of the pulsed interrogation signal by summing the multiple response signals, by averaging the multiple response signals, by determining a moving average of the multiple response signals, and/or by determining a weighted sum of the multiple response signals, for example.

Data storage media 5002 may bear one or more instructions for performing a method as shown in FIG. 43. In an embodiment, data storage media 5002 bear one or more instructions for delivering an interrogation signal containing multiple wavelengths of light. The data storage media may then also bear one or more instructions for detecting a first response signal produced by the eye of the subject responsive to a first wavelength component of the interrogation signal, and detecting a second response signal produced by the eye of the subject responsive to a second wavelength component of the interrogation signal. In another embodiment, the data storage media bear one or more instructions for delivering a first interrogation signal having a first optical wavelength and a second interrogation signal having a second optical wavelength. Data storage media may bear one or more instructions for determining the physiological parameter of the subject by comparing a first response signal sensed from the eye of the subject in response to the first interrogation signal and a second response signal sensed from the eye of the subject in response to the second interrogation signal.

Data storage media 5002 may bear one or more instructions for performing a method as shown in FIG. 44. In one aspect, data storage media bear one or more instructions for delivering the first interrogation signal simultaneously with respect to the second interrogation signal. In another aspect, data storage media bear one or more instructions for delivering the first interrogation signal sequentially with respect to the second interrogation signal. In various embodiments, the data storage media bear one or more instructions for: sending an output signal relating to the determined physiological parameter to an output structure, which may be, for example, a data transmission structure, data storage structure, a display, an audio output, or a visual output. In an aspect, data storage media 5002 bear one or more instructions for sending the output signal to a display adapted to display information relating to the determined physiological parameter. In some embodiments, data storage media bear one or more instructions for sending the output signal to a video monitor, a computer display, a video game display, a telephone display, or to a data processing device.

Data storage media 5002 may include instructions relating to determination of various different physiological parameters, including, for example, a measurement of a substance in the blood of the subject, such as oxygen, glucose, a salt, a protein, or a lipid, a measurement of a substance in an aqueous humor of the subject, such as oxygen, glucose, a salt, a protein, or a lipid, a hormone, a drug, a pulse rate, a measurement of glycosylated hemoglobin, a temperature, a body temperature, a measurement of blood flow, a measurement of a substance in the eye of the subject.

In an aspect, data storage media 5002 bear one or more instructions for performing a method as shown in FIG. 46, including determining the physiological parameter of the subject from the response signal detected from the eye of the subject at one or more set times. In another aspect, data storage media bear one or more instructions for determining the physiological parameter of the subject from the response signal detected from the eye of the subject at a set time interval. In an aspect, data storage media bear one or more instructions for determining the physiological parameter of the subject from the response signal detected from the eye of the subject according to a programmed schedule. The programmed schedule may be personalized for the subject. The programmed schedule may be selected from among at least two pre-programmed schedules based upon at least one attribute of the subject, and/or based upon the physiological parameter.

In an aspect, the data storage media 5002 bear one or more instructions for performing a method as shown in FIG. 47, including reporting information regarding the physiological trend to an interested party, such as the subject, a medical service provider, a family member, a legal guardian or a legal representative. In another aspect, data storage media bear one or more instructions for comparing the physiological parameter determined from the response signal to a previous measurement of a physiological parameter to determine a physiological trend. The data storage media may also bear one or more instructions for reporting information regarding the physiological trend to an interested party, e.g. one or more of the subject, a medical service provider, a family member, a legal guardian or a legal representative. Data storage media may bear one or more instructions for utilizing the physiological parameter determined from the response signal to assess an emotional state of the subject, and/or one or more instructions for utilizing the physiological parameter determined from the response signal to assess the alertness of the subject. Data storage media may bear one or more instructions for utilizing the physiological parameter determined from the response signal in a medical or health-related application, or one or more instructions for utilizing the physiological parameter determined from the response signal in a business or security application.

In one aspect, data storage media 5002 bear one or more instructions for performing a method as shown in FIG. 48, including presenting an input to the subject; and utilizing the physiological parameter determined from the response signal to determine a response of the subject to the input. For example, the input may include information (advertising information, marketing research information, print information, or video information, for example), an auditory stimulus, a visual stimulus, a tactile stimulus, an olfactory stimulus, a gustatory stimulus, a thermal stimulus, a neural stimulus, a drug, a pharmaceutical, a nutraceutical, or a nutrient.

Data storage media 5002 may include instructions 5004 for performing a method as shown in FIG. 49, including delivering an interrogation signal to the eye of the subject with an interrogation signal source and detecting a response signal from the eye of the subject with a response signal sensor are performed unobtrusively, and/or without detection by the subject. Data storage media may include one or more instructions for receiving an input indicative of an instruction from the subject or representative of the subject for information to be measured, receiving an input indicative of authorization from the subject or representative of the subject for information to be measured, or receiving an input indicative of informed consent from the subject or representative of the subject for information to be measured.

Figure 51:
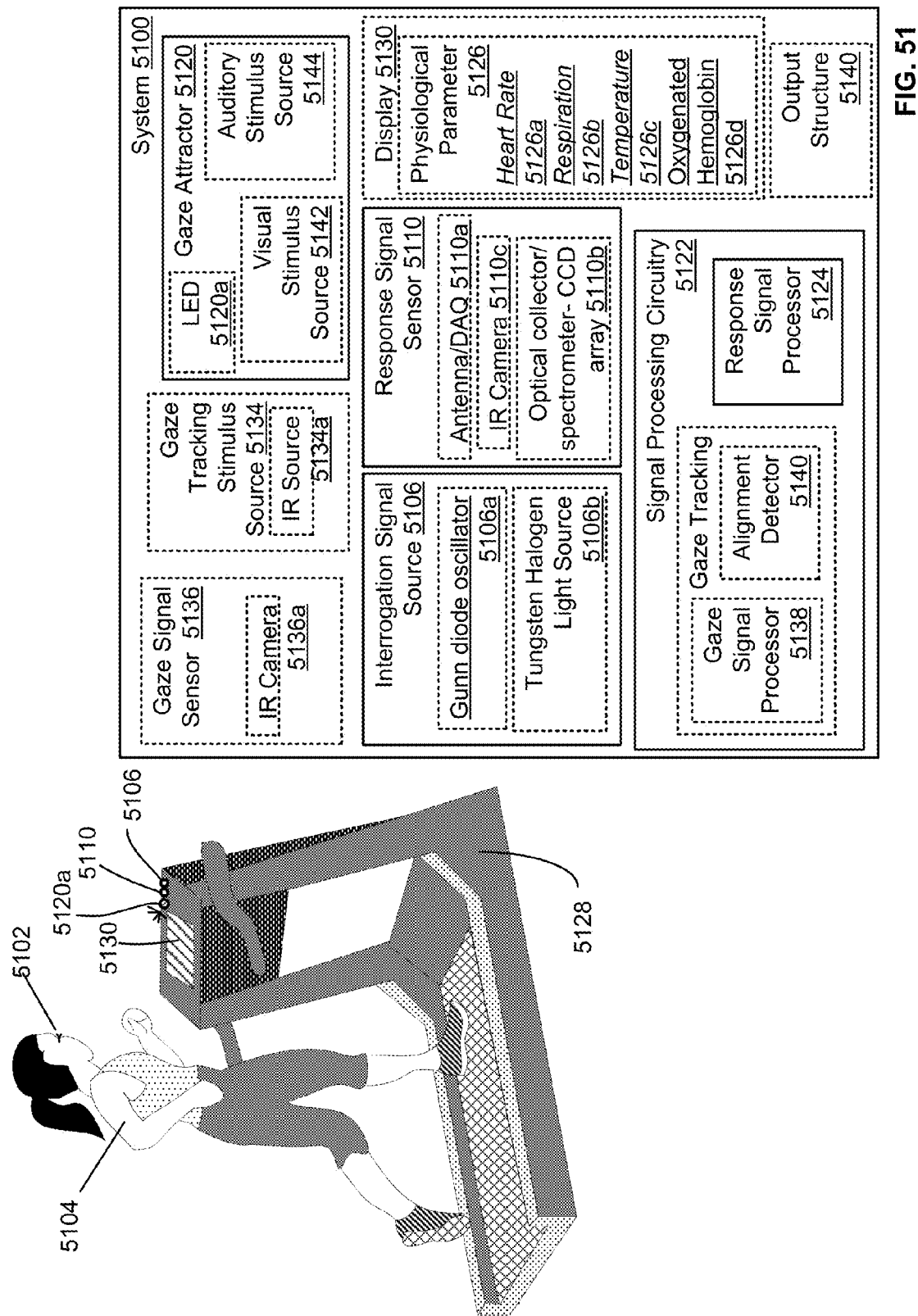
FIG. 51 illustrates an embodiment of a system for sensing information from an eye of a subject.

FIG. 51 depicts a system 5100 for sensing information from an eye 5102 of a subject 5104, which includes an interrogation signal source 5106 for delivering an interrogation signal to eye 5102 of a subject 5104; a response signal sensor 5110 for sensing a response signal produced by the eye 5102 of the subject 5104 responsive to the interrogation signal; a gaze attractor 5120 adapted to attract the gaze of the subject 5104 to thereby cause the eye of the subject to move into alignment with at least one of the interrogation signal source 5106 or the response signal sensor 5110; and signal processing circuitry 5122 including: a response signal processor 5124 configured to process a response signal sensed from the eye of the subject when the eye of the subject is in alignment with respect to the at least one of the interrogation signal source 5106 or the response signal sensor 5110 to determine a physiological parameter 5126 from the response signal. System 5100 is discussed connection with an example of an eye interrogation system incorporated into a treadmill 5128, for monitoring and display of physiological parameters. However, various other implementations of system 5100 will be apparent to a person having ordinary skill in the art, based on the disclosure presented herein.

EXAMPLE 4

An Eye Interrogation System on a Treadmill to Monitor and Display Physiological Parameters A noncontact eye interrogation system 5100 which measures and displays physiological parameters 5126 to a runner is built into treadmill 5128. The eye interrogation system includes gaze attraction and tracking components to align the runner's eyes with an interrogation signal source 5106 and a response signal sensor 5120. The system includes a signal processing circuitry to activate the interrogation source 5106 and response signal sensor 5110 during exercise and to obtain physiological data from the detected signals. The noncontact eye interrogation system 5100 unobtrusively monitors and displays heart rate, respiration rate, body temperature, and oxygen saturation in the blood. In the example shown in FIG. 51, the system may include signal processing circuitry (including hardware and software) that causes the physiological parameter 5126 to be displayed on a liquid crystal display (LCD) 5130 display on the treadmill 5128.

To align the runner's eyes with the interrogation signal source 5106, gaze attractor 5120 is incorporated in the system. A gaze attractor 5120 may be a light that draws attention while the runner exercises, as shown in FIG. 51. For example, the eye interrogation system may have a LED gaze attractor 5120a which flashes and draws the runner's gaze to the vicinity of interrogation source 5106 and response signal sensor 5110 when a physiological parameter 5126 is to be measured. Signal processing circuitry 5122 may activate the LED 5120a and interrogation system according to a preset schedule, e.g. every 10 minutes, or according to the runner's preset preferences. A gaze tracking system is used to detect when the runner looks at the LED gaze attractor 5120a, interrogation signal source 5106 and response signal sensor 5110. The gaze tracking system is comprised of a gaze tracking stimulus source 5134 that is an IR light source 5134a and a gaze signal sensor 5136 that is an IR camera 5136a which detects the reflection of IR light from the eyes of the runner. Eye position, eye rotation, eye gaze position against screen, pupil diameter and eye vergence distance may be monitored. The gaze tracking system includes software and circuitry forming gaze signal processor 5138 to analyze the gaze tracking data and alignment detector 5140 to detect alignment of the runner's gaze with the interrogation source and/or the interrogation detectors. Alignment of the runner's eyes with the interrogation signal source 5106 and response signal sensor 5110 triggers activation of the interrogation signal source 5106 by the signal processing circuitry 5122.

To monitor the runner's heart rate 5126a and respiration 5126b the eye interrogation system is equipped with an interferometry system that detects movement of an individual's chest wall. Construction of an interferometer, data acquisition systems and signal processing algorithms to determine heart rate and respiration are described (see e.g., U.S. Pat. No. 7,272,431 issued to McGrath on Sep. 18, 2007 and Mikhelson et al., *IEEE Transactions on Biomedical Engineering*, 58: 1671-1677, 2011 which are incorporated herein by reference). For example a continuous wave millimeter-wave interferometer is constructed integral to the eye interrogation system. A continuous wave 94-GHz signal is generated by a cavity-tuned Gunn diode oscillator 5106a and transmitted at the runner with a Gaussian (quasi-optical) antenna with a lens that results in a far-field starting at approximately 0.5 meter and a beam divergence of approximately 1.5 degrees. The gaze tracking system (see above) is used to establish alignment of the oscillator and antenna on the runner's chest and to signal activation of the interferometer. Interferometer components include a Gunn diode oscillator 5106a (94 GHz) a circulator, a Gaussian antenna and beam splitters and mixers. To acquire the reflected wave signals a 24 bit data acquisition device (DAQ 5110a) (e.g., "24-Bit, 102.4 kS/s, 8 and 4-Channel Dynamic Signal Acquisition" available from National Instruments, Austin, Tex.; see the Data sheet: "DAQ Device" which is incorporated herein by reference) is used with LabView data acquisition software. The vibration signals may be processed with programs written in MATLAB to derive chest displacements (respiration) and heart beats from the reflected wave signals (see e.g., Mikhelson et al., Ibid.). Heart rate and respiration data are analyzed and displayed by system circuitry and software. The data may be displayed on a LCD on the treadmill and the runner may be alerted when maximum heart rate is exceeded. Abnormal heart rate may also be transmitted to a healthcare worker or medic.

To monitor the runner's temperature 5126c an infrared thermometer is incorporated in the eye interrogation system which remotely measures temperature in the eye. Following alignment of the runner's eye with the infrared thermometer the thermometer is activated. An infrared thermometer comprised of a detector, collecting optical system (e.g., lens and filter) and signal processing circuitry is incorporated in the eye interrogation system. The filter limits the spectrum of infrared radiation detected and the lens' optical characteristics determine the target size within the eye and the allowed distance from the runner's eye. The detector converts infrared energy into an electrical signal which is amplified and processed by the associated signal processors to calculate temperature of the eye. An infrared thermometer suitable for sensitive temperature measurement (i.e., approximately 0.1 degree Centigrade) that may be targeted to the iris/pupil region or to the sclera is described (see e.g., U.S. Pat. No. 5,115,815 issued to Hansen on May 26, 1992 which is incorporated herein by reference). For example an infrared camera 5110c may be used to measure corneal temperature (see e.g., Kessel et al., Investigative Ophthalmology and Visual Science 51: 6593-6597, 2010 which is incorporated herein by reference). An infrared camera 5110c with a focal plane array detector, thermal sensitivity ≤0.09 degrees C. and an accuracy of 0.1 degrees C. is available from Fluke Corp., Everett, Wash. (see e.g., "Fluke Industrial/Electrical Thermal Imagers, Models: Ti25 and Ti10" Datasheet which is incorporated herein by reference). To summarize, during exercise on the treadmill the LED gaze atrractor 5120a lights up and the gaze tracking system detects alignment of the runners' eye with the infrared thermometer. Next the system controller activates the infrared thermometer and signal processors determine eye temperature from the infrared radiation. The runner's temperature data are displayed on display 5130 of treadmill 5128 and may be transmitted to a remote device, e.g., a computer (not shown) for analysis and storage. For example, analysis of corneal eye temperatures shows that they may be correlated with core body temperatures (see e.g., Kessel et al., Ibid.). If safe core body temperatures are exceeded the eye interrogation system may alert the runner on the system LCD and alert health care workers by email.

To measure the runner's oxygenation of hemoglobin 5126d, the eye interrogation system may also incorporate an interrogation light source and response signal sensor to measure oxyhemoglobin and deoxyhemoglobin in the fundus of the eye. An apparatus and methods to measure oxyhemoglobin and deoxyhemoglobin in the eye are described (see e.g. U.S. Pat. No. 6,149,589 issued to Diaconu et al. on Nov. 21, 2000 which is incorporated herein by reference). An interrogation source 5106 that generates wavelengths between 450 nm and 850 nm is integrated in the eye interrogation system (see FIG. 8). For example a tungsten halogen light source with a wavelength range of 360 nm to 2000 nm in wavelength is available from Ocean Optics, Dunedin, Fla. See e.g., the Specification Sheet: "HL-2000 Tungsten Halogen Light Sources" which is incorporated herein by reference. The optical system may include lenses and filters to focus and limit the wavelength spectrum of the light beam. Light reflected from the eye is detected by a response signal sensor 5110 which is also located in the interrogation system. The response signal sensor 5100 may include an optical collector and a spectrometer to determine the reflected spectrum. For example the collector may include a collimating lens assembly with a single aspheric lens with a field of view of approximately 45 degrees (e.g., a 74-DA Collimating Lens (200-2000 nm) is available from Ocean Optics, Dunedin, Fla.). The lens attaches to a spectrometer for increased light throughput and collects collimated light in a straight path of open air and focuses it on to a spectrometer's slit. The spectrometer may be a fiber optic spectrometer with a CCD-array detector and an analog to digital converter with programmable circuitry. For example a miniature fiber optic spectrometer with a 2048-element CCD-array detector with a range of 200-1100 nm and a grating with a spectral range of 625 nm with best efficiency from 530 nm to 1100 nm is available from Ocean Optics, Dunedin, Fla. (see e.g., the Specification Sheet: USB2000+ Miniature Fiber Optic Spectrometer which is incorporated herein by reference). The spectrometer has a microcontroller and USB connector to allow activation and programming of the spectrometer by a computer.

The spectrum of reflected light emanating from the fundus of the eye is detected by the CCD array and electronic signals are processed to derive the absorption spectrum for the runner's eye. Absorption peaks between 500 nm and 600 nm may be analyzed to determine the fraction of oxygenated hemoglobin (see e.g., Dianconu et al., Ibid.). Computation of the reflectance spectra and comparison to reference spectra for oxygenated and deoxygenated hemoglobin permits calculation of the percentage oxygenation of total hemoglobin in the runner's eye. The percent oxyhemoglobin may be displayed on the LCD display 5130 of the treadmill 5128 and the runner may be alerted if the percentage of oxygenated hemoglobin falls below healthy levels. The percent oxyhemoglobin data may also be sent to healthcare workers or exercise physiologists.

In an embodiment, system includes a gaze signal sensor 5136 adapted for receiving a gaze signal containing information indicative of a gaze direction of an eye of the subject; a gaze signal processor 5138 configured to determine the gaze direction of the eye of the subject based upon the gaze signal; and an alignment detector 5140 configured to determine whether the eye of the subject is in alignment with respect to at least one of the interrogation signal source 5106 or the response signal sensor 5110 based at least in part upon the gaze direction.

In an embodiment, the response signal sensor 5110 is adapted to sense a response signal from an interior of the eye of the subject responsive to the interrogation signal, for example, from a lens, aqueous humor, vitreous humor, and/or retina of the eye of the subject responsive to the interrogation signal.

As depicted in FIG. 51, gaze signal sensor 5136 and the response signal sensor 5110 can be different sensors. However, in some embodiments, gaze signal sensor 5136 and the response signal sensor 5110 are the same sensor. In some embodiments, gaze signal sensor 5136 includes an infrared camera or CCD camera.

System 5100 can include an interrogation signal source 5106 that includes a broad spectrum light source and response signal sensor 5110 that includes a spectrometer based on a CCD array. In other embodiments, interrogation signal source 5106 includes a near-infrared light source and response signal sensor 5110 includes a near-infrared camera, interrogation signal source 5106 includes a tunable laser source and response signal sensor 5110 includes a Raman spectrometer based on a CCD camera, interrogation signal source 5106 includes a mid-infrared light source and the response signal sensor 5110 includes a mid-infrared detector, or interrogation signal source 5106 includes a tunable laser source and response signal sensor 5110 includes a broad spectrum pyroelectric detector, for example.

In some embodiments, the response signal is indicative of a feature of the vasculature of the eye of the subject, or indicative of a biometric identification of the subject.

As shown in FIG. 51, system 5110 can include at least one gaze tracking stimulus source 5134 adapted to deliver a gaze tracking stimulus to at least an eye of a subject, wherein the gaze signal is produced in response to the gaze tracking stimulus. In one embodiment, gaze tracking stimulus source 5134 includes an infra-red source. In connection therewith, gaze signal sensor 5136 includes an infra-red sensor. In another embodiment, gaze tracking stimulus source 5134 can include a near infra-red source, and gaze signal sensor 5136 can include a near infra-red sensor.

Gaze tracking stimulus source 5134 may include a single light source, or a plurality of light sources. Gaze signal sensor 5136 can include an optical sensor, optical sensor array, camera, or plurality of gaze signal sensors.

In an embodiment, interrogation signal source 5106 is adapted to produce light having a first polarization, and the response signal sensor is adapted to detect light having a second polarization, wherein the first polarization and the second polarization are the same. In an embodiment, interrogation signal source is adapted to produce light having a first polarization, and the response signal sensor is adapted to detect light having a second polarization, wherein the first polarization and the second polarization are different. See, e.g. discussion in connection with FIG. 12.

In an embodiment, interrogation signal source 5106 is adapted to deliver a pulsed interrogation signal. At least one of the response signal sensor 5110 and signal processing circuitry 5122 is configured to gate detection of the response signal relative to the pulsed interrogation signal. Signal processing circuitry 5122 may be configured to combine multiple response signals produced by the eye of the subject in response to multiple pulses of the pulsed interrogation signal, e.g., by summing or averaging the multiple response signals, or determining a moving average or weighted sum of the multiple response signals. See, e.g., discussion in connection with FIG. 6.

In an embodiment, the interrogation signal source 5106 is adapted to deliver an interrogation signal containing multiple wavelengths of light, as discussed generally in connection with FIG. 7. System 5100 may include at least a first response signal sensor configured to sense a first response signal produced by the eye of the subject responsive to a first wavelength component of the interrogation signal, and a second response signal sensor configured to sense a second response signal produced by the eye of the subject responsive to a second wavelength component of the interrogation signal. In an embodiment, system 5100 includes at least a first interrogation signal source configured to deliver a first interrogation signal having a first optical wavelength and at least a second interrogation signal source configured to deliver a second interrogation signal having a second optical wavelength. Signal processing circuitry 5100 may then be configured to process a first response signal sensed from the eye of the subject in response to the first interrogation signal and a second response signal sensed from the eye of the subject in response to the second interrogation signal by comparing the first and second response signals to determine the physiological parameter. System can be configured to deliver the first interrogation signal simultaneously with respect to the second interrogation signal, or sequentially with respect to the second interrogation signal. Further details regarding this approach are provided in connection with FIG. 7.

In some embodiments, interrogation signal source 5106 and the response signal sensor 5110 are co-aligned. In other embodiments, interrogation signal source 5106 and the response signal sensor 5110 are separately aligned and located.

System 5100 also can also include an output structure 5140 adapted to output a signal relating to the determined physiological parameter 5126. Output structure may include, for example, data storage structure, display, audio output, or visual output, as discussed herein above, and depicted, e.g., in FIG. 8. System may include a display (e.g. display 5130) adapted to display information relating to the determined physiological parameter 5126. The display can be a video monitor, computer display, video game display, telephone display, or terminal of a data processing device, for example. In various embodiments, the display 5130 can be incorporated in a wearable item, an article of furniture, an article of medical or health-care related equipment, an article of exercise equipment (as illustrated in FIG. 51), or a vehicle. Examples of such displays are described in greater detail herein above.

Physiological parameter 5126 may be a measurement of oxygenation, blood glucose, heart rate, glycosylated hemoglobin, temperature, body temperature, blood flow, or a substance in the eye of the subject.

In some embodiments, gaze attractor 5120 includes a visual stimulus source 5142 for delivering a visual stimulus to attract the gaze of the subject. For example, the visual stimulus source 5120 can be a mirror, light source (such as an LED), or video display. In one aspect, the visual stimulus source 5120 is adapted for attachment to various types of displays or other items that the subject may look at, or toward which a subject may turn his or her head or direct his or her gaze during use of, attention to, or interaction with the item. Items to which a visual stimulus source may be attached include a video display, computer display, video game display, television, terminal of a data processing device, smart phone, smart book, book, article of furniture, article of medical equipment, or article of exercise equipment.

Visual stimulus source 5142 may be adapted to produce a visual stimulus that differs from a visual background in some manner, for example, a visual stimulus that includes a different light intensity, different optical wavelength, different temporal pattern of light intensity, different temporal pattern of optical wavelength, different spatial pattern of light intensity, or different spatial pattern of optical wavelength relative to a visual background. Visual stimulus source 5142 may be adapted to produce a visual stimulus that includes an image, a moving image, or text. In one aspect, at least one visual stimulus source 5142 is configured such that when the gaze of the subject is directed toward the visual stimulus the eye of the subject will be brought into alignment with respect to the at least one of the interrogation signal source 5106 or the response signal sensor 5110.

In another aspect, gaze attractor 5120 includes at least one auditory stimulus source 5144 for delivering a localized auditory stimulus to attract the gaze of the subject. At least one auditory stimulus source 5144 can be configured such that when the gaze of the subject is directed toward the auditory stimulus the eye of the subject will be brought into alignment with respect to the at least one of the interrogation signal source 5106 or the response signal sensor 5110. In an embodiment, gaze attractor 5120 includes at least one auditory stimulus source 5144 and at least one visual stimulus source 5142 configured to deliver at least one auditory stimulus and at least one visual stimulus in sequence. In an embodiment, gaze attractor includes at least one auditory stimulus source 5144 and at least one visual stimulus source 5142 configured to deliver at least one auditory stimulus and at least one visual stimulus simultaneously.

Figure 52:
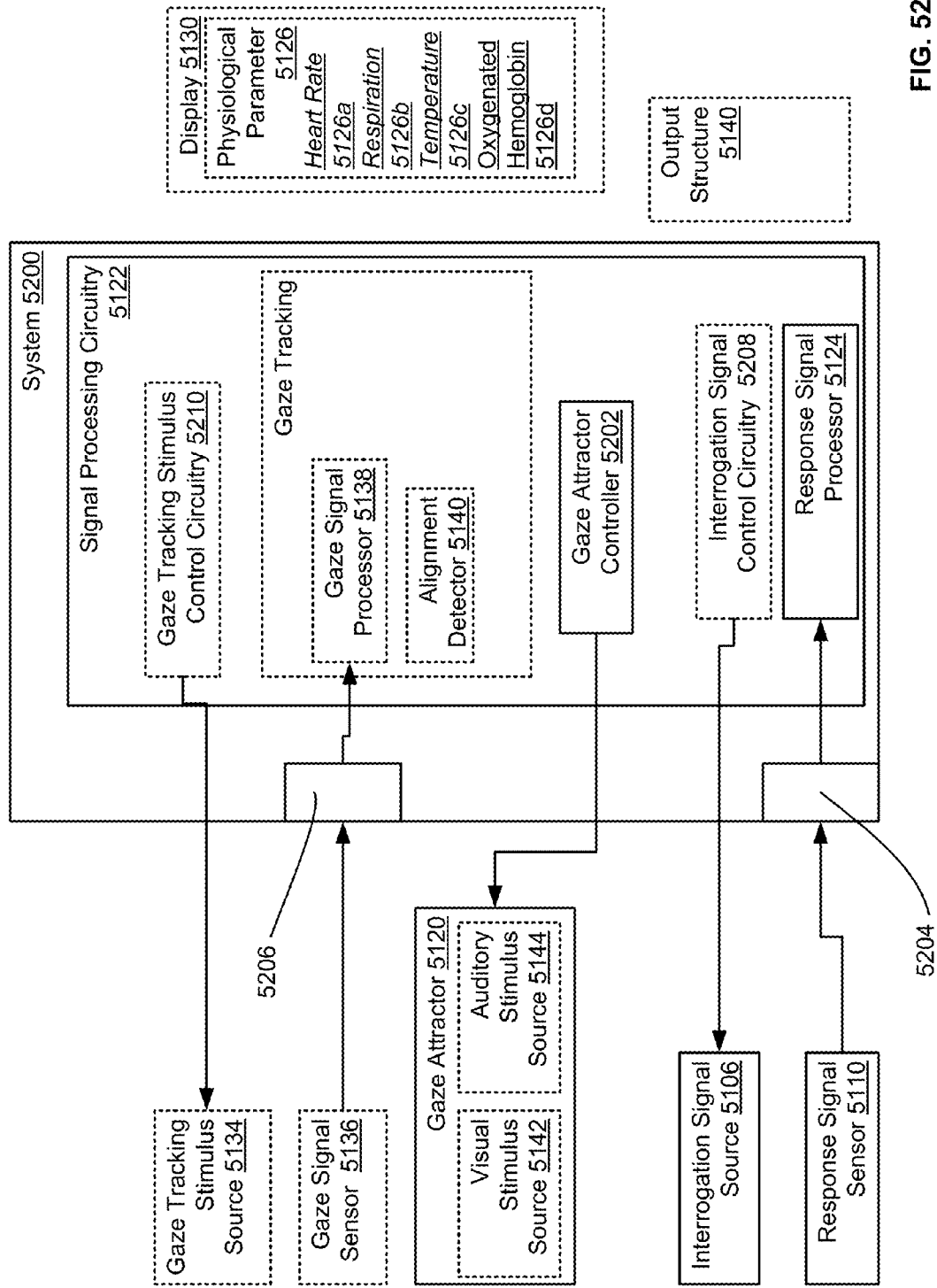
FIG. 52 is a block diagram of a system for controlling the sensing of information from an eye of a subject.

FIG. 52 is a schematic diagram of a system 5200 for controlling the sensing of information from an eye of a subject, including signal processing circuitry 5122 including: a gaze attractor controller 5202 adapted to drive a gaze attractor 5120 to cause the eye of the subject to move into alignment with at least one of an interrogation signal source 5106 or the response signal sensor 5110; a response signal input 5204 adapted to receive a response signal sensed from the eye of the subject by a response signal sensor 5110 responsive to delivery of an interrogation signal to the eye of the subject; and a response signal processor 5124 configured to process a response signal sensed from the eye of the subject when the eye of the subject is in alignment with respect to the at least one of the interrogation signal source 5106 or the response signal sensor 5110 to determine a physiological parameter 5126 from the response signal.

System 5200 may further include a gaze signal input 5206 adapted to receive a gaze signal containing information indicative of a gaze direction of the eye of the subject sensed from at least an eye of the subject; a gaze signal processor 5138 configured to determine the gaze direction of the eye of the subject based upon the gaze signal; and an alignment detector 5140 configured to determine whether the eye of the subject is in alignment with respect to at least one of the interrogation signal source 5106 or the response signal sensor 5110 based at least in part upon the gaze direction.

Response signal processor 5124 can be configured to process the response signal to determine a feature of the vasculature of the eye of the subject, or to determine a biometric identification of the subject, as discussed herein above.

In one aspect, gaze attractor controller 5202 is adapted to drive a visual stimulus source 5142 for delivering a visual stimulus to attract the gaze of the subject. The visual stimulus source may be, for example, a mirror, a light source, or a video display. In one aspect, gaze attractor controller 5202 is adapted to drive the visual stimulus source to produce a visual stimulus that differs from a visual background, which may be, for example, a visual stimulus that includes a different light intensity, different optical wavelength, different temporal pattern of light intensity, different temporal pattern of optical wavelength, different spatial pattern of light intensity, or different spatial pattern of optical wavelength relative to a visual background.

Gaze attractor controller 5202 may be adapted to drive the visual stimulus source 5142 to produce a visual stimulus that includes an image, a moving image, or text. In another aspect, gaze attractor controller 5202 is adapted to drive at least one auditory stimulus source 5144 for delivering a localized auditory stimulus to attract the gaze of the subject. In another aspect, gaze attractor controller 5120 is adapted to drive at least one auditory stimulus source 5144 and at least one visual stimulus source 5142 to deliver at least one auditory stimulus and at least one visual stimulus in sequence. In yet another aspect, gaze attractor controller 5202 is adapted to drive at least one auditory stimulus source 5144 and at least one visual stimulus source 5142 to deliver at least one auditory stimulus and at least one visual stimulus simultaneously.

In an embodiment, system 5200 includes interrogation signal control circuitry 5208 configured to drive production of the interrogation signal by the interrogation signal source 5106.

In an embodiment, system includes gaze tracking stimulus control circuitry 5210 configured to drive production of a gaze tracking stimulus by a gaze tracking stimulus source 5134, wherein the gaze tracking stimulus is adapted to cause production of the gaze signal the eye of the subject. In an embodiment, gaze tracking stimulus control circuitry 5210 is configured to drive production of a gaze tracking stimulus by a plurality of gaze tracking stimulus sources, e.g. as described herein above. Response signal processor 5124 may be adapted to process a response signal sensed from an interior of the eye of the subject responsive to the interrogation signal, e.g., from a lens, aqueous humor, vitreous humor, or retina of the eye of the subject responsive to the interrogation signal.

In an aspect, response signal processor 5124 is configured to process the response signal to determine a feature of the vasculature of the eye of the subject. In one aspect, response signal processor 5124 is configured to process the response signal to determine a biometric identification of the subject.

Gaze signal input 5206 and response signal input 5204 can be separate inputs, as depicted in FIG. 52, or the same input, for example as in FIG. 4. In an embodiment, gaze signal input 5206 is adapted to receive a signal from a camera.

In an embodiment, signal processing circuitry 5122 includes a plurality of gaze signal inputs (generally as depicted in FIG. 12) adapted to receive a plurality of gaze signals containing information indicative of a gaze direction of the eye of the subject sensed from at least an eye of the subject.

In an embodiment, response signal processor 5124 is configured to process the response signal by determining a first response signal at a first polarization, determining a second response signal at a second polarization, and comparing the response signal determined at the first polarization to the response signal determined at the second polarization, wherein the first polarization and the second polarization are different, as discussed herein above, e.g. in connection with FIG. 12.

Response signal processor 4125 can be configured to process the response signal sensed from the eye of the subject by the response signal sensor 5110 when the eye of the subject is in alignment with respect to the at least one of the interrogation signal source 5106 or response signal sensor 5110 to determine a measurement of oxygenation, blood glucose, heart rate, or glycosylated hemoglobin, temperature, body temperature, blood flow, or a substance in the eye of the subject from the response signal, for example.

In one aspect, interrogation signal control circuitry 5208 is configured to drive production of a pulsed interrogation signal by the interrogation signal source, as described generally herein above in connection with FIG. 6. Signal processing circuitry 5122 may be configured to gate detection of the response signal relative to the pulsed interrogation signal. Signal processing circuitry 5122 may be configured to combine multiple response signals produced by the eye of the subject in response to multiple pulses of the pulsed interrogation signal, for example by summing or averaging the multiple response signals, or determining a moving average or weighted sum of the multiple response signals.

In one aspect, a system 5200 includes interrogation signal control circuitry 5208 configured to drive production of a first interrogation signal having a first optical wavelength and production of a second interrogation signal having a second optical wavelength. Signal processing circuitry 5122 may then be configured to process a first response signal sensed from the eye of the subject in response to the first interrogation signal and a second response signal sensed from the eye of the subject in response to the second interrogation signal by comparing the first and second response signals in order to determine the physiological parameter. Signal processing circuitry 5122 may be configured to drive production of the first interrogation signal simultaneously with respect to the second interrogation signal, or configured to drive production of the first interrogation signal sequentially with respect to the second interrogation signal.

In another aspect, system 5200 includes an output structure 5140 adapted to output a signal relating to the determined physiological parameter. Output structure can include, for example, a data transmission structure, data storage structure, display, audio output, or visual output, as described herein above. In an aspect, system 5200 includes a display 5130 adapted to display information relating to the determined physiological parameter 5126.

Figure 53:
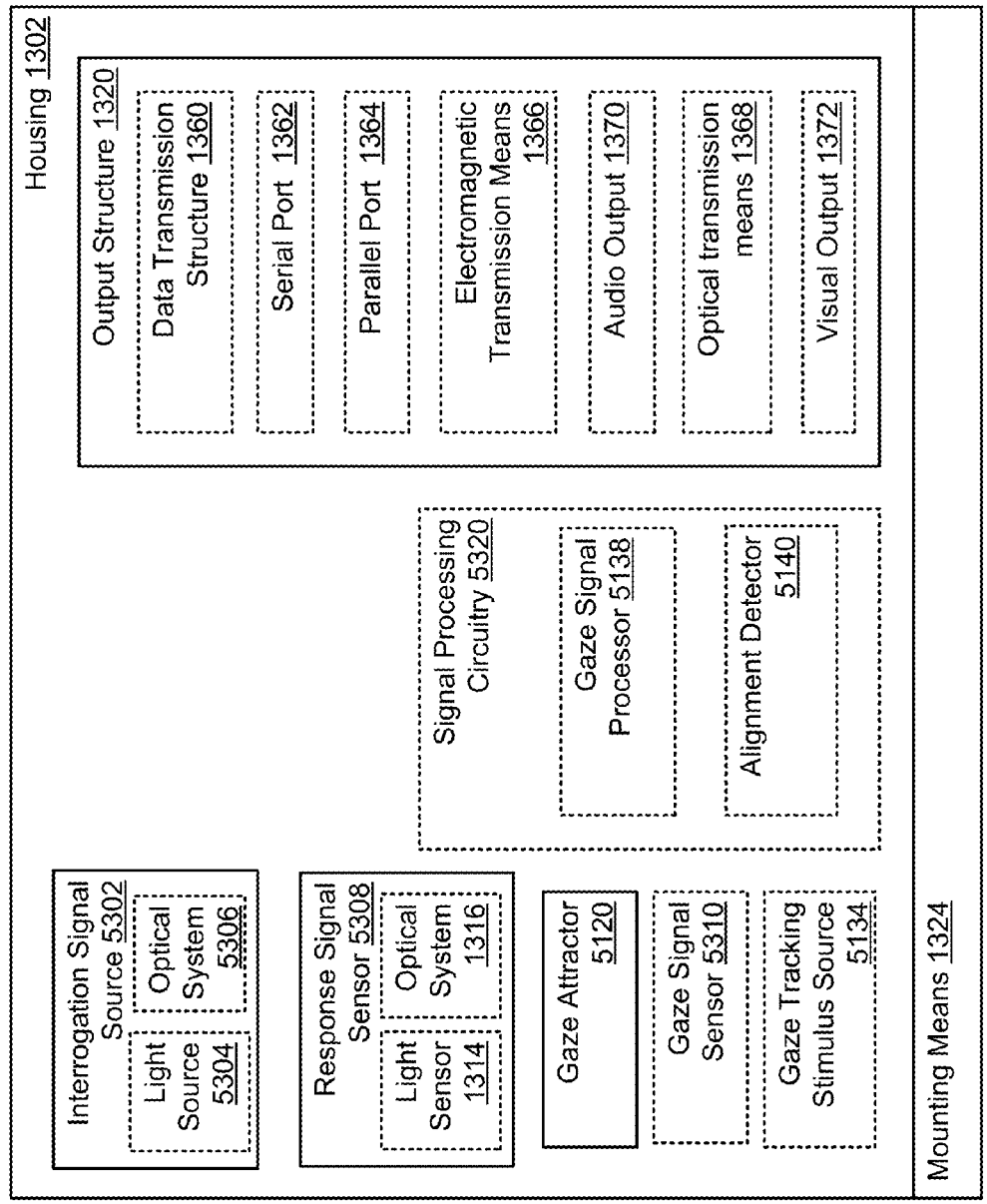
FIG. 53 is a block diagram of an embodiment of a system for sensing information from an eye of a subject.

FIG. 53 depicts a system 5300 that includes a housing 1302; an interrogation signal source 5302 housed in the housing 1302 and adapted for delivering an interrogation signal to an eye of a subject, the interrogation signal source 5302 including at least one light source 5304 and at least one optical system 5306; a response signal sensor 5308 housed within the housing 1302 and adapted for sensing a response signal produced by the eye of the subject responsive to the interrogation signal, the response signal containing information regarding a physiological parameter of the subject; a gaze attractor 5120 adapted to attract the gaze of the subject to thereby cause the eye of the subject to move into alignment with at least one of the interrogation signal source 5302 or the response signal sensor 5308; an output structure 1320 adapted for transmitting an output signal; mounting means 1324 adapted for mounting the housing with respect to a display in such a manner that the interrogation signal source 5302 and response signal sensor 5308 are alignable with the eye of the subject during normal use of the display by the subject.

In an aspect, mounting means 1324 is adapted for mounting the housing 1302 with respect to the display such that during normal use of the display by the subject, the interrogation signal source 5302 and response signal sensor 5308 are positioned within the visual field of at least one eye of the subject. In an aspect, mounting means 1324 is adapted for mounting the housing 1302 with respect to the display such that the interrogation signal source 5302 and response signal sensor 5308 are oriented in substantially the same direction as the display surface of the display.

In an embodiment, system 5300 includes a gaze signal sensor 5310 adapted for receiving a gaze signal containing information indicative of a gaze direction of an eye of the subject. Gaze signal sensor 5310 may include, for example, an optical sensor, an optical sensor array, a camera, and/or a plurality of gaze signal sensors.

System 5300 may also include a gaze signal sensor processor 5138 configured to determine the gaze direction of the eye of the subject based upon the gaze signal; and an alignment detector 5140 configured to determine whether the eye of the subject is in alignment with respect to at least one of the interrogation signal source 5302 or the response signal sensor 5308 based at least in part upon the gaze direction.

Gaze signal sensor 5310 and the response signal sensor 5308 can be the same sensor, or different sensors. Gaze signal sensor 5310 may include, for example, an infrared camera or a CCD camera.

In an embodiment, interrogation signal source 5302 includes a broad spectrum light source and the response signal sensor 5308 includes a spectrometer based on a CCD array. In other embodiments, interrogation signal source 5302 includes a near-infrared light source and response signal sensor 5308 includes a near-infrared camera, interrogation signal source 5302 includes a tunable laser source and the response signal sensor 5308 includes a Raman spectrometer based on a CCD camera, interrogation signal source 5302 includes a mid-infrared light source and response signal sensor 5308 includes a mid-infrared detector, or interrogation signal source 5302 includes a tunable laser source and response signal sensor 5308 includes a broad spectrum pyroelectric detector.

In an embodiment, system 5300 includes at least one gaze tracking stimulus source 5134 adapted to deliver a gaze tracking stimulus to at least an eye of a subject, wherein the gaze signal is produced in response to the gaze tracking stimulus. In an embodiment, gaze tracking stimulus source 5134 includes an infra-red source; gaze signal sensor 5310 may then include an infra-red sensor. In an embodiment, gaze tracking stimulus source 5134 includes a near infra-red source and gaze signal sensor 5310 includes a near infra-red sensor. In some embodiments, gaze tracking stimulus source 5134 includes a plurality of light sources.

In an aspect, response signal sensor 5308 is adapted to sense a response signal from an interior of the eye of the subject responsive to the interrogation signal, e.g., from a lens, aqueous humor, vitreous humor, or retina of the eye of the subject. The response signal may be indicative of a feature of the vasculature of the eye of the subject, or indicative of a biometric identification of the subject, as discussed herein above. In various embodiments of the system, the physiological parameter is a measurement of oxygenation, blood glucose, heart rate, glycosylated hemoglobin, temperature, body temperature, blood flow, or a substance in the eye of the subject, for example.

In an embodiment, interrogation signal source 5302 is adapted to produce light having a first polarization, and the response signal sensor 5308 is adapted to detect light having a second polarization, and wherein the first polarization and the second polarization are the same. In an embodiment, interrogation signal source 5302 is adapted to produce light having a first polarization, wherein the response signal sensor 5308 is adapted to detect light having a second polarization, and wherein the first polarization and the second polarization are different. In one aspect, interrogation signal source 5302 is adapted to deliver a pulsed interrogation signal. Response signal sensor 5308 may be configured to gate detection of the response signal relative to the pulsed interrogation signal. System may include signal processing circuitry 5320 adapted to process the response signal. In an embodiment, interrogation signal source 5302 is adapted to deliver a pulsed interrogation signal, and the signal processing circuitry 5320 is configured to gate detection of the response signal relative to the pulsed interrogation signal. Signal processing circuitry 5320 may be configured to combine multiple response signals produced by the eye of the subject in response to multiple pulses of the pulsed interrogation signal, for example, by summing or averaging the multiple response signals, or by determining a moving average or weighted sum of the multiple response signals.

In an embodiment, interrogation signal source 5302 is adapted to deliver an interrogation signal containing multiple wavelengths of light. System 5300 may include at least a first response signal sensor configured to sense a first response signal produced by the eye of the subject responsive to a first wavelength component of the interrogation signal, and a second response signal sensor configured to sense a second response signal produced by the eye of the subject responsive to a second wavelength component of the interrogation signal (not shown in FIG. 53, but described and depicted elsewhere herein).

In an embodiment, system 5200 includes at least a first interrogation signal source configured to deliver a first interrogation signal having a first optical wavelength and at least a second interrogation signal source configured to deliver a second interrogation signal having a second optical wavelength. Signal processing circuitry 5320 may be configured to process a first response signal sensed from the eye of the subject in response to the first interrogation signal and a second response signal sensed from the eye of the subject in response to the second interrogation signal by comparing the first and second response signals to determine the physiological parameter. System may be configured to deliver the first interrogation signal simultaneously with respect to the second interrogation signal, or sequentially with respect to the second interrogation signal.

Interrogation signal source 5302 and the response signal sensor 5308 can be co-aligned, or separately aligned and located, as described herein above.

Output structure 1320 may include various structures, for example, a data transmission structure 1360, serial port 1362, parallel port 1364, electromagnetic transmission means 1366, optical transmission means 1368, an audio output 1370, or visual output 1372. Output structure may be adapted to transmit an output signal to the display. Output structure 1320 may be adapted to transmit an output signal to a data processing device, and the display may be controlled by the data processing device, for example. For example, such a display may be configured to display information relating to the determined physiological parameter. A display to which housing 1302 is attached via mounting means 1324 may be a video monitor, computer display, video game display, telephone display, or terminal of a data processing device. The display may be incorporated in a wearable item, an article of furniture, an article of medical or health-care related equipment, an article of exercise equipment, or a vehicle. Examples of such displays are described in greater detail herein above.

In an embodiment, response signal 5308 is indicative of a feature of the vasculature of the eye of the subject. In an embodiment, the response signal may be indicative of a biometric identification of the subject. In an aspect, gaze attractor 5120 includes a visual stimulus source for delivering a visual stimulus to attract the gaze of the subject, as discussed herein above. Visual stimulus source may be a mirror, light source, or video display, for example. In an aspect, visual stimulus source is adapted for attachment to a video display. In an aspect, visual stimulus source is adapted to produce a visual stimulus that differs from a visual background, e.g., that includes a different light intensity, different optical wavelength, different temporal pattern of light intensity, different temporal pattern of optical wavelength, different spatial pattern of light intensity, or different spatial pattern of optical wavelength relative to a visual background. In various embodiments, visual stimulus source is adapted to produce a visual stimulus that includes an image, a moving image, or text. In an aspect, visual stimulus source is configured such that when the gaze of the subject is directed toward the visual stimulus the eye of the subject will be brought into alignment with respect to the at least one of the interrogation signal source 5302 or the response signal sensor 5308. In an aspect, gaze attractor 5120 includes at least one auditory stimulus source for delivering a localized auditory stimulus to attract the gaze of the subject, as discussed herein above. In an aspect, the at least one auditory stimulus source is configured such that when the gaze of the subject is directed toward the auditory stimulus the eye of the subject will be brought into alignment with respect to the at least one of the interrogation signal source 5302 or the response signal sensor 5308. In an aspect, gaze attractor 5120 includes at least one auditory stimulus source and at least one visual stimulus source configured to deliver at least one auditory stimulus and at least one visual stimulus in sequence. Gaze attractor 5120 may include at least one auditory stimulus source and at least one visual stimulus source configured to deliver at least one auditory stimulus and at least one visual stimulus simultaneously.

Figure 54:
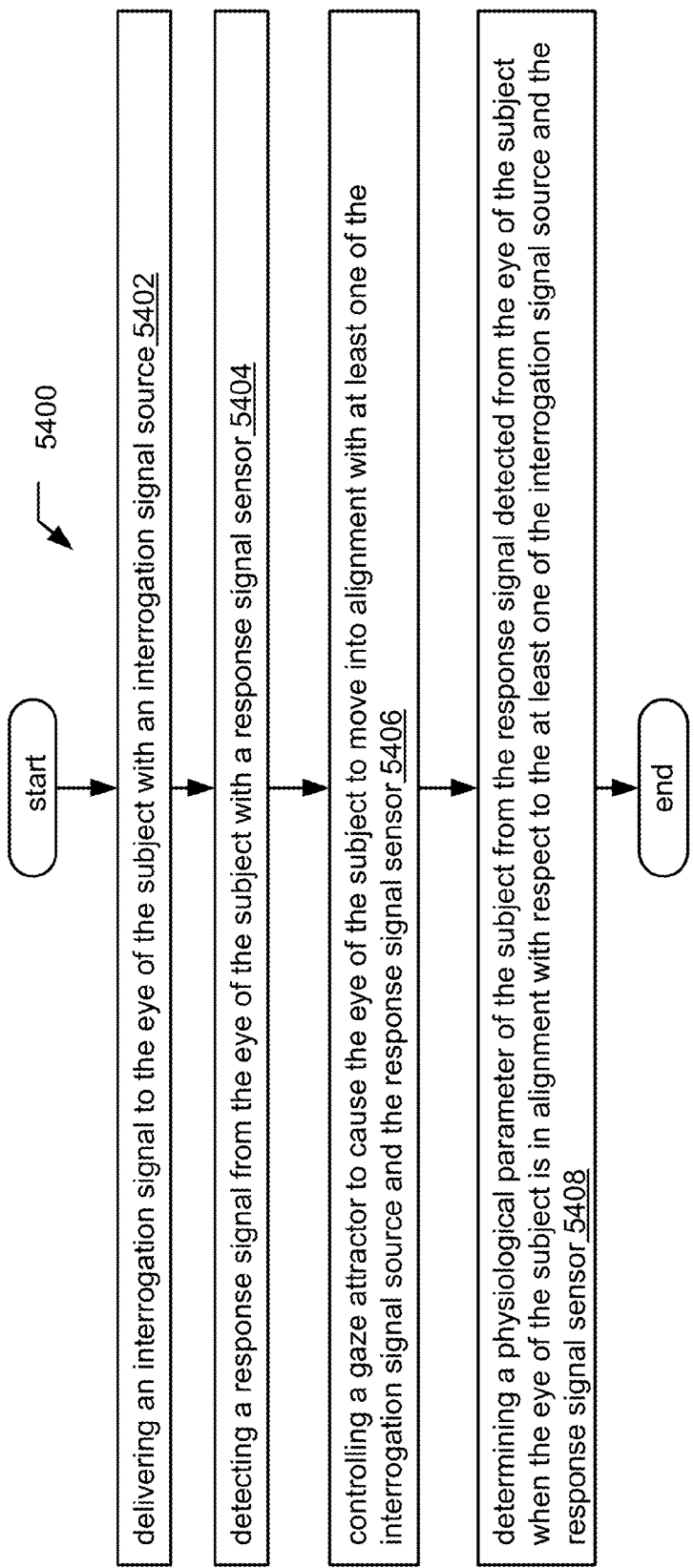
FIG. 54 is a flow diagram of a method of measuring information from an eye of a subject.

FIG. 54 is a flow chart of a method 5400 of measuring information from an eye of a subject, including delivering an interrogation signal to the eye of the subject with an interrogation signal source 5402; detecting a response signal from the eye of the subject with a response signal sensor 5404; controlling a gaze attractor to cause the eye of the subject to move into alignment with at least one of the interrogation signal source and the response signal sensor 5406; and determining a physiological parameter of the subject from the response signal detected from the eye of the subject when the eye of the subject is in alignment with respect to the at least one of the interrogation signal source and the response signal sensor 5408.

Figure 55:
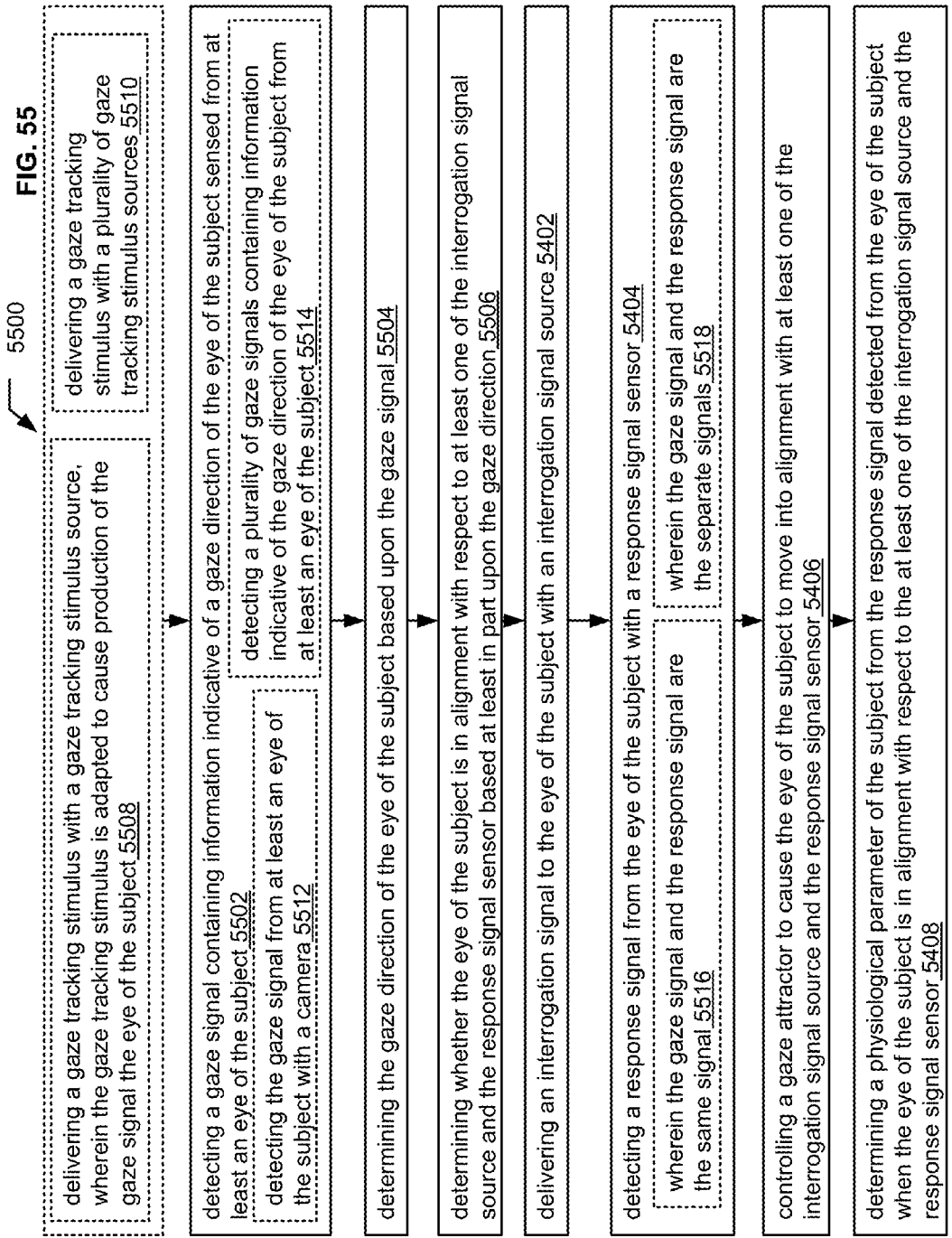
FIG. 55 is a flow diagram of a method of measuring information from an eye of a subject.

FIG. 55 illustrates a further method 5500, which includes detecting a gaze signal containing information indicative of a gaze direction of the eye of the subject sensed from at least an eye of the subject 5502; determining the gaze direction of the eye of the subject based upon the gaze signal 5504; and determining whether the eye of the subject is in alignment with respect to at least one of the interrogation signal source and the response signal sensor based at least in part upon the gaze direction 5506.

In an aspect, method 5500 (and other related methods) may include delivering a gaze tracking stimulus with a gaze tracking stimulus source, wherein the gaze tracking stimulus is adapted to cause production of the gaze signal by the eye of the subject 5508. The method may include delivering a gaze tracking stimulus with a plurality of gaze tracking stimulus sources 5510. In an embodiment, the method may include detecting the gaze signal from at least an eye of the subject with a camera 5512, or detecting a plurality of gaze signals containing information indicative of the gaze direction of the eye of the subject from at least an eye of the subject 5514. In an aspect, the gaze signal and the response signal are the same signal 5516. Alternatively, the gaze signal and the response signal may be the separate signals 5518.

Figure 56:
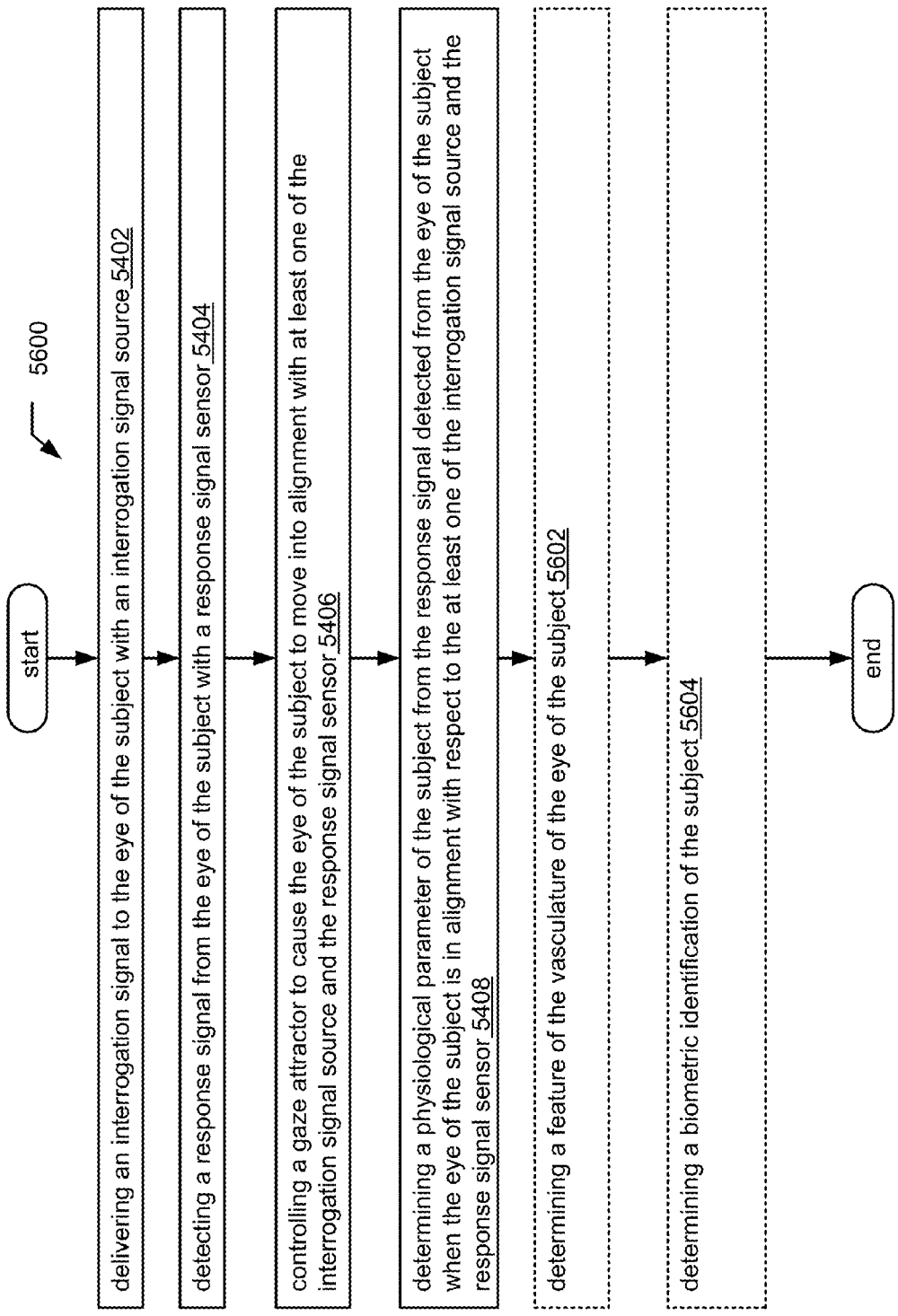
FIG. 56 is a flow diagram of a method of measuring information from an eye of a subject.

As shown in FIG. 56, in an embodiment, a method 5600 includes determining a feature of the vasculature of the eye of the subject 5602. In an embodiment, method 5600 includes determining a biometric identification of the subject 5604.

Figure 57:
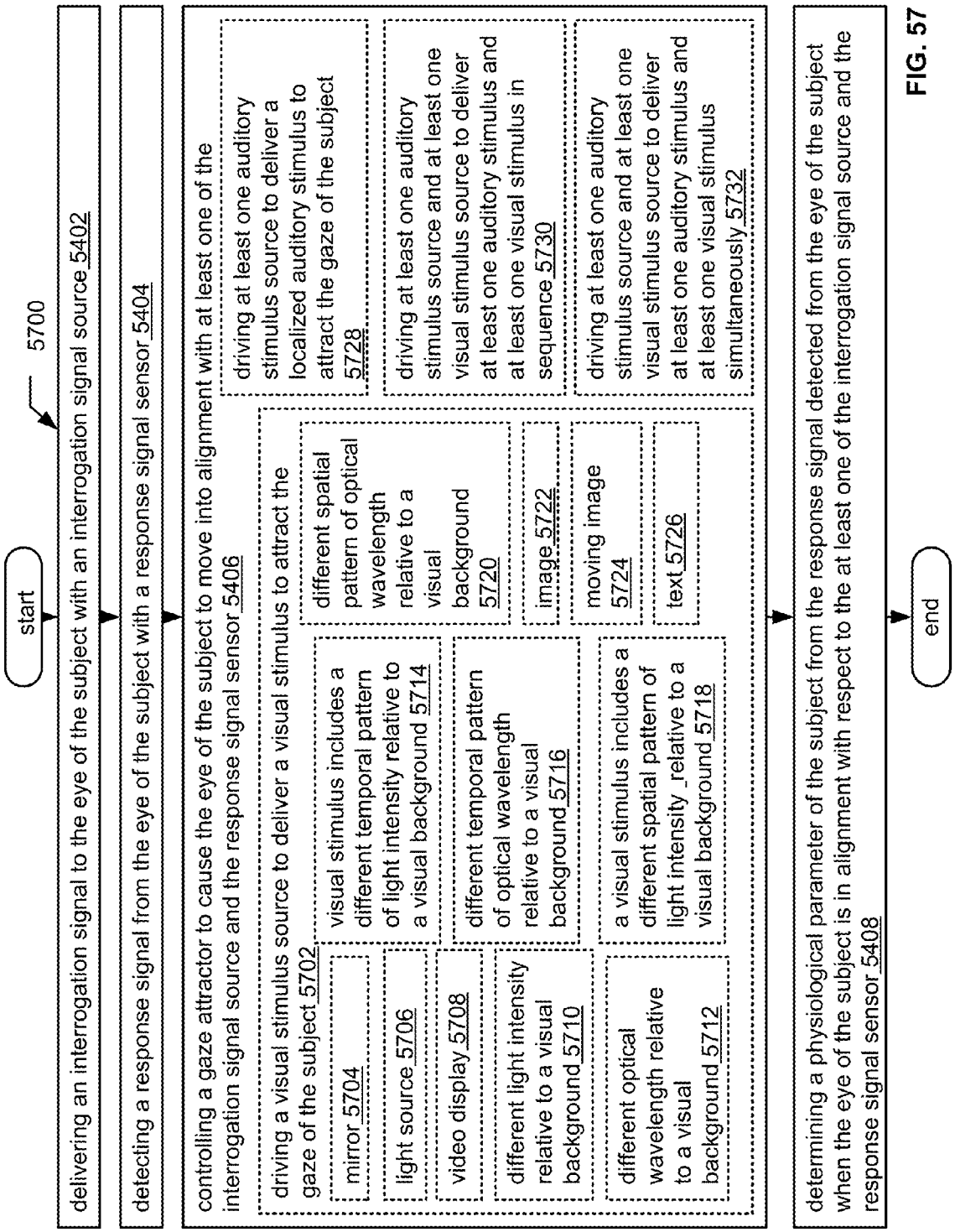
FIG. 57 is a flow diagram of a method of measuring information from an eye of a subject.

In an embodiment, in a method 5700 depicted in FIG. 57, controlling the gaze attractor includes driving a visual stimulus source to attract the gaze of the subject 5702, such as a mirror 5704, a light source 5706, or a video display 5708 to deliver a visual stimulus. Controlling the gaze attractor can include driving the visual stimulus source to produce a visual stimulus that includes a different light intensity 5710, different optical wavelength 5712, different temporal pattern of light intensity 5714, different temporal pattern of optical wavelength 5716, different spatial pattern of light intensity 5718, or different spatial pattern of optical wavelength 5720 relative to a visual background. Controlling the gaze attractor can include driving the visual stimulus source to produce a visual stimulus that includes an image 5722, a moving image 5724, or text 5726. Controlling the gaze attractor can include driving at least one auditory stimulus source to deliver a localized auditory stimulus to attract the gaze of the subject 5728. In an embodiment, controlling the gaze attractor includes driving at least one auditory stimulus source and at least one visual stimulus source to deliver at least one auditory stimulus and at least one visual stimulus in sequence 5730. In an embodiment, controlling the gaze attractor includes driving at least one auditory stimulus source and at least one visual stimulus source to deliver at least one auditory stimulus and at least one visual stimulus simultaneously 5732.

Figure 58:
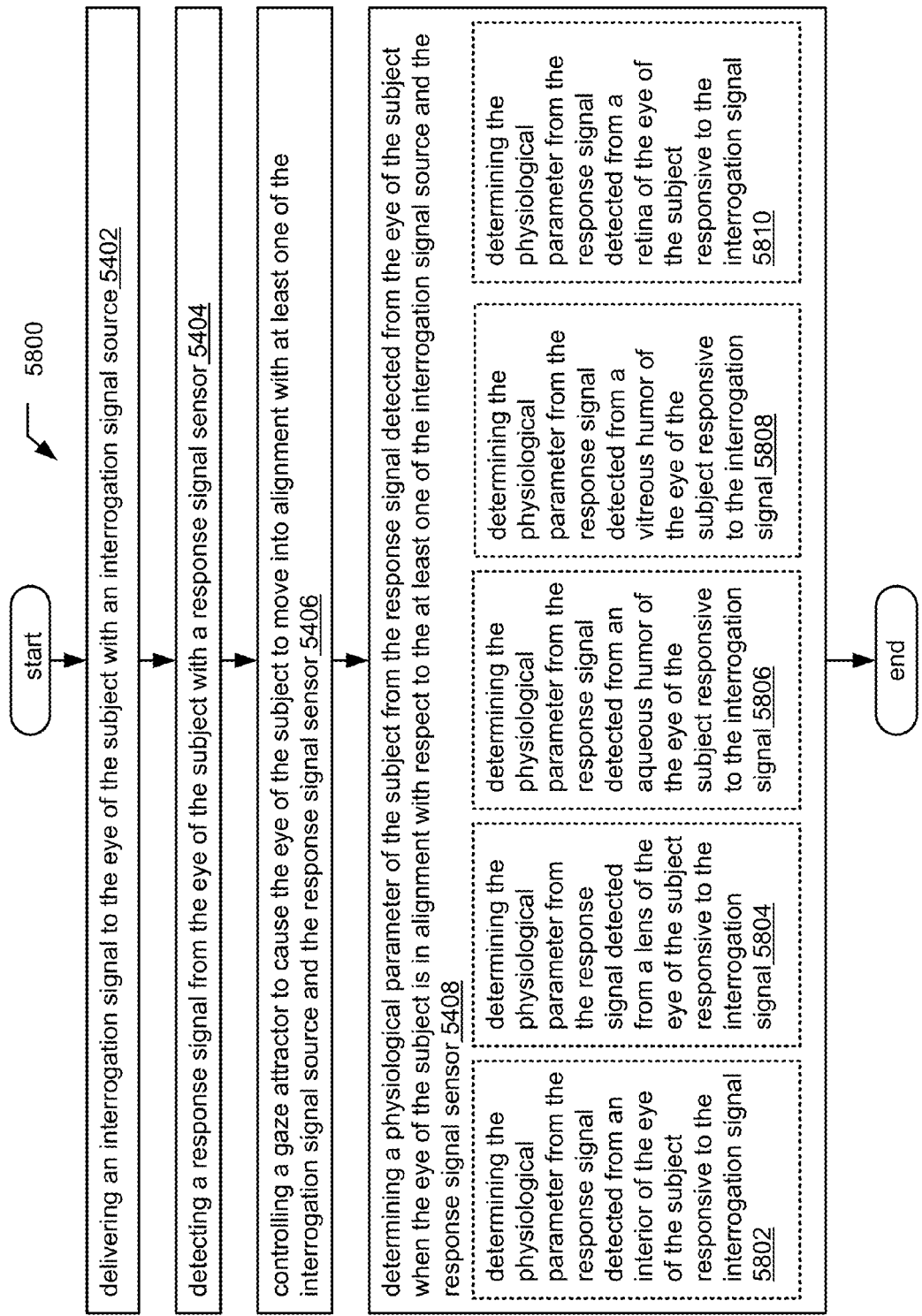
FIG. 58 is a flow diagram of a method of measuring information from an eye of a subject.

As shown in FIG. 58, a method 5800 includes determining the physiological parameter from the response signal detected from an interior of the eye of the subject responsive to the interrogation signal 5802, e.g., from a lens 5804, aqueous humor 5806, vitreous humor 5808, or retina 5810 of the eye of the subject responsive to the interrogation signal.

Figure 59:
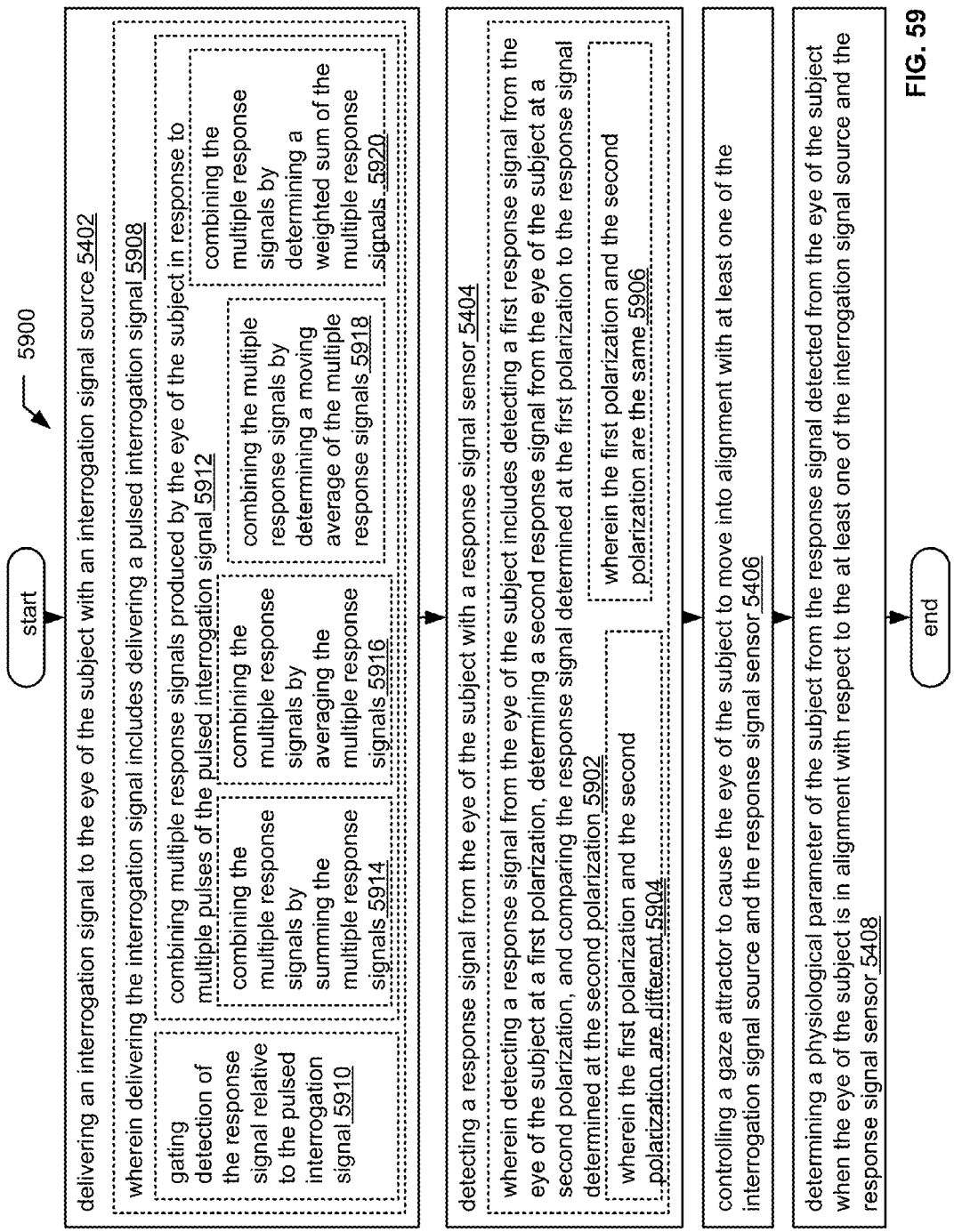
FIG. 59 is a flow diagram of a method of measuring information from an eye of a subject.

As shown in FIG. 59, in a method 5900, detecting a response signal from the eye of the subject includes detecting a first response signal from the eye of the subject at a first polarization, determining a second response signal from the eye of the subject at a second polarization, and comparing the response signal determined at the first polarization to the response signal determined at the second polarization 5902. Depending upon the intended application, the first polarization and the second polarization may be different as shown at 5904, or the same as shown at 5906. In an embodiment, delivering the interrogation signal includes delivering a pulsed interrogation signal 5908. The method may further include gating detection of the response signal relative to the pulsed interrogation signal 5910. In an embodiment, the method includes combining multiple response signals produced by the eye of the subject in response to multiple pulses of the pulsed interrogation signal 5912. The method may include combining the multiple response signals by summing 5914 or averaging 5916 the multiple response signals, or by determining a moving average 5918 or weighted sum 5920 of the multiple response signals.

Figure 60:
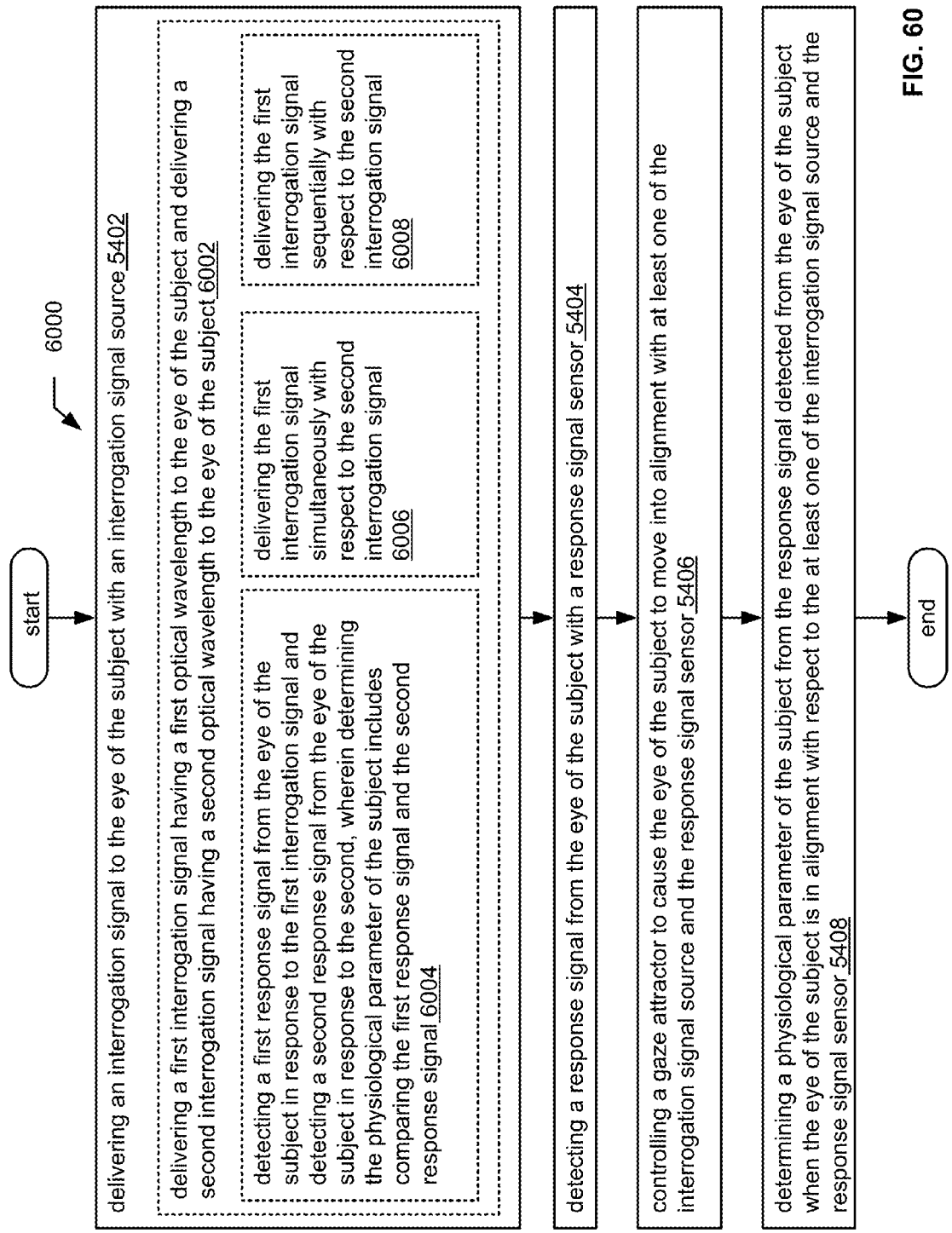
FIG. 60 is a flow diagram of a method of measuring information from an eye of a subject.

A shown in FIG. 60, in an embodiment, method 6000 includes delivering a first interrogation signal having a first optical wavelength to the eye of the subject and delivering a second interrogation signal having a second optical wavelength to the eye of the subject 6002. The method may also include detecting a first response signal from the eye of the subject in response to the first interrogation signal and detecting a second response signal from the eye of the subject in response to the second, wherein determining the physiological parameter of the subject includes comparing the first response signal and the second response signal 6004. For example, it may include delivering the first interrogation signal simultaneously with respect to the second interrogation signal 6006, or delivering the first interrogation signal sequentially with respect to the second interrogation signal 6008.

Figure 61:
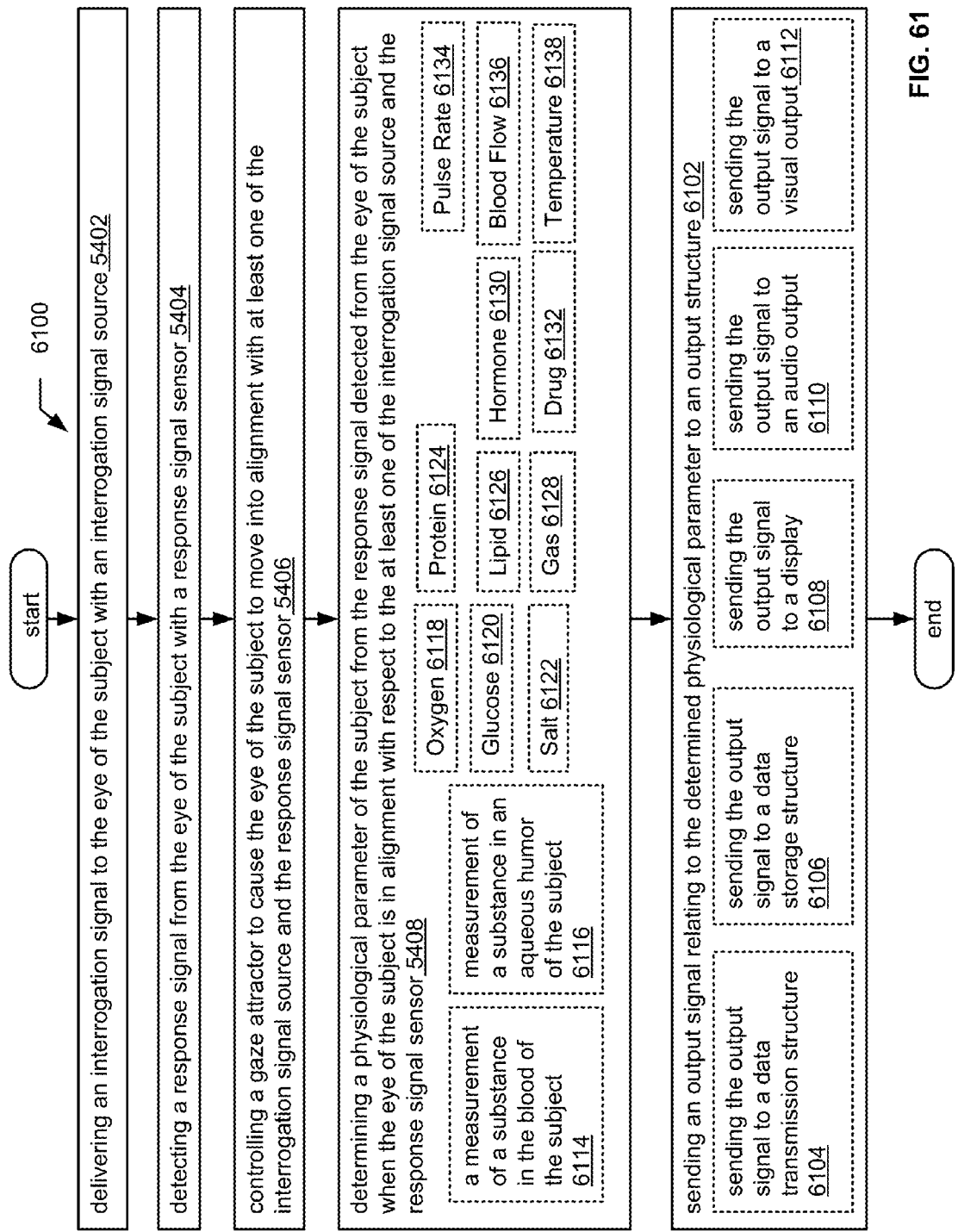
FIG. 61 is a flow diagram of a method of measuring information from an eye of a subject.

As shown in FIG. 61, in an embodiment, a method 6100 includes sending an output signal relating to the determined physiological parameter to an output structure 6102, which may be, for example, a data transmission structure 6104, data storage structure 6106, display 6108, audio output 6110, or visual output 6112. As described elsewhere herein, the physiological parameter determined at step 5408 may be, for example, a measurement of a substance in the blood of the subject 6114, a measurement of a substance in an aqueous humor of the subject 6116, oxygen 6118, glucose 6120, a salt 6122, a protein 6124, a lipid 6126, a gas 6128, a hormone 6130, a drug 6132, a pulse rate 6134, a blood flow 6136, or a temperature 6138.

Figure 62:
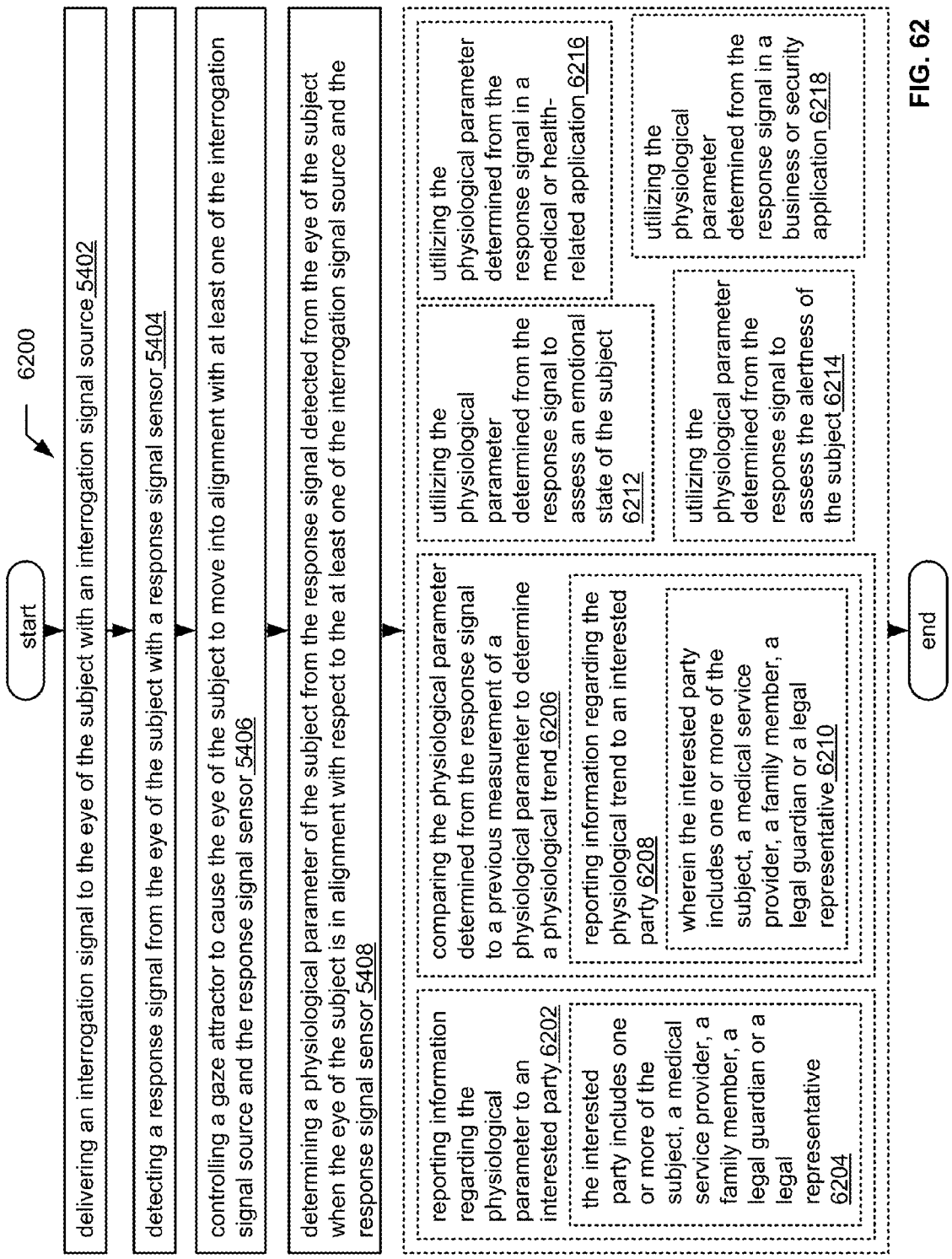
FIG. 62 is a flow diagram of a method of measuring information from an eye of a subject.

As shown in FIG. 62, in an aspect, a method 6200 includes reporting information regarding the physiological parameter to an interested party 6202, such as one or more of the subject, a medical service provider, a family member, a legal guardian or a legal representative 6204. In an aspect, method 6200 includes comparing the physiological parameter determined from the response signal to a previous measurement of a physiological parameter to determine a physiological trend 6206. The method may further include reporting information regarding the physiological trend to an interested party 6208, such as one or more of the subject, a medical service provider, a family member, a legal guardian or a legal representative 6210. In an aspect, method 6200 includes utilizing the physiological parameter determined from the response signal to assess an emotional state 6212 or the alertness 6214 of the subject. In an aspect, the method includes utilizing the physiological parameter determined from the response signal in a medical or health-related application 6216. In another aspect, the method includes utilizing the physiological parameter determined from the response signal in a business or security application 6218.

Figure 63:
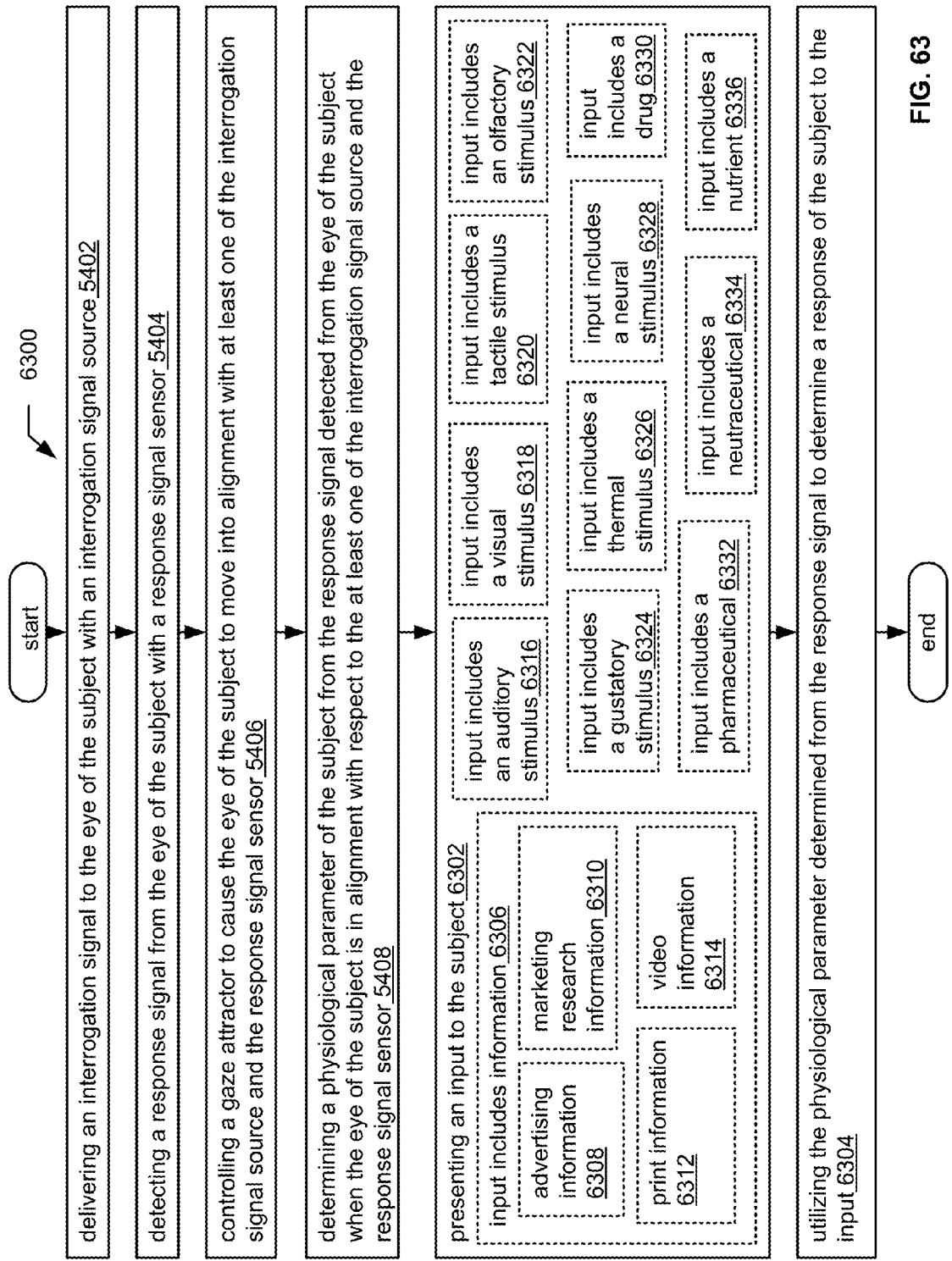
FIG. 63 is a flow diagram of a method of measuring information from an eye of a subject.

As shown in FIG. 63, in an embodiment, a method 6300 includes presenting an input to the subject 6302; and utilizing the physiological parameter determined from the response signal to determine a response of the subject to the input 6304. For example, the input may include information 6306 (e.g., advertising information 6308, marketing research information 6310, print information 6312, or video information 6314), an auditory stimulus 6316, a visual stimulus 6318, a tactile stimulus 6320, an olfactory stimulus 6322, a gustatory stimulus 6324, a thermal stimulus 6326, a neural stimulus 6328, a drug 6330, a pharmaceutical 6332, a nutraceutical 6334, or a nutrient 6336.

Figure 64:
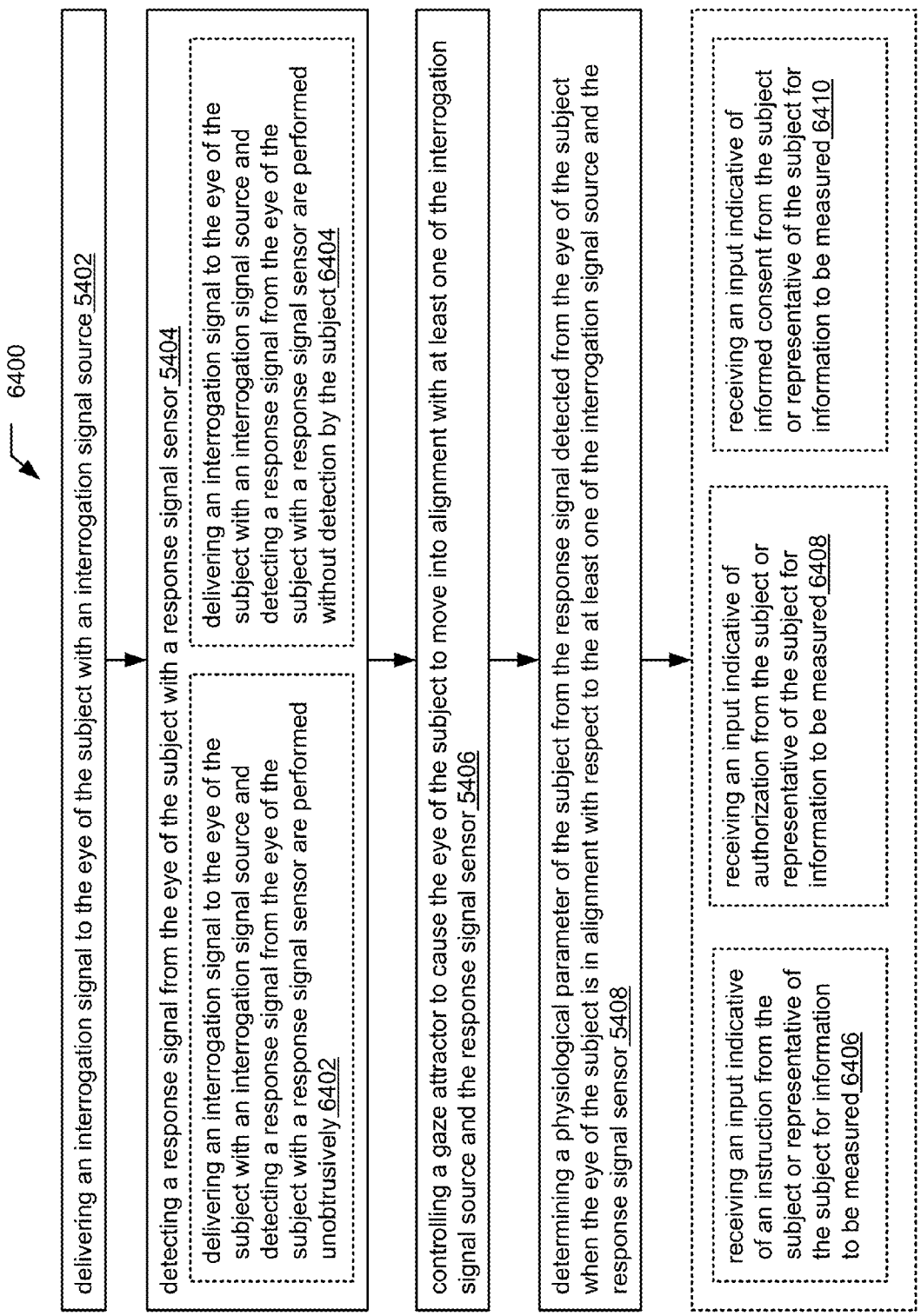
FIG. 64 is a flow diagram of a method of measuring information from an eye of a subject.

As shown in FIG. 64, in aspect of a method 6400, delivering an interrogation signal to the eye of the subject with an interrogation signal source and detecting a response signal from the eye of the subject with a response signal sensor are performed unobtrusively 6402, or without detection by the subject 6404, as discussed herein above. Method 6400 may also include receiving an input indicative of an instruction from the subject or representative of the subject for information to be measured 6406, receiving an input indicative of authorization from the subject or representative of the subject for information to be measured 6408, or receiving an input indicative of informed consent from the subject or representative of the subject for information to be measured 6410.

Figure 65:
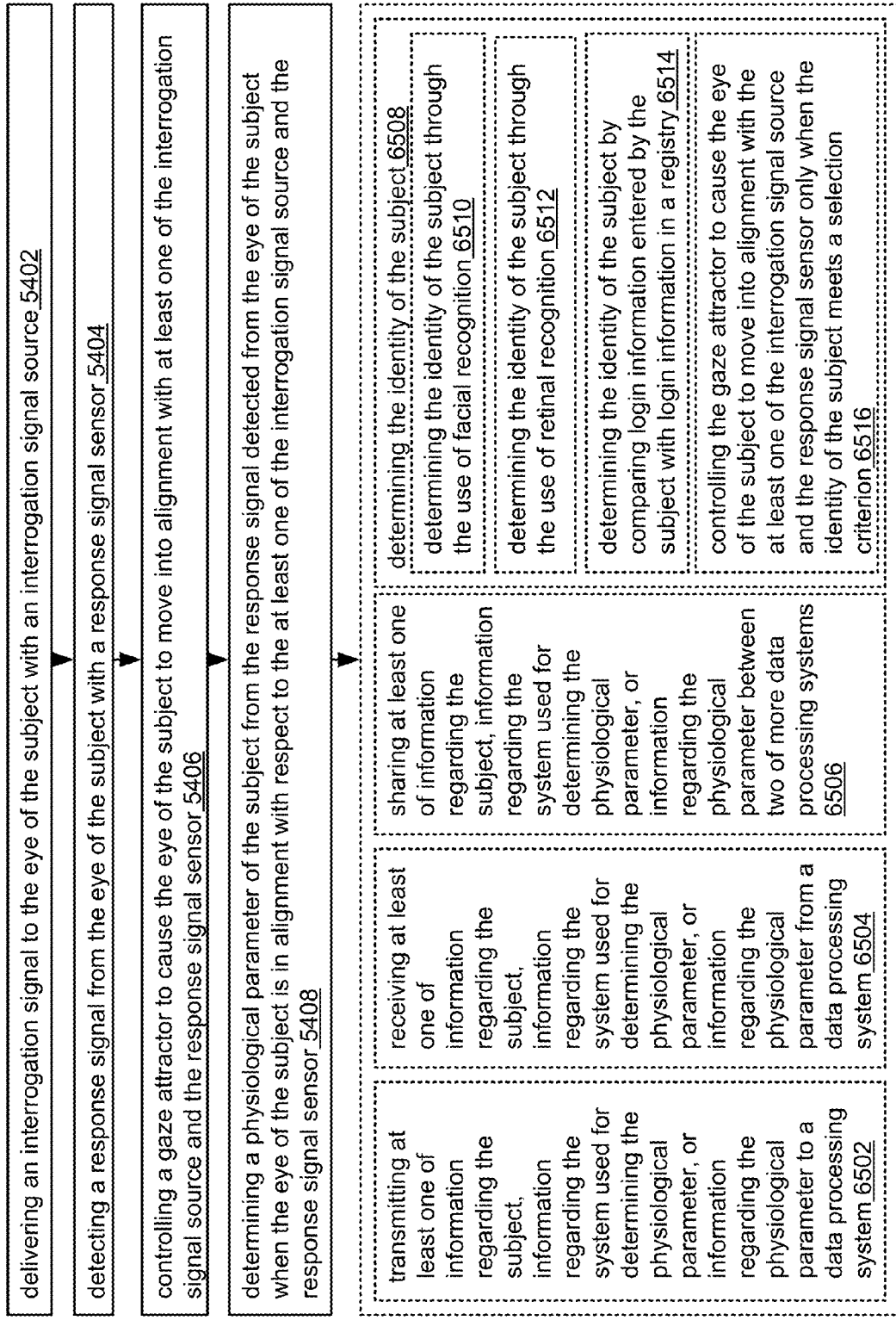
FIG. 65 is a flow diagram of a method of measuring information from an eye of a subject.

As shown in FIG. 65, a method may 6500 may include transmitting at least one of information regarding the subject, information regarding the method used for determining the physiological parameter, or information regarding the physiological parameter to a data processing system 6502, receiving at least one of information regarding the subject, information regarding the method used for determining the physiological parameter, or information regarding the physiological parameter from a data processing system 6504, or sharing at least one of information regarding the subject, information regarding the method used for determining the physiological parameter, or information regarding the physiological parameter between two of more data processing systems 6506. In an embodiment, method include determining the identity of the subject 6508, for example, through the use of facial recognition 6510, through the use of retinal recognition 6512, or by comparing login information entered by the subject with login information in a registry 6514. In an embodiment, the method includes controlling the gaze attractor to cause the eye of the subject to move into alignment with the at least one of the interrogation signal source and the response signal sensor only when the identity of the subject meets a selection criterion. Determining whether the identify of the subject meets a selection critereion is performed generally as discussed herein above, e.g. in connection with FIG. 20.

Figure 66:
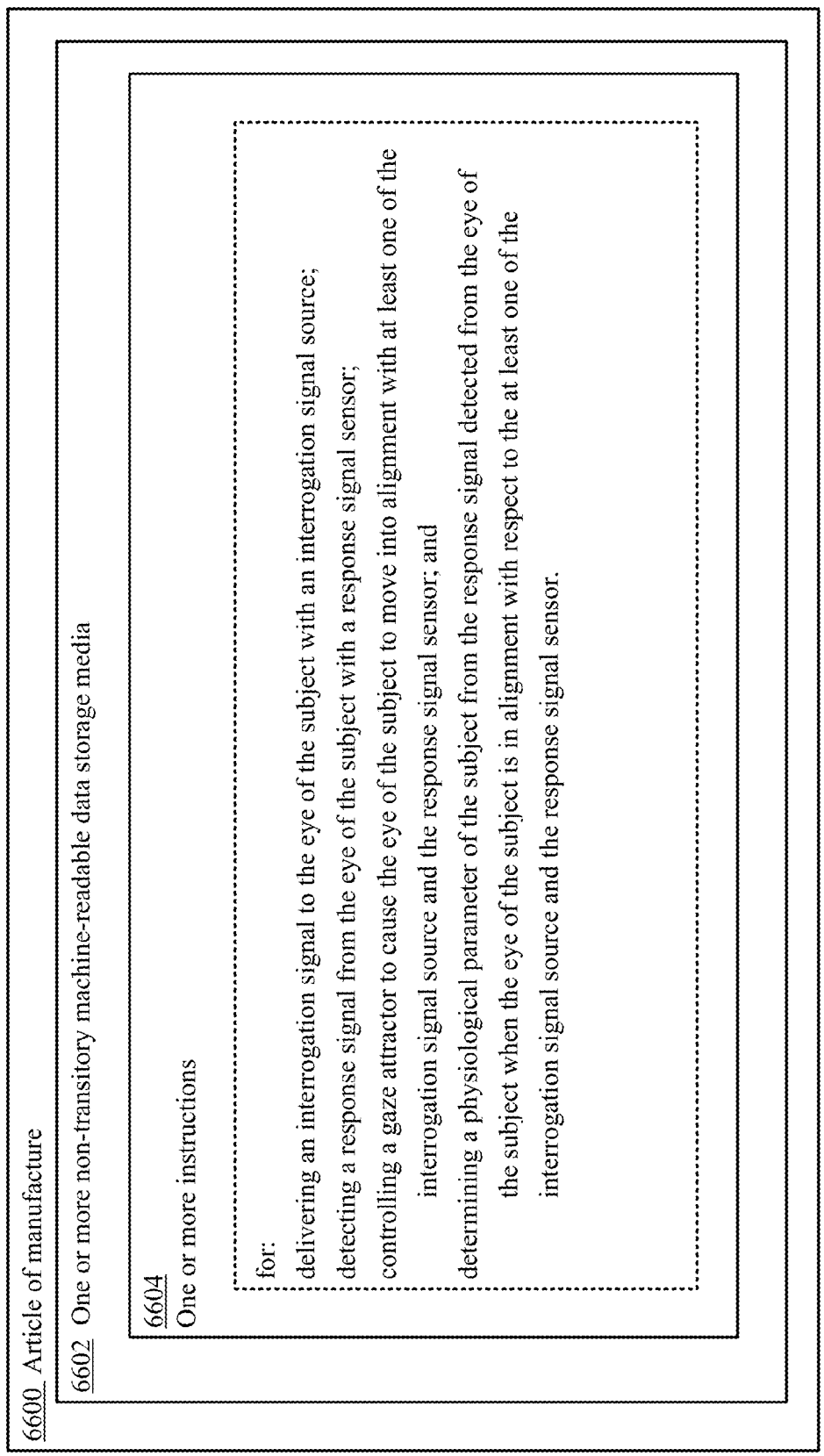
FIG. 66 illustrates an article of manufacture including non-transitory machine-readable data storage media bearing instructions for performing a method of measuring information from an eye of a subject.

FIG. 66 depicts an article of manufacture 6600 including one or more non-transitory machine-readable data storage media 6602 bearing one or more instructions 6604 for: delivering an interrogation signal to the eye of the subject with an interrogation signal source; detecting a response signal from the eye of the subject with a response signal sensor; controlling a gaze attractor to cause the eye of the subject to move into alignment with at least one of the interrogation signal source and the response signal sensor; and determining a physiological parameter of the subject from the response signal detected from the eye of the subject when the eye of the subject is in alignment with respect to the at least one of the interrogation signal source and the response signal sensor, e.g., a method as shown in FIG. 54.

In an embodiment, data storage media 6602 may bear one or more instructions for detecting a gaze signal containing information indicative of a gaze direction of the eye of the subject sensed from at least an eye of the subject; and determining the gaze direction of the eye of the subject based upon the gaze signal; determining whether the eye of the subject is in alignment with respect to at least one of the interrogation signal source and the response signal sensor based at least in part upon the gaze direction, e.g., as in FIG. 55.

In an embodiment, data storage media 6602 may bear one or more instructions for determining a feature of the vasculature of the eye of the subject or determining a biometric identification of the subject, e.g. as in FIG. 56.

In an embodiment, data storage media 6602 may bear one or more instructions for performing method steps as shown in FIG. 57, e.g. where the one or more instructions for controlling the gaze attractor include one or more instructions for driving a visual stimulus source to deliver a visual stimulus (e.g., a mirror, light source, or video display) to attract the gaze of the subject. In various embodiments, the one or more instructions for controlling the gaze attractor include one or more instructions for driving the visual stimulus source to produce a visual stimulus that includes a different light intensity, a different optical wavelength, a different temporal pattern of light intensity, a different temporal pattern of optical wavelength, a different spatial pattern of light intensity or a different spatial pattern of optical wavelength relative to a visual background. In addition, the one or more instructions for controlling the gaze attractor may include one or more instructions driving the visual stimulus source to produce a visual stimulus that includes an image, a moving image, or text. In an embodiment, the one or more instructions for controlling the gaze attractor include one or more instructions for driving at least one auditory stimulus source to deliver a localized auditory stimulus to attract the gaze of the subject. In an aspect, the one or more instructions for controlling the gaze attractor include one or more instructions for driving at least one auditory stimulus source and at least one visual stimulus source to deliver at least one auditory stimulus and at least one visual stimulus in sequence. In another aspect, the one or more instructions for controlling the gaze attractor include one or more instructions for driving at least one auditory stimulus source and at least one visual stimulus source to deliver at least one auditory stimulus and at least one visual stimulus simultaneously.

In an embodiment, the data storage media 6602 bear one or more instructions for performing method steps as shown in FIG. 55, including one or more instructions for delivering a gaze tracking stimulus with a gaze tracking stimulus source, wherein the gaze tracking stimulus is adapted to cause production of the gaze signal the eye of the subject, or one or more instructions for delivering a gaze tracking stimulus with a plurality of gaze tracking stimulus sources. In an embodiment, the data storage media bear one or more instructions for detecting the gaze signal from at least an eye of the subject with a camera. In an embodiment, the data storage media bear one or more instructions for detecting a plurality of gaze signals containing information indicative of the gaze direction of the eye of the subject from at least an eye of the subject.

In an embodiment, the data storage media 6602 may bear one or more instructions for determining the physiological parameter from the response signal detected from an interior of the eye (e.g., from a lens, aqueous humor, vitreous humor, or retina) of the subject responsive to the interrogation signal, e.g. as in the method of FIG. 58.

In an embodiment, data storage media 6602 bear one or more instructions for performing method steps as shown in FIG. 59, e.g. where the one or more instructions for detecting a response signal from the eye of the subject include one or more instructions for detecting a first response signal from the eye of the subject at a first polarization, determining a second response signal from the eye of the subject at a second polarization, and comparing the response signal determined at the first polarization to the response signal determined at the second polarization. The first polarization and the second polarization may be different, or the same as discussed above. In an embodiment, one or more instructions for delivering the interrogation signal includes one or more instructions for delivering a pulsed interrogation signal.

The data storage media may bear one or more instructions for gating detection of the response signal relative to the pulsed interrogation signal. The data storage media may bear one or more instructions for combining multiple response signals produced by the eye of the subject in response to multiple pulses of the pulsed interrogation signal, e.g. by summing or averaging the multiple response signals, or by determining a moving average or weighted sum of the multiple response signals.

The data storage media 6002 may bear one or more instructions for delivering a first interrogation signal having a first optical wavelength to the eye of the subject and delivering a second interrogation signal having a second optical wavelength to the eye of the subject, as shown in FIG. 60. In addition, data storage media 6002 may bear one or more instructions for detecting a first response signal from the eye of the subject in response to the first interrogation signal and detecting a second response signal from the eye of the subject in response to the second, wherein determining the physiological parameter of the subject includes comparing the first response signal and the second response signal. The data storage media 6002 may bear one or more instructions for delivering the first interrogation signal simultaneously with respect to the second interrogation signal. The data storage media 6002 may bear one or more instructions for delivering the first interrogation signal sequentially with respect to the second interrogation signal.

The data storage media 6002 may bear one or more instruction for performing a method as shown in FIG. 61, including one or more instructions for sending an output signal relating to the determined physiological parameter to an output device, which may be, for example, a data transmission structure, data storage structure, display, audio output, or visual output. The physiological parameter may be a measurement of a substance in the blood of the subject (e.g. oxygen, glucose, or glycosylated hemoglobin), a measurement of a substance in an aqueous humor of the subject (e.g., oxygen, glucose, or glycosylated hemoglobin), a pulse rate, a temperature, or a blood flow, for example.

In an embodiment, the data storage media 6002 bear one or more instructions for performing a method as shown in FIG. 62, including one or more instructions for comparing the physiological parameter determined from the response signal to a previous measurement of a physiological parameter to determine a physiological trend. In addition, the data storage media may bear one or more instructions for reporting information regarding the physiological trend to an interested party (for example, one or more of the subject, a medical service provider, a family member, a legal guardian or a legal representative). In an aspect, the data storage media 6002 bear one or more instructions for utilizing the physiological parameter determined from the response signal to assess an emotional state of the subject. In an aspect, the data storage media 6002 bear one or more instructions for utilizing the physiological parameter determined from the response signal to assess the alertness of the subject. In an aspect, the data storage media 6002 bear one or more instructions for utilizing the physiological parameter determined from the response signal in a medical or health-related application. In another aspect, the data storage media 6002 bear one or more instructions for utilizing the physiological parameter determined from the response signal in a business or security application.

In an aspect, the data storage media 6002 bear one or more instructions for performing a method as shown in FIG. 63, including one or more instructions for presenting an input to the subject; and utilizing the physiological parameter determined from the response signal to determine a response of the subject to the input. The one or more instructions for presenting an input to the subject may include one or more instructions for presenting information (e.g., advertising information, marketing research information, print information, or video information), or presenting a stimulus (e.g., an auditory stimulus, visual stimulus, tactile stimulus, olfactory stimulus, gustatory stimulus, thermal stimulus, neural stimulus, drug, pharmaceutical, nutraceutical, or nutrient).

In an aspect, the data storage media 6002 bear one or more instructions for methods as shown in FIG. 64, including one or more instructions for receiving an input indicative of an instruction from the subject or representative of the subject for information to be measured. In an aspect, the data storage media 6002 bear one or more instructions for receiving an input indicative of authorization from the subject or representative of the subject for information to be measured. In an aspect, the data storage media 6002 bear one or more instructions for receiving an input indicative of informed consent from the subject or representative of the subject for information to be measured.

In various embodiments, the data storage media 6002 bear one or more instructions for performing a method as shown in FIG. 65, including one or more instructions for transmitting at least one of information regarding the subject, information regarding the method used for determining the physiological parameter, or information regarding the physiological parameter to a data processing system, receiving at least one of information regarding the subject, information regarding the method used for determining the physiological parameter, or information regarding the physiological parameter from a data processing system, or sharing at least one of information regarding the subject, information regarding the method used for determining the physiological parameter, or information regarding the physiological parameter between two of more data processing systems. In an aspect, the data storage media 6002 bear one or more instructions for determining the identity of the subject, for example through the use of facial recognition, through the use of retinal recognition, or by comparing login information entered by the subject with login information in a registry.

Figure 67:
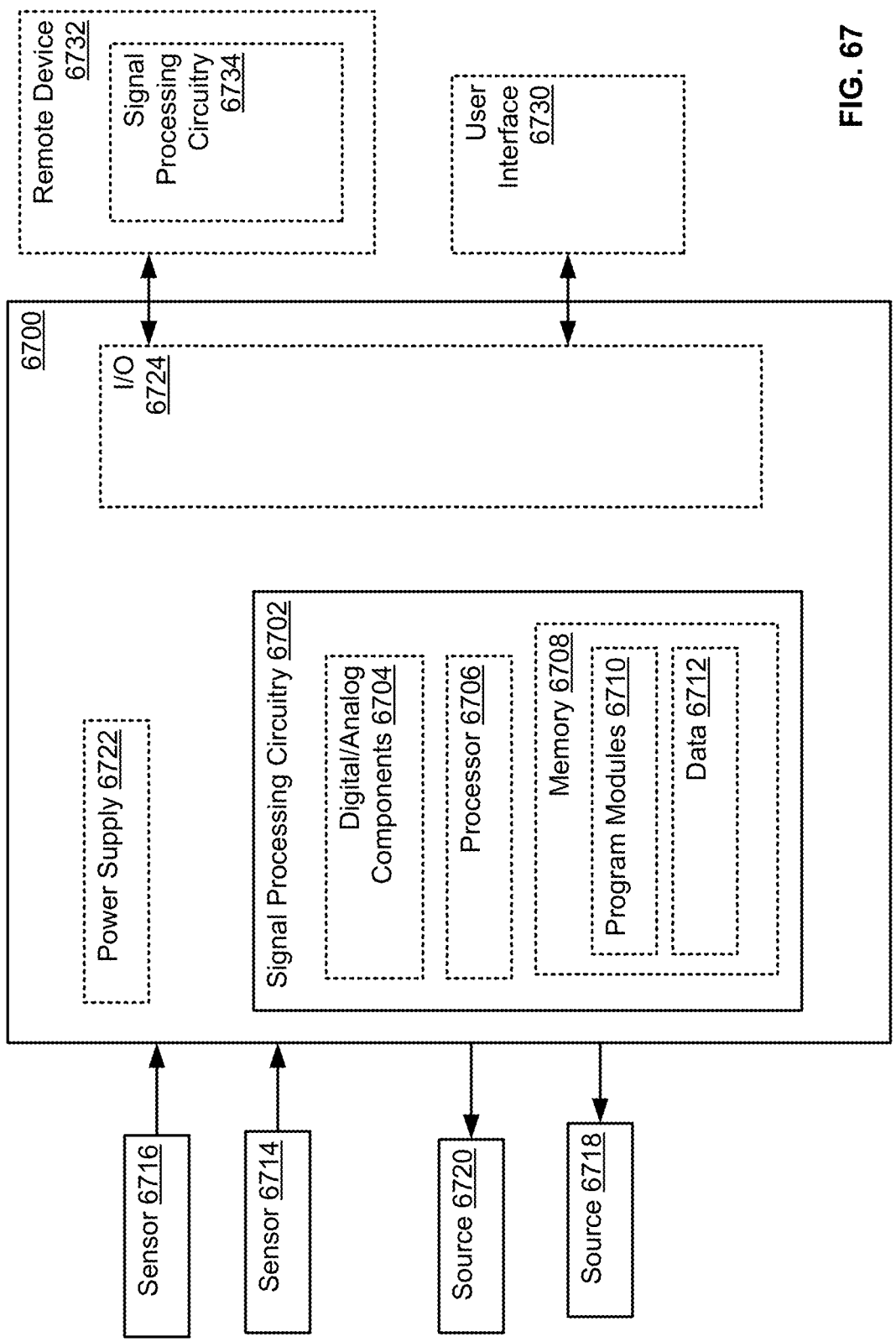
FIG. 67 is a generalized block diagram of an embodiment of a system.

Although specific embodiments are described herein, those skilled in the art will appreciate that methods and systems as described herein can be implemented in various ways. FIG. 67 depicts a generic system 6700, illustrating components of systems described herein above. Reference is made throughout to "signal processing circuitry." Signal processing circuitry, as used herein, for example, such as signal processing circuitry 6702 illustrated in FIG. 67, may include any or all of digital and/or analog components 6704, one or more processor 6706 (e.g. a microprocessor), and memory 6708, which may store program module 6710 and/or data 6712. Systems as described herein may receive signals from various sensors (e.g., sensors 6714 and 6716 depicted in FIG. 67) and send control signals to various types of signal sources used for interrogating the eye to determine eye position or physiological parameters (e.g. sources 6718 and 6720). System 6700 may include other components as known to those skilled in the art, e.g. one or more power supply 6722, and I/O structure 6724. I/O structure permits communication with various types of user interface devices (represented by user interface 6730) and various types of remote device 6732, which may have signal processing capability conferred by signal processing circuitry 6743 and may perform some or all of the signal processing tasks required by system 6700, or which may perform additional processing of data generated by 6700, e.g. determination of appropriate medical treatment based on physiological parameters.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof, limited to patentable subject matter under 35 U.S.C. §101; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc), and/or any non-electrical analog thereto, such as optical or other analogs (e.g., graphene based circuitry). Those skilled in the art will also appreciate that examples of electro-mechanical systems include but are not limited to a variety of consumer electronics systems, medical devices, as well as other systems such as motorized transport systems, security systems, and/or communication/computing systems. Those skilled in the art will recognize that electro-mechanical as used herein is not necessarily limited to a system that has both electrical and mechanical actuation except as context may dictate otherwise. In a general sense, those skilled in the art will recognize that the various aspects described herein which can be implemented, individually and/or collectively, by a wide range of hardware, software, firmware, and/or any combination thereof can be viewed as being composed of various types of "electrical circuitry."

Those skilled in the art will recognize that at least a portion of the devices and/or processes described herein can be integrated into an image processing system. Those having skill in the art will recognize that a typical image processing system generally includes one or more of a system unit housing, a video display, memory such as volatile or non-volatile memory, processors such as microprocessors or digital signal processors, computational entities such as operating systems, drivers, applications programs, one or more interaction devices (e.g., a touch pad, a touch screen, an antenna, etc), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configured by," "configurable to," "operable/operative to," "adapted/adaptable," "able to," "conformable/conformed to," etc. Those skilled in the art will recognize that such terms (e.g. "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for sensing information from an eye of a subject, comprising:
   a gaze signal sensor adapted for receiving a gaze signal containing information indicative of a gaze direction of the eye of the subject;
   an interrogation signal source for delivering the interrogation signal to the eye of the subject;
   a response signal sensor for sensing a response signal produced by the eye of the subject responsive to the interrogation signal; and
   signal processing circuitry including:
      a gaze signal processor configured to determine the gaze direction of the eye of the subject based upon the gaze signal;
      an alignment detector configured to determine whether the eye of the subject is in alignment with respect to at least one of the interrogation signal source and the response signal sensor based at least in part upon the gaze direction; and
      a response signal processor configured to process the response signal sensed from the eye of the subject by the response signal sensor when the eye of the subject is in alignment with respect to the at least one of the interrogation signal source and the response signal sensor to determine a physiological parameter from the response signal.

2. A system for controlling the sensing of information from an eye of a subject, comprising:
   signal processing circuitry including:
      a gaze signal input adapted to receive a gaze signal containing information indicative of a gaze direction of the eye of the subject sensed from at least the eye of the subject;
      a response signal input adapted to receive a response signal sensed from the eye of the subject by a response signal sensor responsive to delivery of an interrogation signal to the eye of the subject;
      a gaze signal processor configured to determine the gaze direction of the eye of the subject based upon the gaze signal;
      an alignment detector configured to determine whether the eye of the subject is in alignment with respect to at least one of the interrogation signal source and the response signal sensor based at least in part upon the gaze direction; and
      a response signal processor configured to process the response signal sensed from the eye of the subject by the response signal sensor when the eye of the subject is in alignment with respect to the at least one of the interrogation signal source and the response signal sensor to determine a physiological parameter from the response signal.

3. The system of claim 1, wherein the gaze signal sensor includes at least one of a camera, an infrared camera, a CCD camera, an optical sensor, and an optical sensor array.

4. The system of claim 1, wherein the interrogation signal source includes at least one of an optical signal source, an acoustic signal source, a broad spectrum light source, a near-infrared light source, a tunable laser source, and a mid-infrared light source.

5. The system of claim 1, wherein the response signal sensor includes at least one of an optical sensor, an acoustic sensor, a spectrometer based on a CCD array, a near-infrared camera, a Raman spectrometer based on a CCD camera, a mid-infrared detector, and a broad spectrum pyroelectric detector.

6. The system of claim 1, including at least one gaze tracking stimulus source adapted to deliver a gaze tracking stimulus to at least the eye of the subject, wherein the gaze signal is produced in response to the gaze tracking stimulus, and wherein the gaze tracking stimulus source includes at least one of an infra-red source and a near infra-red source.

7. The system of claim 1, wherein the interrogation signal source is adapted to deliver a pulsed interrogation signal, and wherein the signal processing circuitry is configured to combine multiple response signals produced by the eye of the subject in response to multiple pulses of the pulsed interrogation signal by at least one of summing the multiple response signals, averaging the multiple response signals, determining a moving average of the multiple response signals, and determining a weighted sum of the multiple response signals.

8. The system of claim 1, including at least a first response signal sensor, and a second response signal sensor, wherein the interrogation signal source is adapted to deliver an interrogation signal containing multiple wavelengths of light, and wherein the first response signal sensor is configured to sense a first response signal produced by the eye of the subject responsive to a first wavelength component of the interrogation signal, and the second response signal sensor is configured to sense a second response signal produced by the eye of the subject responsive to a second wavelength component of the interrogation signal.

9. The system of claim 1, including at least a first interrogation signal source configured to deliver a first interrogation signal having a first optical wavelength and at least a second interrogation signal source configured to deliver a second interrogation signal having a second optical wavelength, wherein the signal processing circuitry is configured to process a first response signal sensed from the eye of the subject in response to the first interrogation signal and a second response signal sensed from the eye of the subject in response to the second interrogation signal by comparing the first and second response signals to determine the physiological parameter.

10. The system of claim 1, including at least one of an output structure adapted to output a signal relating to the determined physiological parameter and a display adapted to display information relating to the determined physiological parameter.

11. The system of claim 10, wherein the output structure includes at least one of a data transmission structure, a data storage structure, a display, an audio output, and a visual output.

12. The system of claim 10, wherein the display includes at least one of a video monitor, a computer display, a video game display, a telephone display, a terminal of a data processing device, a display incorporated in a wearable item, a display incorporated in an article of furniture, a display incorporated in an article of medical or health-care related equipment, a display incorporated in an article of exercise equipment and a display incorporated in a vehicle.

13. The system of claim 2, including:
 interrogation signal control circuitry configured to drive production of the interrogation signal by an interrogation signal source; and
 gaze tracking stimulus control circuitry configured to drive production of a gaze tracking stimulus by at least one gaze tracking stimulus source.

14. The system of claim 2, wherein the response signal processor is configured to process the response signal sensed from the eye of the subject by the response signal sensor when the eye of the subject is in alignment with respect to the at least one of the interrogation signal source and the response signal sensor to determine a measurement of at least one of oxygenation, blood glucose, a heart rate, glycosylated hemoglobin, a temperature, a body temperature, a blood flow, and a substance in the eye of the subject from the response signal.

15. The system of claim 2, including interrogation control circuitry configured to drive production of a pulsed interrogation signal by an interrogation signal source, and wherein the signal processing circuitry is configured to gate detection of the response signal relative to the pulsed interrogation signal.

16. The system of claim 2, including interrogation control circuitry configured to drive production of a pulsed interrogation signal by an interrogation signal source, and wherein the signal processing circuitry is configured to combine multiple response signals produced by the eye of the subject in response to multiple pulses of the pulsed interrogation signal by at least one of summing the multiple response signals, averaging the multiple response signals, determining a moving average of the multiple response signals, and determining a weighted sum of the multiple response signals.

17. The system of claim 2, including at least one of an output structure adapted to output a signal relating to the determined physiological parameter and a display adapted to display information relating to the determined physiological parameter.

18. The system of claim 1, wherein the interrogation signal source is adapted to produce light having a first polarization, wherein the response signal sensor is adapted to detect light having a second polarization, and where the first polarization and the second polarization are different.

19. The system of claim 1, wherein the interrogation signal source is adapted to produce light having a first polarization, wherein the response signal sensor is adapted to detect light having a second polarization, and where the first polarization and the second polarization are the same.

20. The system of claim 1, wherein interrogation signal source and the response signal sensor are separately co-aligned.

21. The system of claim 1, wherein interrogation signal source and the response signal sensor are separately aligned and located.

22. The system of claim 2, including gaze tracking stimulus control circuitry configured to drive production of a gaze tracking stimulus by a plurality of gaze tracking stimulus sources.

23. The system of claim 2, including interrogation signal control circuitry configured to drive production of a first interrogation signal having a first optical wavelength and production of a second interrogation signal having a second optical wavelength.

* * * * *